US006096757A

United States Patent [19]

Bishop et al.

[11] Patent Number: 6,096,757

[45] Date of Patent: Aug. 1, 2000

[54] METHOD FOR TREATING PROLIFERATIVE DISEASES

[75] Inventors: Walter R. Bishop, Pompton Plains, N.J.; Joseph J. Catino, Guilford, Conn.; Ronald J. Doll, Maplewood, N.J.; Ashit Ganguly, Upper Montclair, N.J.; Viyyoor M. Girijavallabhan, Parsippany, N.J.; Paul Kirschimeier, Basking Ridge, N.J.; Ming Liu, Fanwood, N.J.; Loretta L. Nielsen, Millington, N.J.; David L. Cutler, Morristown, N.J.

[73] Assignee: Schering Corporation, Kenilworth, N.J.

[21] Appl. No.: 09/217,335

[22] Filed: Dec. 21, 1998

Related U.S. Application Data

[60] Provisional application No. 60/068,423, Dec. 22, 1997, provisional application No. 60/098,339, Aug. 28, 1998, and provisional application No. 60/106,096, Oct. 29, 1998.

[51] Int. Cl.$^7$ .................................... A61K 31/44

[52] U.S. Cl. .................................... 514/290

[58] Field of Search .................................... 514/290

[56] References Cited

U.S. PATENT DOCUMENTS

| | | | |
|---|---|---|---|
| 5,340,828 | 8/1994 | Graham et al. | 514/357 |
| 5,416,091 | 5/1995 | King | 514/290 |
| 5,661,152 | 8/1997 | Bishop et al. | 514/254 |
| 5,719,148 | 2/1998 | Bishop et al. | 514/228 |
| 5,801,175 | 9/1998 | Alfonso et al. | 514/254 |
| 5,874,442 | 2/1999 | Doll et al. | 514/290 |

FOREIGN PATENT DOCUMENTS

| | | |
|---|---|---|
| 0856315 | 8/1998 | European Pat. Off. . |
| WO 92/11034 | 7/1992 | WIPO . |
| WO 95/10516 | 4/1995 | WIPO . |
| WO 97/23478 | 7/1997 | WIPO . |
| WO 97/38664 | 10/1997 | WIPO . |
| WO 97/38697 | 10/1997 | WIPO . |
| WO 97/45412 | 12/1997 | WIPO . |
| WO 98/35554 | 8/1998 | WIPO . |
| WO 98/44797 | 10/1998 | WIPO . |
| WO98/54966 | 12/1998 | WIPO . |

OTHER PUBLICATIONS

Gibbs, vol. 65, 1–4, Apr. 5, 1991.

Sepp–Lorenzo et al., Cancer Research 55, 5302–5309, Nov. 15, 1995.

Moasser, et al., Proc. Natl. Acad. Sci. USA, vol. 95, pp. 1369–1374, Feb. 1998.

Travis, Science, vol. 260, pp. 1877–1878, Jun. 25, 1993.

Kohl, et al., Nature Medicine, vol. 1, pp. 792–797, No. 8, Aug. 1995.

Kohl, et al., Proc. Natl. Acad. Sci. USA, vol. 91, pp. 9141–9145, Sep. 1994.

Levitzki, Current Opinion In Cell Biology vol. 8, pp. 239–244, 1996.

Bernhard, et al., Cancer Research 56, 1727–1730, Apr. 15, 1996.

DeVita, et al., "Cancer, Principles & Practice of Oncology," 5$^{th}$ Ed. pp.445–446, Lippencott–Raven (Phila., 1997).

Liu, et al., Cancer Research 58, 4947–4956, Nov. 1, 1998.

Nagasu, et al., Cancer Research 55, 5310–5314, Nov. 1995.

"SCH66336 Plus Gemictabine For All Advanced Malignancies" (print–out from Internet, 1999).

Shi, et al., "Enhanced efficacy of the farnesly protein transferase inhibitor SCH66336 in combination with paclitaxel", *Proceedings of the American Association For Cancer Research Annual Meeting*, 1999 (Abstract No. 3457).

Schlitzer, "Hemmstoffe der Farnesyltransferase: Ein neuer Ansatz zur Entwicklung potentieller Krebstherapeutika," *Pharmazie in Unserer Zeit*, vol. 27, No. 6, Nov. 1998 pp. 278–288.

Omer et al.: "CA1A2X–competitive inhibitors of farnesyltransferase as anti–cancer agents," *Trends in Pharmacological Sciences*, vol. 18, No. 11, Nov. 1, 1997, pp. 437–445.

Miller et al., Increased radioresistance of Ejras–transformed human osteosarcoma cells and its modulation by lovastatin, an inhibitor of p21ras isoprenylation, (Abstract from Int. J. Cancer, 53 (2): 302–7 (Jan. 21, 1993).

Hausheer et al., "Ab initio quantum mechanica l and x–ray crystallographic studies of gemcitabine and 2'–deoxycytosine", Comput. Chem., 20(4), 459–467, 1996.

*Primary Examiner*—James H. Reamer
*Attorney, Agent, or Firm*—James M. Gould; Henry C. Jeanette

[57] ABSTRACT

Methods are provided for treating proliferative diseases, especially cancers, comprising administering (1) a farnesyl protein transferase inhibitor in conjunction with (2) an antineoplastic agent and/or radiation therapy.

21 Claims, 38 Drawing Sheets

METHOD FOR TREATING PROLIFERATIVE DISEASES

This application claims priority under 35 U.S.C. §119(e) to provisional application No. 60/068,423 filed Dec. 22, 1997, and a provisional application Ser. No. 60/098,339 filed Aug. 28, 1998, and a provisional application of Ser. No. 60/106,096 filed Oct. 29, 1998.

FIELD OF THE INVENTION

This invention describes novel methods of treating subjects afflicted with proliferative diseases such as cancers, tumors, or metastatic disease. In particular, this invention provides methods of inhibiting the proliferation of cells, more specifically cancer cells, comprising the combined use of (1) a farnesyl protein transferase ("FPT") inhibitor and (2) an antineoplastic agent and/or radiation therapy.

BACKGROUND OF THE INVENTION

Oncogenes frequently encode protein components of signal transduction pathways which lead to stimulation of cell growth and mitogenesis. Mutation and/or overexpression of certain oncogenes is frequently associated with cellular tranformation and human cancer. To acquire transforming potential, the precursor of the ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors. Mutated, oncogenic forms of ras are frequently found in many human cancers, most notably in more than 50% of colon and pancreatic carcinomas (Kohl et al., Science, Vol. 260, 1934 to 1937, (1993)). Proteins other than ras may play a part in tumorigenicity and may also require farnesylation for biological activity.

International Patent Publication Number WO92/11034 (published Jul. 9, 1992) discloses a method of increasing the sensitivity of a tumor to an antineoplastic agent (in cases where the tumor is resistant to the antineoplastic agent), by the concurrent administration of the antineoplastic agent and (inter alia) a potentiating agent of the formula:

A

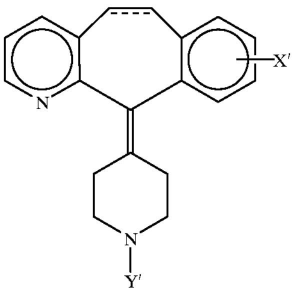

wherein the dotted line represents an optional double bond, X' is hydrogen or halo, and Y' is hydrogen, substituted carboxylate or substituted sulfonyl. For example, Y' can be, amongst others, —COOR' wherein R' is C-1 to C-6 alkyl or substituted ally, phenyl, substituted phenyl, C-7 to C-12 aralkyl or substituted aralkyl, 2-, 3- or 4-piperidyl or N-substituted piperidyl. Y' can also be, amongst others, $SO_2R'$ wherein R' is C-1 to C-6 alkyl, phenyl, substituted phenyl, C-7 to C-12 aralkyl or substituted aralkyl. Examples of such potentiating agents include 11-(4-piperidylidene)-5H-benzo[5,6]cyclohepta[1,2-b]pyridines such as Loratadine. Antineoplastic agents exemplified are: vinca alkaloids, epipodophyllotoxins, anthracycline antibiotics, actinomycin D, plicamycin, puromycin, gramicidin D, taxol, colchicine, cytochalasin B, emetine, maytansine, and amsacrine. The WO92/11034 publication focuses on potentiating the antineoplastic agents through a specific mechanism of action: inhibition of multiple drug resistance.

In view of the need for improved treatments for proliferative diseases, particularly cancers, novel methods of treatment would be a welcome contribution to the art. The present invention provides just such methods of treatment.

SUMMARY OF THE INVENTION

The present invention provides methods of treating proliferative disease in a patient (e.g., a mammal such as a human) in need of such treatment, said treatment comprising administering, concurrently or sequentially, an effective amount of (1) a farnesyl protein transferase (FPT) inhibitor, and (2) an antineoplastic agent and/or radiation therapy. The methods of the present invention are particularly useful for the treatment of various cancers, especially epithelial cancers, e.g., prostate cancer, lung cancer, breast cancer, colorectal cancer, and pancreatic cancer. In preferred embodiments, the FPT inhibitor is combined with one of the following antineoplastic agents: gemcitabine, paclitaxel (Taxol®), 5-Fluorouracil (5-FU), cyclophosphamide (Cytoxan®), temozolomide, or Vincristine.

For instance, in a preferred embodiment, the present invention provides a method of treating cancer, comprising administering, concurrently or sequentially, an effective amount of (1) a farnesyl protein transferase (FPT) inhibitor, and (2) gemcitabine. In a particularly preferred embodiment, the cancer to be treated is a pancreatic cancer.

In another preferred embodiment, the present invention provides a method of treating cancer, comprising administering, concurrently or sequentially, an effective amount of (1) a farnesyl protein transferase (FPT) inhibitor, and (2) a microtubule affecting agent (e.g., paclitaxel).

In view of International Patent Publication WO92/11034, the present specification includes provision of a method of treating proliferative disease, said treatment comprising administering, concurrently or sequentially, an effective amount of (1) an FPT inhibitor, and (2) an antineoplastic agent and/or radiation therapy; with the proviso that when the FPT inhibitor is a compound of the formula:

A

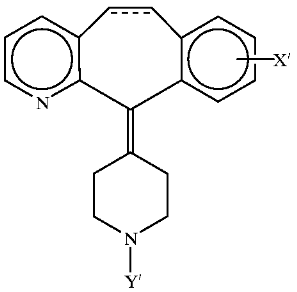

wherein:

the dotted line represents an optional double bond;

X' is hydrogen or halo; and

Y' is hydrogen, —COOR' wherein R' is $C_1$ to $C_{12}$ alkyl or substituted alkyl, phenyl, substituted phenyl, $C_7$ to $C_{12}$ arylalkyl or substituted arylalkyl, 2-, 3- or 4-piperidyl or N-substituted piperidyl, wherein the substituents on said substituted $C_1$ to $C_{12}$ alkyl are selected from amino and substituted amino, and the substituents on the substituted amino are selected from $C_1$ to $C_6$ alkyl, the substituents on said substituted phenyl and on said substituted aryl moiety of the $C_7$ to $C_{12}$ arylalkyl are selected from $C_1$ to $C_6$ alkyl and halo, and the substituent on said N-substituted piperidyl is $C_1$ to $C_4$ alkyl, or $—SO_2R'$ wherein R' is $C_1$ to $C_{12}$ alkyl, phenyl, substituted phenyl, $C_7$ to $C_{12}$ arylalkyl or substituted arylalkyl, wherein the substituents on said substituted phenyl and on said substituted aryl moiety of the $C_7$ to $C_{12}$ arylalkyl are selected from $C_1$ to $C_6$ alkyl and halo;

then the antineoplastic agent is not selected from vinca alkaloids, epipodophyllotoxins, anthracycline antibiotics, actinomycin D, plicamycin, puromycin, gramicidin D, taxol, colchicine, cytochalasin B, emetine, maytansine, or amsacrine.

BRIEF DESCRIPTION OF THE DRAWINGS

The FPT Inhibitory Compound in FIGS. 1 through 38 (sometimes referred to as "Compound X") is as follows:

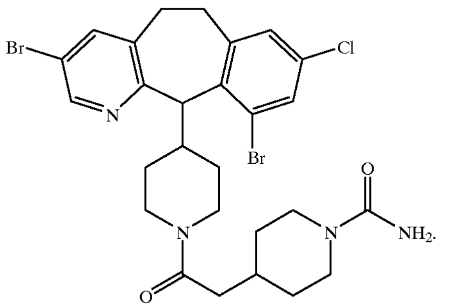

(+)-enantiomer

FIGS. 1 through 15 show three examples where clear synergy was observed. Similar results were observed in the DLD-1 colon, HTB177 lung, PA-1 ovarian, LNCaP prostate, AsPC-1 pancreatic and PANC-1 pancreatic models (data not shown). Clear Antagonism was observed in one cell line MDA-MB-231 (FIGS. 16–20). Mixed results were seen in MDA-MB-468 (FIGS. 21–35).

Figure 1:
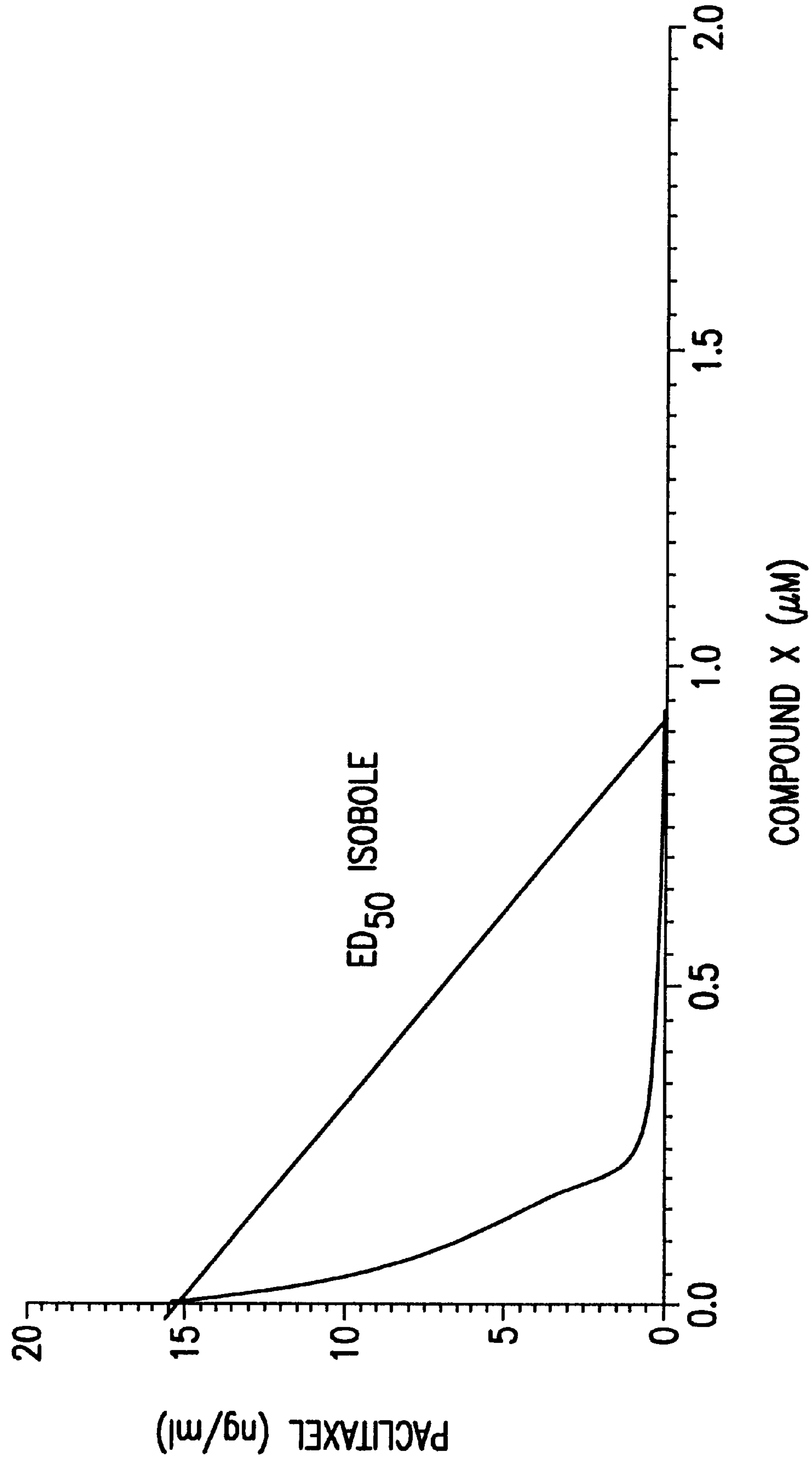

More specifically, FIG. 1 shows an isobologram for MiaPaCa2 pancreatic tumor cells treated with an FPT inhibitory compound and paclitaxel in vitro. The x-axis indicates the amount of paclitaxel expressed as ng/ml. The y-axis indicates the amount of Compound X in $\mu$M units. When the experimental curve falls below the straight diagonal line, as is the case here, this represents a synergistic interaction. (See, e.g., O'Connell, M. A., and Wolfinger, R. D., J. Computational and Graphical Statistics 6: 224–241, 1997, and Berenbaum, M. C., Pharmacol. Rev. 41: 93–141, 1989)

Figure 2:
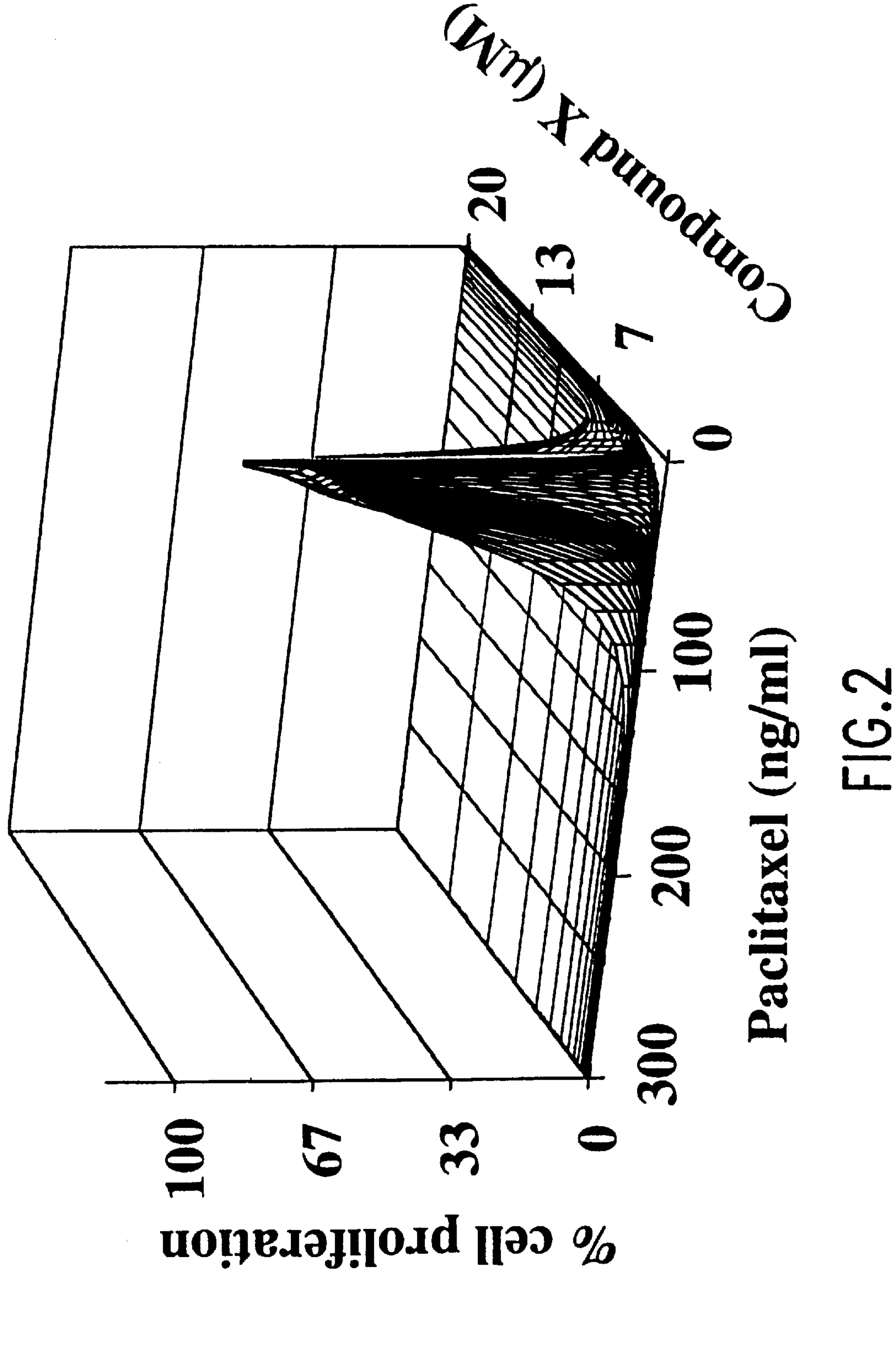

FIG. 2 shows a 3-dimensional cell proliferation model from which FIG. 1 was derived.

Figure 3:
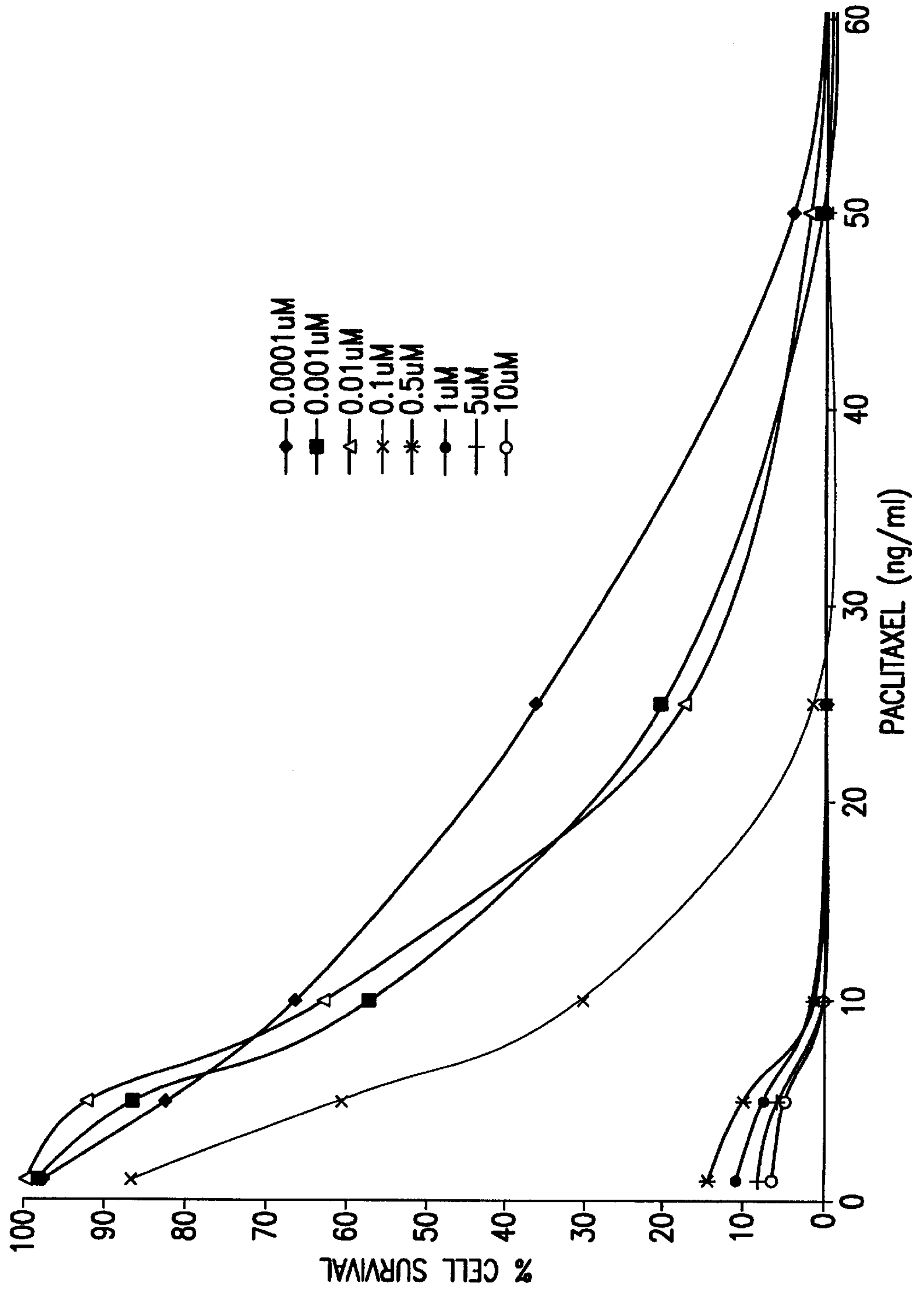

FIG. 3 shows a dose response curve before statistical analysis for drug interactions of paclitaxel (dosages expressed as ng/ml along the x-axis) and Compound X (dosages in $\mu$M units as indicated in the box to the right of the curves) in MiaPaCa2 cells. The y-axis indicates percentage of cell survival.

Figure 4:
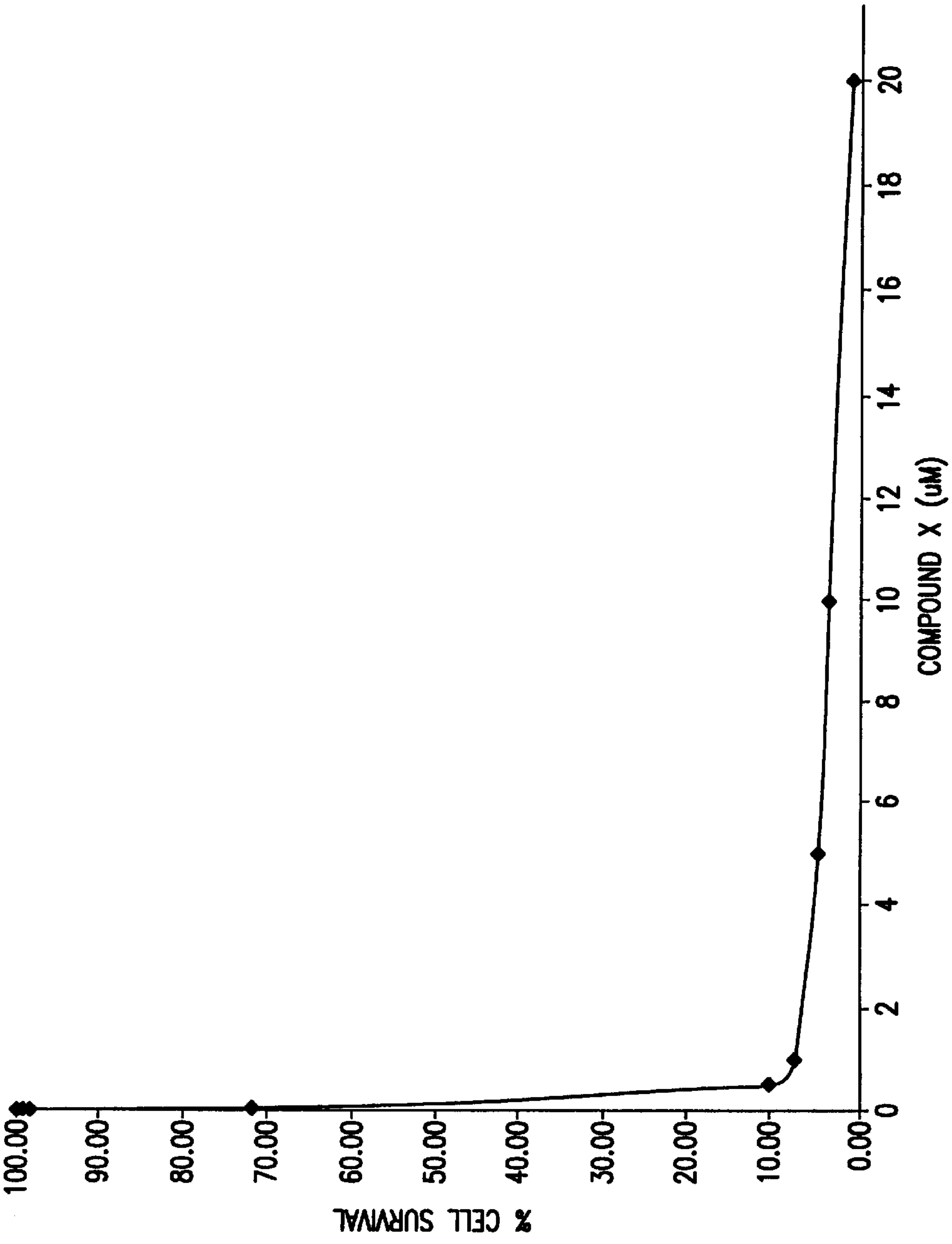

FIG. 4 shows a dose response curve before statistical analysis for Compound X (dosages in $\mu$M units as indicated along the x-axis) in MiaPaCa2 cells, with the y-axis indicating percentage of cell survival.

Figure 5:
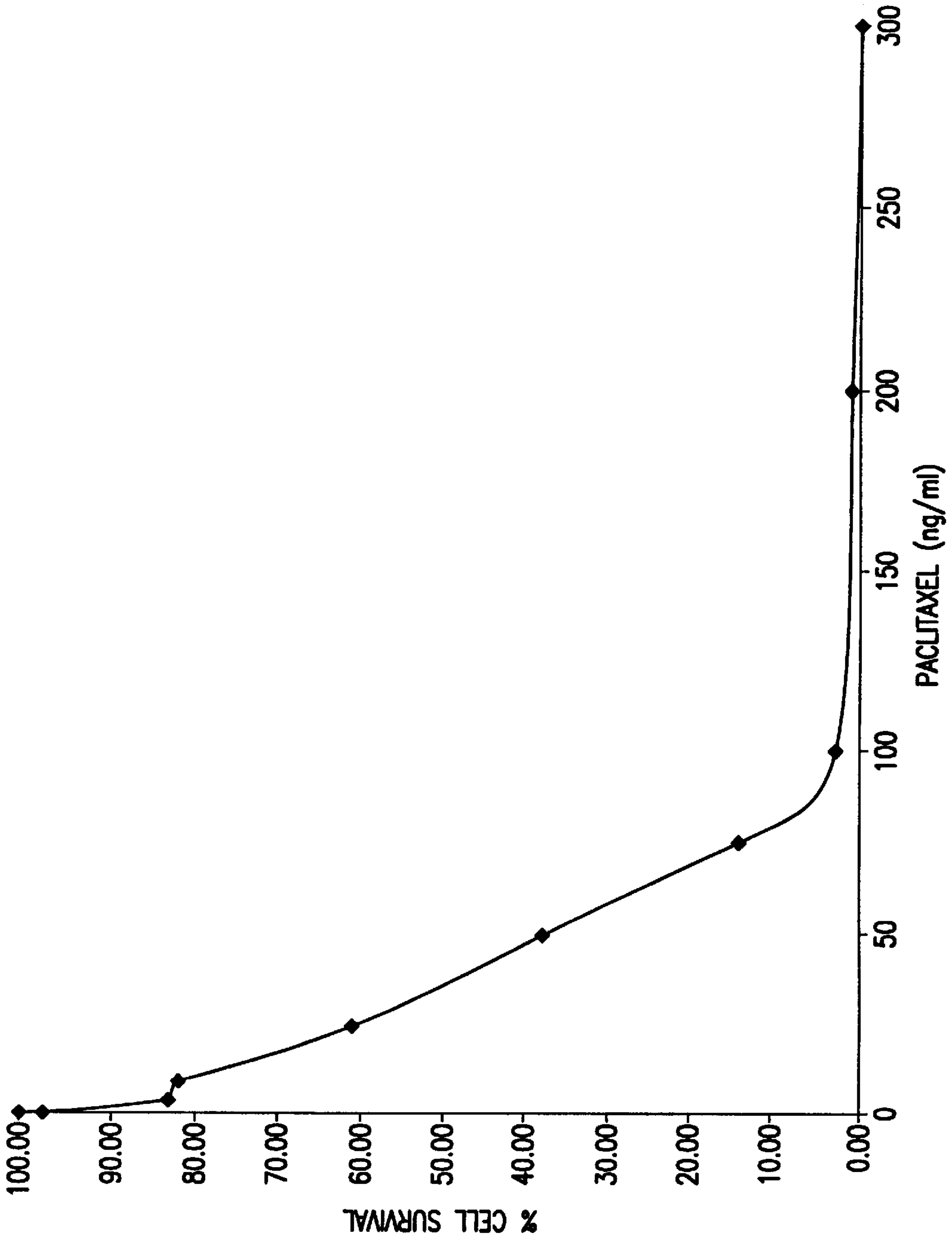

FIG. 5 shows a dose response curve before statistical analysis for paclitaxel (dosages expressed as ng/ml as indicated along the x-axis) in MiaPaCa2 cells, with the y-axis indicating percentage of cell survival.

Figure 6:
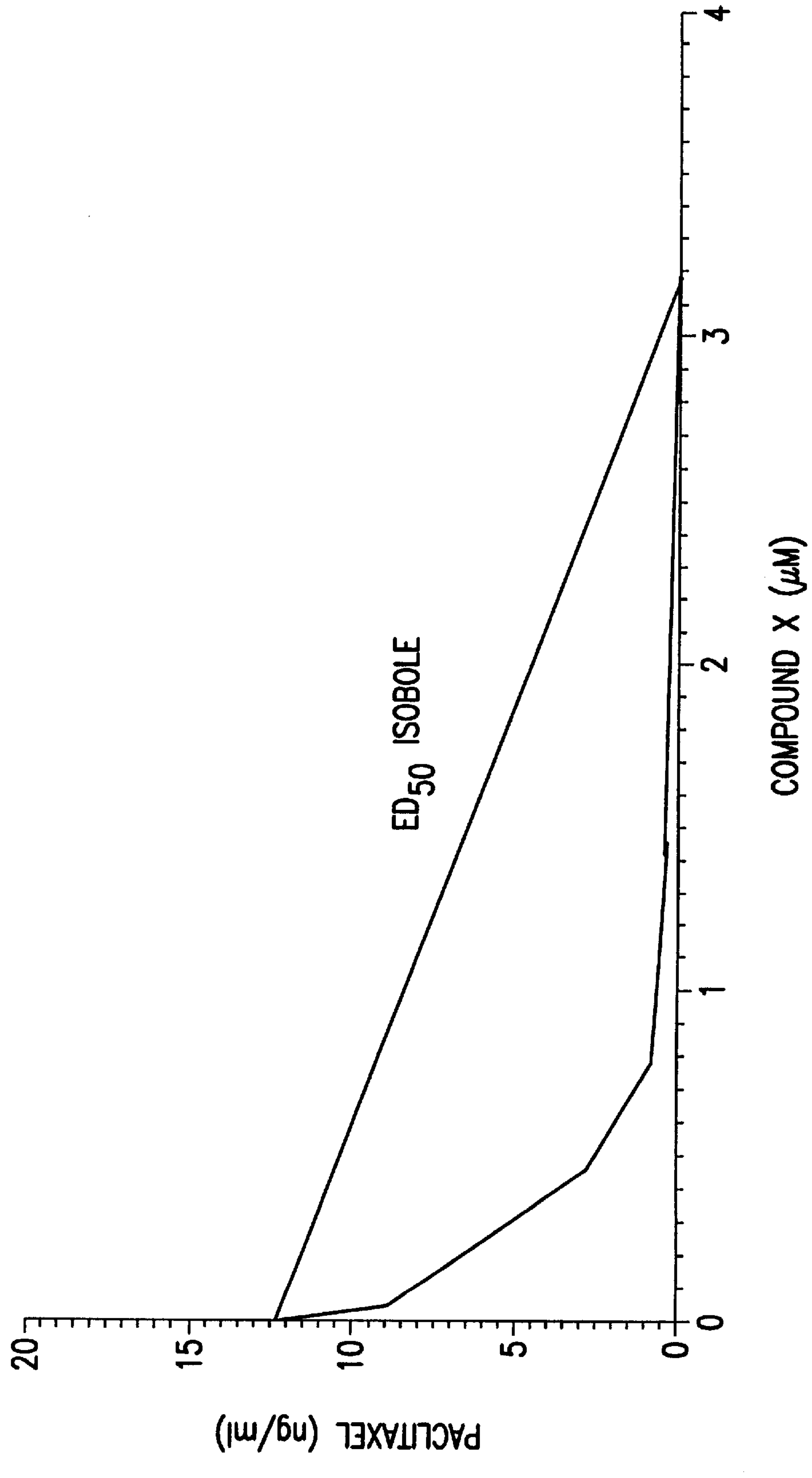

FIG. 6 shows an isobologram for DU-145 prostate tumor cells treated with an FPT inhibitory compound and paclitaxel in vitro. The x-axis indicates the amount of paclitaxel expressed as ng/ml. The y-axis indicates the amount of Compound X in $\mu$M units.

Figure 7:
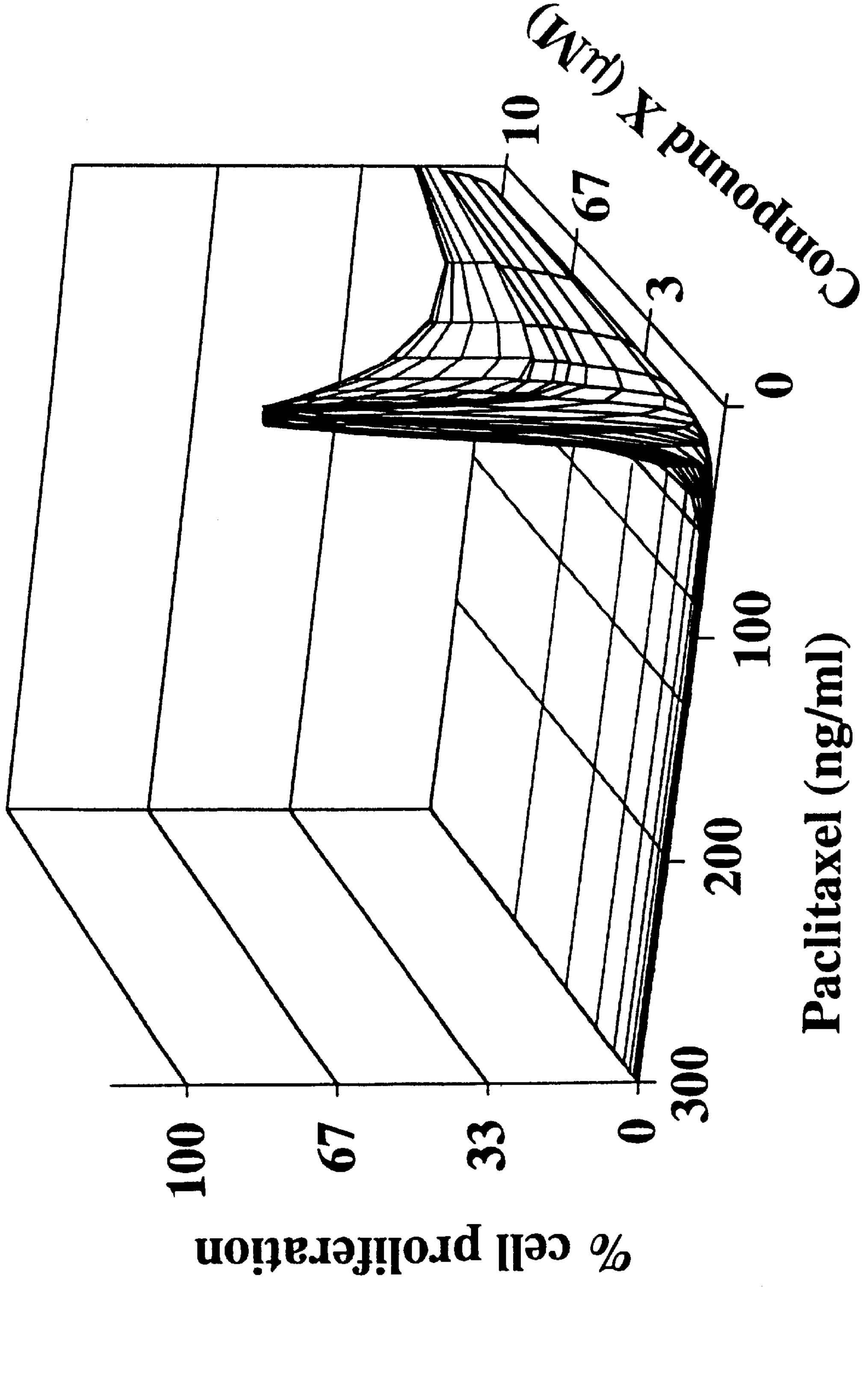

FIG. 7 shows a 3-dimensional model from which FIG. 6 was generated.

Figure 8:
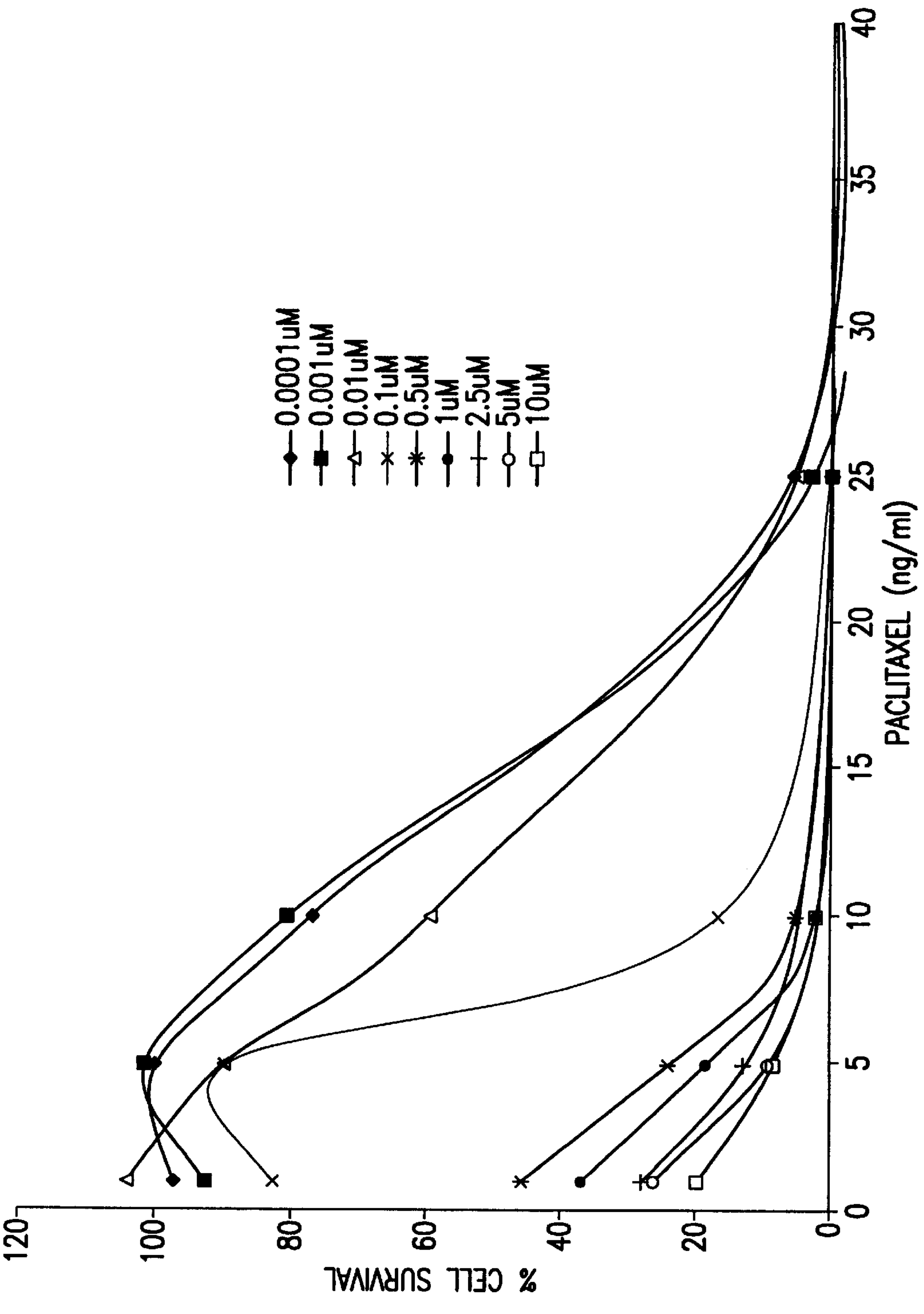

FIG. 8 shows a dose response curve before statistical analysis for drug interactions of paclitaxel (dosages expressed as ng/ml along the x-axis) and Compound X (dosages in $\mu$M units as indicated in the box to the right of the curves) in DU-145 cells. The y-axis indicates percentage of cell survival.

Figure 9:
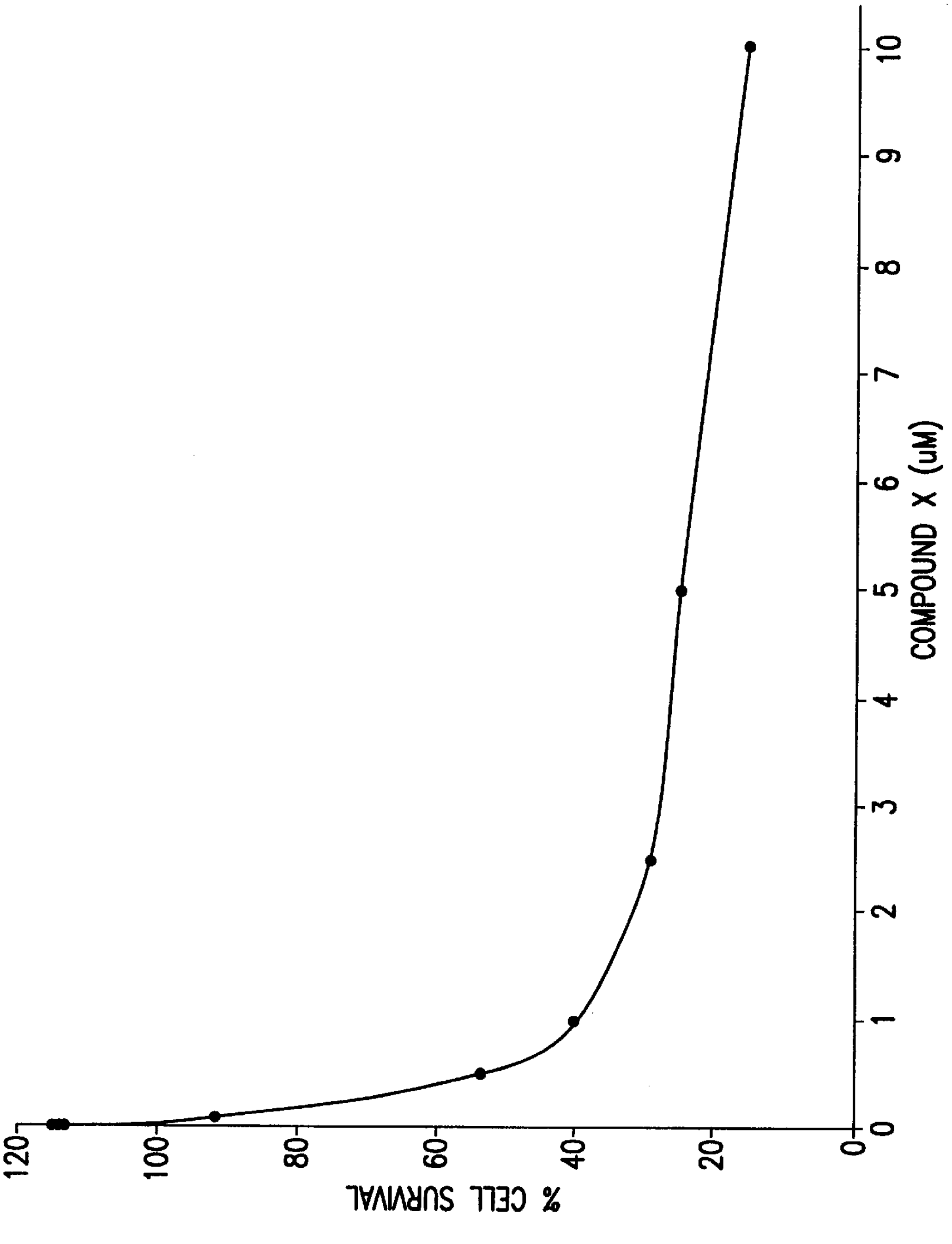

FIG. 9 shows a dose response curve before statistical analysis for Compound X (dosages in $\mu$M units as indicated along the x-axis) in DU-145 cells, with the y-axis indicating percentage of cell survival.

Figure 10:
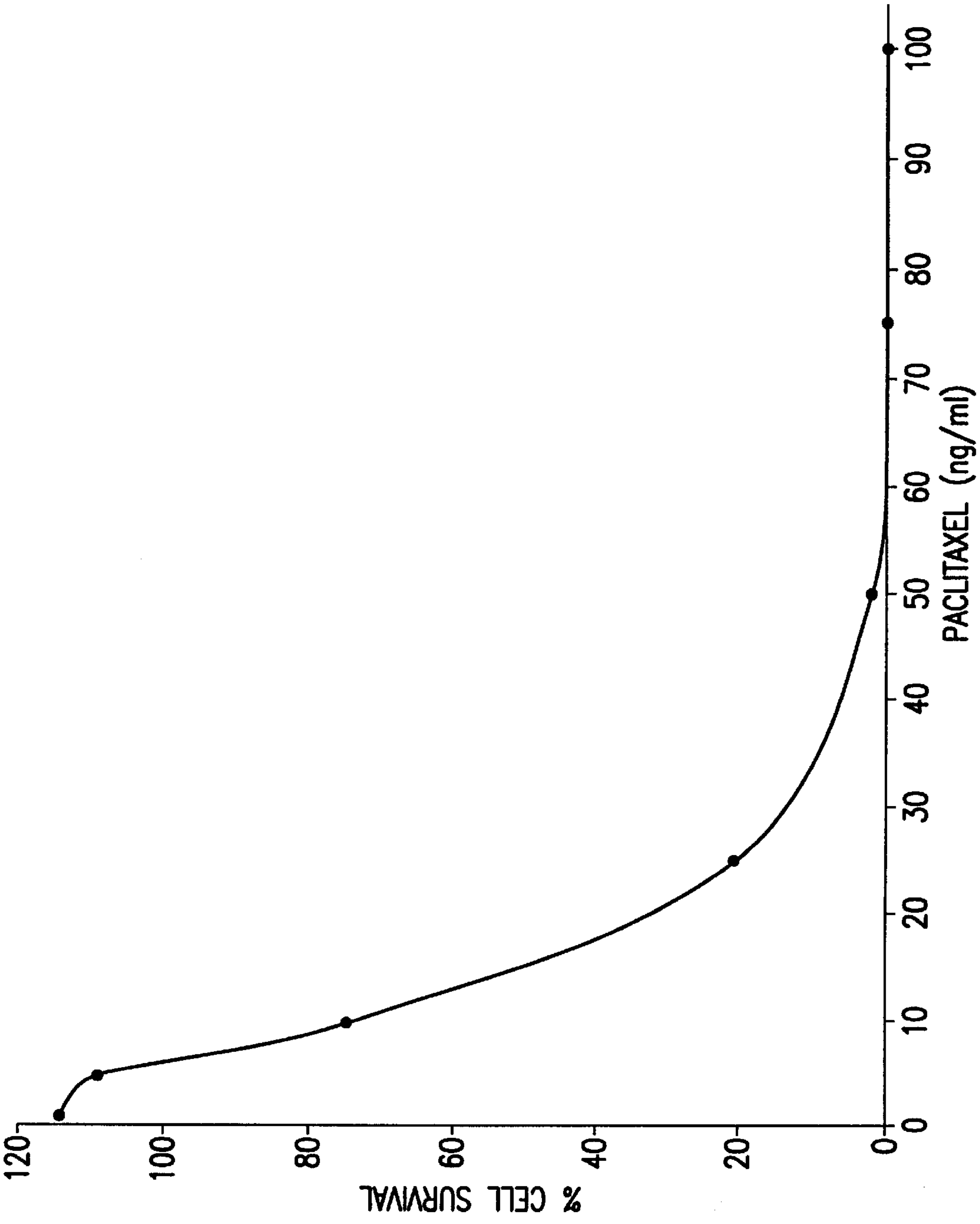

FIG. 10 shows a dose response curve before statistical analysis for paclitaxel (dosages expressed as ng/ml as indicated along the x-axis) in DU-145 cells, with the y-axis indicating percentage of cell survival.

Figure 11:
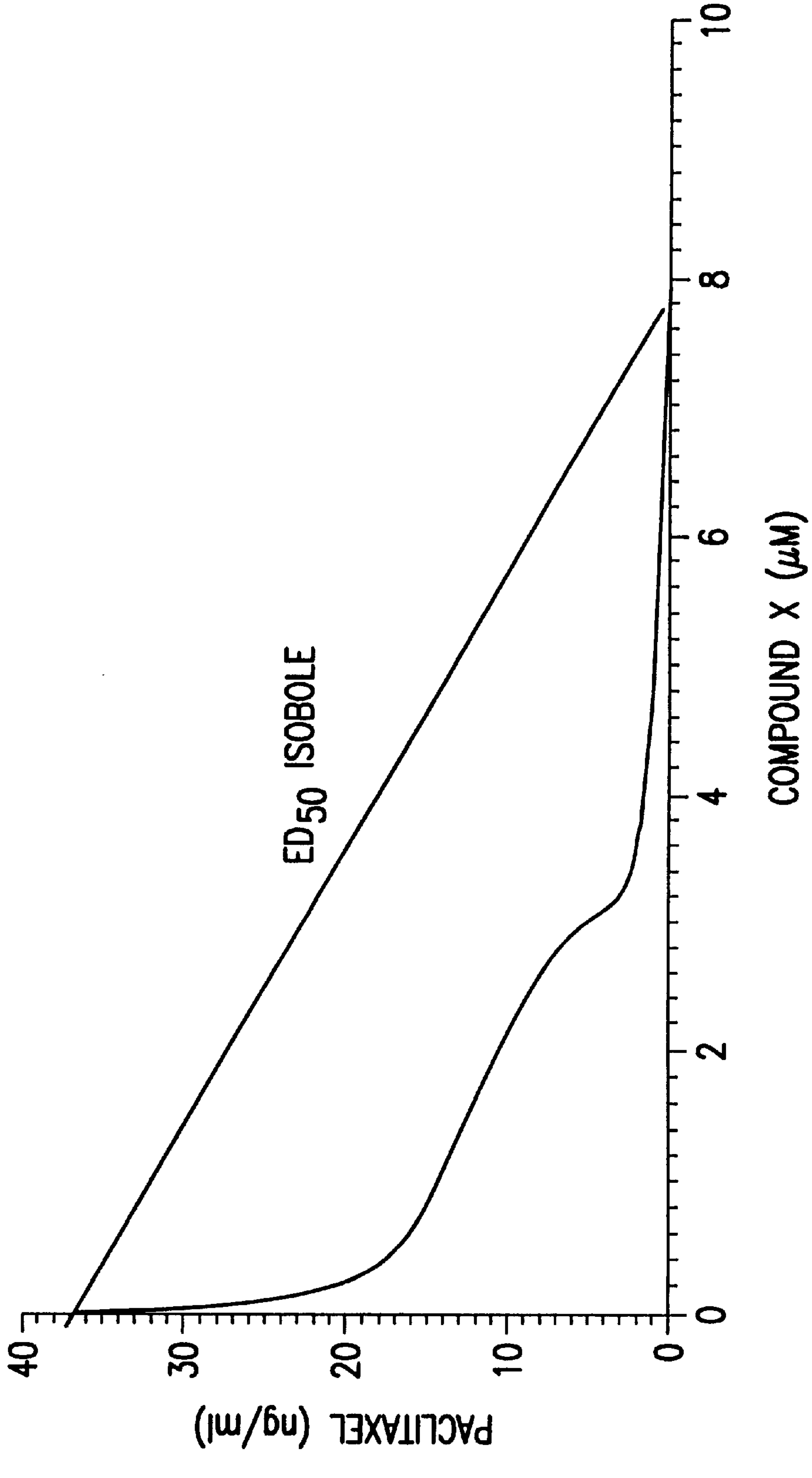

FIG. 11 shows an isobologram for MidT#2-1 mouse mammary tumor cells treated with an FPT inhibitory compound and paclitaxel in vitro. The x-axis indicates the amount of paclitaxel expressed as ng/ml. The y-axis indicates the amount of Compound X in $\mu$M units.

Figure 12:
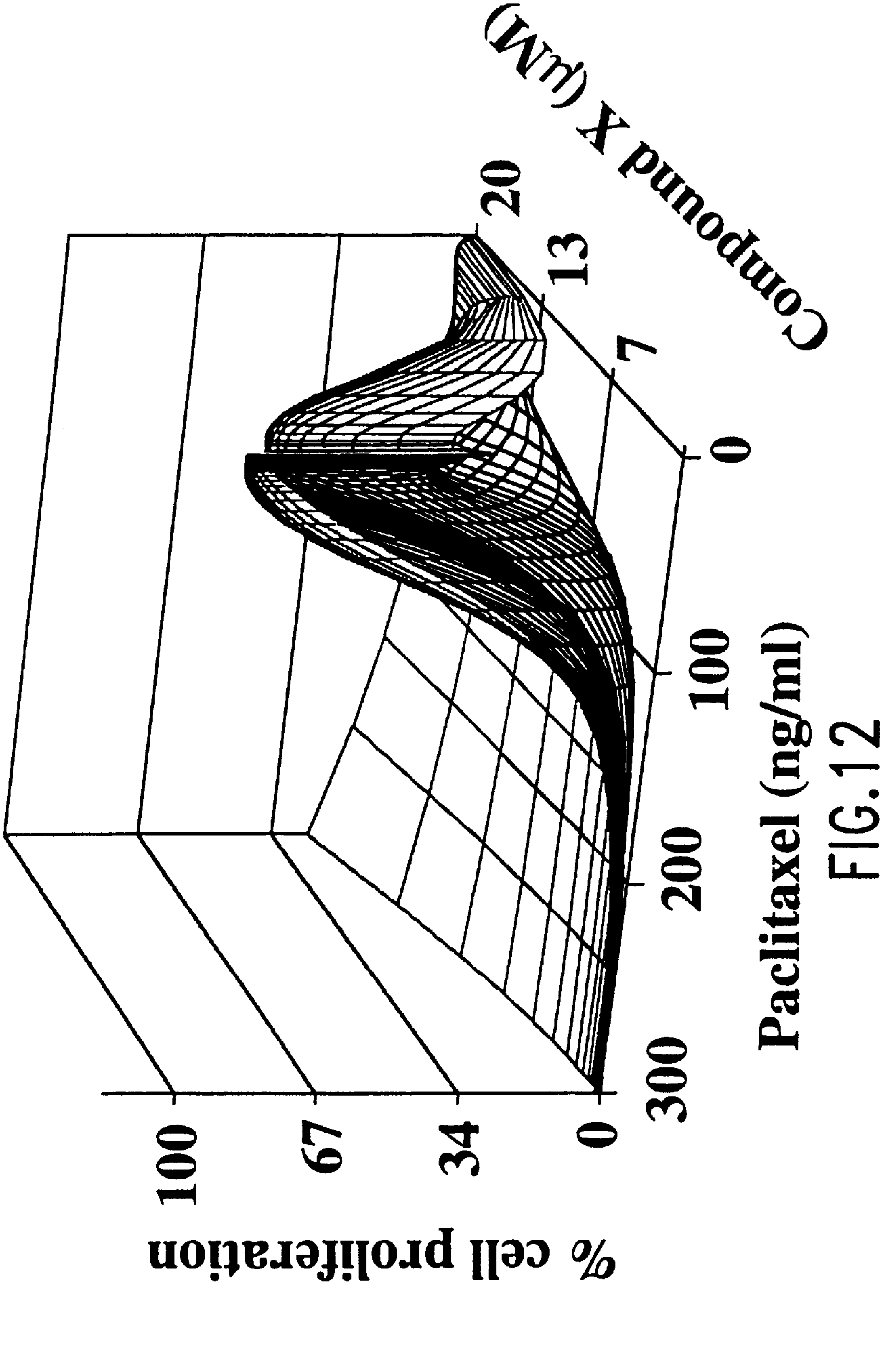

FIG. 12 shows a 3-dimensional cell proliferation model from which FIG. 11 is derived.

Figure 13:
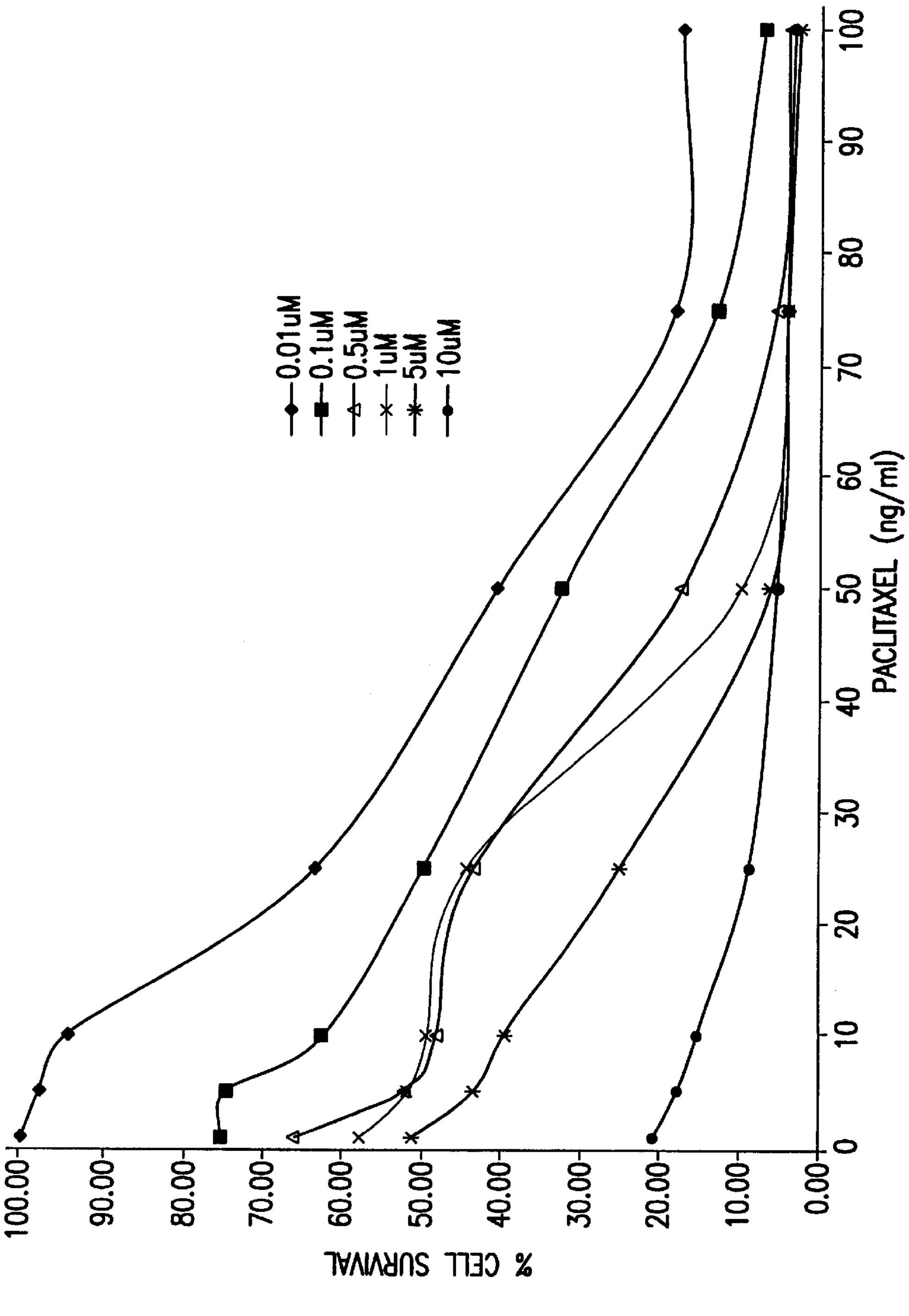

FIG. 13 shows a dose response curve before statistical analysis for drug interactions of paclitaxel (dosages expressed as ng/ml along the x-axis) and Compound X (dosages in $\mu$M units as indicated in the box to the right of the curves) in MidT#2-1 cells. The y-axis indicates percentage of cell survival.

Figure 14:
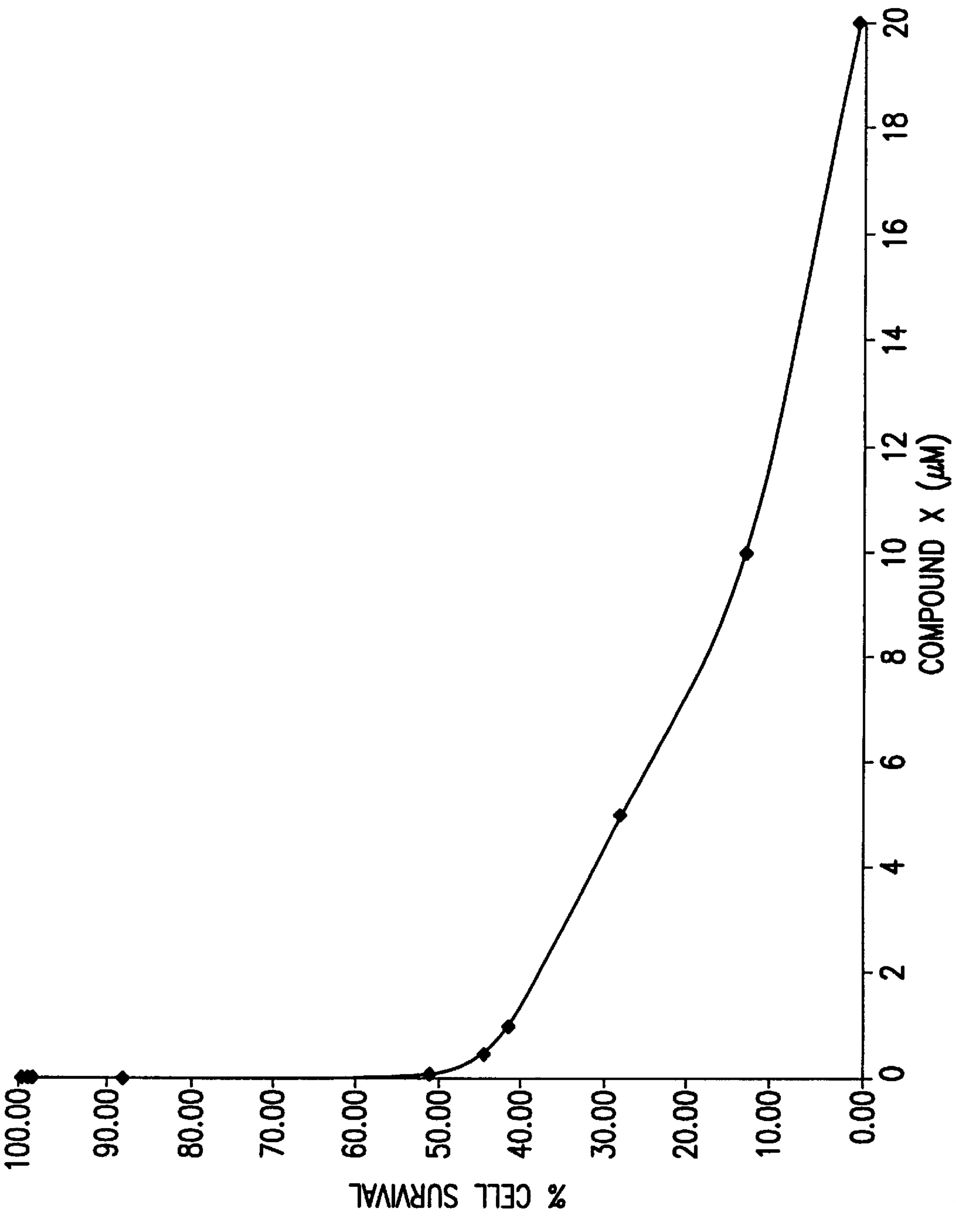

FIG. 14 shows a dose response curve before statistical analysis for Compound X (dosages in $\mu$M units as indicated along the x-axis) in MidT#2-1 cells, with the y-axis indicating percentage of cell survival.

Figure 15:
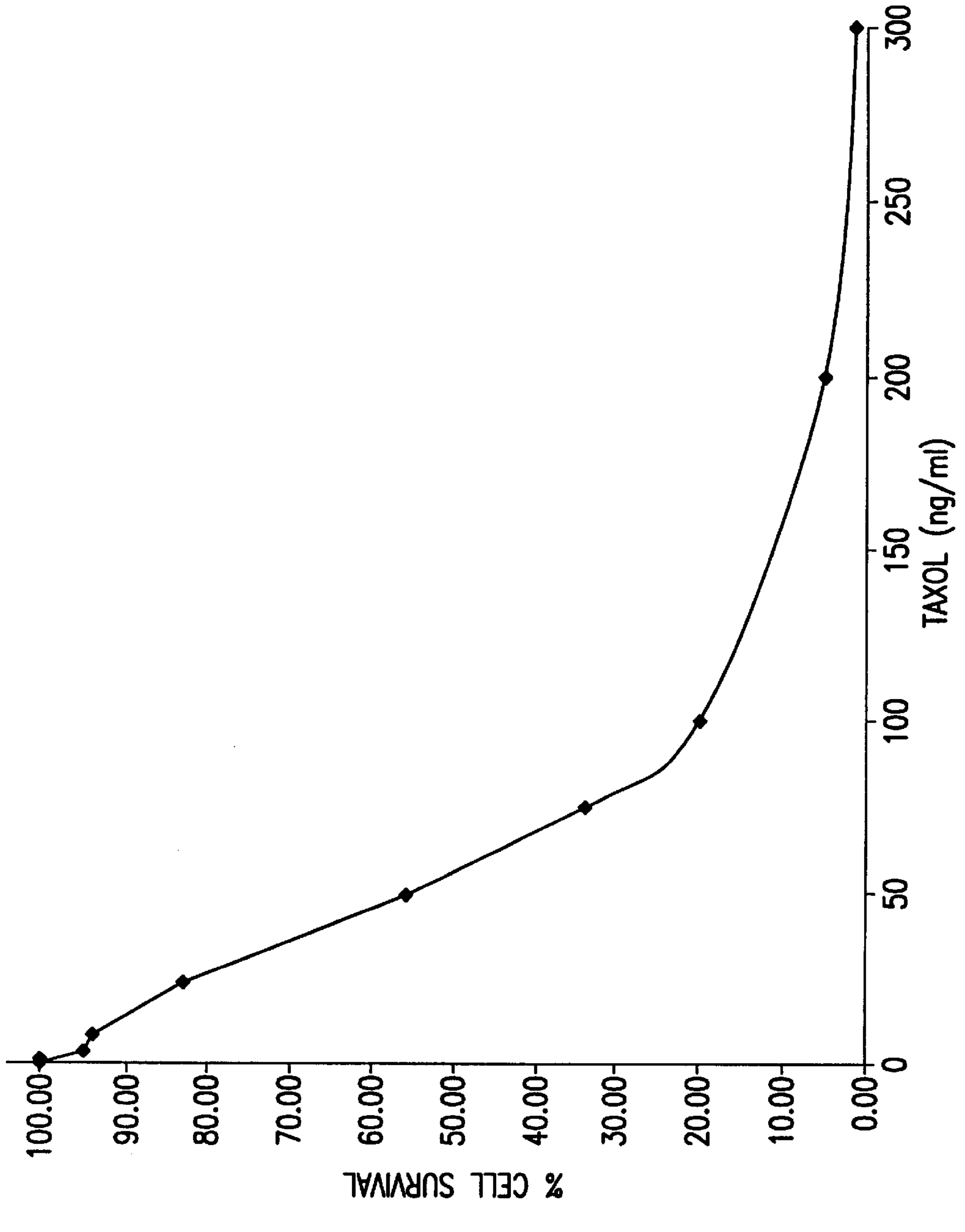

FIG. 15 shows a dose response curve before statistical analysis for paclitaxel (dosages expressed as ng/ml as indicated along the x-axis) in MidT#2-1 cells, with the y-axis indicating percentage of cell survival.

Figure 16:
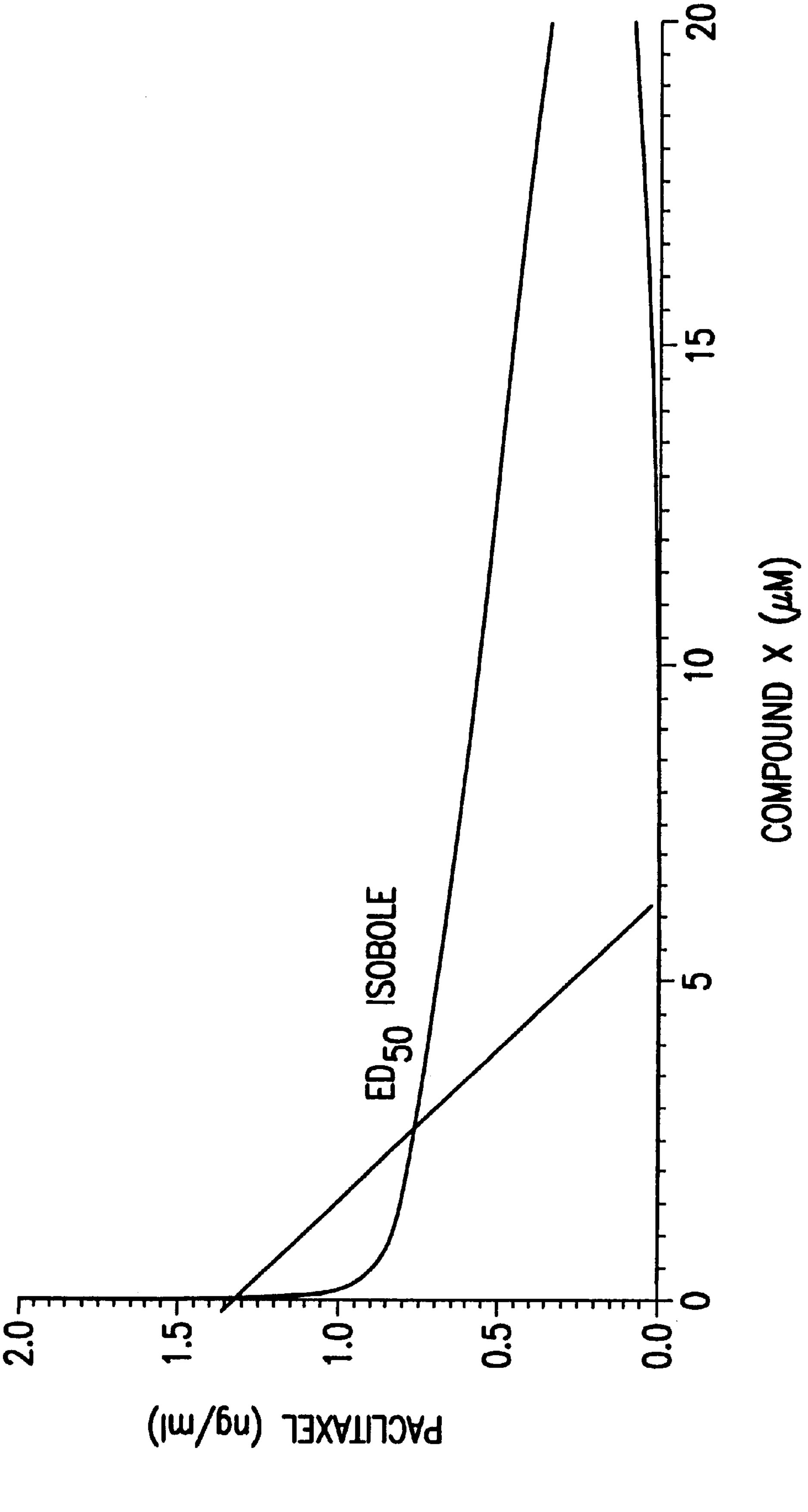

FIG. 16 shows an isobologram for MDA-MB-231 breast tumor cells treated with a FPT inhibitory compound and paclitaxel in vitro. The x-axis indicates the amount of paclitaxel expressed as ng/ml. The y-axis indicates the amount of Compound X in $\mu$M units.

Figure 17:
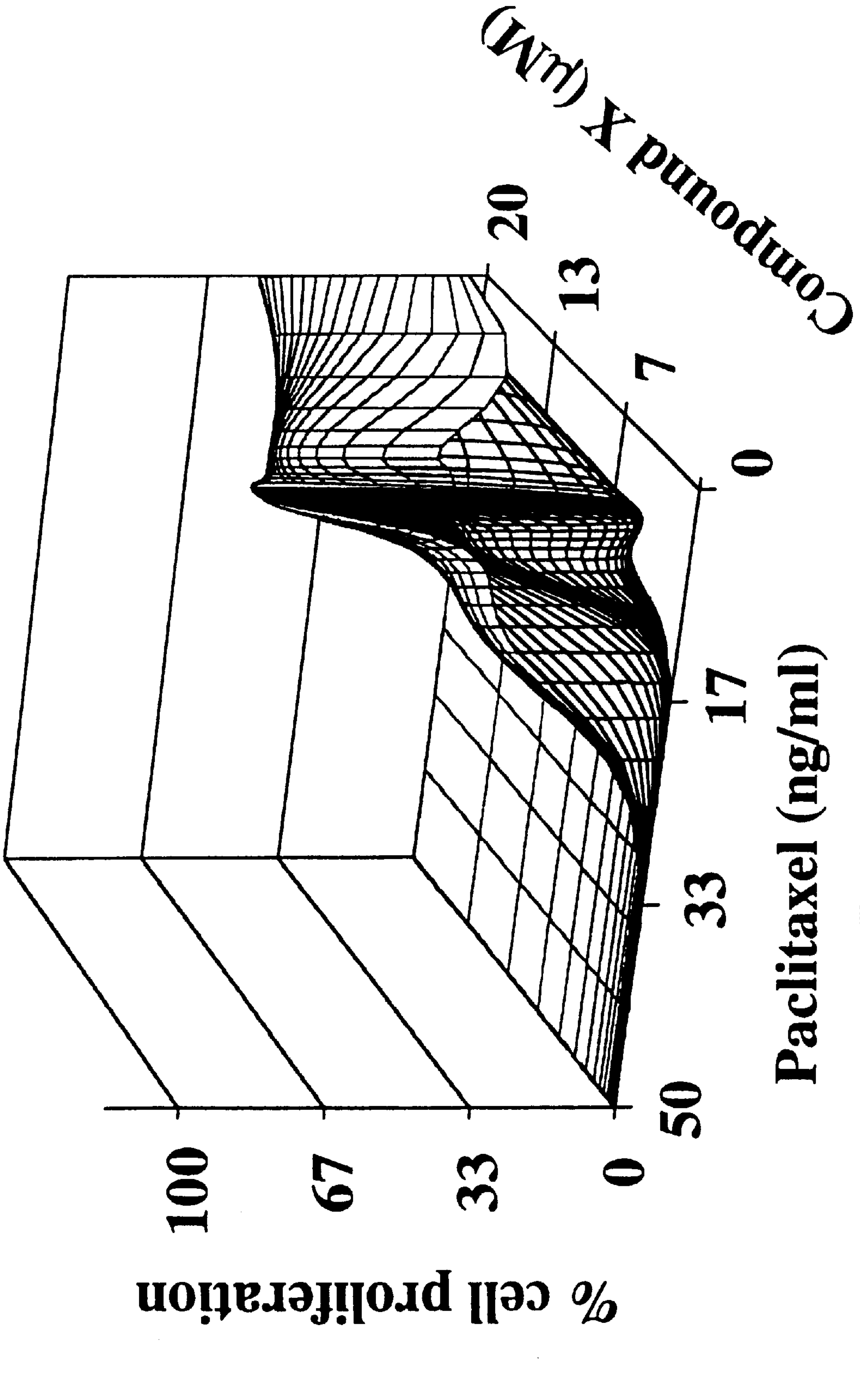

FIG. 17 shows a 3-dimensional cell proliferation model from which FIG. 16 was generated.

Figure 18:
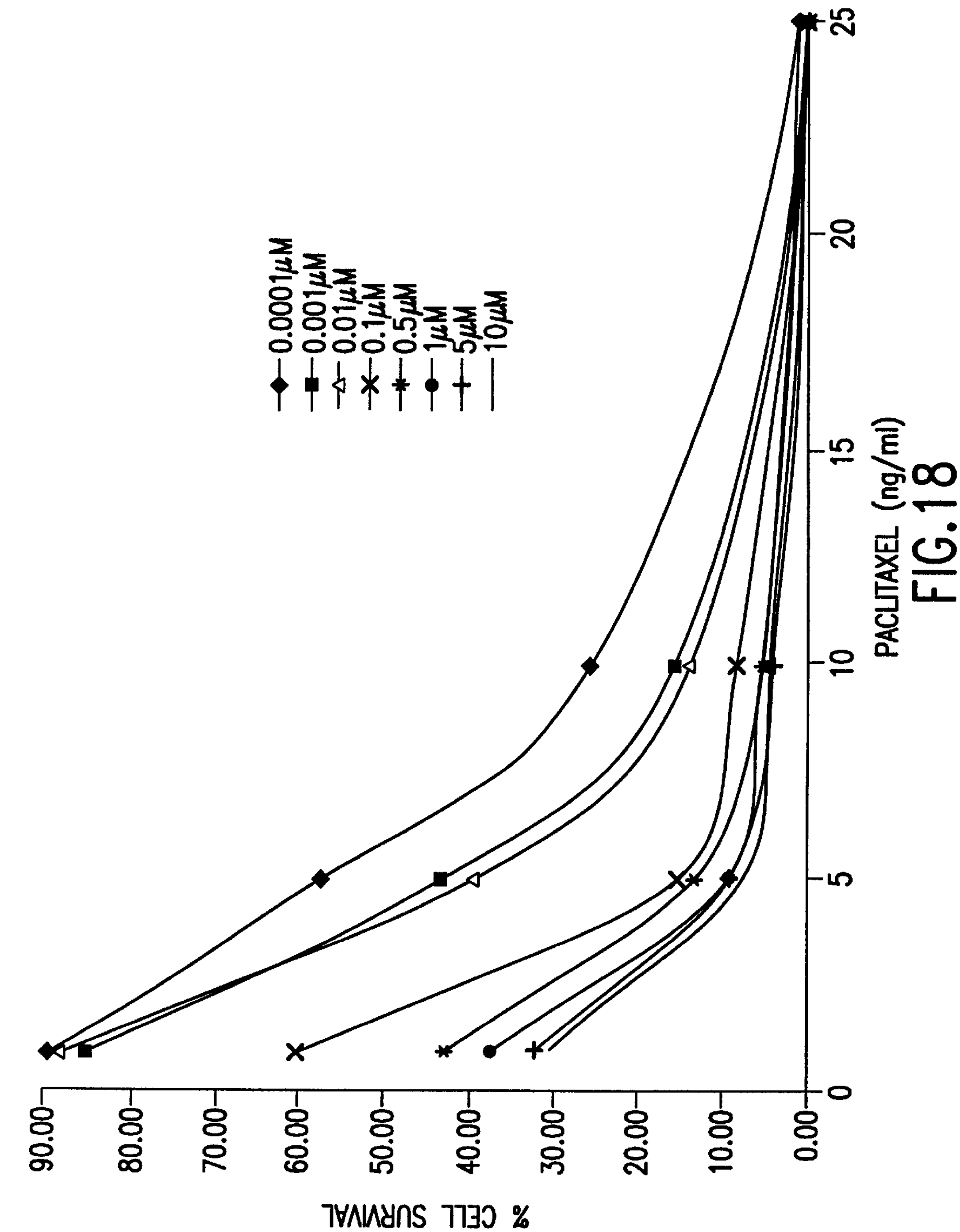

FIG. 18 shows a dose response curve before statistical analysis for drug interactions of paclitaxel (dosages expressed as ng/ml along the x-axis) and Compound X (dosages in $\mu$M units as indicated in the box to the right of the curves) in MDA-MB-231 cells. The y-axis indicates percentage of cell survival.

Figure 19:
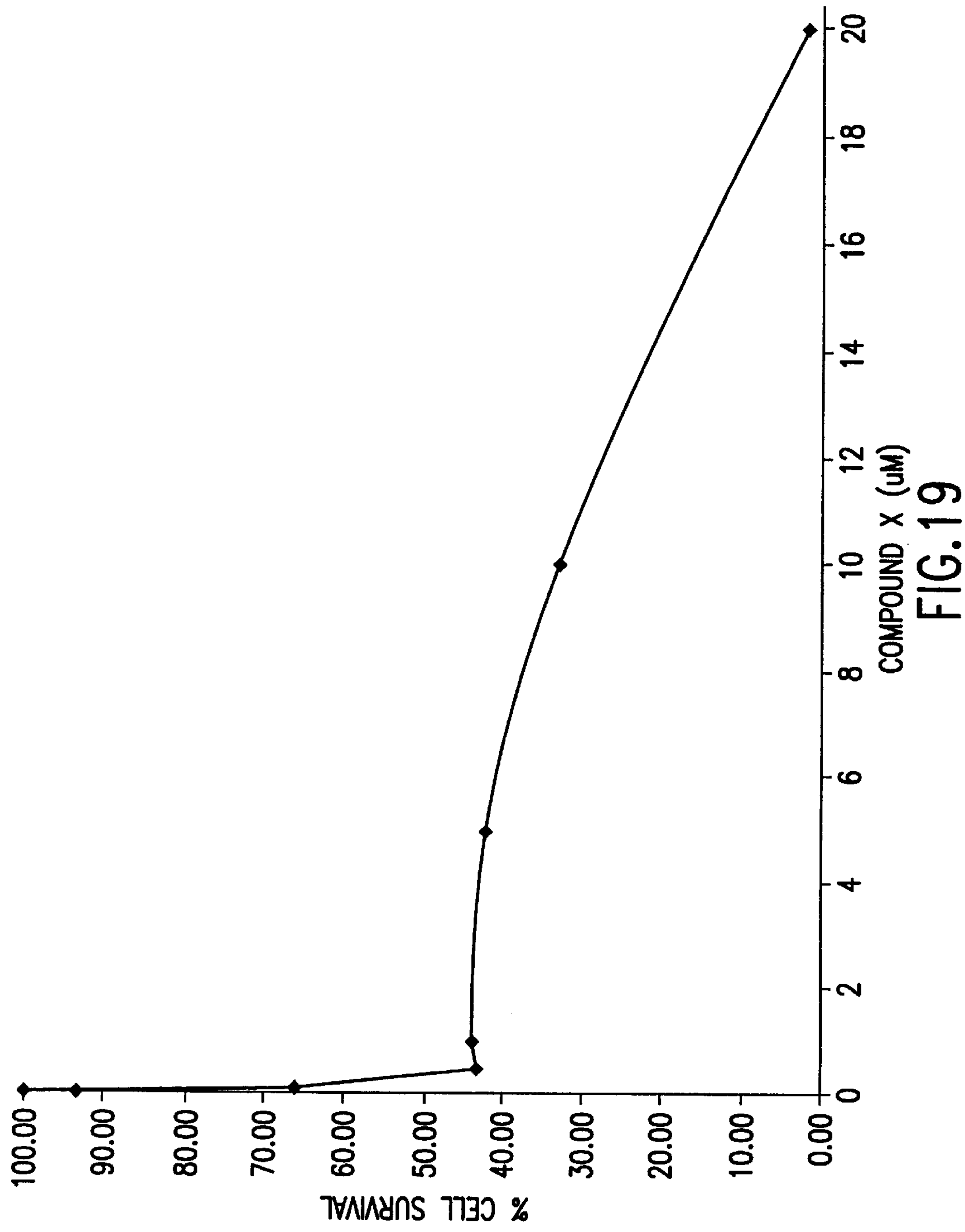

FIG. 19 shows a dose response curve before statistical analysis for Compound X (dosages in $\mu$M units as indicated along the x-axis) in MDA-MB-231 cells, with the y-axis indicating percentage of cell survival.

Figure 20:
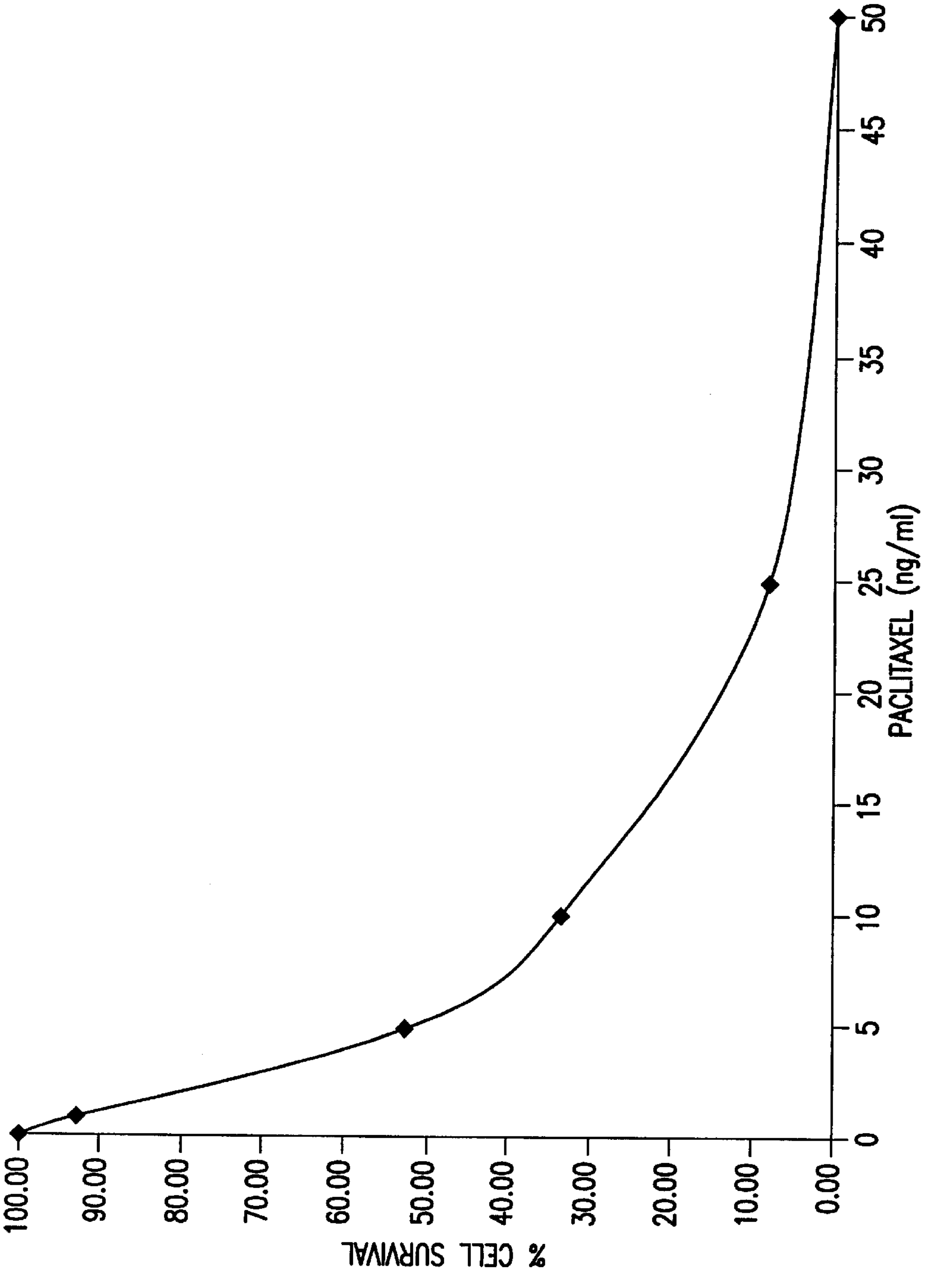

FIG. 20 shows a dose response curve before statistical analysis for paclitaxel (dosages expressed as ng/ml as indicated along the x-axis) in MDA-MB-231 cells, with the y-axis indicating percentage of cell survival.

Figure 21:
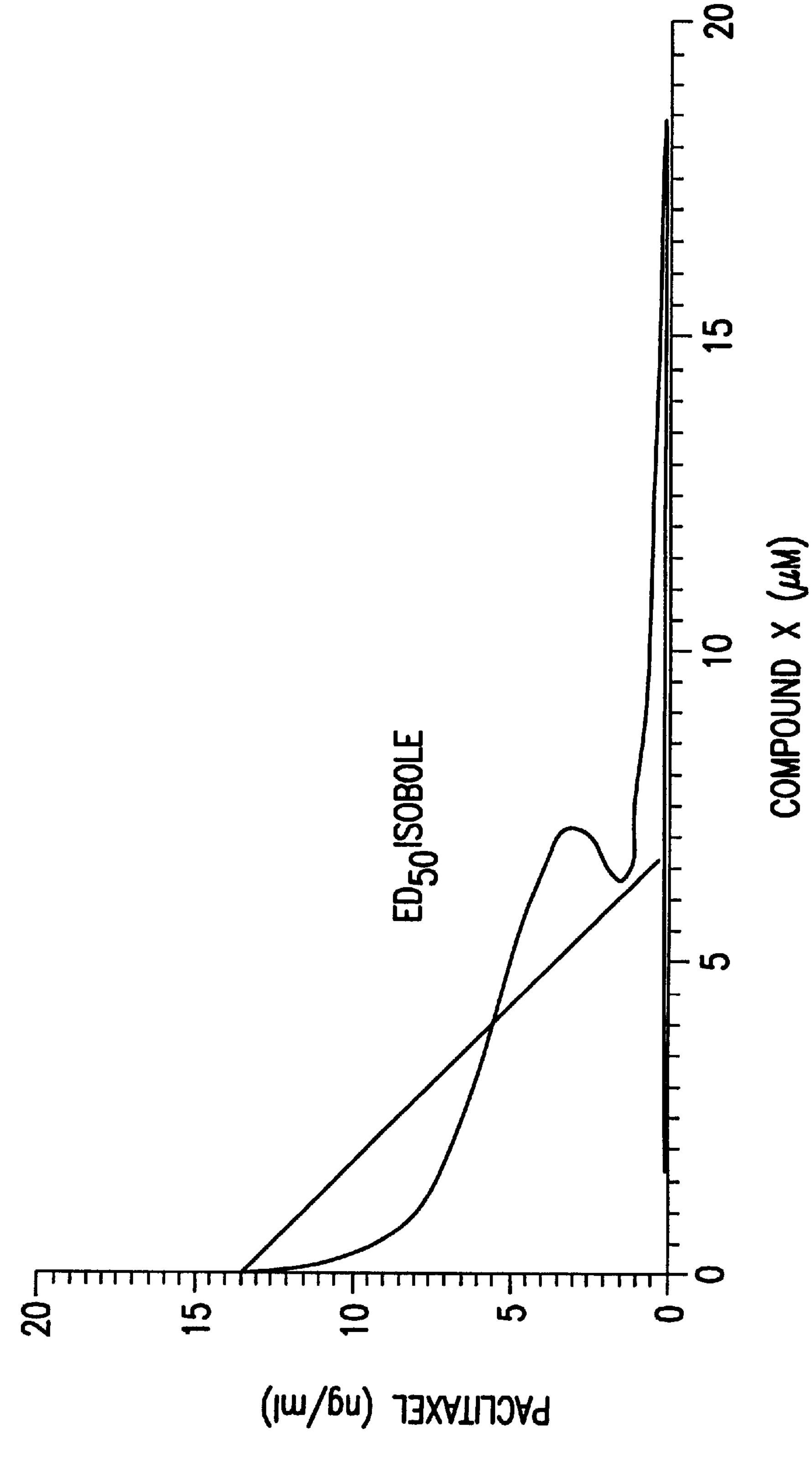

FIG. 21 shows an isobologram for Study #1 of MDA-MB-468 breast tumor cells treated with a FPT inhibitory compound and paclitaxel in vitro. (Example E herein). The x-axis indicates the amount of paclitaxel expressed as ng/ml. The y-axis indicates the amount of Compound X in μM units.

Figure 22:
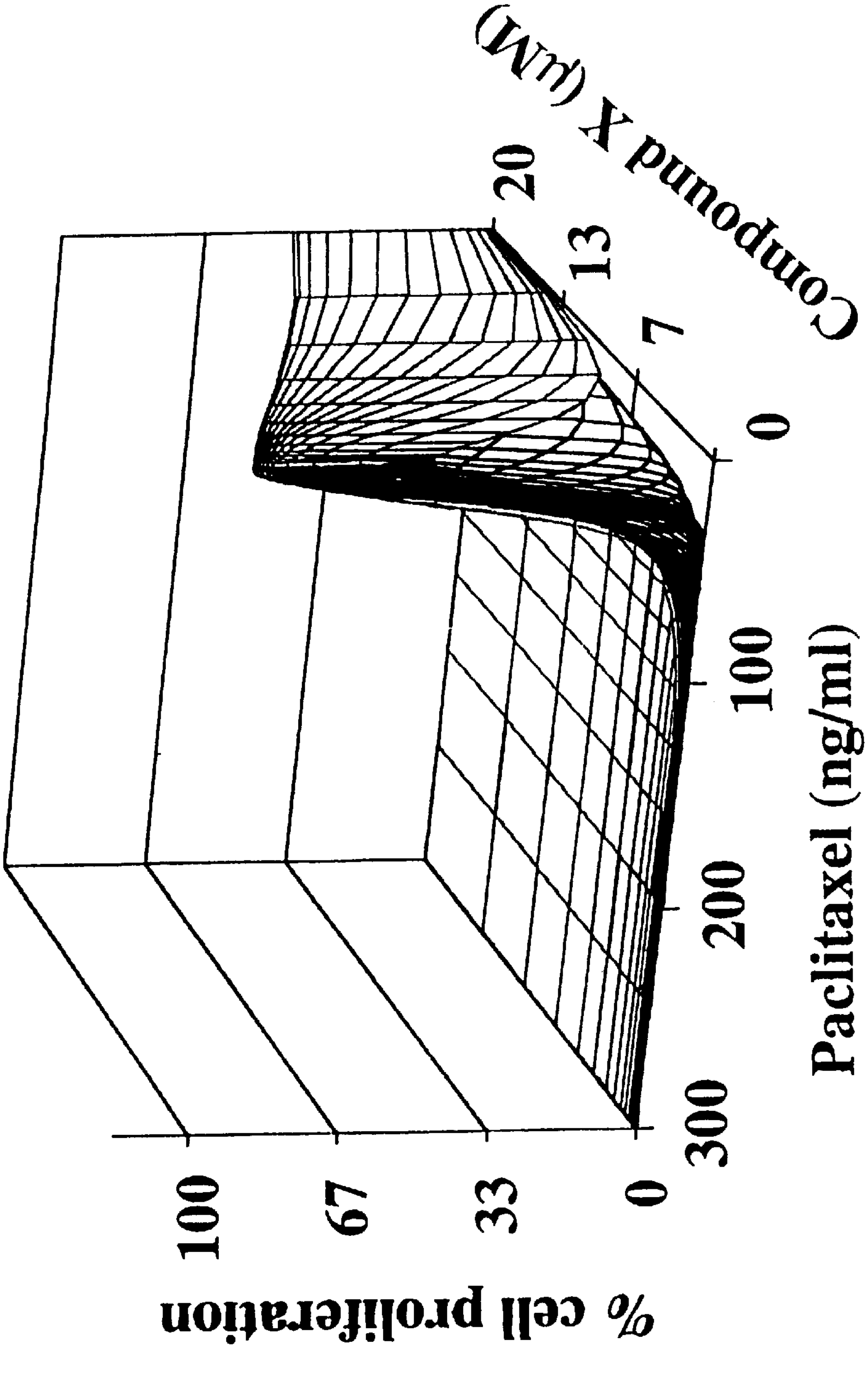

FIG. 22 shows a 3-dimensional cell proliferation model from which FIG. 21 was generated.

Figure 23:
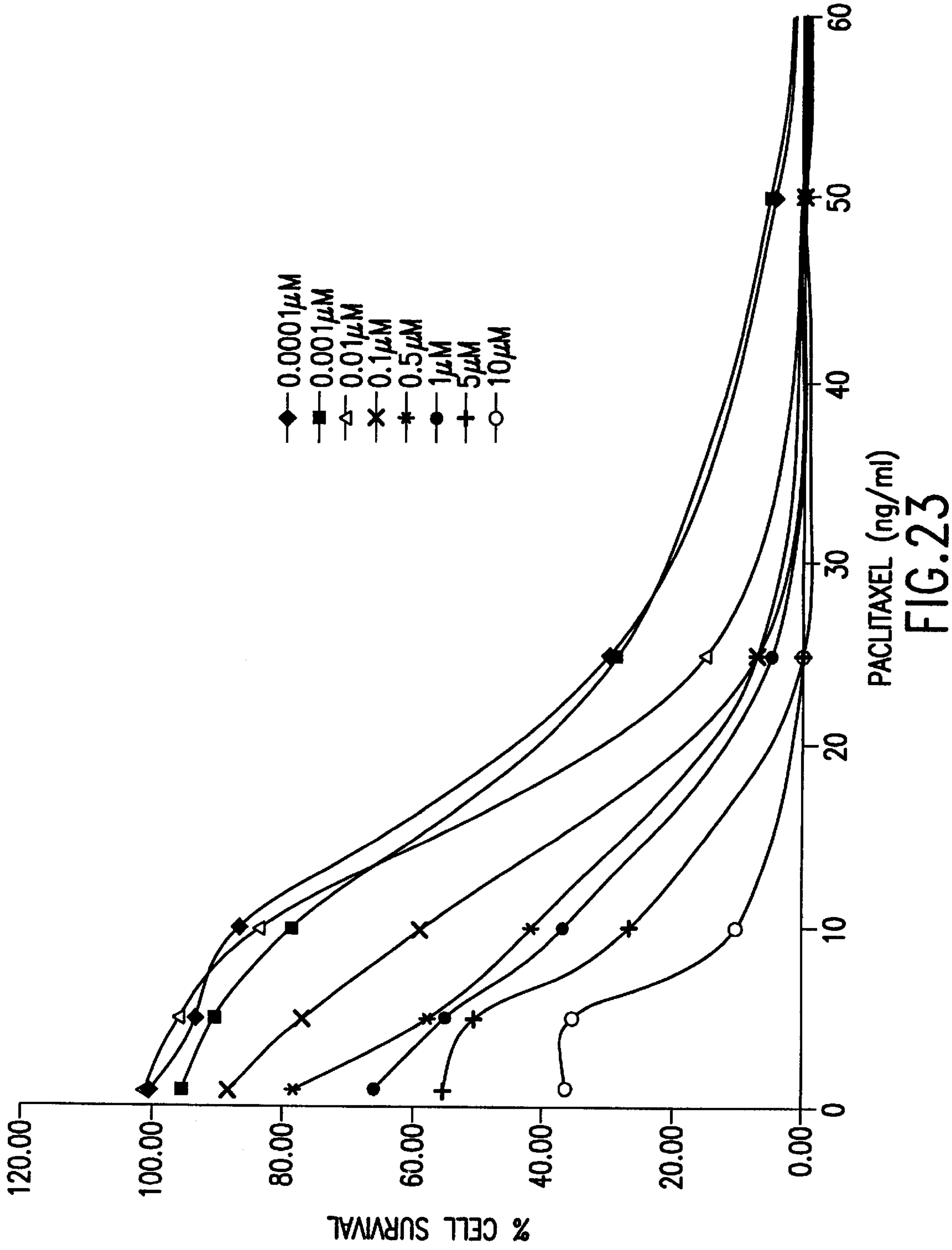

FIG. 23 shows a dose response curve before statistical analysis for drug interactions of paclitaxel (dosages expressed as ng/ml along the x-axis) and Compound X (dosages in μM units as indicated in the box to the right of the curves) in MDA-MB-468 cells. The y-axis indicates percentage of cell survival.

Figure 24:
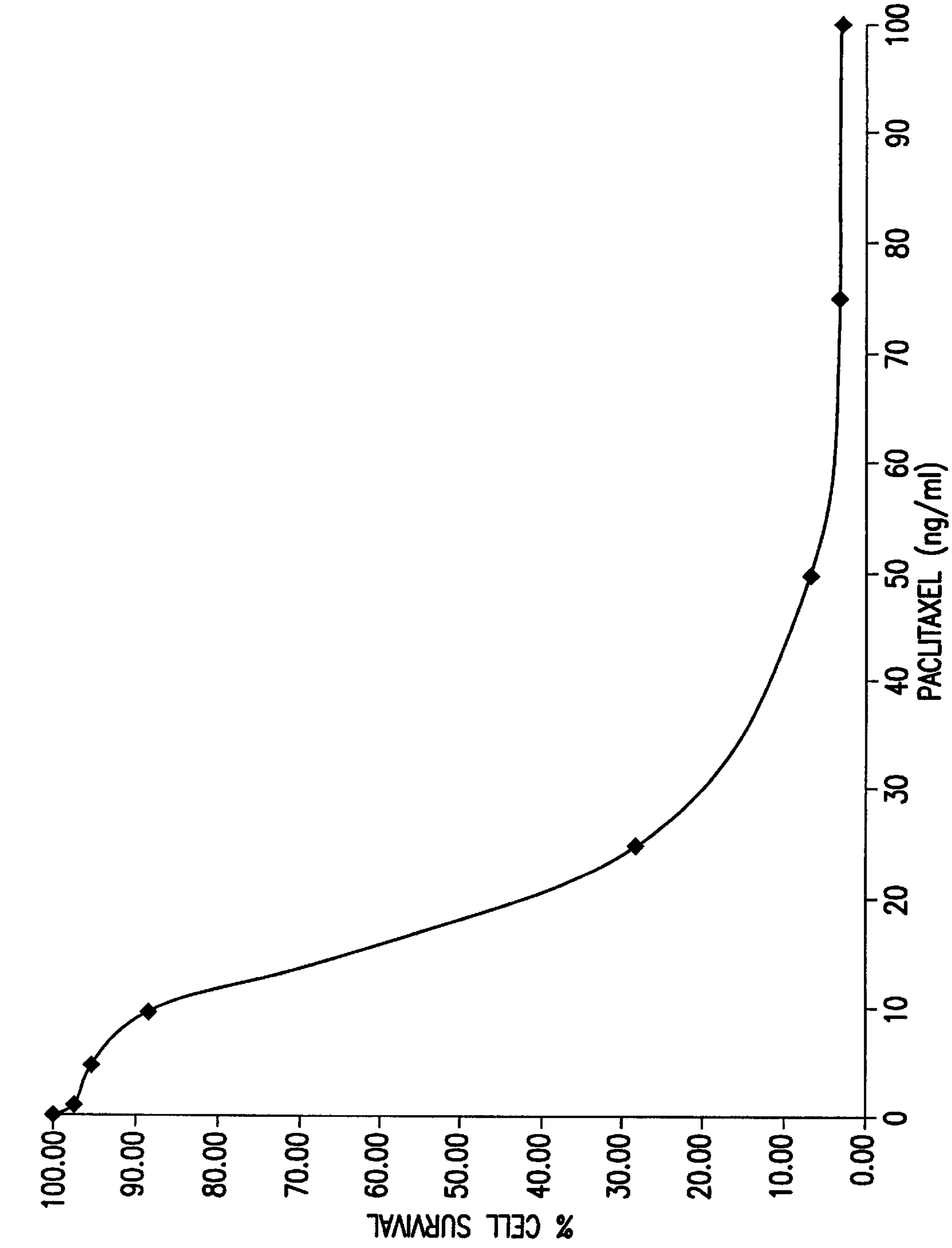

FIG. 24 shows a dose response curve before statistical analysis for paclitaxel (dosages expressed as ng/ml as indicated along the x-axis) in MDA-MB-468 cells, with the y-axis indicating percentage of cell survival.

Figure 25:
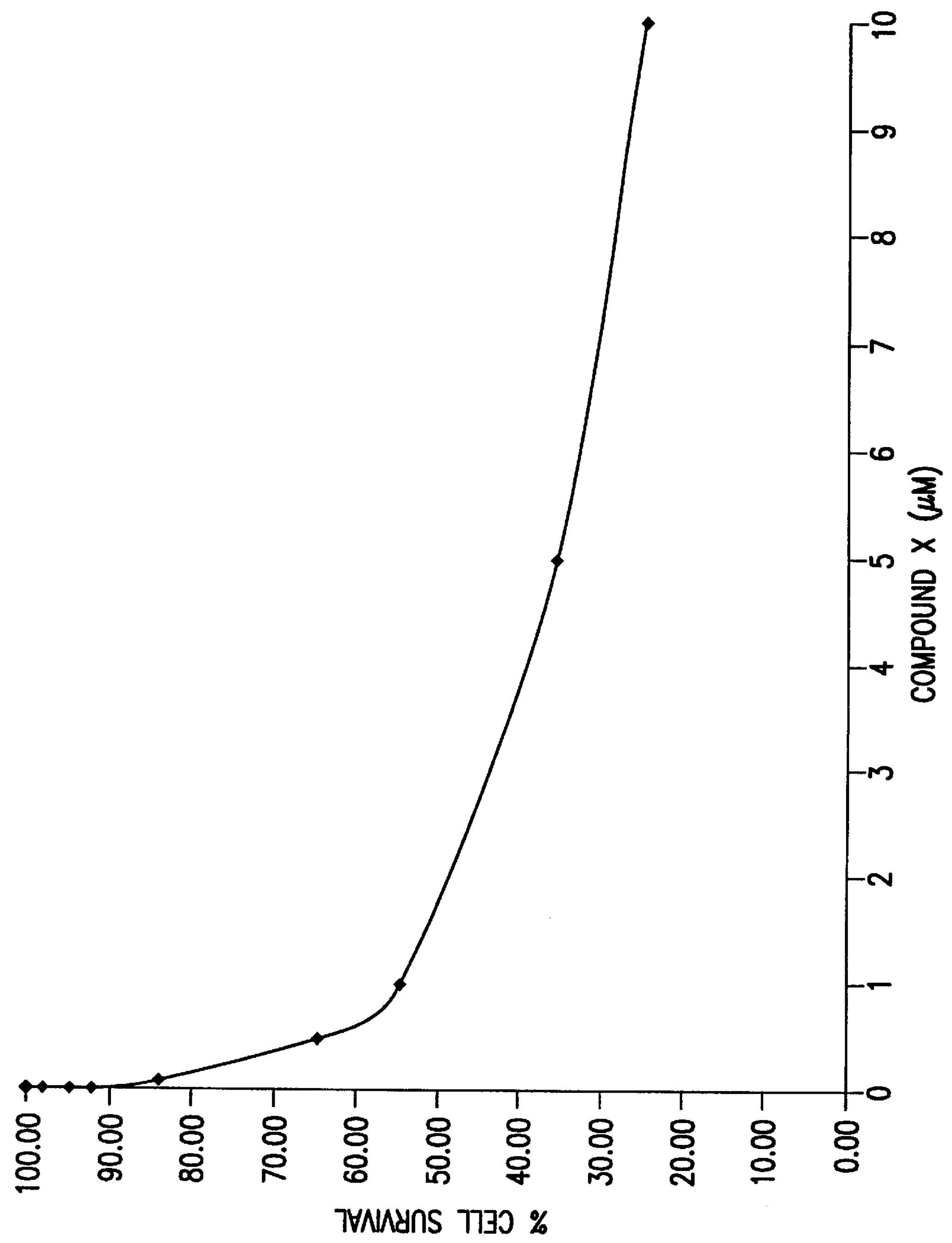

FIG. 25 shows a dose response curve before statistical analysis for Compound X (dosages in μM units as indicated along the x-axis) in MDA-MB-468 cells, with the y-axis indicating percentage of cell survival.

Figure 26:
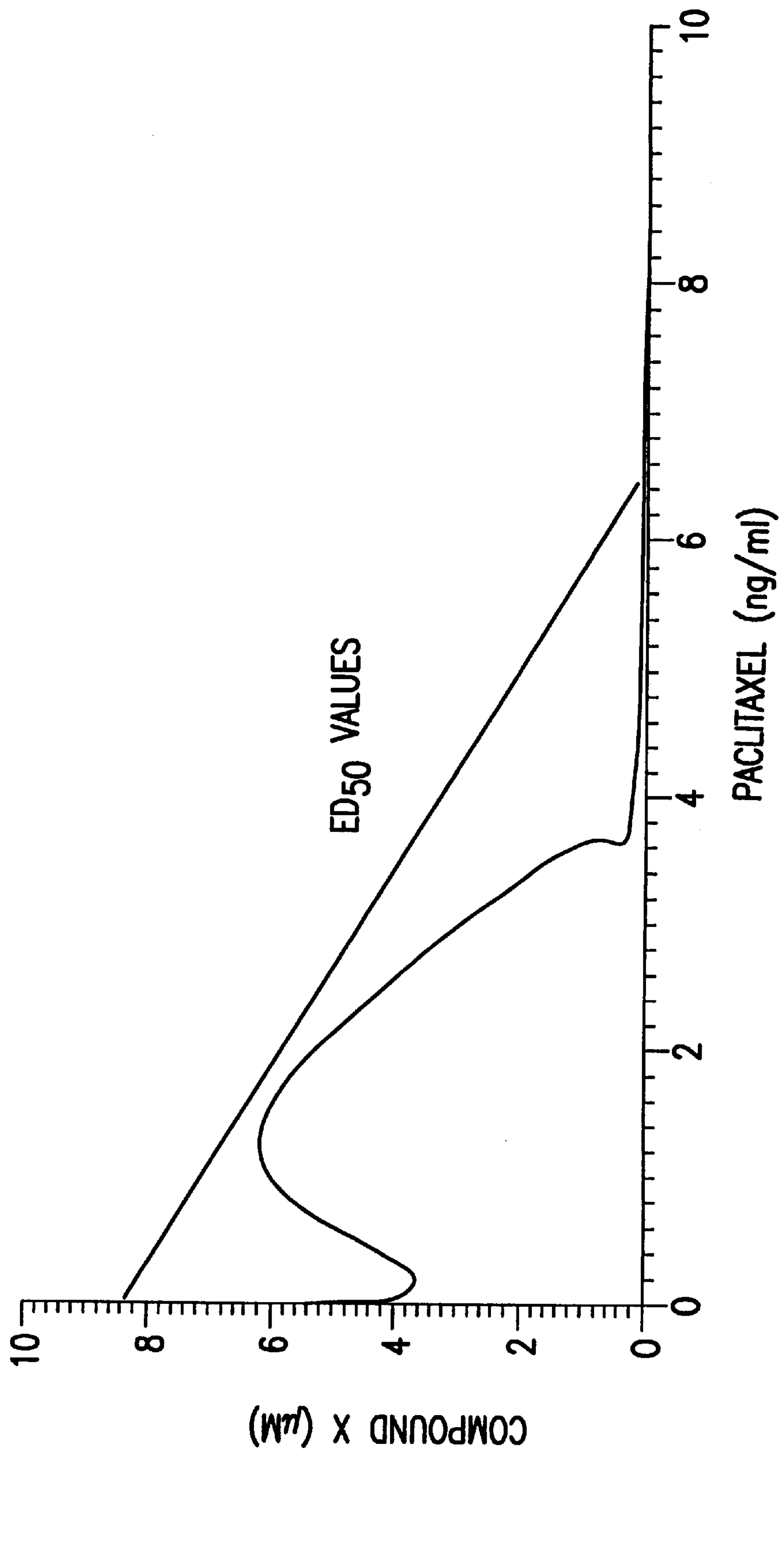

FIG. 26 shows an isobologram for Study #2 of MDA-MB-468 breast tumor cells treated with a FPT inhibitory compound and paclitaxel in vitro. (Example F herein). The x-axis indicates the amount of paclitaxel expressed as ng/ml. The y-axis indicates the amount of Compound X in μM units.

Figure 27:
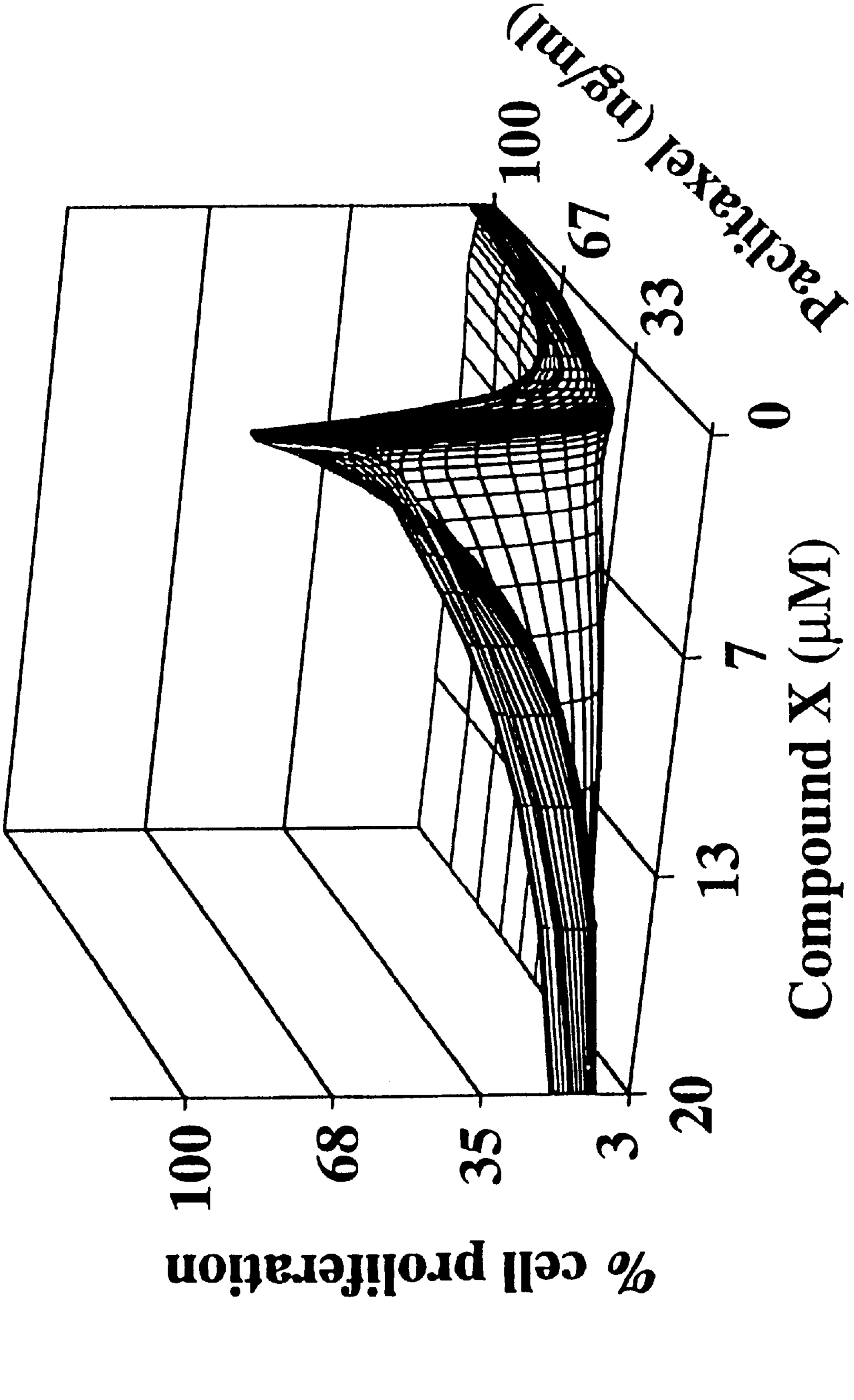

FIG. 27 shows a 3-dimensional cell proliferation model from which FIG. 26 was generated.

Figure 28:
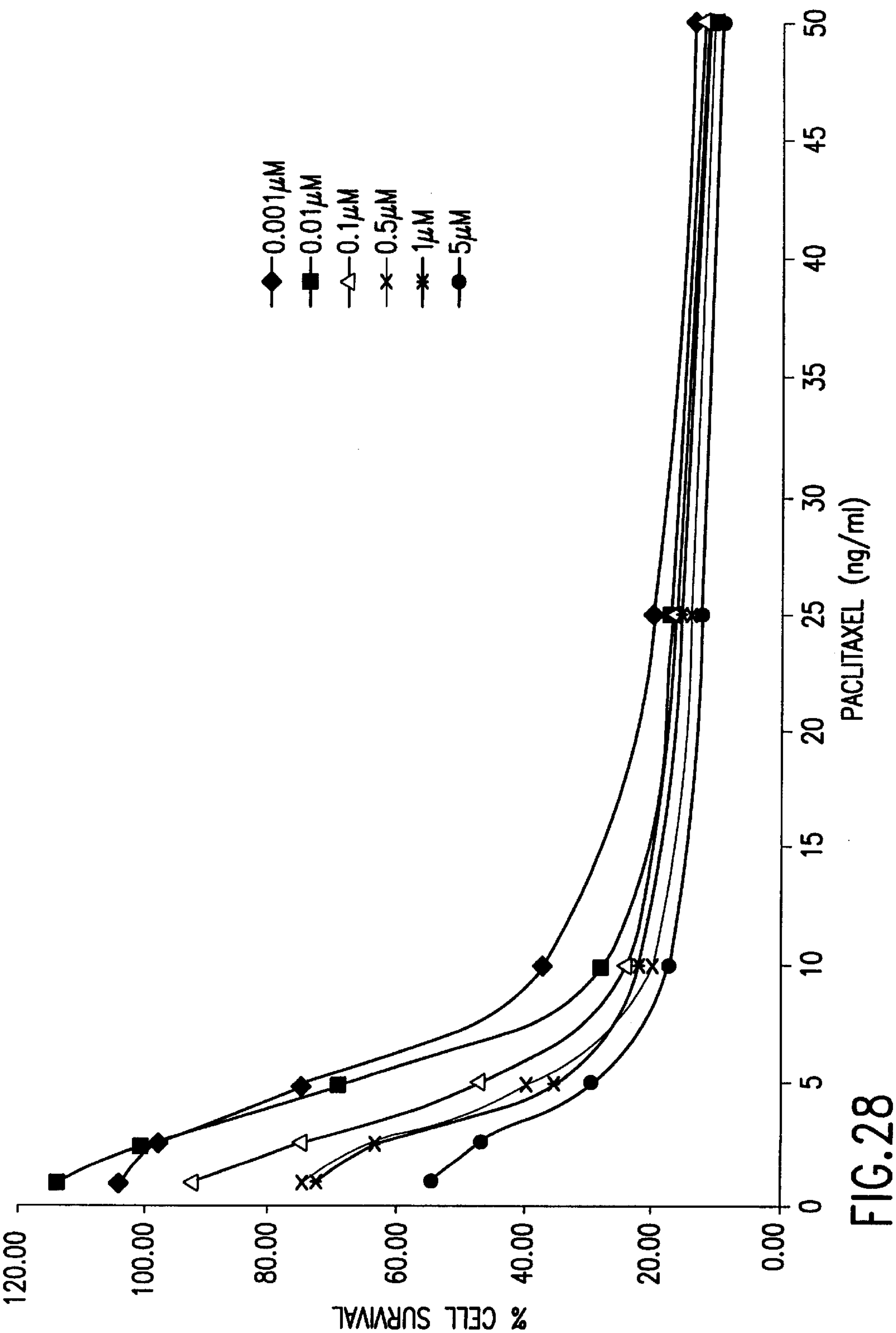

FIG. 28 shows a dose response curve before statistical analysis for drug interactions of paclitaxel (dosages expressed as ng/ml along the x-axis) and Compound X (dosages in μM units as indicated in the box to the right of the curves) in MDA-MB-468 cells. The y-axis indicates percentage of cell survival.

Figure 29:
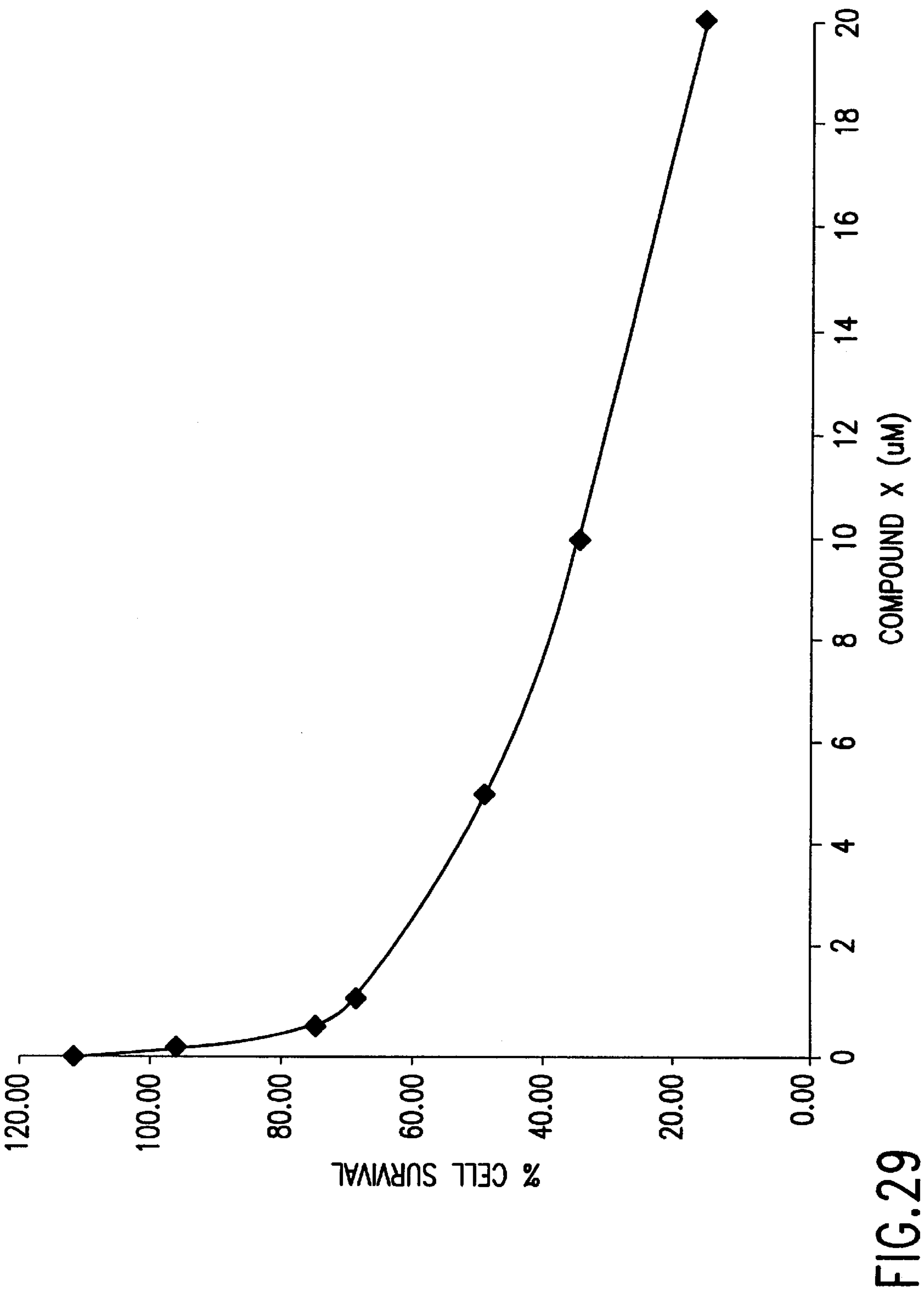

FIG. 29 shows a dose response curve before statistical analysis for Compound X (dosages in μM units as indicated along the x-axis) in MDA-MB-468 cells, with the y-axis indicating percentage of cell survival.

Figure 30:
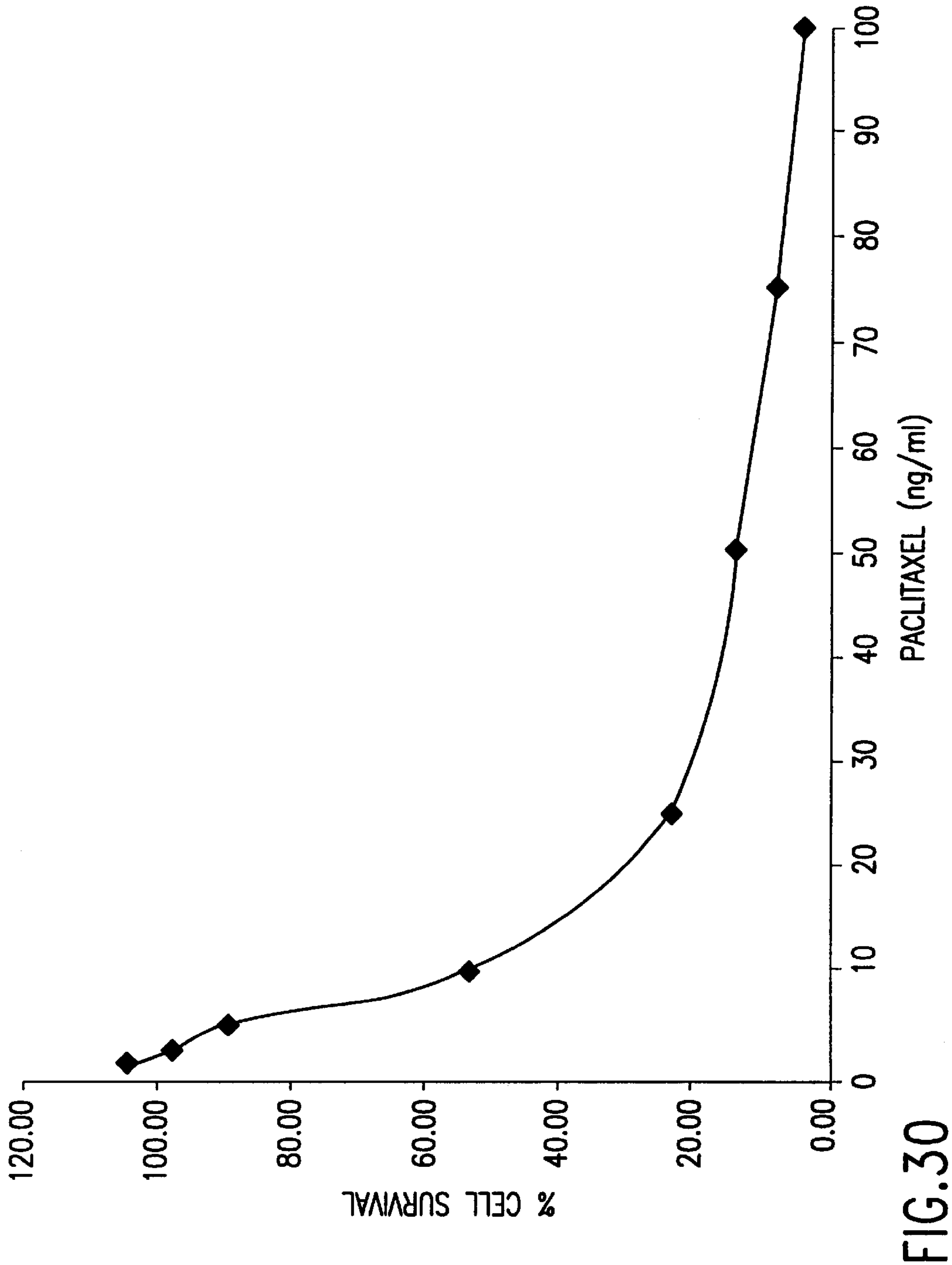

FIG. 30 shows a dose response curve before statistical analysis for paclitaxel (dosages expressed as ng/ml as indicated along the x-axis) in MDA-MB-468 cells, with the y-axis indicating percentage of cell survival.

Figure 31:
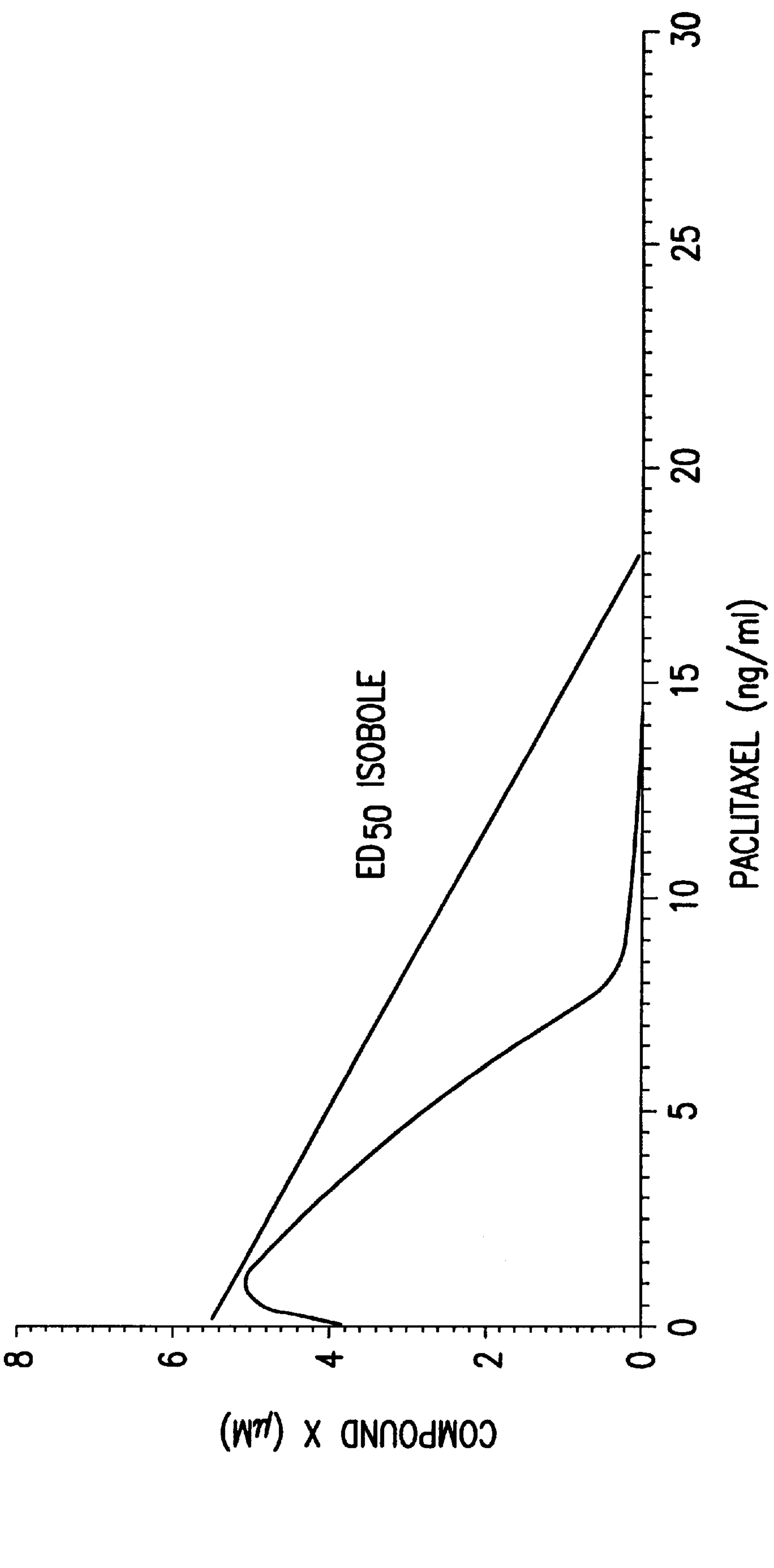

FIG. 31 shows an isobologram for Study #3 of MDA-MB-468 breast tumor cells treated with a FPT inhibitory compound and paclitaxel in vitro. (Example G herein). The x-axis indicates the amount of paclitaxel expressed as ng/ml. The y-axis indicates the amount of Compound X in μM units.

Figure 32:
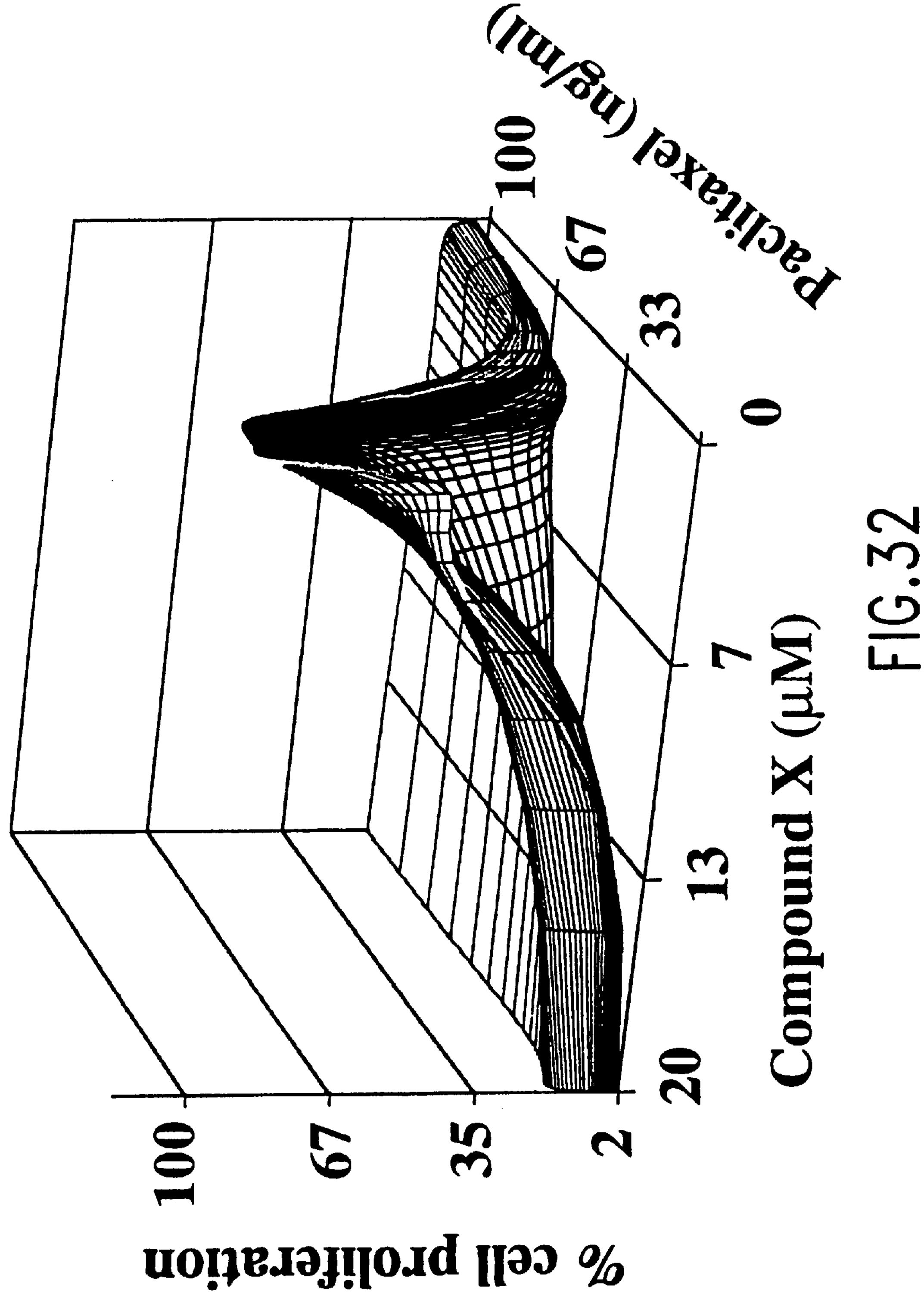

FIG. 32 shows a 3-dimensional cell proliferation model from which FIG. 31 was generated.

Figure 33:
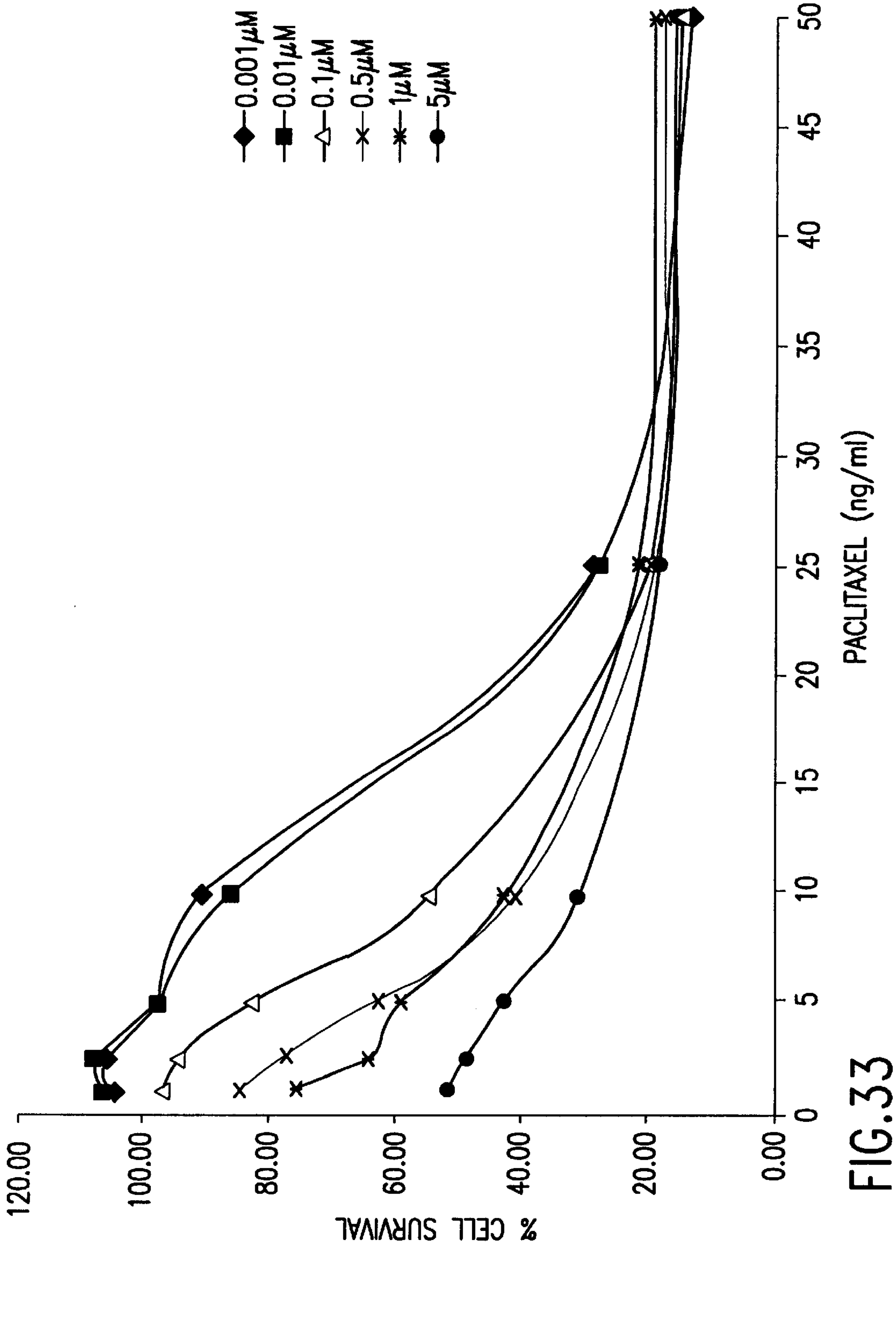

FIG. 33 shows a dose response curve before statistical analysis for drug interactions of paclitaxel (dosages expressed as ng/ml along the x-axis) and Compound X (dosages in μM units as indicated in the box to the right of the curves) in MDA-MB-468 cells. The y-axis indicates percentage of cell survival.

Figure 34:
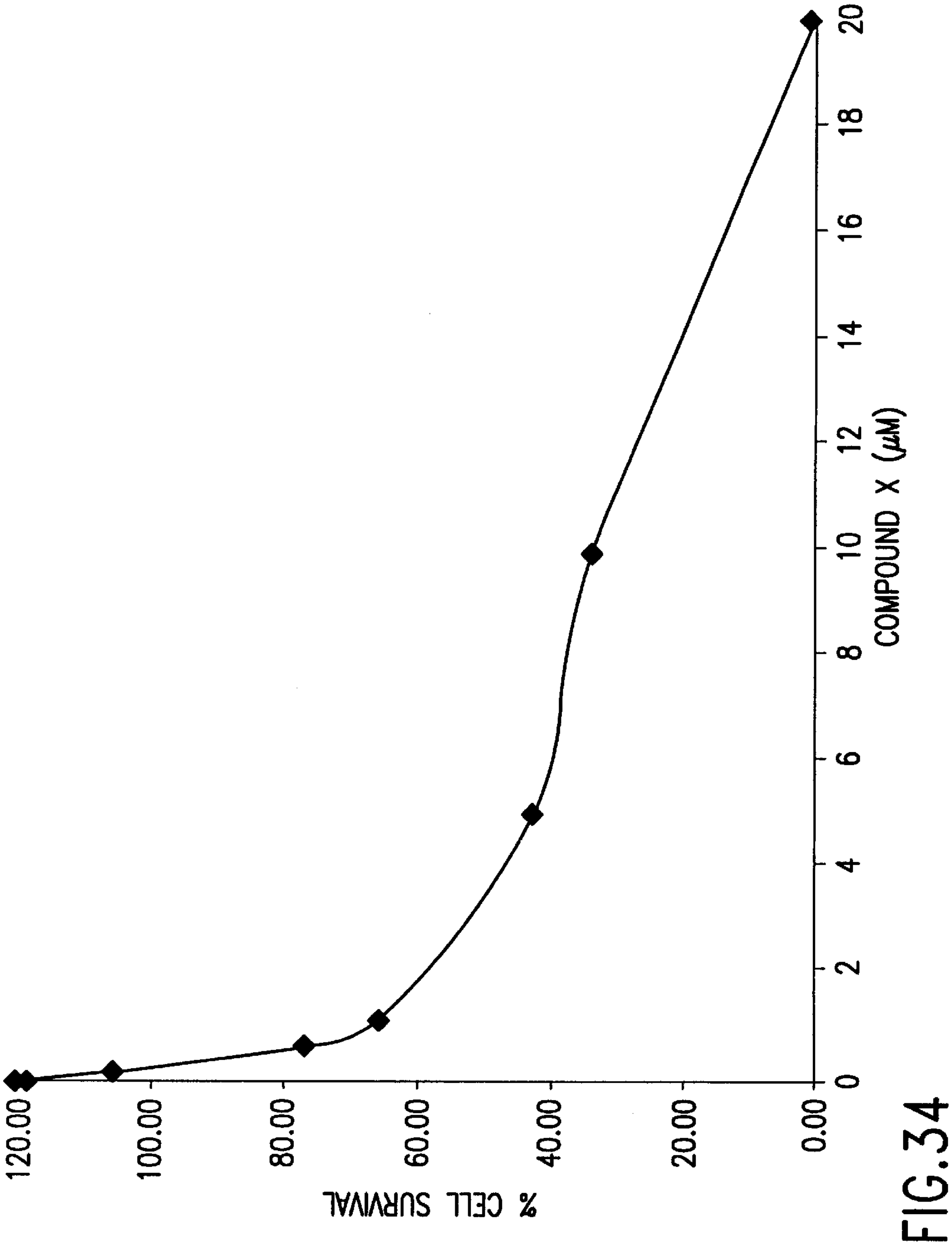

FIG. 34 shows a dose response curve before statistical analysis for Compound X (dosages in μM units as indicated along the x-axis) in MDA-MB-468 cells, with the y-axis indicating percentage of cell survival.

Figure 35:
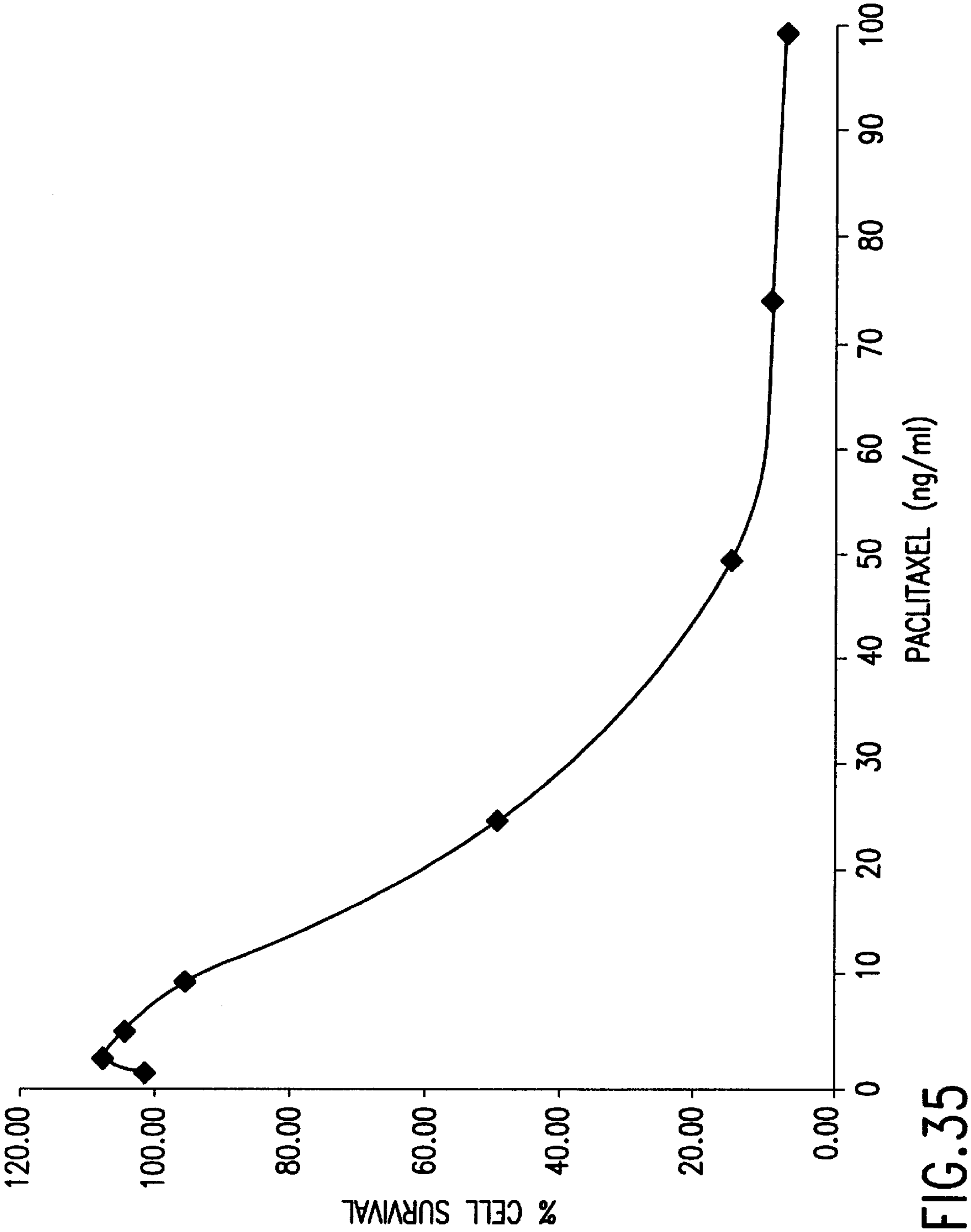

FIG. 35 shows a dose response curve before statistical analysis for paclitaxel (dosages expressed as ng/ml as indicated along the x-axis) in MDA-MB-468 cells, with the y-axis indicating percentage of cell survival.

Figure 36:
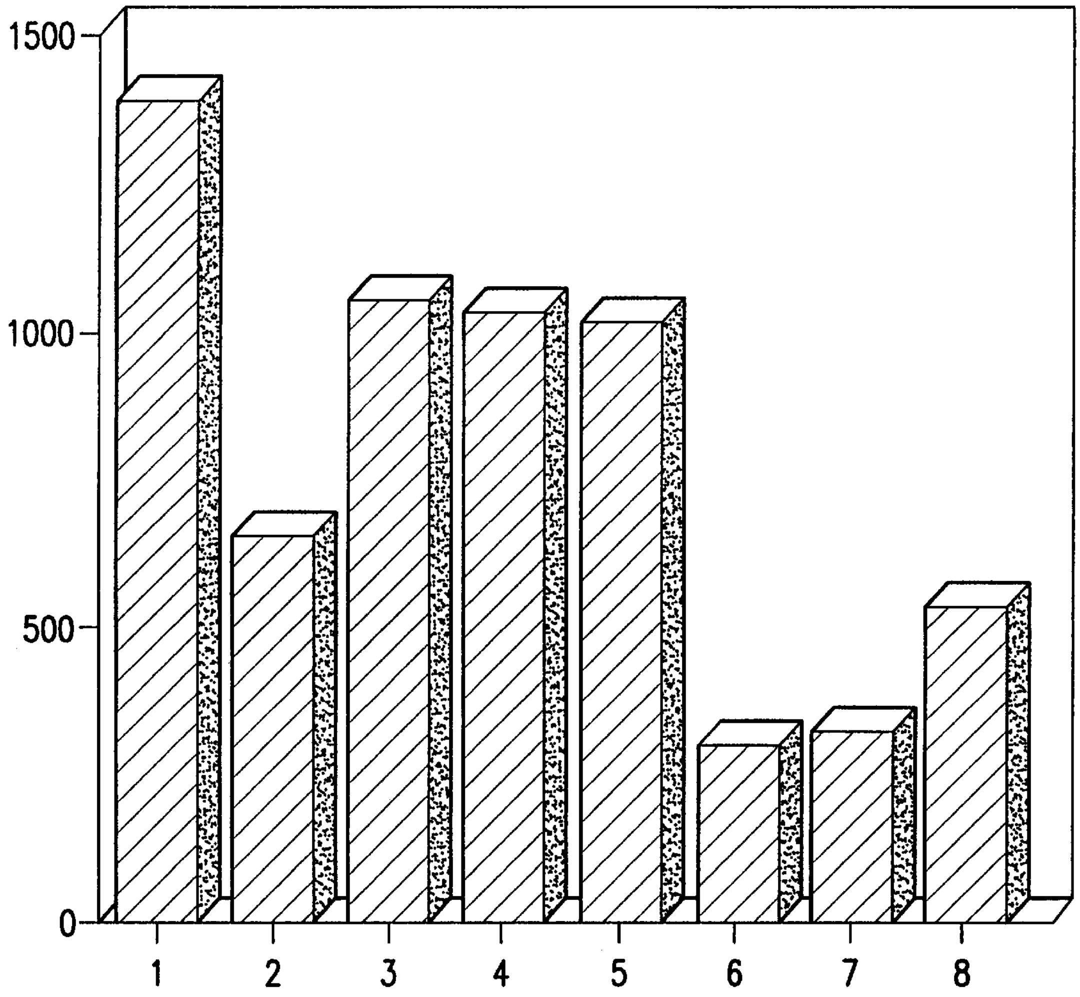

FIG. 36 graphically represents the data provided in Table 2, which is set forth later on in the present specification. The Y-axis (vertical axis, numbers 0–1500) represents the tumor volume, in cubic millimeters ($mm^3$), on day 25. The X-axis (horizontal axis, numbers 1–8) represents the substances administered. Numbers 1–8 represent: 1 is the vehicle; 2 is the FPT Inhibitory Compound (identified as "Compound X" in Table 2); 3 is Cytoxan; 4 is 5-FU; 5 is Vincristine; 6 is the FPT Inhibitory Compound plus Cytoxan; 7 is the FPT Inhibitory Compound plus 5-FU; and 8 is the FPT Inhibitory Compound plus Vincristine. FIG. 36 represents experiments wherein HTB177 cells were implanted subcutaneously in nude mice on day 0. The FPT Inhibitory Compound, dosed orally at 40 mpk, four times a day on days 1–26, resulted in 68% tumor growth inhibition. Chemo-therapeutic agents were administered intraperitoneally on day 13. When used as single agents the cytotoxics yielded 9%, 28% and 7% inhibition for Cytoxan (Cyclophosphamide) (200 mpk), 5-Fluorouracil (5-FU) (50 mpk), and Vincristine (1 mpk), respectively. When the FPT Inhibitory Compound X (40 mpk) was used in combination with the cytotoxics, tumor growth inhibition of 81%, 80% and 80% was observed for the combination with Cytoxan, 5-FU and Vincristine, respectively. These results indicate that enhanced efficacy is observed when the FPT Compound is combined with the cytotoxic chemotherapeutic agents compared to treatment with single agents. Similar results were observed when the FPT compound was dosed using a twice a day schedule. The data in FIG. 36 represented by bars 6, 7 and 8 had a P value <0.05 compared to each single agent treatment.

Figure 37:
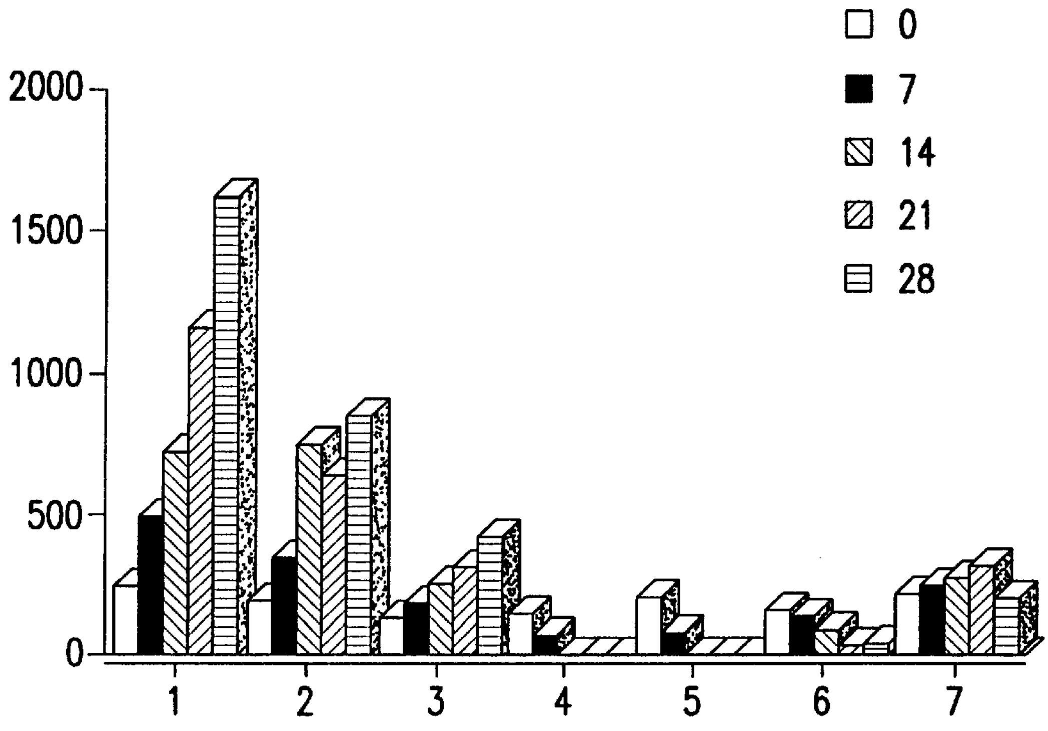

FIG. 37 graphically represents tumor regression data. The Y-axis (vertical axis, numbers 0–2000) represents the tumor volume in cubic millimeters ($mm^3$). The X-axis (horizontal axis, numbers 1–7) represents the substances administered. Numbers 1–7 represent: 1 is 20% HPBCD (vehicle); 2 is the FPT Inhibitory Compound X dosed at 2.5 mpk; 3 is the FPT Inhibitory Compound X dosed at 10 mpk; 4 is the FPT Inhibitory Compound X dosed at 20 mpk; 5 is the FPT Inhibitory Compound X dosed at 30 mpk; 6 is the FPT Inhibitory Compound X dosed at 10 mpk and Cytoxan dosed at 200 mpk; and 7 is Cytoxan dosed at 200 mpk. The number of days (0, 7, 14, 21 or 28) represented by a particular bar in the graph is indicate done of the patterns set forth in the legend in the upper right portion of FIG. 37. The data in FIG. 37 was obtained from the evaluation of the FPT Inhibitory compound in a transgenic mouse model in which an activated H-Ras oncogene is expressed from whey acidic promoter (Nielsen et al., Evaluation of the wap-ras Transgenic Mouse as a Model System for Testing Anticancer Drugs, Cancer Research 52, 3733–3738, Jul. 1, 1992). Since the transgene is carried on the Y chromosome, male transgenics reproducibly develop tumors (breast and salivary gland) at about 1.5 to 2 months of age. This model has been run in a therapeutic mode in which treatment was initiated after mice had developed palpable tumors (mean tumor size at the start of dosing was 200 $mm^3$). Mice were dosed orally four times a day with 2.5, 10, 20 or 30 mpk of the FPT Inhibitory Compound for 4 weeks. Some mice were also treated by weekly intraperitoneal injection with Cytoxan (Cyclophosphamide) at 200 mpk. Growth curves for the various treatment groups are shown in the bar graph in FIG. 37. In the vehicle-treated control group, tumors grew throughout the course of the experiment to a volume of >1500 $mm^3$ by the end of the study. Cytoxan alone resulted in near complete inhibition of tumor growth but no significant tumor regression. The FPT Inhibitory Compound at the 20 and 30 mpk dose levels resulted in significant tumor regression. The FPT Inhibitory Compound at 2.5 or 10 mpk slowed the rate of tumor growth but did not result in tumor regression. Surprisingly, while Cytoxan or 10 mpk of the FPT Inhibitory Compound as single agents did not result in tumor regressions, the combination of these treatments resulted in significant tumor regression. This indicates that, when used in combination with a standard chemotherapeutic agent such as Cytoxan, greater tumor responses can be obtained at lower doses of the FPT Inhibitory Compound.

Figure 38:
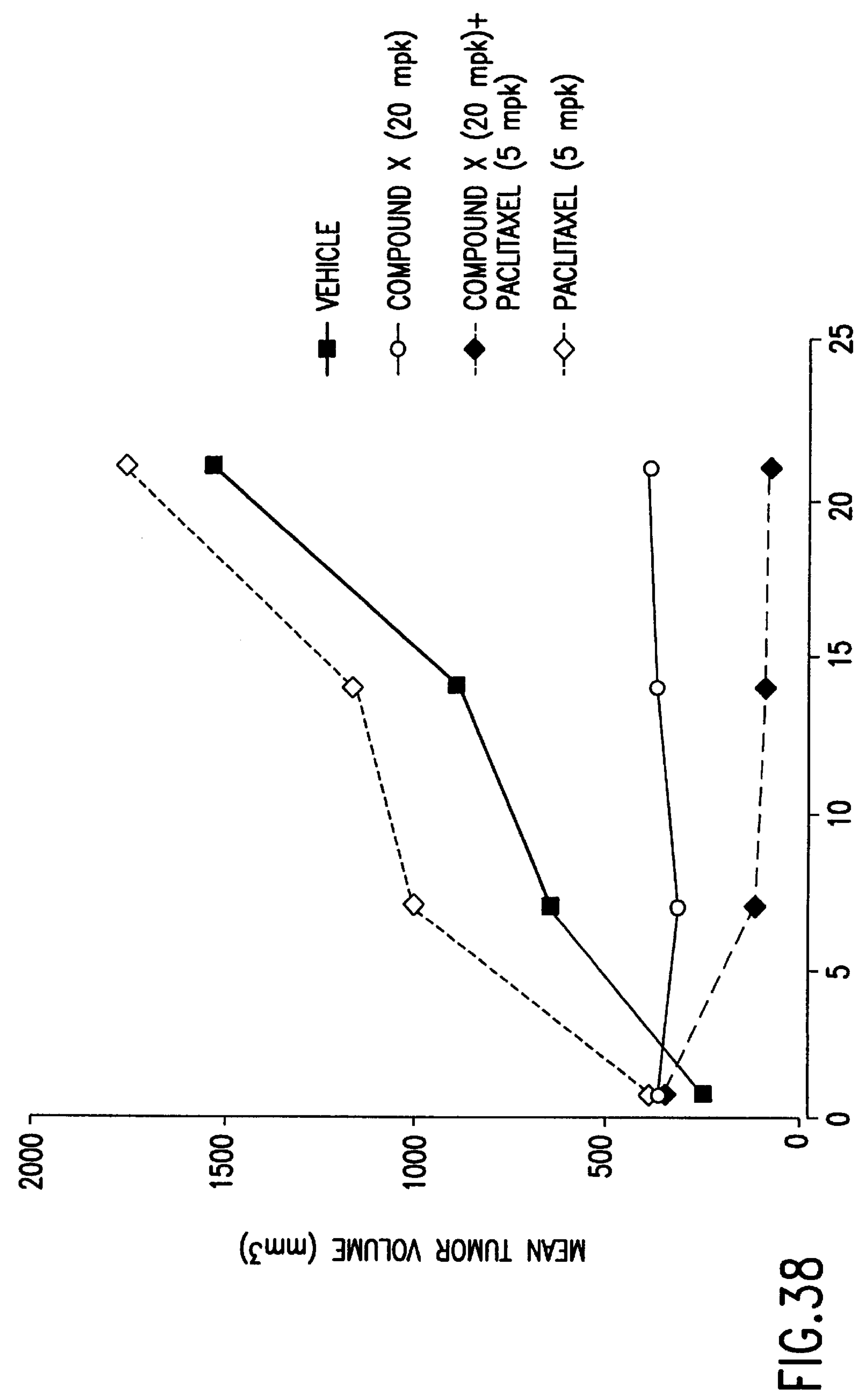

FIG. 38 shows data for combination therapy (in the Wap-ras transgenic model) with Compound X and paclitaxel relative to mean tumor volume (expressed in $mm^3$ along the y-axis) over time. The curve with white boxes represents paclitaxel alone (5 mpk), the white circles represent Compound X alone (20 mpk), the cross-hatched boxes represent the combination of paclitaxel (5 mpk) plus Compound X (20 mpk), and the black boxes represent vehicle without drug.

DETAILED DESCRIPTION OF THE INVENTION

The present invention provides a method of treating proliferative diseases, especially cancers, by combining (1) a method for inhibiting FPT (using the FPT inhibitors described herein) with (2) a method for treating cancer (using a chemotherapeutic agent and/or radiation).

The FPT inhibitors are compounds which: (i) potently inhibit FPT (but preferably not geranylgeranyl protein transferase I, in vitro); (ii) block the phenotypic change induced by a form of transforming H-ras which is a farnesyl acceptor (but preferably not by a form of transforming H-ras engineered to be a geranyl—geranyl acceptor); (iii) block intracellular farnesylation of ras; and (iv) block abnormal cell growth.

The method of treating proliferative diseases, according to this invention, includes a method for treating (inhibiting) the abnormal growth of cells, including transformed cells, in a patient in need of such treatment (e.g., a mammal such as a human), by administering, concurrently or sequentially, an effective amount of an FPT inhibitor and an effective amount of a chemotherapeutic agent and/or radiation. Abnormal growth of cells means cell growth independent of normal regulatory mechanisms (e.g., loss of contact inhibition), including the abnormal growth of: (1) tumor cells (tumors) expressing an activated ras oncogene; (2) tumor cells in which the ras protein is activated as a result of oncogenic mutation in another gene; and (3) benign and malignant cells of other proliferative diseases.

In preferred embodiments, the methods of the present invention include methods for treating or inhibiting tumor growth in a patient in need of such treatment (e.g., a mammal such as a human) by administering, concurrently or sequentially, (1) an effective amount of an FPT inhibitor and (2) an effective amount of an antineoplastic agent and/or radiation therapy. Examples of tumors which may be treated include, but are not limited to, epithelial cancers, e.g., prostate cancer, lung cancer (e.g., lung adenocarcinoma), pancreatic cancers (e.g., pancreatic carcinoma such as, for example, exocrine pancreatic carcinoma), breast cancers, colon cancers (e.g., colorectal carcinomas, such as, for example, colon adenocarcinoma and colon adenoma), ovarian cancer, and bladder carcinoma. Other cancers that can be treated include melanoma, myeloid leukemias (for example, acute myelogenous leukemia), sarcomas, thyroid follicular cancer, and myelodysplastic syndrome.

The methods of treating proliferative diseases, according to this invention, also include a method for treating (inhibiting) proliferative diseases, both benign and malignant, wherein ras proteins are aberrantly activated as a result of oncogenic mutation in other genes—i.e., the ras gene itself is not activated by mutation to an oncogenic form. This method comprises administering, concurrently or sequentially, an effective amount of an FPT inhibitor and an effective amount of an antineoplastic agent (and/or radiation therapy) to a patient in need of such treatment (e.g., a mammal such as a human). Examples of such proliferative diseases which may be treated include: the benign proliferative disorder neurofibromatosis, or tumors in which ras is activated due to mutation or overexpression of tyrosine kinase oncogenes (e.g., neu, src, abl, lck, lyn, fyn).

As used herein the following terms have the following meanings unless indicated otherwise:

antineoplastic agent—a chemotherapeutic agent effective against cancer;

concurrently—(1) simultaneously in time, or (2) at different times during the course of a common treatment schedule; and sequentially—(1) administration of one component of the method ((a) FPT inhibitor, or (b) antineoplastic agent and/or radiation therapy) followed by administration of the other component; after adminsitration of one component, the second component can be administered substantially immediately after the first component, or the second component can be administered after an effective time period after the first component; the effective time period is the amount of time given for realization of maximum benefit from the administration of the first component.

CHEMOTHERAPEUTIC AGENTS

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimnetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxycoformycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645–1742, USA); the disclosure of which is incorporated herein by reference thereto.

MICROTUBULE AFFECTING AGENTS

As explained above, the present invention also provides methods of treating diseased cells by contacting the cells with a FPT inhibitor and a microtubule affecting agent (e.g., paclitaxel, a paclitaxel derivative or a paclitaxel-like compound). As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science,* 274:2009) estramustine, nocodazole, MAP4, and the like. Examples of such agents are also described in the scientific and patent literature, see, e.g., Bulinski (1997) *J. Cell Sci.* 110:3055–3064; Panda (1997) *Proc. Natl. Acad. Sci.* USA 94:10560–10564; Muhlradt (1997) Cancer Res. 57:3344–3346; Nicolaou (1997) *Nature* 387:268–272; Vasquez (1997) *Mol. Biol. Cell* 8:973–985; Panda (1996) *J. Biol. Chem.* 271:29807–29812.

Particularly preferred agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) *Oncology,* 6: 17–23, Horwitz (1992) *Trends Pharmacol. Sci.* 13: 134–146, Rowinsky (1990) *J. Natl. Canc. Inst.* 82: 1247–1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see *Lopes* (1997) *Cancer Chemother. Pharmacol.* 41:37–47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

In a preferred embodiment, compounds with possible tubulin polymerization activity are screened in vitro. In a preferred embodiment, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) *Lab. Anim. Sci.,* 45(2):145–150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) *J. Molec. Biol.,* 89: 737–758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

FPT INHIBITORS

Classes of compounds that can be used as the FPT inhibitor include: oligopeptides, peptido-mimetic compounds, farnesylated peptido-mimetic compounds, fused-ringed tricyclic benzocycloheptapyridines, carbonyl piperazinyl compounds, carbonyl piperidinyl compounds, farnesyl derivatives, and natural products and derivatives.

Some of the compounds are oligopeptides, especially tetrapeptides, or derivatives thereof, based on the formula Cys-$Xaa_1$-$Xaa_2$-$Xaa_3$, where $Xaa_3$ represents a serine, methionine or glutamine residue, and $Xaa_1$ and $Xaa_2$ can represent a wide variety of amino acid residues, but especially those with an aliphatic side-chain. Their derivatives may or may not have three peptide bonds; thus it has been found that reduction of a peptide bond —CO—NH— to a secondary amine grouping, or even replacement of the nitrogen atoms in the peptide chain with carbon atoms (provided that certain factors such as general shape of the molecule and separation of the ends are largely conserved) affords compounds that are frequently more stable than the oligopeptides and, if active, have longer activity. Such compounds are referred to herein as peptido-mimetic compounds.

Examples of compounds that are FPT inhibitors and the documents directed to those compounds are given below.

Oligopeptides (mostly tetrapeptides but also pentapeptides) including the formula Cys-$Xaa_1$-$Xaa_2$-$Xaa_3$: EPA 461,489; EPA 520,823; EPA 528,486; and WO 95/11917.

Peptido-mimetic compounds—especially Cys-Xaa-Xaa-Xaa-mimetics: EPA 535,730; EPA 535,731; EPA 618,221; WO 94/09766; WO 94/10138; WO 94/07966; U.S. Pat. No. 5,326,773; U.S. Pat. No. 5,340,828; U.S. Pat. No. 5,420,245; WO 95/20396; U.S. Pat. No. 5,439,918; and WO 95/20396.

Farnesylated peptido-mimetic compounds—specifically farnesylated Cys-Xaa-Xaa-Xaa-mimetic: GB-A 2,276,618.

Other peptido-mimetic compounds: U.S. Pat. No. 5,352,705; WO 94/00419; WO 95/00497; WO 95/09000; WO 95/09001; WO 95/12612; WO 95/25086; EPA 675,112; and FR-A 2,718,149.

With regard to the use of peptido-mimetic compounds as FPT inhibitors, it is noted that data based on combining a particular peptido-mimetic FTI compound with several different chemotherapeutic agents (e.g., taxol (paclitaxel), doxorubicin, cisplatin, and vinblastine) in breast cancer cell lines MDA-MB-468 and MCF-7 are presented in Moasser, MM, et al. Proc. Natl. Acad. Sci. USA 95: 1369–1374, 1998. (See also Kohl et al, Nature Medicine 1: 792 (1995) for identification of the subject compound as a peptido-mimetic compound). Fused-ring tricyclic benzocycloheptapyridines: WO 95/10514; WO 95/10515; WO 95/10516; WO 96/30363; WO 96/30018; WO 96/30017; WO 96/30362; WO 96/31111; WO 96/31478; WO 96/31477; WO 96/31505; WO 97/23478; International Patent Application No. PCT/US97/17314 (WO 98/15556); International Patent Application No. PCT/US97/15899 (WO 98/11092); International Patent Application No. PCT/US97/15900 (WO 98/11096); International Patent Application No. PCT/US97/15801 (WO 98/11106); International Patent Application No. PCT/US97/15902 (WO 98/11097); International Patent Application No. PCT/US97/15903 (WO 98/11098); International Patent Application No. PCT/US97/15904; International Patent Application No. PCT/US97/15905 (WO 98/11099); International Patent Application No. PCT/US97/15906 (WO 98/11100); International Patent Application No. PCT/US97/15907 (WO 98/11093); International Patent Application No. PCT/US97/19976 (WO 98/11091); U.S. application Ser. No. 08/877,049; U.S. application Ser. No. 08/877,366; U.S. application Ser. No. 08/877,399; U.S. application Ser. No. 08/877,336; U.S. application Ser. No. 08/877,269; U.S. application Ser. No. 08/877,050; U.S. application Ser. No. 08/877,052; U.S. application Ser. No. 08/877,051; U.S. application Ser. No. 08/877,498; U.S. application Ser. No. 08/877,057; U.S. application Ser. No. 08/877,739; U.S. application Ser. No. 08/877,677; U.S. application Ser. No. 08/877,741; U.S. application Ser. No. 08/877,743; U.S. application Ser. No. 08/877,457; U.S. application Ser. No. 08/877,673; and U.S. application Ser. No. 08/876,507.

Farnesyl derivatives: EPA 534,546; WO 94/19357; WO 95/08546; EPA 537,007; and WO 95/13059.

Natural products and derivatives: WO 94/18157; U.S. Pat. No. 5,430,055; GB-A 2,261,373; GB-A 2,261,374; GB-A 2,261,375; U.S. Pat. No. 5,420,334; U.S. Pat. No. 5,436,263.

Other compounds: WO 94/26723; WO 95/08542; U.S. Pat. No. 5,420,157; WO 95/21815; WO 96/31501; WO 97/16443; WO 97/21701; U.S. Pat. No. 5,578,629; U.S. Pat. No. 5,627,202; WO 96/39137; WO 97/18813; WO 97/27752WO 97/27852; WO 97/27853; WO 97/27854; WO 97/36587; WO 97/36901; WO 97/36900; WO 97/36898; WO 97/36897; WO 97/36896; WO 97/36892; WO 97/36891; WO 97/36890; WO 97/36889; WO 97/36888; WO 97/36886; WO 97/36881; WO 97/36879; WO 97/36877; WO 97/36876; WO 97/36875; WO 97/36605; WO 97/36593; WO 97/36592; WO 97/36591; WO 97/36585; WO 97/36584; and WO 97/36583.

A plasmid encoding an α- and β-unit of an FPT, and describing an assay therefor: WO 94/10184.

All of the foregoing documents directed to compounds that are FPT inhibitors are incorporated herein by reference thereto.

A review of many such compounds is given by Graham in *Exp. Opin. Ther. Patents* (1995) 5(12): 1269–1285.

It will be understood that the breadth of a chemical formula in a patent specification may not enable one to classify all compounds therein under one of the headings above. For example, the monoterpenyl chain in the farnesyl derivatives may be extended, e.g. by a number of methylene groups or even another isoprene residue.

The tetrapeptides of the formula Cys-$Xaa_1$-$Xaa_2$-$Xaa_3$ have an amino-terminal cysteine residue. A tetrapeptide of that type forms the carboxyl-terminal of ras. Such tetrapeptides are capable of binding with FPT and competing with ras. Compounds of similar structure but having at least one of the carbonyl groups of the tetrapeptide replaced by a hydrocarbyl group such as a methylene group and classified above as peptido-mimetic compounds are also capable of binding with FPT and competing with ras, but are generally more resistant to enzymatic degradation in vivo.

FPT INHIBITORS—EXEMPLIFIED COMPOUNDS

The following documents disclose compounds that are FPT inhibitors that can be used in this invention. The documents also disclose methods of inhibiting abnormal cell growth (e.g., tumors) using the compounds disclosed in the document. The radicals and formulae designations defined herein for a particular document apply only to the compounds described in that document.

WO 95/10516 published Apr. 20, 1995 and WO 96/30363 published Oct. 3, 1996 disclose compounds of formula 1.0:

(1.0)

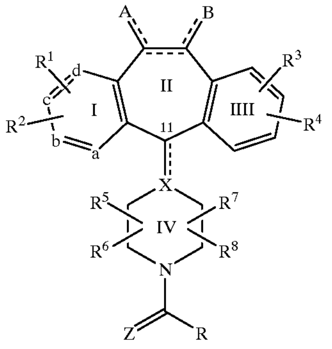

or a pharmaceutically acceptable salt or solvate thereof, wherein:

one of a, b, c and d represents N or $NR^9$ wherein $R^9$ is $O^-$, $—CH_3$ or $—(CH_2)_nCO_2H$ wherein n is 1 to 3, and the remaining a, b, c and d groups represent $CR^1$ or $CR^2$; or each of a, b, c, and d is independently selected from $CR^1$ and $CR^2$;

each $R^1$ and each $R^2$ is independently selected from H, halo, $—CF_3$, $—OR^{10}$, $—COR^{10}$, $—SR^{10}$, $—S(O)_tR^{11}$ (wherein t is 0, 1 or 2), —SCN, $—N(R^{10})_2$, $—NO_2$, $—OC(O)R^{10}$, $—CO_2R^{11}$, $—OCO_2R^{11}$, —CN, $—NHC(O)R^{10}$, $—NHSO_2R^{10}$, $—CONHR^{10}$, $—CONHCH_2CH_2OH$, $—NR^{10}COOR^{11}$, $—SR^{11}C(O)OR^{11}$,

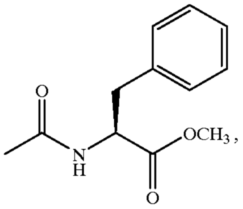

$—SR^{11}N(R^{75})_2$ (wherein each $R^{75}$ is independently selected from H and $—C(O)OR^{11}$), benzotriazol-1-yloxy, tetrazol-5-ylthio, substituted tetrazol-5-ylthio, alkynyl, alkenyl and alkyl, said alkyl or alkenyl group optionally being substituted with halo, $—OR^{10}$ or $—CO_2R^{10}$;

$R^3$ and $R^4$ are the same or different and each independently represents H or any of the substituents of $R^1$ and $R^2$, or $R^3$ and $R^4$ taken together represent a saturated or unsaturated $C_5$–$C_7$ ring fused to the benzene ring;

each of $R^5$, $R^6$, $R^7$ and $R^8$ independently represents H, $—CF_3$, $—COR^{10}$, alkyl or aryl, said alkyl or aryl optionally being substituted with $—OR^{10}$, $—SR^{10}$, $—S(O)_tR^{11}$, $—NR^{10}COOR^{11}$, $—N(R^{10})_2$, $—NO_2$, $—COR^{10}$, $—OCOR^{10}$, $—OCO_2R^{11}$, $—CO_2R^{10}$, or $OPO_3R^{10}$, or one of $R^5$, $R^6$, $R^7$ and $R^8$ can be taken in combination with $R^{40}$ as defined below to represent $—(CH_2)_r—$ wherein r is 1 to 4 which can be substituted with lower alkyl, lower alkoxy, $—CF_3$ or aryl, or $R^5$ is combined with $R^6$ to represent =O or =S and/or $R^7$ is combined with $R^8$ to represent =O or =S;

$R^{10}$ represents H, alkyl, aryl, or aralkyl;

$R^{11}$ represents alkyl or aryl;

X represents N, CH or C, which C may contain an optional double bond, represented by the dotted line, to carbon atom 11;

the dotted line between carbon atoms 5 and 6 represents an optional double bond, such that when a double bond is present, A and B independently represent $—R^{10}$, halo, $—OR^{11}$, $—OCO_2R^{11}$ or $—OC(O)R^{10}$, and when no double bond is present between carbon atoms 5 and 6, each of A and B independently represents $H_2$, $—(OR^{11})_2$, (H and halo), dihalo, (alkyl and H), $(alkyl)_2$, (H and $—OC(O)R^{10}$), (H and $—OR^{10}$), =O, (aryl and H), $=NOR^{10}$, or $—O—(CH_2)_p—O—$ wherein p is 2, 3 or 4;

R represents $R^{40}$, $R^{42}$, $R^{44}$, or $R^{54}$, as defined below;

$R^{40}$ represents H, aryl, alkyl, cycloalkyl, alkenyl, alkynyl or —D wherein —D represents

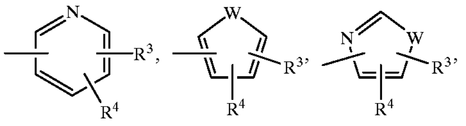

-continued

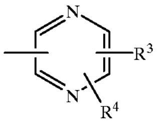 or 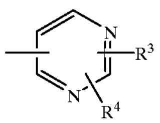

wherein $R^3$ and $R^4$ are as previously defined and W is O, S or $NR^{10}$ wherein $R^{10}$ is as defined above; said $R^{40}$ cycloalkyl, alkenyl and alkynyl groups being optionally substituted with from 1–3 groups selected from halo, $—CON(R^{11})_2$, aryl, $—CO_2R^{10}$, $—OR^{12}$, $—SR^{12}$, $—N(R^{10})_2$, $—N(R^{10})CO_2R^{11}$, $—COR^{12}$, $—NO_2$ or D, wherein —D, $R^{10}$ and $R^{11}$ are as defined above and $R^{12}$ represents $R^{10}$, $—(CH_2)_mOR^{10}$ or $—(CH_2)_qCO_2R^{10}$ wherein $R^{10}$ is as previously defined, m is 1 to 4 and q is 0 to 4; said alkenyl and yl $R^{40}$ groups not containing —OH, —SH or $—N(R^{10})_2$ on a carbon containing a double or triple bond respectively; or $R^{40}$ represents phenyl substituted with a group selected from $—SO_2NH_2$, $—NHSO_2CH_3$, $—SO_2NHCH_3$, $—SO_2CH_3$, $—SOCH_3$, $—SCH_3$, and $—NHSO_2CF_3$, which group is preferably located in the para position of the phenyl ring; or $R^{40}$ sents a group selected from

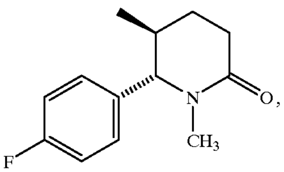

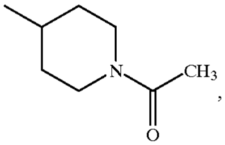, 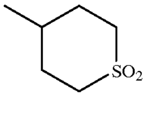,

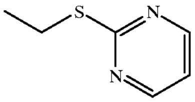, 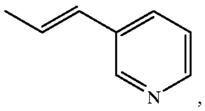,

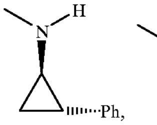 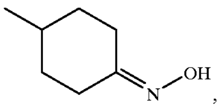,

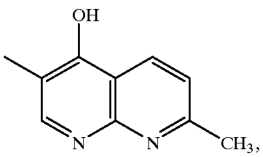 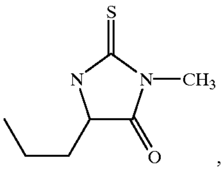,

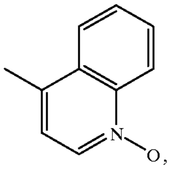 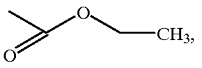

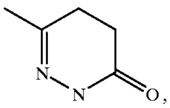 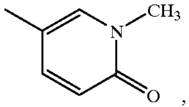, or

-continued

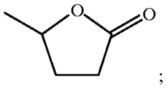

;

$R^{42}$, represents

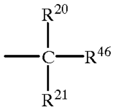

wherein $R^{20}$, $R^{21}$ and $R^{46}$ are each independently selected from the group consisting of:

(1) H;

(2) $—(CH_2)_qSC(O)CH_3$ wherein q is 1 to 3;

(3) $—(CH_2)_qOSO_2CH_3$ wherein q is 1 to 3;

(4) —OH;

(5) —CS—$(CH_2)_w$-(substituted phenyl) wherein w is 1 to 3 and the substitutents on said situted phenyl group are the same substitutents as described under (12) below for substituted phenyl;

(6) $—NH_2$;

(7) —NHCBZ;

(8) $—NHC(O)OR^{22}$ wherein $R^{22}$ is an alkyl group having from 1 to 5 carbon atoms, or $R^{22}$ represents phenyl substituted with 1 to 3 alkyl groups;

(9) alkyl;

(10) $—(CH_2)_k$-phenyl wherein k is 1 to 6;

(11) phenyl;

(12) substituted phenyl wherein the substituents are selected from the group consisting of: halo, $NO_2$, —OH, $—OCH_3$, $—NH_2$, $—NHR^{22}$, $—N(R^{22})_2$, alkyl, $—O(CH_2)_t$-phenyl (wherein t is from 1 to 3), and $—O(CH_2)_t$-substituted phenyl (wherein t is from 1 to 3);

(13) naphthyl;

(14) substituted naphthyl, wherein the substituents are as defined for substituted phenyl under (12) above;

(15) bridged polycyclic hydrocarbons having from 5 to 10 carbon atoms;

(16) cycloalkyl having from 5 to 7 carbon atoms;

(17) heteroaryl;

(18) hydroxyalkyl;

(19) substituted pyridyl or substituted pyridyl N-oxide wherein the substituents are selected from methylpyridyl, morpholinyl, imidazolyl, 1-piperidinyl, 1-(4-methylpiperazinyl), $—S(O)_tR^{11}$, and any of the substituents given under (12) above for substituted phenyl, and said substitutents are bound to a ring carbon by replacement of the hydrogen bound to said carbon;

(20)

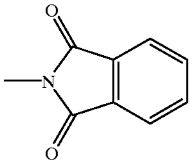

;

-continued (21)

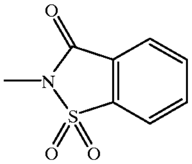

;

(22)

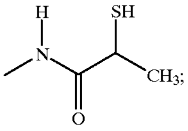

(23) —NHC(O)—$(CH_2)_k$-phenyl or —NH(O)—$(CH_2)_k$— (substituted phenyl), wherein said k is as defined under (10) above;

(24) piperidine Ring V:

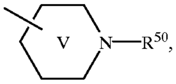

wherein $R^{50}$ represents H, alkyl, alkylcarbonyl, alkoxycarbonyl, haloalkyl, or $—C(O)NH(R^{10})$ wherein $R^{10}$ is H or alkyl;

(25) $—NHC(O)CH_2C_6H_5$ or $—NHC(O)CH_2$-(substituted $C_6H_5$);

(26) $—NHC(O)OC_6H_5$;

(27)

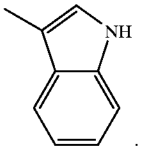

;

(28)

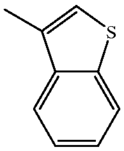

;

(29)

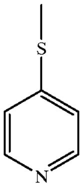

;

(30) —OC(O)-heteroaryl (for example pyridine-4-carbonyloxy);

(31) —O-alkyl (e.g., $—OCH_3$);

(32) $—CF_3$;

(33) —CN;

(34) a heterocycloalkyl group of the formula

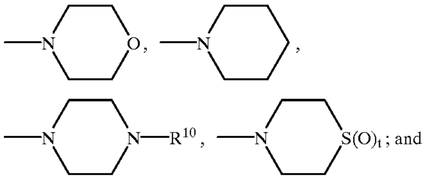

(35) a piperidinyl group of the formula

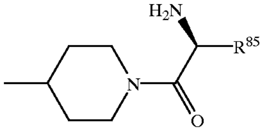

wherein $R^{85}$ is H, alkyl, or alkyl substituted by —OH or —$SCH_3$; or $R^{20}$ and $R^{21}$ taken together form an =O group and the remaining $R^{46}$ is as defined above; or two of $R^{20}$, $R^{21}$ and $R^{46}$ taken together form piperidine Ring V

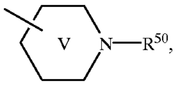

wherein $R^{50}$ is as defined under (24) above;

with the proviso that $R^{46}$, $R^{20}$ and $R^{21}$ are selected such that the carbon atom to which they are bound is not bonded to more than one heteroatom;

$R^{44}$ represents —$NR^{25}R^{48}$ wherein $R^{25}$ represents heteroaryl, N-methylpiperidinyl or aryl, and $R^{48}$ represents H or alkyl;

$R^{54}$ represents an N-oxide heterocyclic group of the formula (i), (ii), (iii) or (iv):

(i)

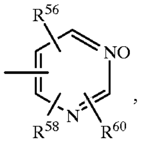

(ii)

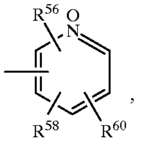

(iii)

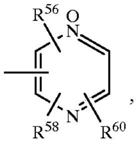

, or

-continued (iv)

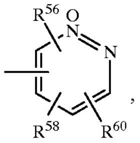

wherein $R^{56}$, $R^{58}$, and $R^{60}$ are the same or different and each is independently selected from H, halo, —$CF_3$, —$OR^{10}$, —$C(O)R^{10}$, —$SR^{10}$, —$S(O)_eR^{11}$ (wherein e is 1 or 2), —$N(R^{10})_2$, —$NO_2$, —$CO_2R^{10}$, —$OCO_2R^{11}$, —$OCOR^{10}$, alkyl, aryl, alkenyl and alkynyl, which alkyl may be substituted with —$OR^{10}$, —$SR^{10}$ or —$N(R^{10})_2$ and which alkenyl may be substituted with $OR^{11}$ or $SR^{11}$; or $R^{54}$ represents an N-oxide heterocyclic group of the formula (ia), (iia), (iiia) or (iva):

(ia)

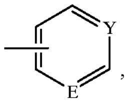

(iia)

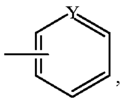

(iiia)

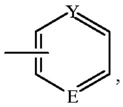

, or (iva)

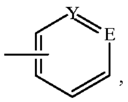

wherein Y represents $N^+$-$O^-$ and E represents N; or $R^{54}$ represents an alkyl group substituted with one of said N-oxide heterocyclic groups (i), (ii), (iii), (iv), (ia), (iia), (iiia) or (iva); and Z represents O or S such that R can be taken in combination with $R^5$, $R^6$, $R^7$ or $R^8$ as defined above, or R represents $R^{40}$, $R^{42}$, $R^{44}$ or $R^{54}$.

WO 95/10516 and WO 96/30363 also disclose compounds of the formulas:

-continued (5.0)

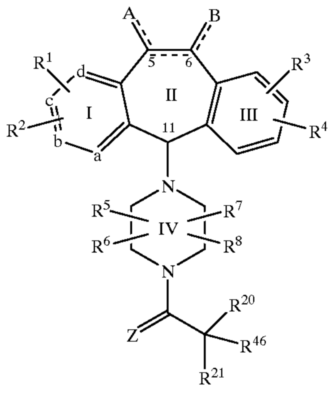

;

(5.1)

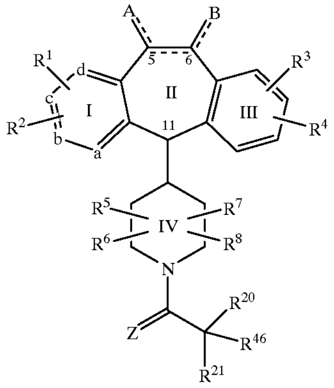

;

(5.2)

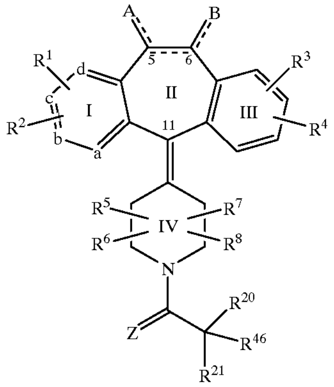

;

(5.3)

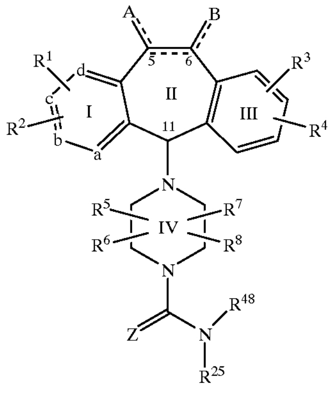

;

(5.3A)

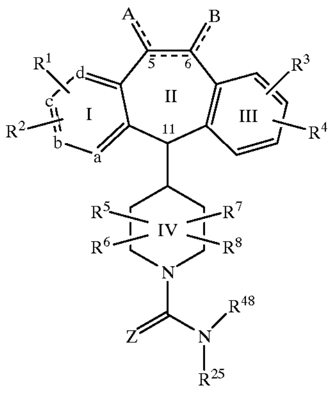

or (5.3B)

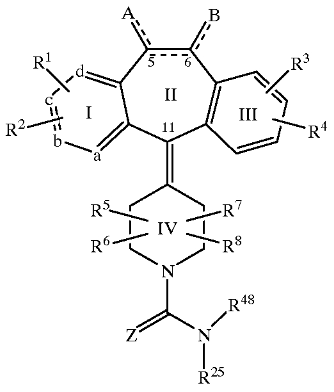

or a pharmaceutically acceptable salt or solvate thereof, wherein all the substituents are as defined for formula 1.0 of WO 95/10516 and WO 96/30363, and wherein for the compounds of Formula 5.2 the substituents $R^{20}$, $R^{21}$, and $R^{46}$ are selected such that when one of said substituents $R^{20}$, $R^{21}$, and $R^{46}$ is selected from the group consisting of: (1) H, (2) —OH, (3) —$NH_2$, (4) —$NHC(O)OR^{22}$, (5) alkyl, (6) phenyl, (7) heteroaryl, (8) hydroxyalkyl, (9) substituted pyridyl, (10) substituted phenyl and (11) —O-alkyl, then the remaining two of said substituents $R^{20}$, $R^{21}$ and $R^{46}$ cannot both be H when: (a) $R^1$ and $R^2$ are both H, and (b) the double bond between C-5 and C-6 is absent, and (c) both A and B are $H_2$, and (d) $R^4$ is H, and (e) $R^3$ is H or Cl at C-8.

WO 96/30363 also disclose the compounds:

(5.200)

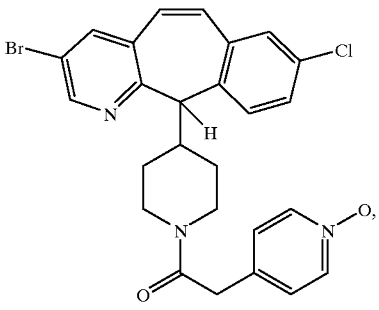

-continued
(5.201)
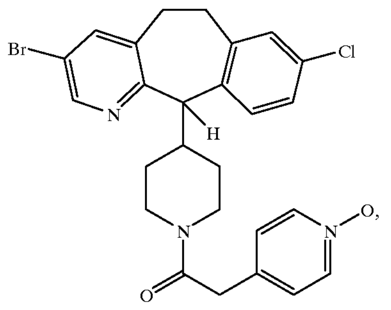
(5.202)
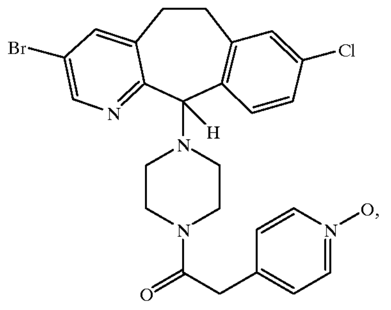
(5.203)
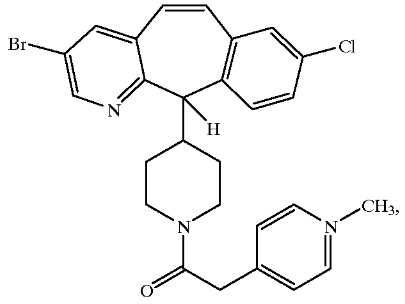
(5.204)
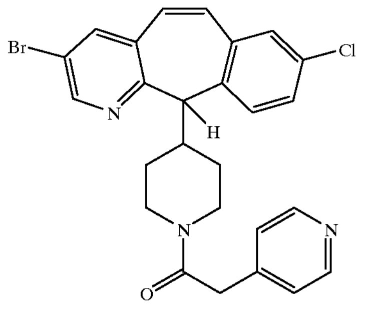
,
-continued
(5.205)
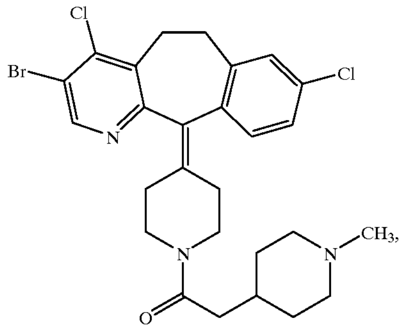
(5.206)
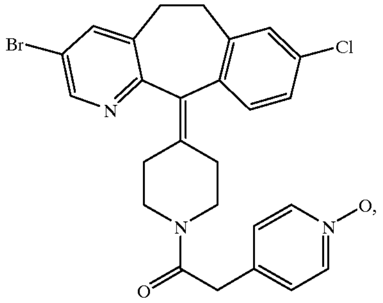
(5.207)
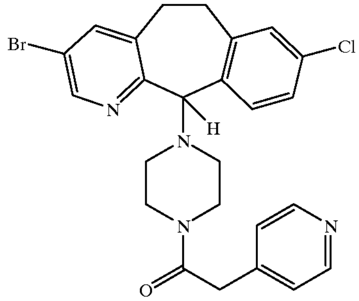
,
(5.208)
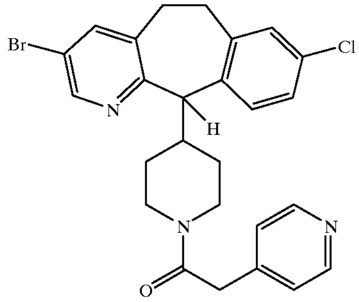
, -continued
(5.209)
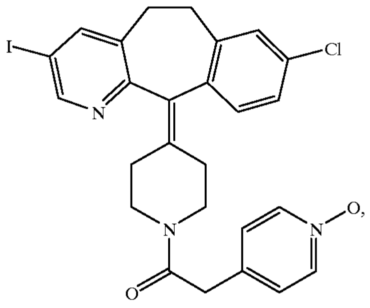
(5.210)
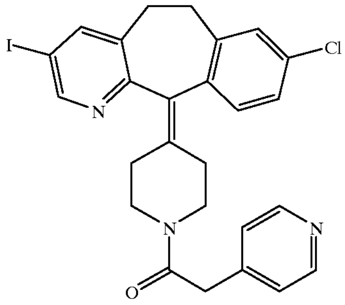
,
(5.211)
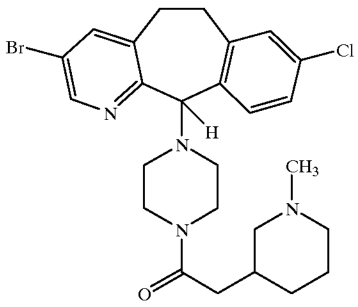
,
(5.212)
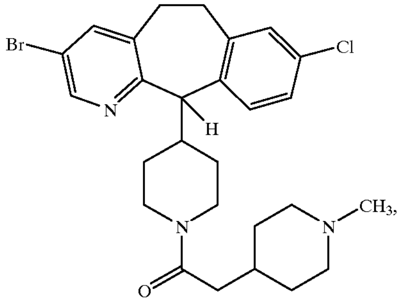
(5.214)
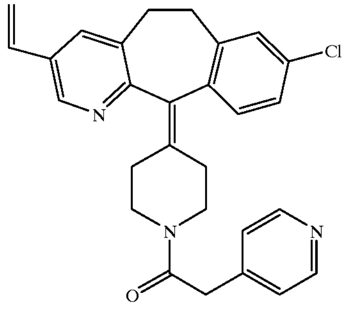
,
-continued
(5.213)
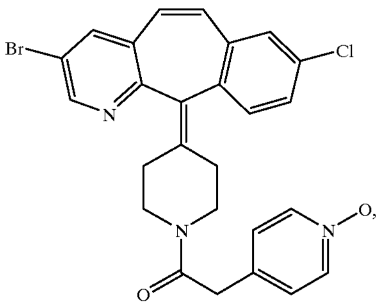
(5.215)
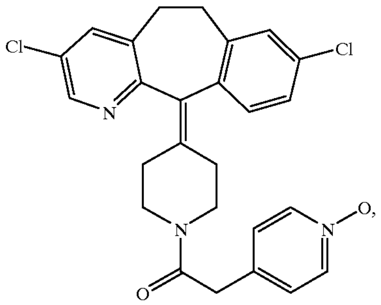
(5.217)
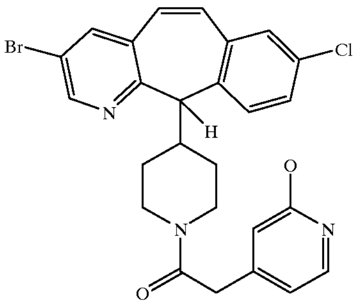
,
(5.216)
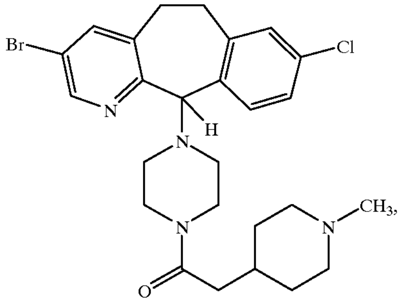
(5.218)
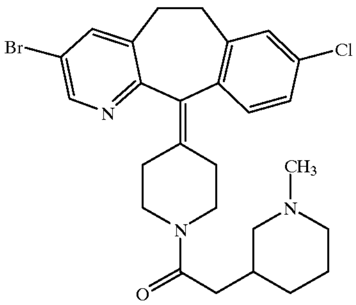
, -continued (5.219)

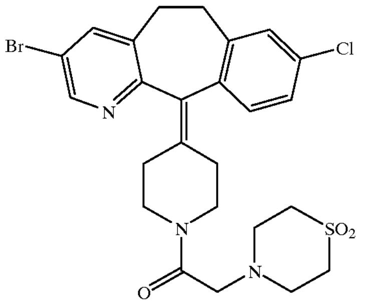

, and (5.220)

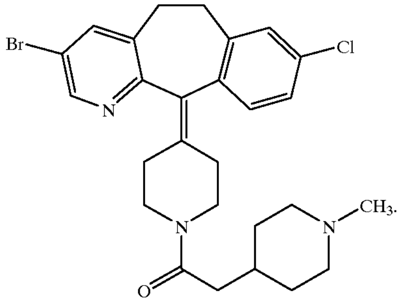

WO 95/10515 published Apr. 20, 1995 discloses compounds of formula 1.0:

(1.0)

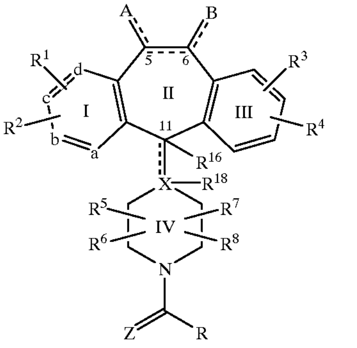

or a pharmaceutically acceptable salt or solvate thereof, wherein:

one of a, b, c and d represents N or $NR^9$ wherein $R^9$ is $O^-$ (i.e., $NR^9$ is an N-oxide group), —$CH_3$ or —$(CH_2)_nCO_2H$ wherein n is 1 to 3, and the remaining a, b, c and d groups represent $CR^1$ or $CR^2$;

each $R^1$ and each $R^2$ is independently selected from H, halo, —$CF_3$, —$OR^{10}$, —$COR^{10}$, —$SR^{10}$, —$N(R^{10})_2$, —$NO_2$, —$OC(O)R^{10}$, —$CO_2R^{11}$, —$OCO_2R^{11}$, benzotriazol-1-yloxy, CN, alkynyl, alkenyl and alkyl, said alkyl or alkenyl group optionally being substituted with halo, —$OR^{10}$ or —$CO_2R^{10}$;

$R^3$ and $R^4$ are the same or different and each independently represents H or any of the substituents of $R^1$ and $R^2$, or $R^3$ and $R^4$ together can represent a saturated or unsaturated $C_5$–$C_7$ ring fused to the benzene ring (Ring III);

each of $R^5$, $R^6$, $R^7$ and $R^8$ independently represents H, —$CF_3$, alkyl or aryl, said alkyl or aryl optionally being substituted with —$OR^{10}$, —$SR^{10}$, —$N(R^{10})_2$, —$NO_2$, —$COR^{10}$, —$OCOR^{10}$, —$OCO_2R^{11}$, —$CO_2R^{10}$, or $OPO_3R^{10}$, or one of $R^5$, $R^6$, $R^7$ and $R^8$ can be taken in combination with R as defined below to represent —$(CH_2)_r$—, wherein r is 1 to 4, which can be substituted with lower alkyl, lower alkoxy, —$CF_3$ or aryl;

$R^{10}$ represents H, alkyl, aryl, or aralkyl;

$R^{11}$ represents alkyl or aryl;

$R^{16}$ and $R^{18}$ represent H and F respectively, or F and H respectively, when the bond to X is a single bond and X is carbon; or each of $R^{16}$ and $R^{18}$ represents H when the bond to X is a single bond;

X represents N or C, which C may contain an optional double bond (represented by the dotted line) to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, each of A and B independently represents $H_2$, —$(OR^{11})_2$, (H and halo), dihalo, (alkyl and H), $(alkyl)_2$, (H and —$OC(O)R^{10}$), (H and —$OR^{10}$), =O, (aryl and H), =$NOR^{10}$ or —O—$(CH_2)_p$—O— wherein p is 2, 3 or 4;

Z represents O; and

R represents —$SR^{65}$ wherein $R^{65}$ is alkyl, aryl, heteroaryl, 2-, 3-, or 4-piperidyl or N-substituted piperidyl, wherein the substituent on said N-substituted piperidyl is $C_1$ to $C_4$ alkyl, alkylcarbonyl or —$C(O)NH(R^{10})$ wherein $R^{10}$ is H or alkyl; or R represents —$OR^{20}$ wherein $R^{20}$ is $C_1$ to $C_{12}$ alkyl, substituted $C_1$ to $C_{12}$ alkyl, phenyl, substituted phenyl, $C_7$ to $C_{12}$ phenylalkyl, $C_7$ to $C_{12}$ phenylalkyl wherein the phenyl moiety is substituted, heteroaryl, or $R^{20}$ is 2-, 3-, or 4-piperidyl or N-substituted piperidyl, wherein the substituents on said substituted $C_1$ to $C_{12}$ alkyl are selected from amino and substituted amino, with the proviso that said amino or said substituted amino for said $C_1$ to $C_{12}$ alkyl is not on $C_1$, and the substitutents on said substituted amino are selected from $C_1$ to $C_6$ alkyl, the substituents on said substituted phenyl and on said substituted phenyl moiety of the $C_7$ to $C_{12}$ phenylalkyl are selected from $C_1$ to $C_6$ alkyl and halo, and the substituent on said N-substituted piperidyl is $C_1$ to $C_4$ alkyl, alkylcarbonyl or —$C(O)NH(R^{10})$ wherein $R^{10}$ is H or alkyl.

WO 95/10515 also disclose compounds of formulas 1.1, 1.2, and 1.3:

(1.1)

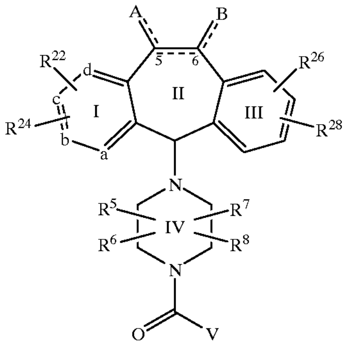

or a pharmaceutically acceptable salt or solvate thereof, wherein:

a, b, c, d, A, B, $R^5$, $R^6$, $R^7$, and $R^8$ are as defined for Formula 1.0 of WO 95/10515;

$R^{22}$ and $R^{24}$ are the same or different and each independently represents any of the substituents of $R^1$ and $R^2$ for Formula 1.0 of WO 95/10515;

$R^{26}$ and $R^{28}$ are the same or different and each independently represents any of the substituents of $R^3$ and $R^4$ for Formula 1.0 of WO 95/10515;

V represents —$OR^{30}$ or —$SR^{70}$;

$R^{30}$ represents aralkyl, aryl, heteroaryl, alkyl, 2-, 3-, or 4-piperidyl or N-substituted piperidyl, wherein the substituent on said N-substituted piperidyl is $C_1$ to $C_4$ alkyl, alkylcarbonyl or —C(O)NH($R^{10}$) wherein $R^{10}$ is H or alkyl;

$R^{70}$ represents aryl, heteroaryl, 2-, 3-, or 4-piperidyl or N-substituted piperidyl, wherein the substituent on said N-substituted piperidyl is $C_1$ to $C_4$ alkyl, alkylcarbonyl or —C(O)NH($R^{10}$) wherein $R^{10}$ is H or alkyl; and the dotted line between carbons 5 and 6 represents an optional double bond;

(1.2)

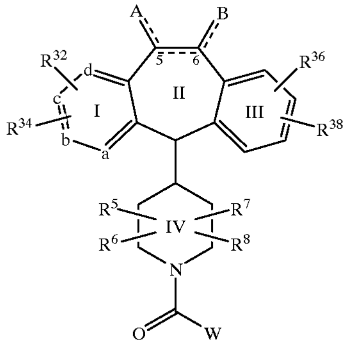

or a pharmaceutically acceptable salt or solvate thereof, wherein:

a, b, c, d, A, B, $R^5$, $R^6$, $R^7$, and $R^8$ are as defined for Formula 1.0 of WO 95/10515;

$R^{32}$ and $R^{34}$ are the same or different and each independently represents any of the substituents of $R^1$ and $R^2$ for Formula 1.0 of WO 95/10515;

$R^{36}$ and $R^{38}$ are the same or different and each independently represents any of the substituents of $R^3$ and $R^4$ for Formula 1.0 of WO 95/10515;

W represents —$OR^{40}$ or —$SR^{70}$;

$R^{40}$ represents alkyl, aryl, heteroaryl, or 2-, 3-, or 4-piperidyl or N-substituted piperidyl, wherein the substituent on said N-substituted piperidyl is $C_1$ to $C_4$ alkyl, alkylcarbonyl or —C(O)NH($R^{10}$) wherein $R^{10}$ is H or alkyl;

$R^{70}$ represents aryl, heteroaryl, 2-, 3-, or 4-piperidyl or N-substituted piperidyl, wherein the substituent on said N-substituted piperidyl is $C_1$ to $C_4$ alkyl, alkylcarbonyl or —C(O)NH($R^{10}$) wherein $R^{10}$ is H or alkyl; and the dotted line between carbons 5 and 6 represents an optional double bond; and (1.3)

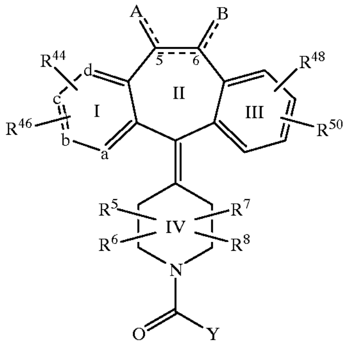

or a pharmaceutically acceptable salt or solvate thereof, wherein:

a, b, c, d, A, B, $R^5$, $R^6$, $R^7$, and $R^8$ are as defined for Formula 1.0 of WO 95/10515;

$R^{44}$ and $R^{46}$ are the same or different and each independently represents any of the substituents of $R^1$ and $R^2$ of Formula 1.0 of WO 95/10515;

$R^{48}$ and $R^{50}$ are the same or different and each independently represents any of the substituents of $R^3$ and $R^4$ of Formula 1.0 of WO 95/10515;

Y represents —$OR^{52}$ or —$SR^{70}$;

$R^{52}$ represents aralkyl, aryl, heteroaryl, alkyl, or 2-, 3-, or 4-piperidyl or N-substituted piperidyl, wherein the substituent on said N-substituted piperidyl is $C_1$ to $C_4$ alkyl, alkylcarbonyl or —C(O)NH($R^{10}$) wherein $R^{10}$ is H or alkyl;

$R^{70}$ represents aryl, heteroarylalkyl, 2-, 3-, or 4-piperidyl or N-substituted piperidyl, wherein the substituent on said N-substituted piperidyl is $C_1$ to $C_4$ alkyl, alkylcarbonyl or —C(O)NH($R^{10}$) wherein $R^{10}$ is H or alkyl; and the dotted line between carbons 5 and 6 represents an optional double bond; and with the provisos that: (a) when Y represents —$OR^{52}$, and when there is a single bond between carbon atoms 5 and 6, and when both $R^{44}$ and $R^{46}$ are hydrogen, and when both $R^{48}$ and $R^{50}$ are H, then $R^{52}$ is not phenyl; and (b) when Y represents —$OR^{52}$, and when there is a single bond between carbon atoms 5 and 6, and when both $R^{44}$ and $R^{46}$ are hydrogen, and when $R^{48}$ is Cl at the C-8 position and $R^{50}$ is H, then $R^{52}$ is not ethyl.

WO 96/30018 published Oct. 3, 1996 discloses compounds of the formulas:

(800.00)

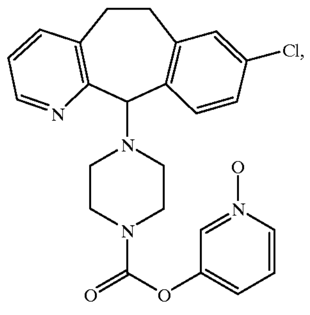

-continued
(801.00)
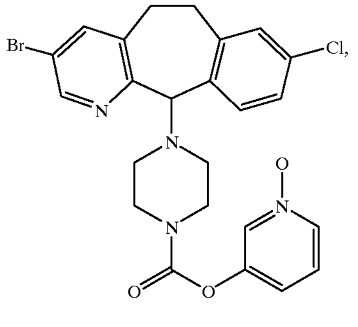
(802.00)
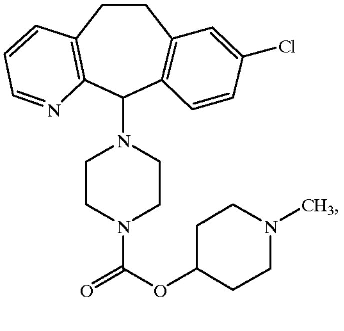
(803.00)
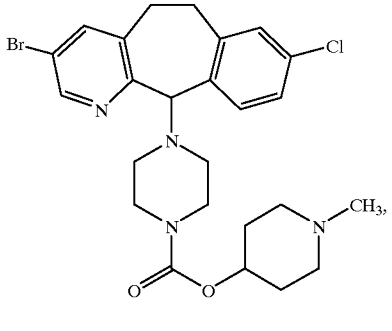
(804.00)
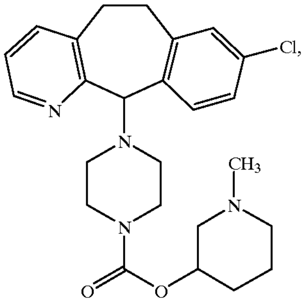
and
-continued
(805.00)
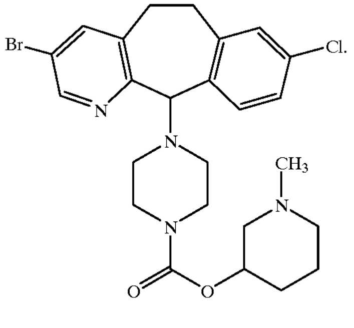
WO 96/30017 published Oct. 3, 1996 discloses compounds of formulas (Ia), (Ib) and (Ic):
(Ia)
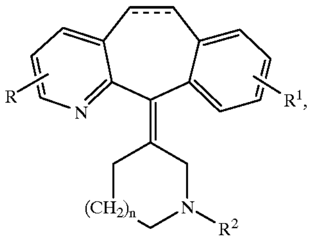
(Ib)
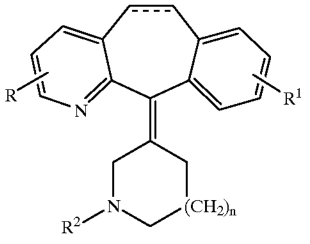
and
(Ic)
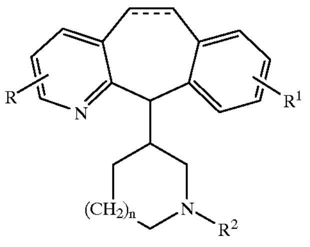
wherein:
R and $R^1$ are independently selected from H, $(C_1–C_6)$alkyl, halo, OH, $(C_1–C_6)$alkoxy, $NH_2$, $(C_1–C_6)$alkylamino, di$(C_1–C_6)$alkylamino, $CF_3$, $SO_3H$, $CO_2R^3$, $NO_2$, $SO_2NH_2$, and $CONHR^4$;

$R^2$ is $R^5C(O)$—, $R^5CH_2C(O)$—, $R^5C(R^6)_2C(O)$—, $R^5SO_2$—, $R^5CH_2SO_2$—, $R^5SCH_2C(O)$—, $R^5OC(O)$—, $R^5NHC(O)$—, $R^5C(O)C(O)$— or $R^5SC(O)$—;

$R^3$ is $(C_1-C_6)$alkyl or aryl;

$R^4$ is $(C_1-C_6)$alkyl;

$R^5$ is $(C_1-C_6)$alkyl, aryl, aryl$(C_1-C_6)$alkyl, aryl$(C_2-C_6)$ alkenyl, heteroaryl, heteroaryl$(C_1-C_6)$alkyl, heteroaryl $(C_2-C_6)$alkenyl or heterocycloalkyl;

each $R^6$ independently represents $(C_1-C_6)$alkyl, or both $R^6$ groups together with the carbon atom to which they are attached comprise a $(C_3-C_7)$-carbocyclic ring;

n is 0 or 1; and the dotted line represents an optional double bond;

and pharmaceutically acceptable salts thereof.

WO 96/30362 published Oct. 3, 1996 discloses a compound of formula (7.0a), (7.0b) or (7.0c):

(7.0a)

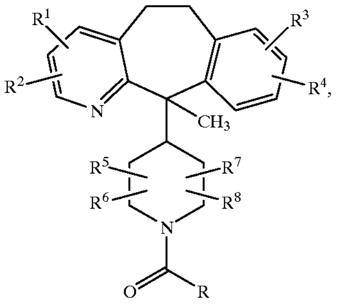

(7.0b)

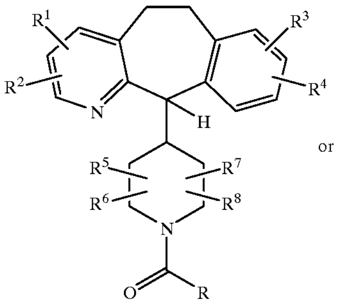

or (7.0)c

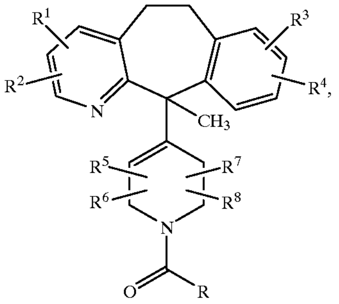

or a pharmaceutically acceptable salt or solvate thereof, wherein:

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COOR^{11}$,

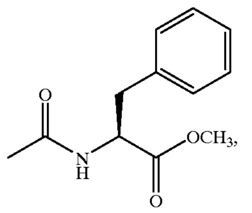

—$SR^{11}C(O)OR^{11}$ (e.g., —$SCH_2CO_2CH_3$), —$SR^{11}N(R^{75})_2$ wherein each $R^{75}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5-C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$—, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or one of $R^5$, $R^6$, $R^7$ and $R^8$ can be taken in combination with $R^{40}$ as defined below to represent —$(CH_2)_r$— wherein r is 1 to 4 which can be substituted with lower alkyl, lower alkoxy, —$CF_3$ or aryl, or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

R represents $R^{40}$, $R^{42}$, $R^{44}$, or $R^{54}$, as defined below;

$R^{40}$ represents H, aryl, alkyl, cycloalkyl, alkenyl, alkynyl or —D wherein —D represents

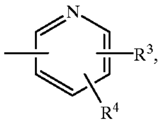, 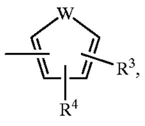, 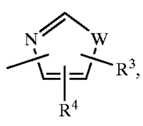,

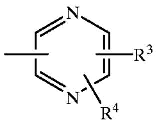 or 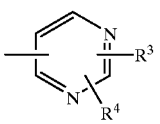

wherein $R^3$ and $R^4$ are as previously defined and W is O, S or $NR^{10}$ wherein $R^{10}$ is as defined above; said $R^{40}$ cycloalkyl, alkenyl and alkynyl groups being optionally substituted with from 1–3 groups selected from halo, —$CON(R^{10})_2$, aryl, —$CO_2R^{10}$, —$OR^{12}$, —$SR^{12}$, —$N(R^{10})_2$, —$N(R^{10})CO_2R^{11}$, —$COR^{12}$, —$NO_2$ or D, wherein —D, $R^{10}$ and $R^{11}$ are as defined above and $R^{12}$ represents $R^{10}$, —$(CH_2)_mOR^{10}$ or —$(CH_2)_qCO_2R^{10}$ wherein $R^{10}$ is as previously defined, m is 1 to 4 and q is 0 to 4; said alkenyl and alkynyl $R^{40}$ groups not containing —OH, —SH or —$N(R^{10})_2$ on a carbon containing a double or triple bond respectively; or $R^{40}$ represents phenyl substituted with a group selected from —$SO_2NH_2$, —$NHSO_2CH_3$, —$SO_2NHCH_3$, —$SO_2CH_3$, —$SOCH_3$, —$SCH_3$, or —$NHSO_2CF_3$, preferably, said group is located in the para (p-) position of the phenyl ring; or $R^{40}$ represents a group selected from

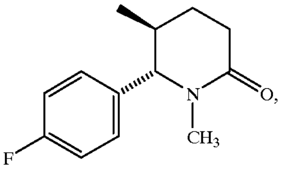
,
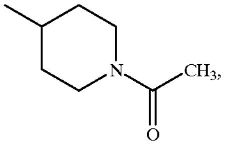
,
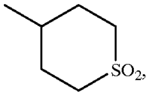
,
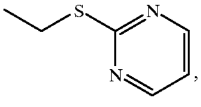
,
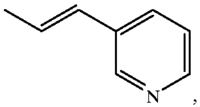
,
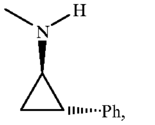
,
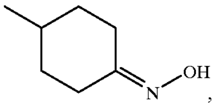
,
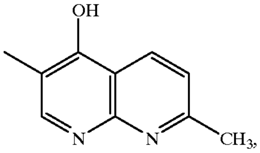
,
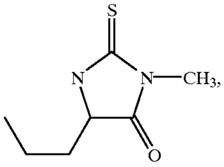
,
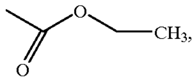
,
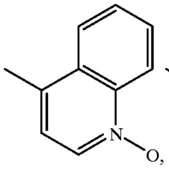
,
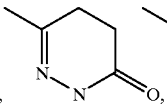
,
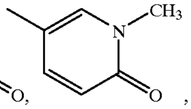
, or
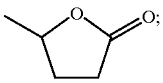
;

$R^{42}$ represents

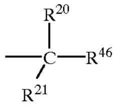

wherein $R^{20}$, $R^{21}$ and $R^{46}$ are each independently selected from the group consisting of:

(1) H;

(2) $-(CH_2)_qSC(O)CH_3$ wherein q is 1 to 3 (e.g., $-CH_2SC(O)CH_3$);

(3) $-(CH_2)_qOSO_2CH_3$ wherein q is 1 to 3 (e.g., $-CH_2OSO_2CH_3$);

(4) —OH;

(5) $-CS(CH_2)_w$(substituted phenyl) wherein w is 1 to 3 and the substitutents on said substituted phenyl group are the same substitutents as described below for said substituted phenyl (e.g., —C—S—$CH_2$-4-methoxyphenyl);

(6) $-NH_2$;

(7) —NHCBZ (wherein CBZ stands for carbonylbenzyloxy—i.e., CBZ represents $-C(O)OCH_2C_6H_5$);

(8) $-NHC(O)OR^{22}$ wherein $R^{22}$ is an alkyl group having from 1 to 5 carbon atoms (e.g., $R^{22}$ is t-butyl thus forming —NHBOC wherein BOC stands for tert-butyloxycarbonyl—i.e., BOC represents $-C(O)OC(CH_3)_3$), or $R^{22}$ represents phenyl substituted with 1 to 3 alkyl groups (e.g., 4-methylphenyl);

(9) alkyl (e.g., ethyl);

(10) $-(CH_2)_k$phenyl wherein k is 1 to 6, usually 1 to 4 and preferably 1 (e.g., benzyl);

(11) phenyl;

(12) substituted phenyl (i.e., phenyl substituted with from 1 to 3 substituents, preferably one) wherein the substituents are selected from the group consisting of: halo (e.g., Br, Cl, or I, with Br being preferred); $NO_2$; —OH; $-OCH_3$; $-NH_2$; $-NHR^{22}$; $-N(R^{22})_2$; alkyl (e.g., alkyl having from 1 to 3 carbons with methyl being preferred); $-O(CH_2)_t$phenyl (wherein t is from 1 to 3 with 1 being preferred); and $-O(CH_2)_t$substituted phenyl (wherein t is from 1 to 3 with 1 being preferred); examples of substituted phenyls include, but are not limited to, p-bromophenyl, m-nitrophenyl, o-nitrophenyl, m-hydroxy-phenyl, o-hydroxyphenyl, methoxyphenyl, p-methylphenyl, m-methyl-phenyl, and $-OCH_2C_6H_5$;

(13) naphthyl;

(14) substituted naphthyl, wherein the substituents are as defined for substituted phenyl above;

(15) bridged polycyclic hydrocarbons having from 5 to 10 carbon atoms (e.g., adamantyl and norbornyl);

(16) cycloalkyl having from 5 to 7 carbon atoms (e.g., cyclopentyl, and cyclohexyl);

(17) heteroaryl (e.g., pyridyl, and pyridyl N-oxide);

(18) hydroxyalkyl (e.g., $-(CH_2)_vOH$ wherein v is 1 to 3, such as, for example, $-CH_2OH$);

(19) substituted pyridyl or substituted pyridyl N-oxide wherein the substituents are selected from methylpyridyl, morpholinyl, imidazolyl, 1-piperidinyl, 1-(4-methylpiperazinyl), $-S(O)_tR^{11}$, or any of the substituents given above for said substituted phenyl, and said substitutents are bound to a ring carbon by replacement of the hydrogen bound to said carbon;

(20)

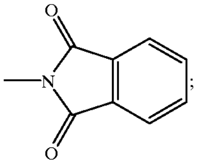
;

(21)

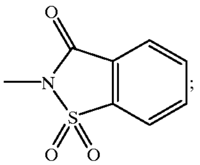
;

(22)

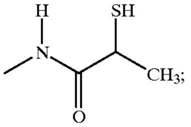
;

(23) $-NHC(O)-(CH_2)_k$-phenyl or $-NH(O)-(CH_2)_k$-substituted phenyl, wherein said k is as defined above (i.e., 1–6, usually 1–4 and preferably 1);

(24) piperidine Ring V:

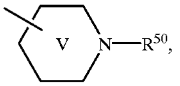

wherein $R^{50}$ represents H, alkyl (e.g., methyl), alkylcarbonyl (e.g., $CH_3C(O)$—), alkyloxycarbonyl (e.g., —C(O)O—t—$C_4H_9$, —$C(O)OC_2H_5$, and —$C(O)OCH_3$), haloalkyl (e.g., trifluromethyl), or —C(O)NH($R^{10}$) wherein $R^{10}$ is H or alkyl; Ring V includes

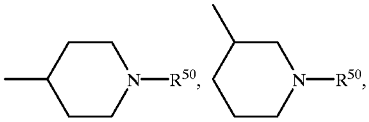

and

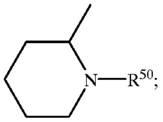

examples of Ring V include:

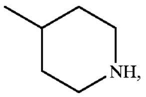

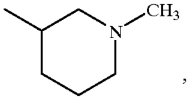

,

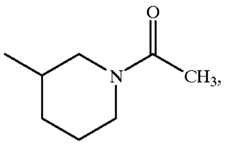

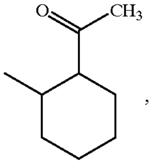

,

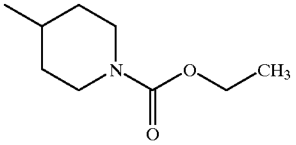

and

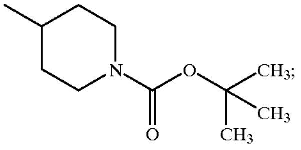

(25) —$NHC(O)CH_2C_6H_5$ or —$NHC(O)CH_2$-substituted-$C_6H_5$, for example —$NHC(O)CH_2$-p-hydroxyphenyl, —$NHC(O)CH_2$-m-hydroxyphenyl, and —$NHC(O)CH_2$-o-hydroxyphenyl;

(26) —$NHC(O)OC_6H_5$;

(27)

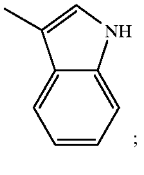

;

-continued (28)

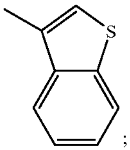

;

(29)

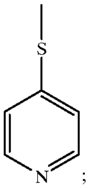

;

(30) —OC(O)-heteroaryl, for example

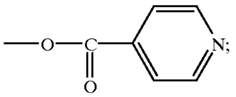

(31) —O-alkyl (e.g., —$OCH_3$);

(32) —$CF_3$;

(33) —CN;

(34) a heterocycloalkyl group of the formula

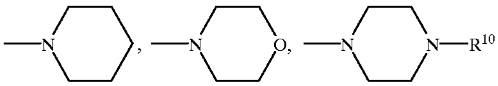

or

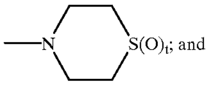

(35) a piperidinyl group of the formula

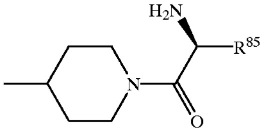

wherein $R^{85}$ is H, all or alkyl substituted by —OH or —$SCH_3$; or $R^{20}$ and $R^{21}$ taken together form a =O group and the remaining $R^{46}$ is as defined above; or two of $R^{20}$, $R^{21}$ and $R^{46}$ taken together form piperidine Ring V

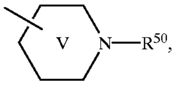

wherein $R^{50}$ and Ring V are as defined above;

with the proviso $R^{46}$, $R^{20}$, and $R^{21}$ are selected such that the carbon atom to which they are bound does not contain more than one heteroatom (i.e., $R^{46}$, $R^{20}$, and $R^{21}$ are selected such that the carbon atom to which they are bound contains 0 or 1 heteroatom);

$R^{44}$ represents

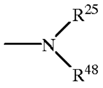

wherein $R^{25}$ represents heteroaryl (e.g., pyridyl or pyridyl N-oxide) or aryl (e.g., phenyl and substituted phenyl); and $R^{48}$ represents H or alkyl (e.g., methyl);

$R^{54}$ represents an N-oxide heterocyclic group of the formula (i), (ii), (iii) or (iv):

(i)

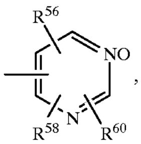

, (ii)

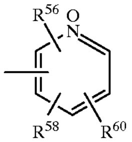

, (iii)

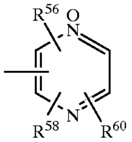

or (iv)

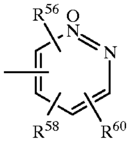

wherein $R^{56}$, $R^{58}$, and $R^{60}$ are the same or different and each is independently selected from H, halo, $—CF_3$, $—OR^{10}$, $—C(O)R^{10}$, $—SR^{10}$, $—S(O)_eR^{11}$ (wherein e is 1 or 2), $—N(R^{10})_2$, $—NO_2$, $—CO_2R^{10}$, $—OCO_2R^{11}$, $—OCOR^{10}$, alkyl, aryl, alkenyl or alkynyl, which alkyl may be substituted with $—OR^{10}$, $—SR^{10}$ or $—N(R^{10})_2$ and which alkenyl may be substituted with $OR^{11}$ or $SR^{11}$; or $R^{54}$ represents an N-oxide heterocyclic group of the formula (ia), (iia), (iiia) or (iva):

(ia)

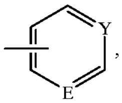

, (iia)

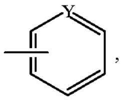

,

-continued (iiia)

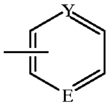

or (iva)

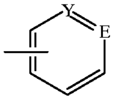

wherein Y represents $N^+$-$O^-$ and E represents N; or $R^{54}$ represents an alkyl group substituted with one of said N-oxide heterocyclic groups (i), (ii), (iii), (iv), (ia), (iia), (iiia) or (iva).

WO 96/31111 published Oct. 10, 1996 discloses compounds of the formula:

(1.0)

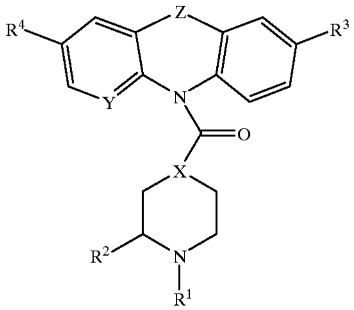

or a pharmaceutically acceptable salt or solvate thereof, wherein:

(1) $R^1$ is a group selected from:

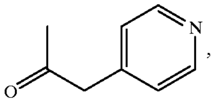

, (a)

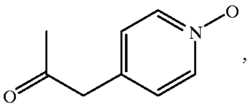

, (b)

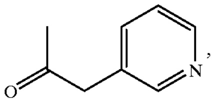

, (c)

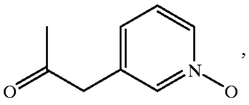

, (d)

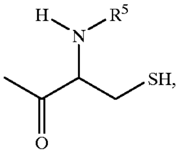

(e)

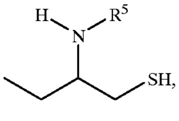

(f)

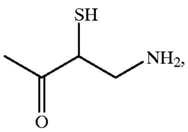

(g)

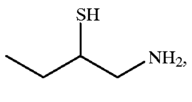

(h)

-continued

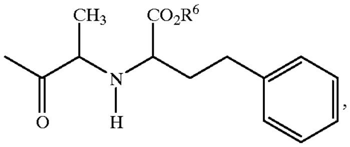, (i)

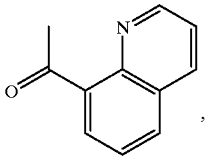, 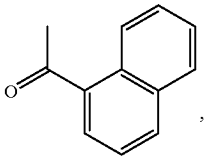, (j) (k)

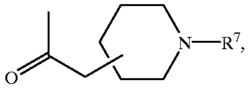 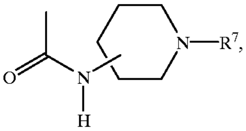

(l) (m)

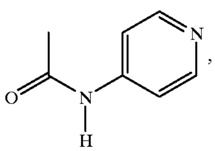, 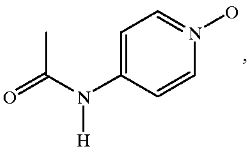, (n) (o)

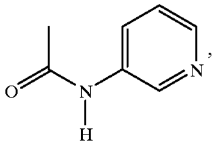, 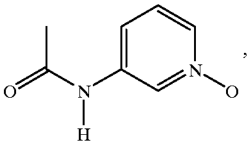, (p) (q)

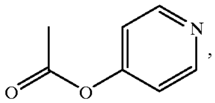, 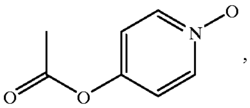, (r) (s)

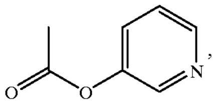, 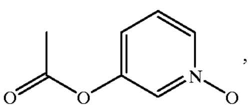, (t) (u)

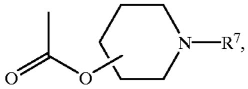 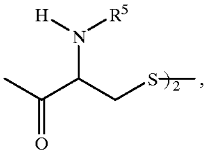, (v) (w)

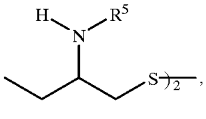, 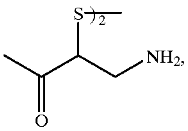

(x) (y)

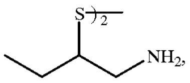 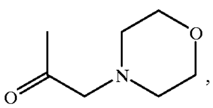, and (z) (z.1)

-continued

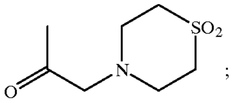;

(z.2)

$R^2$ is selected from:

(1) H;

(2) $C_1$ to $C_8$ alkyl;

(3) $C_2$ to $C_8$ alkenyl;

(4) $C_2$ to $C_8$ alkynyl;

(5) —$CONR^8R^9$; and (6) —$COOR^8$;

wherein said alkyl, alkenyl, or alkynyl is optionally substituted with one or more groups independently selected from:

(a) aryl, aralkyl, heteroaryl, heteroarylalkyl, and heterocycloalkyl, said aryl, aralkyl, heteroarylalkyl, heteroaryl or heterocycloalkyl optionally being substituted with one or more of: $C_1$ to $C_4$ alkyl, $(CH_2)_tOR^8$ wherein t is 1 to 4, $(CH_2)_tNR^8R^9$ wherein t is 1 to 4, halogen;

(b) $C_3$ to $C_6$ cycloalkyl;

(c) —$OR^8$;

(d) —$SR^8$;

(e) —$S(O)R^8$;

(f) —$SO_2R^8$;

(g) —$NR^8R^9$;

(h) —$NR^8$—CO—$R^9$;

(i) —$NR^8$—CO—$NR^9R^{10}$;

(j) —O—CO—$NR^8R^9$;

(k) —O—CO—$OR^8$;

(l) —CO—$NR^8R^9$;

(m) —$SO_2$—$NR^8R^9$;

(n) —$NR^8$—$SO_2$—$OR^9$; and (o) —CO—$R^8$;

$R^3$ is selected from H, halogen and $C_1$ to $C_6$ alkyl;

$R^4$ is selected from H, halogen and $C_1$ to $C_6$ alkyl;

$R^5$ is selected from: H, $C_1$–$C_6$ alkyl, (aa)

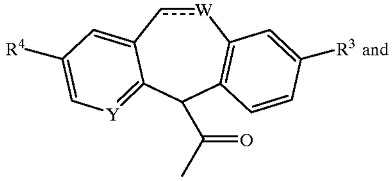 and (bb)

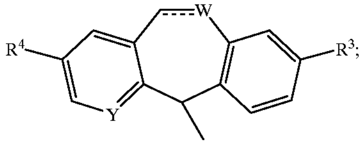;

$R^6$ selected from H or $C_1$ to $C_6$ alkyl;

$R^7$ is selected from H, $C_1$ to $C_6$ alkyl, haloalkyl, and —$C(O)R^{11}$ wherein $R^{11}$ is selected from $C_1$ to $C_6$ alkyl, $C_1$ to $C_6$ alkoxy or —$NHR^{12}$ (wherein $R^{12}$ is $C_1$ to $C_6$ alkyl or H), or R7 is an acyl radical of a naturally occurring amino acid;

$R^8$, $R^9$ and $R^{10}$ are independently selected from H, $C_1$ to $C_4$ alkyl, $C_3$ to $C_6$ cycloalkyl, heteroaryl, heteroarylalkyl, heterocycloalkyl, aralkyl, and aryl; said alkyl, cycloalkyl, heteroaryl, heteroarylalkyl, heterocycloalkyl, aralkyl, or aryl optionally being substituted with $C_1$ to $C_4$ alkoxy, aralkyl, aryl, heteroaryl, heteroarylalkyl, cyclopropyl, heterocycloalkyl, halogen, —OH, —C(O)$R^{13}$, —$SO_2R^{13}$, or —$NR^{14}R^{15}$ wherein $R^{13}$ is selected from $C_1$ to $C_4$ alkyl and aralkyl, and wherein $R^{14}$ and $R^{15}$ are independently selected from H, $C_1$ to $C_4$ alkyl and aralkyl, with the provisos that:

$R^8$ may not be H in substituent (e), (f), or (k), $R^9$ may not be H in substituent (h) or (n), and $R^8$, $R^9$, or $R^{10}$ may not be $CH_2OH$ or $CH_2NR^{14}R^{15}$ when $R^{10}$ is directly attached to a heteroatom which is O, S, or N;

$R^{16}$ is selected from H, arylalkyl and $C_1$ to $C_6$ alkyl;

optionally, when $R^8$ and $R^9$ are bound to the same nitrogen, $R^8$ and $R^9$, together with the nitrogen to which they are bound, form a 5 to 7 membered heterocycloalkyl ring;

optionally, when $R^9$ and $R^{10}$ are bound to the same nitrogen, $R^9$ and $R^{10}$, together with the nitrogen to which they are bound, form a 5 to 7 membered heterocycloalkyl ring;

---- represents an optional bond;

W is CH when the optional bond is present, or $CH_2$, O, or S when the optional bond is absent;

X is selected from CH and N;

Y is selected from N and CH; and

Z is selected from —CO—$NR^{16}$—, —$NR^{16}$—CO—, —$CH_2$—$CH_2$—, and —CH═CH—.

WO 96/31478 published Oct. 10, 1996 discloses compounds of formula (1.0):

(1.0)

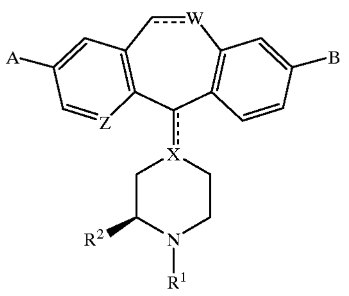

wherein:

A and B are independently selected from H, halo or $C_1$–$C_6$ alkyl;

Z is N or CH;

W is CH, $CH_2$, O or S, wherein the dotted line to W represents a double bond which is present when W is CH;

X is C, CH or N, wherein the dotted line connecting X to the tricyclic ring system represents a double bond which is present when X is C;

$R^1$ is selected from:

1) a group of the formula:

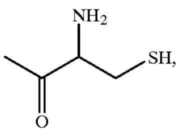

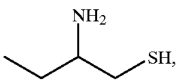

-continued

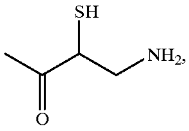

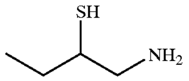

or disulfide dimers thereof;

2) a group of the formula:

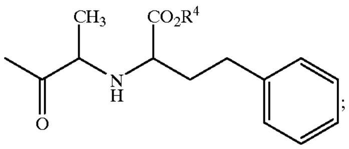

3) a group of the formula:

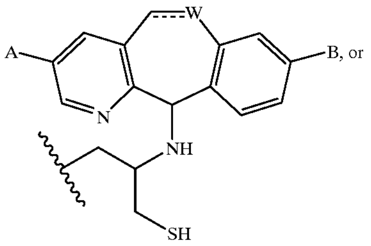

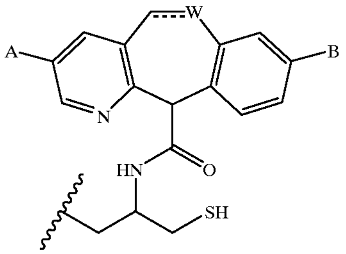

wherein W, A and B are as defined above;

4) a group of the formula:

(159.0)

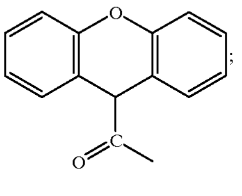

5) a group of the formula:

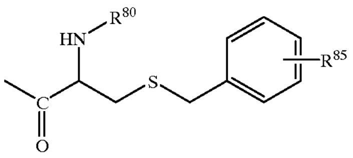

wherein $R^{80}$ is selected from H or —C(O)$OR^{90}$ wherein $R^{90}$ is a $C_1$–$C_6$ alkyl group (e.g., —$C(CH_3)_3$), and $R^{85}$ is a $C_1$–$C_6$ alkoxy group (e.g., p—$OCH_3$); and 6) a group of the formula:

(82.0)

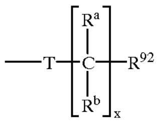

wherein:

(a) T is selected from:

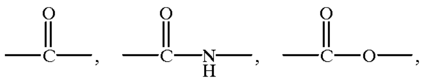

—$SO_2$—, or a single bond;

(b) x is 0, 1, 2, 3, 4, 5 or 6;

(c) each $R^a$ and each $R^b$ is independently selected from H, aryl, alkyl, alkoxy, aralkyl, amino, alkylamino, heterocycloalkyl, —$COOR^{60}$, —$NH\{C(O)\}_zR^{60}$ (wherein z is 0 or 1), or —$(CH)_wS(O)_mR^{60}$ (wherein w is 0, 1, 2 or 3, and m is 0, 1 or 2); or $R^a$ and $R^b$ taken together resent cycloalkyl, =N—O-alkyl, =O or heterocycloalkyl; with the proviso that for the same carbon, $R^a$ is not selected from alkoxy, amino, alkylamino or —$NH\{C(O)\}_zR^{60}$ when $R^b$ is selected from alkoxy, amino, alkylamino or —$NH\{C(O)\}_zR^{60}$; and with the proviso that when T is a single bond, for the first carbon containing $R^a$ and $R^b$, $R^a$ and $R^b$ are not selected from alkoxy, alkylamino, amino or —$NHR^{60}$ (i.e., —$NH\{C(O)\}_zR^{60}$ wherein z is 0) (i.e., $R^a$ and $R^b$ on the first carbon bound to T, when T is a single bond, are not alkoxy, alkylamino, amino or —$NHR^{60}$); and (d) $R^{92}$ can represent H, alkyl, aryl, aryloxy, arylthio, aralkoxy, aralkyl, heteroaryl or heterocycloalkyl;

$R^{60}$ represents H, alkyl, aryl or aralkyl;

$R^4$ is H or $C_1$–$C_6$ alkyl;

$R^2$ is selected from: H, —$C(O)OR^6$, —$C(O)NR^6R^7$, $C_1$–$C_8$ alkyl, $C_2$–$C_8$ alkenyl, $C_2$–$C_8$ alkynyl, substituted $(C_{1-C8})$alkyl, substituted $(C_2$–$C_8)$alkenyl, substituted $(C_2$–$C_8)$alkynyl, wherein said substituted groups have one or more substituents selected from:

1) aryl, arylalkyl, heteroarylalkyl, heteroaryl, heterocycloalkyl, B-substituted aryl, B-substituted arylalkyl, B-substituted heteroarylalkyl, B-substituted heteroaryl or B-substituted heterocycloalkyl, wherein B is selected from $C_1$–$C_4$ alkyl, —$(CH_2)_nOR^6$, —$(CH_2)_nNR^6R^7$ and halo;

2) $C_3$–$C_6$ cycloalkyl;

3) —$OR^6$;

4) —SH or —$S(O)_tR^6$;

5) —$NR^6R^7$;

6) —$N(R^6)$—$C(O)R^7$;

7) —$N(R^6)$—$C(O)NR^7R^{12}$;

8) —O—$C(O)NR^6R^7$;

9) —O—$C(O)OR^6$;

10) —$SO_2NR^6R^7$;

11) —$N(R^6)$—$SO_2$—$R^7$;

12) —$C(O)NR^6R^7$;

13) —$C(O)OR^6$; and provided where $R^1$ is D, $R^2$ is not H, and where $R^1$ is D and $R^2$ is $C_{1-C8}$ alkyl, the substituents on said alkyl group are not substituents 3), 4), 5), 9), or 13); D is —C(O)—$CH_2$—$R^5$, —C(O)—O—$R^5$ or —C(O)—NH—$R^5$, wherein $R^5$ is pyridyl, pyridyl N-oxide,

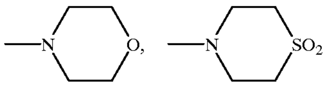

or a piperidinyl group of the formula

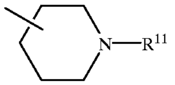

wherein $R^{11}$ represents H, $C_1$–$C_6$ alkyl, haloalkyl or —C(O)—$R^9$ wherein $R^9$ is $C_1$–$C_6$ alkyl, $C_1$–$C_6$ alkoxy or —$NH(R^{10})$ wherein $R^{10}$ is H or alkyl, or the group —C(O)—$R^9$ represents an acyl radical of a naturally occurring amino acid;

$R^6$, $R^7$ and $R^{12}$ are independently selected from H, $C_1$–$C_4$ alkyl, $(C_3$–$C_6)$cycloalkyl, aryl, arylalkyl (i.e., aralkyl), heteroaryl, heteroarylalkyl, heterocycloalkyl, substituted $(C_1$–$C_4)$alkyl, substituted $(C_3$–$C_6)$cycloalkyl, substituted aryl, substituted arylalkyl, substituted heteroaryl, substituted heteroarylalkyl or substituted heterocycloalkyl, wherein said substituted groups have one or more substituents (e.g., 1–3) selected from: $C_1$–$C_4$ alkoxy, aralkyl, heteroarylalkyl, —$NO_2$, $C_3$–$C_{10}$-alkoxyalkoxy (e.g., —O—$(C_1$–$C_4)$alkyl-O-$(C_1$–$C_4)$alkyl), $(C_3$–$C_6)$ cycloalkyl (e.g., cyclopropyl or cyclohexyl), aryl, —CN, nitrophenyl, methylenedioxyphenyl, heteroaryl, heterocycloalkyl, halo, —OH, —$C(O)R^{14}$, —$C(O)NR^6R^7$, —$N(R^6)C(O)R^{14}$, —$S(O)_tR^{14}$ (e.g., —S—$(C_1$–$C_4)$alkyl and —$SO_2R^{14}$) or —$NR^{95}R^{15}$; provided that $R^6$, $R^7$ and $R^{12}$ are not —$CH_2OH$ or —$CH_2NR^{95}R^{15}$ when said $R^6$, $R^7$ or $R^{12}$ is directly bonded to a heteroatom, and further provided that $R^6$ is not H for groups 4) and 9), and $R^7$ is not H for group 6);

optionally, when $R^6$ and $R^7$ are bound to the same nitrogen, $R^6$ and $R^7$ together with the nitrogen to which they are bound, form a 5 to 7 membered heterocycloalkyl ring which optionally contains O, $NR^6$, or $S(O)_t$ wherein t is 0, 1 or 2;

optionally, when $R^7$ and $R^{12}$ are bound to the same nitrogen, $R^7$ and $R^{12}$ together with the nitrogen to which they are bound, form a 5 to 7 membered heterocycloalkyl ring which optionally contains O, $NR^6$, or $S(O)_t$ wherein t is 0, 1 or 2;

$R^{95}$ and $R^{15}$ are independently H, $C_1$–$C_4$ alkyl or arylalkyl;

$R^{14}$ is $C_1$–$C_4$ alkyl, aryl or arylalkyl;

n=0, 1, 2, 3 or 4; and t=0, 1 or 2;

or pharmaceutically acceptable salts thereof.

WO 96/31477 published Oct. 10, 1996 discloses compounds of formula (1.0):

(1.0)
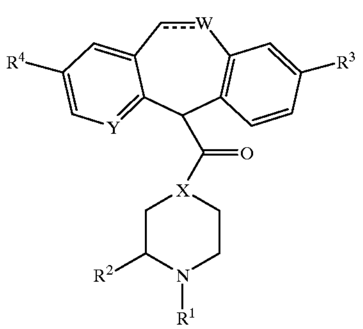
or a pharmaceutically acceptable salt or solvate thereof, wherein:
(1) $R^1$ is a group selected from:
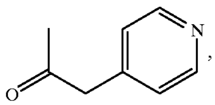
(a)
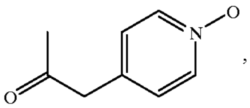
(b)
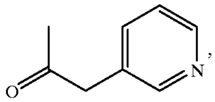
(c)
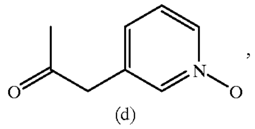
(d)
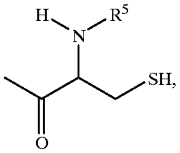
(e)
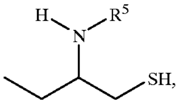
(f)
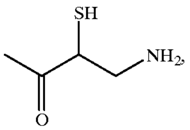
(g)
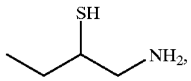
(h)
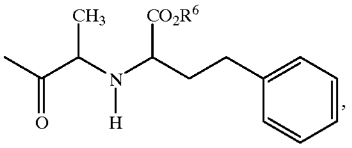
(i)
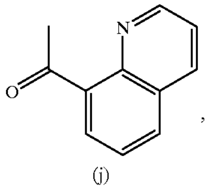
(j)
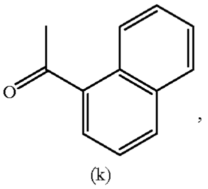
(k)
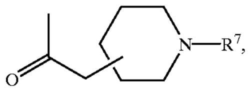
(l)
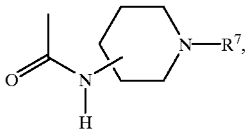
(m)
-continued
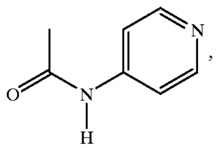
(n)
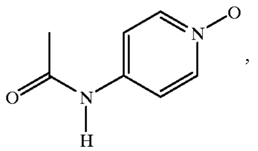
(o)
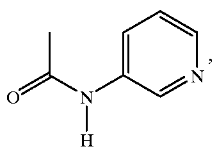
(p)
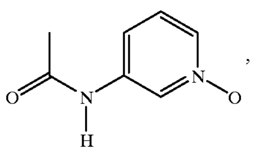
(q)
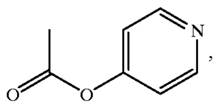
(r)
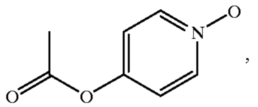
(s)
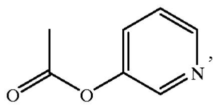
(t)
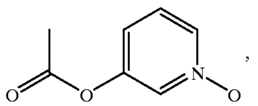
(u)
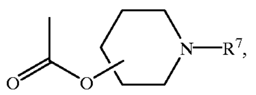
(v)
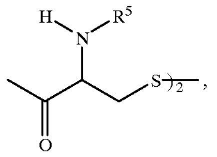
(w)
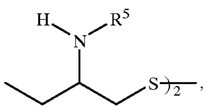
(x)
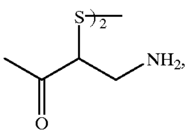
(y)
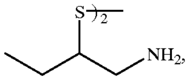
(z)
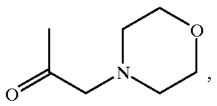
(z.1)
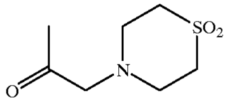
(z.2)
or
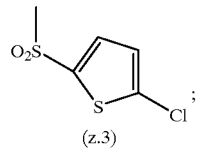
(z.3)
;
$R^2$ is selected from: (1) H, (2) $C_1$ to $C_8$ alkyl, (3) $C_2$ to $C_8$ alkenyl, (4) $C_2$ to $C_8$ alkynyl,
(5)
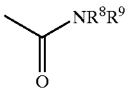
or
(6)
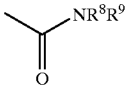
wherein said alkyl, alkenyl, or alkynyl is optionally substituted with one or more groups independently selected from:

(a) aryl, aralkyl, heteroaryl, heteroarylalkyl or heterocycloalkyl; said aryl, aralkyl, heteroaryl, heteroarylalkyl or heterocycloalkyl optionally substituted with one or more groups independently selected from:

(1) $C_1$ to $C_4$ alkyl, (2) $(CH_2)_tOR^8$ wherein t is 1 to 4, (3) $(CH_2)_tNR^8R^9$ wherein t is 1 to 4, or (4) halogen, (b) $C_3$ to $C_6$ cycloalkyl, (c) $—OR^8$, (d) $—SR^8$, (e) $—S(O)R^8$, (f) $—SO_2R^8$, (g) $—NR^8R^9$, (h)

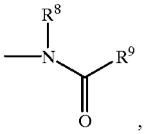

, (i)

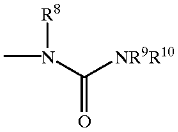

, (j)

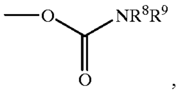

, (k)

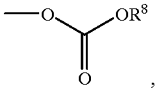

, (l)

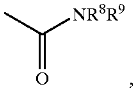

, (m)

$—SO_2—NR^8R^9$, (n)

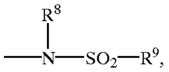

or (o)

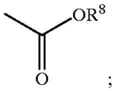

;

$R^3$ is selected from H, halogen or $C_1$ to $C_6$ alkyl (e.g., methyl);

$R^4$ is selected from H, halogen or $C_1$ to $C_6$ alkyl (e.g., methyl);

$R^5$ is selected from: H, (aa)

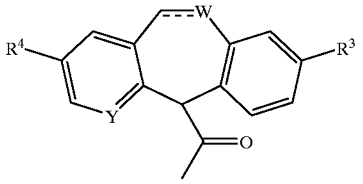

or (bb)

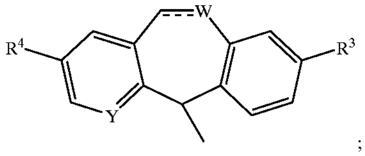

;

$R^6$ is selected from H or $C_1$ to $C_6$ alkyl (preferably methyl or ethyl);

$R^7$ is selected from H, $C_1$ to $C_6$ alkyl, haloalkyl, or $—C(O)R^{11}$ wherein $R^{11}$ is selected from $C_1$ to $C_6$ alkyl, $C_1$ to $C_6$ alkoxy or $—NHR^{12}$ (wherein $R^{12}$ is $C_1$ to $C_6$ alkyl or H), or $R^7$ is an acyl radical of a naturally occurring amino acid;

$R^8$, $R^9$ and $R^{10}$ are independently selected from H, $C_1$ to $C_4$ alkyl, $C_3$ to $C_6$ cycloalkyl, heteroaryl, heteroarylalkyl, heterocycloalkyl, aryl or aralkyl; said alkyl, cycloalkyl, heteroaryl, heteroarylalkyl, heterocycloalkyl, aryl or aralkyl are optionally substituted with $C_1$ to $C_4$ alkyl aryl, heteroaryl, heterocycloalkyl, cyclopropyl, halogen, —OH, $—C(O)R^{13}$, $—SO_2R^{13}$, or $—NR^{14}R^{15}$ wherein $R^{13}$ is selected from $C_1$ to $C_4$ alkyl or aralkyl, and wherein $R^{14}$ and $R^{15}$ are independently selected from H, $C_1$ to $C_4$ alkyl or aralkyl; with the proviso that $R^8$ is not H in substituents (e), (f) or (k), and with the proviso that $R^9$ is not H in substituent (h) or (n), and with the proviso that $R^8$, $R^9$, or $R^{10}$ is not $—CH_2OH$ or $—CH_2NR^{14}R^{15}$ when $R^8$, $R^9$, or $R^{10}$ is directly attached to a heteroatom (e.g., O, S or N);

optionally, when $R^8$ and $R^9$ are bound to the same nitrogen, $R^8$ and $R^9$, together with the nitrogen to which they are bound, form a 5 to 7 membered heterocycloalkyl ring;

optionally, when $R^9$ and $R^{10}$ are bound to the same nitrogen, $R^9$ and $R^{10}$, together with the nitrogen to which they are bound, form a 5 to 7 membered heterocycloalkyl ring;

---- represents an optional bond;

W is selected from CH when the optional bond is present, or O, S or $CH_2$ when the optional bond is absent;

X is selected from CH or N; and

Y is selected from N or CH.

WO 96/31505 published Oct. 10, 1996 discloses compounds of formula (1.0):

(1.0)

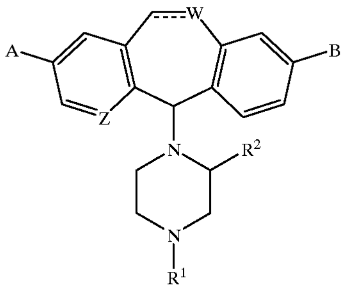

wherein:

A and B are independently selected from H, halo or $C_1$–$C_6$ alkyl;

Z is N or CH;

W is CH, $CH_2$, O or S, wherein the dotted line to W represents a double bond which is present when W is CH;

$R^1$ is selected from the group consisting of:

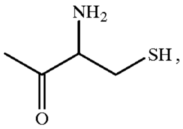,
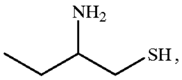,

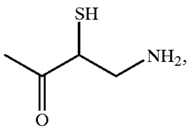,
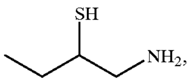,

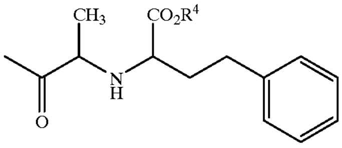,

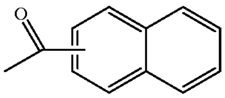,
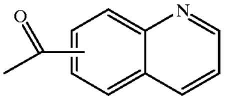,

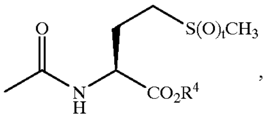,

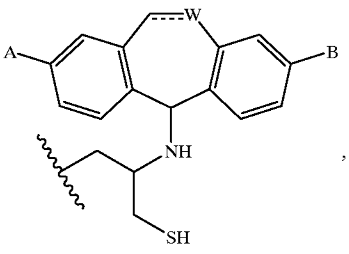,

-continued

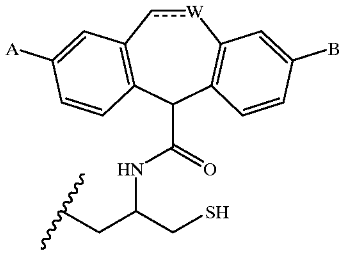, wherein W, A and B are as defined above; or $R^1$ is a group D, wherein D is —C(O)—$(CH_2)_s$—$R^5$, —C(O)O— $(CH_2)_m$—$R^5$ or —C(O)NH—$(CH_2)_m$—$R^5$, wherein $R^5$ is aryl, (such as phenyl, B-substituted phenyl wherein B is as defined below), heteroaryl, (such as pyridyl or pyridyl N-oxide), heterocycloalkyl, or a group of the formula

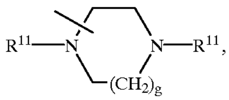,
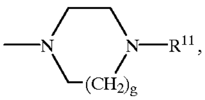,

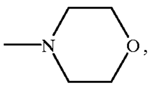,
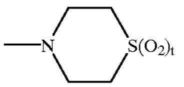 or

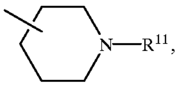, wherein g=1 or 2, and $R^{11}$ represents H, $C_1$–$C_6$ alkyl, haloalkyl or —C(O)—$R^9$ wherein $R^9$ is $C_1$–$C_6$ alkyl, $C_1$–$C_6$ alkoxy or —NH($R^{10A}$) wherein $R^{10A}$ is H or alkyl, or the group —C(O)—$R^9$ represents an acyl radical of a naturally occurring amino acid; or $R^1$ is a group of the formula:

(82.0)

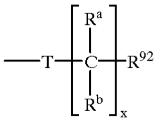

wherein:

(a) T is selected from:

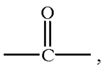,
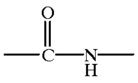,
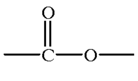,

—$SO_2$—, or a single bond;

(b) x is 0, 1, 2, 3, 4, 5 or 6;

(c) each $R^a$ and each $R^b$ is independently selected from H, aryl, aryl, alkoxy, aralkyl, amino, alkylamino, heterocyloalkyl, —$COOR^{60}$, —NH{C(O)}$_z$$R^{60}$ (wherein z is 0 or 1), or —$(CH)_w$$S(O)_t$$R^{60}$ (wherein w is 0, 1, 2 or 3, and t is 0, 1 or 2); or $R^a$ and $R^b$ taken together can represent cycloalkyl, =N—O-alkyl, =O or heterocycloalkyl; with the proviso that for the same carbon, $R^a$ is not selected from alkoxy, amino, alkylamino or —NH{C(O)}$_z$$R^{60}$ when $R^b$ is selected from alkoxy, amino, alkylamino or —NH{C(O)}$_z$$R^{60}$; and with the proviso that when T is a single bond, for the first carbon containing $R^a$ and $R^b$, $R^a$ and $R^b$ are not selected from alkoxy, alkylamino, amino or —$NHR^{60}$ (i.e., —$NH\{C(O)\}_zR^{60}$ wherein z is 0) (i.e., $R^a$ and $R^b$ on the first carbon bound to T, when T is a single bond, are not alkoxy, alkylamino, amino or —$NHR^{60}$); and (d) $R^{92}$ can represent H, alkyl, aryl, aryloxy, arylthio, aralkoxy, aralkyl, heteroaryl or heterocycloalkyl;

$R^{60}$ represents H, alkyl, aryl or aralkyl;

$R^4$ is H or $C_1$–$C_6$ alkyl;

$R^2$ is selected from: —$C(O)OR^6$, —$C(O)NR^6R^7$, $C_1$–$C_8$ alkyl, $C_2$–$C_8$ alkenyl, $C_2$–$C_8$ yl, substituted ($C_1$–$C_8$)alkyl, substituted ($C_2$–$C_8$)alkenyl, substituted ($C_2$–$C_8$)alkynyl, wherein said substituted groups have one or more substituents selected from:

1) aryl, heteroaryl, heterocycloalkyl, B-substituted aryl, B-substituted heteroaryl or B-substituted heterocycloalkyl, wherein B is selected from $C_1$–$C_4$ alkyl, phenyl, —$(CH_2)_nOR^6$, —$(CH_2)_nNR^6R^7$ and halo;

2) $C_3$–$C_6$ cycloalkyl;

3) —$OR^6$;

4) —$S(O)_tR^6$;

5) —$NR^6R^7$;

6) —$N(R^6)$—$C(O)R^7$;

7) —$N(R^6)$—$C(O)NR^7R^{12}$;

8) —O—$C(O)NR^6R^7$;

9) —O—$C(O)OR^6$;

10) —$SO_2NR^6R^7$;

11) —$N(R^6)$—$SO_2$-$R^7$;

12) —$C(O)NR^6R^7$;

13) —$C(O)OR^6$; and provided that: where $R^1$ is D, $R^2$ is not H; where $R^1$ is D and $R^2$ is $C_1$–$C_8$ alkyl, the substituents on said alkyl group are not substituents 4), 5), 9) or 13); and where $R^1$ is D, and $R^2$ is $C_1$–$C_8$ alkyl substituted by the group —$OR^6$, $R^6$ is not H, alkyl, aryl, substituted aryl, aryl-substituted alkyl or nitrophenylsubstituted alkyl;

$R^6$, $R^7$ and $R^{12}$ are independently selected from H, $C_1$–$C_4$ alkyl, ($C_3$–$C_6$)cycloalkyl, aryl, arylalkyl (i.e., aralkyl), heteroaryl, heteroarylalkyl, heterocycloalkyl, substituted ($C_1$–$C_4$)alkyl, substituted ($C_3$–$C_6$)cycloalkyl, substituted aryl, substituted arylalkyl, substituted heteroaryl, substituted heteroarylalky or substituted heterocycloalkyl, wherein said substituted groups have one or more substituents (e.g., 1–3) selected from: $C_1$–$C_4$ alkoxy, aralkyl, heteroarylalkyl, —$NO_2$, ($C_3$–$C_{10}$)alkoxyalkoxy (e.g., —O—($C_1$–$C_4$)alkyl-O-($C_1$–$C_4$)alkyl), ($C_3$–$C_6$)cycloalkyl (e.g., cyclopropyl or cyclohexyl), aryl, —CN, nitro-phenyl, methylenedioxyphenyl, heteroaryl, heterocycloalkyl, halo, —OH, —COOH, —$C(O)R^{14}$, —$C(O)OR^{14}$, —$C(O)NR^6R^7$ (e.g., —$C(O)NR^{10}R^{15}$), —$N(R^6)C(O)R^{14}$, —$S(O)_tR^{14}$ (e.g., —S—($C_1$–$C_4$) and —$SO_2R^{14}$) or —$NR^{10}R^{15}$; provided that $R^6$, $R^7$ and $R^{12}$ are not —$CH_2OH$ or —$CH_2NR^{10}R^{15}$ when said $R^6$, $R^7$ or $R^{12}$ is directly bonded to a heteroatom, and further provided that $R^6$ is not H for groups 4) and 9), and $R^7$ is not H for group 6);

optionally, when $R^6$ and $R^7$ are bound to the same nitrogen, $R^6$ and $R^7$ together with the nitrogen to which they are bound, form a 5 to 7 membered heterocycloalkyl ring which optionally contains O, $NR^6$ (e.g., $NR^8$), or $S(O)_t$ (e.g., S) wherein t is 0, 1 or optionally, when $R^7$ and $R^{12}$ are bound to the same nitrogen, $R^7$ and $R^{12}$ together with the nitrogen to which they are bound, form a 5 to 7 membered heterocycloalkyl ring which optionally contains O, $NR^6$ (e.g., $NR^8$), or $S(O)_t$ (e.g., S) wherein t is 0, 1 or 2;

$R^8$, $R^{10}$ and $R^{15}$ are independently H, $C_1$–$C_4$ alkyl or arylalkyl;

$R^{14}$ is $C_1$–$C_4$ alkyl, aryl or arylalkyl;

m=0, 1, 2 or 3;

n=0, 1, 2, 3 or 4;

s=1, 2 or 3; and t=0, 1 or 2;

or pharmaceutically acceptable salts thereof.U.S.

WO 97/23478 published Jul. 3, 1997 discloses the compounds:

(1.0)

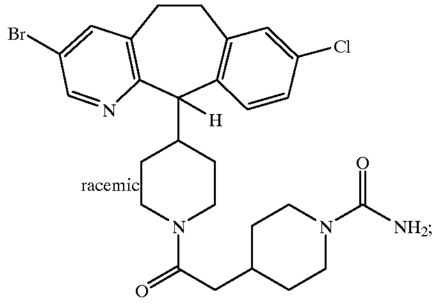

(2.0)

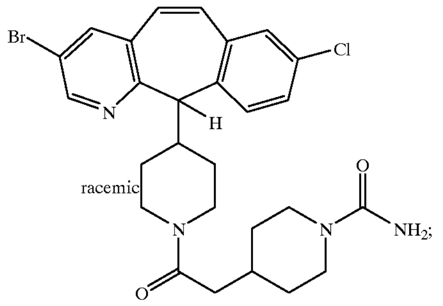

(3.0)

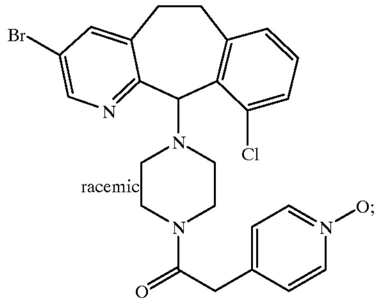

(5.0)

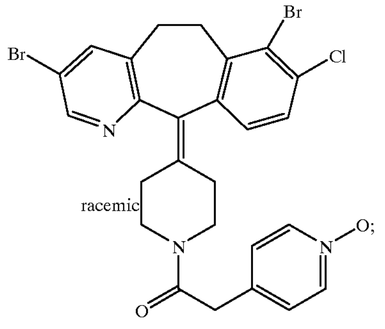

-continued
(6.0)
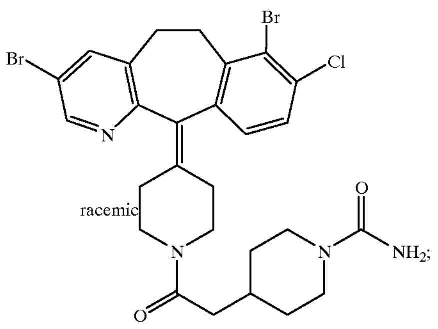
(7.0)
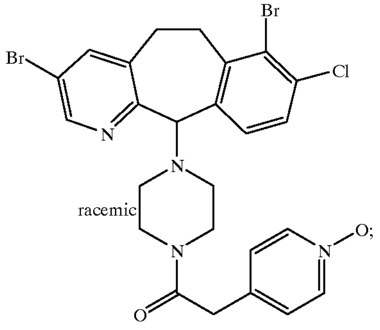
(7.0A)
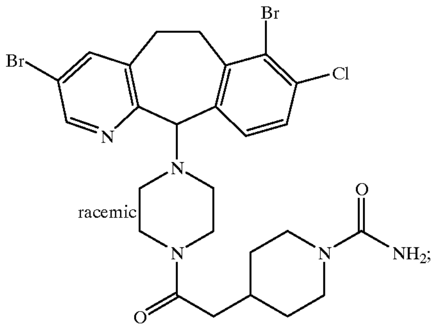
(8.0)
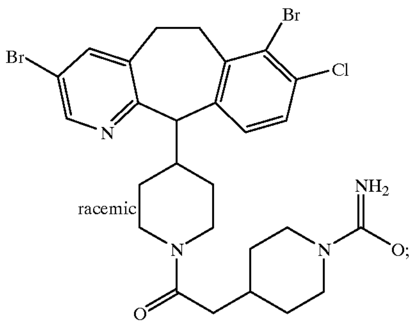
-continued
(8.0A)
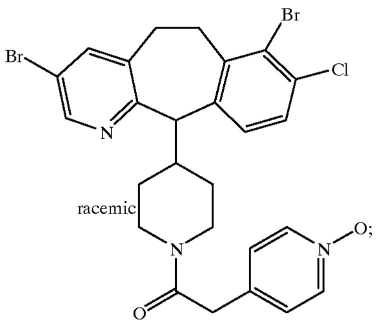
(9.0)
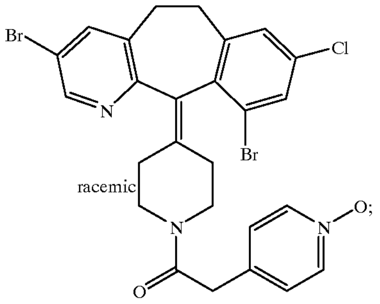
(10.0)
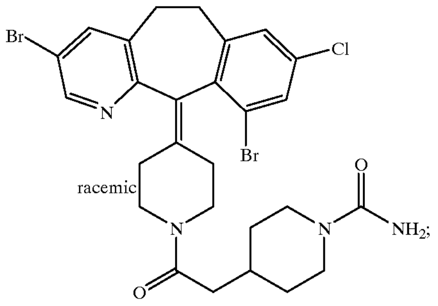
(11.0)
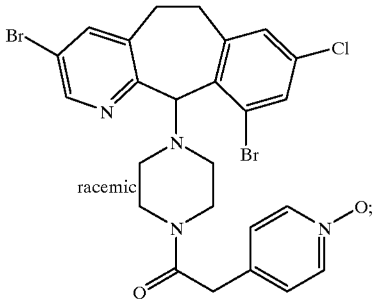
(12.0)
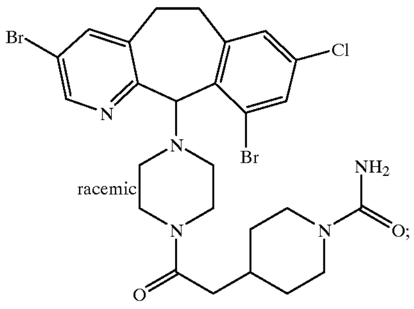

-continued
(13.0)
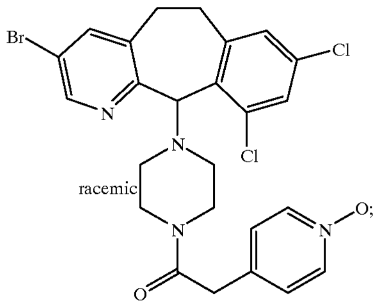
racemic
(14.0)
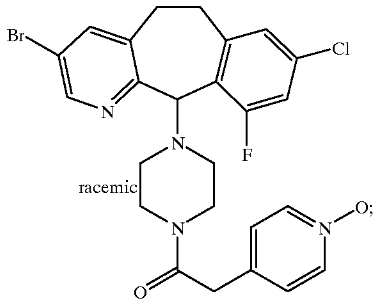
racemic
(15.0)
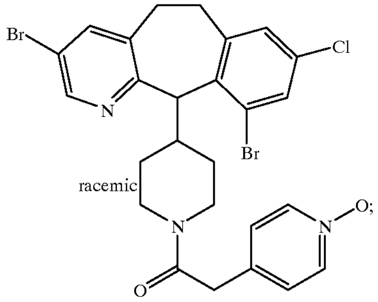
racemic
(16.0)
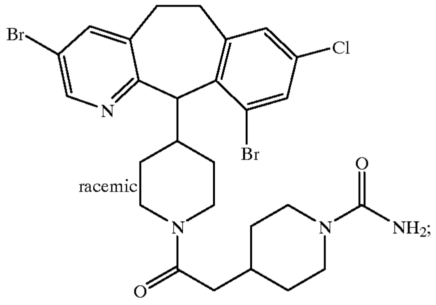
racemic
(17.0)
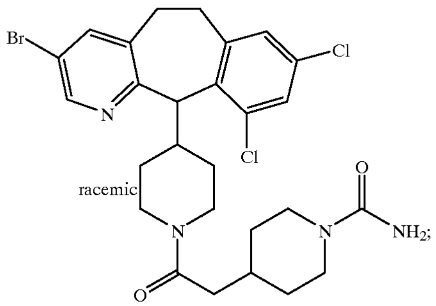
racemic
-continued
(18.0)
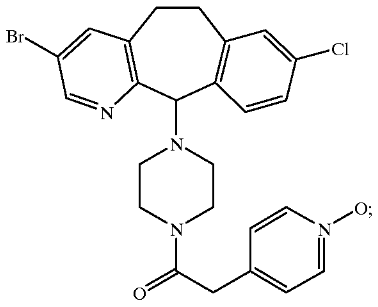
(+)-enantiomer
(19.0)
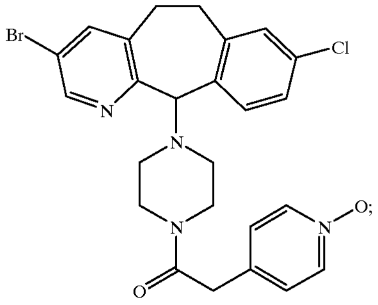
(-)-enantiomer
(20.0)
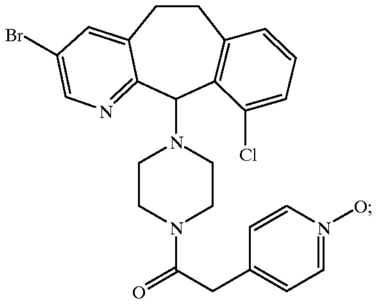
(+)-enantiomer
(21.0)
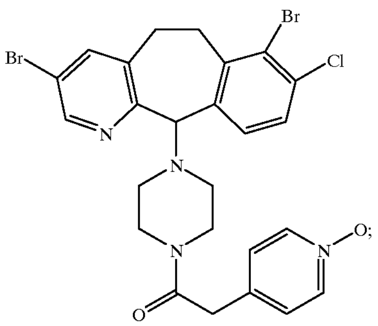
(+)-enantiomer -continued
(22.0)
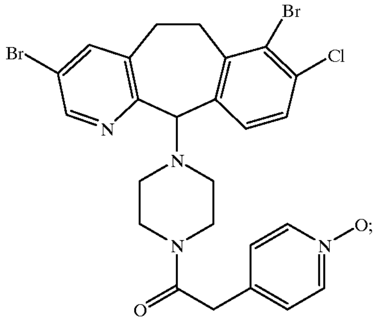
(-)-enantiomer
(23.0)
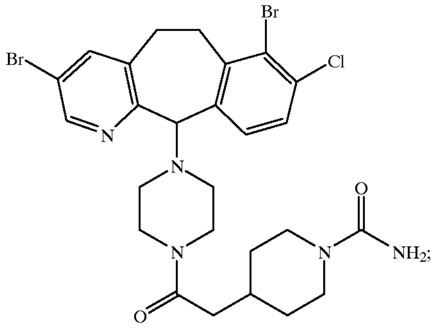
(-)-enantiomer
(24.0)
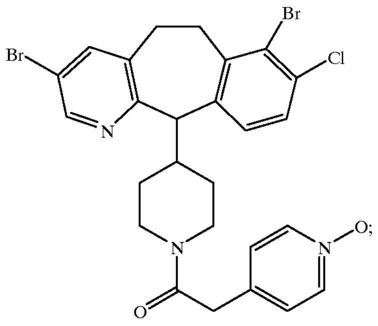
(+)-enantiomer
(25.0)
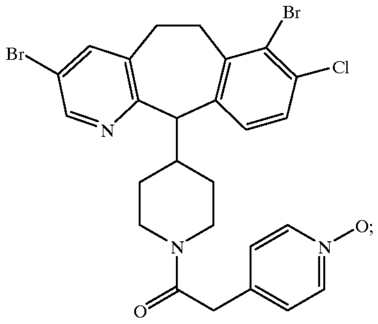
(-)-enantiomer
-continued
(26.0)
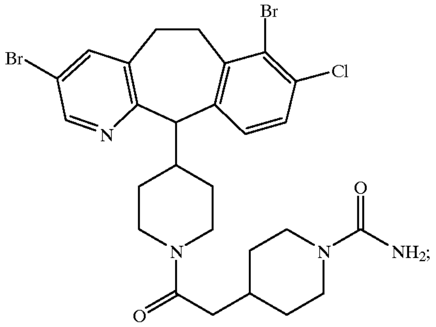
(+)-enantiomer
(27.0)
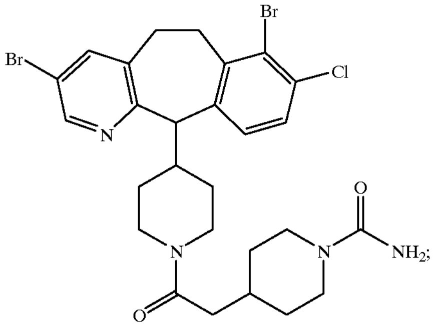
(-)-enantiomer
(28.0)
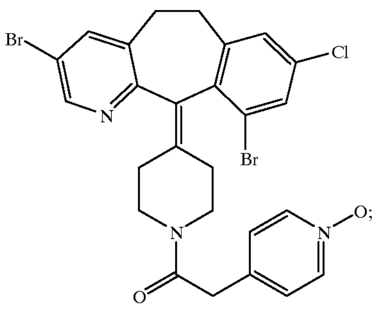
(-)-enantiomer
(29.0)
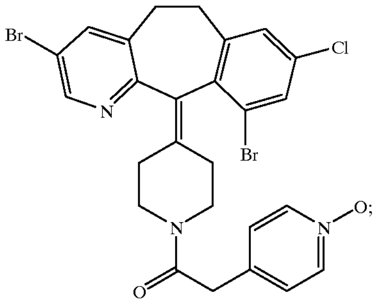
(+)-enantiomer -continued
(30.0)
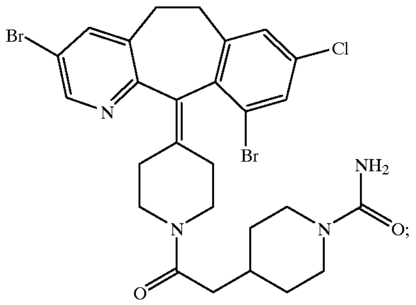
(-)-enantiomer
(31.0)
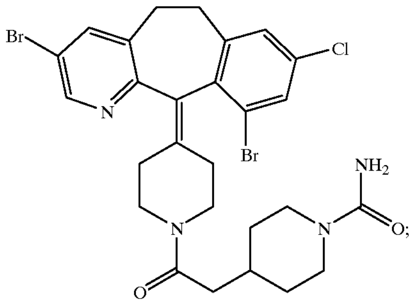
(+)-enantiomer
(32.0)
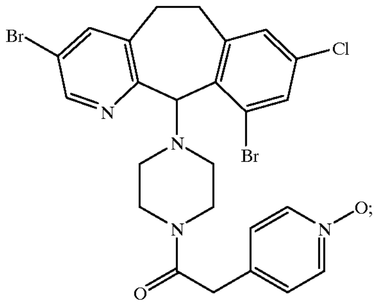
(+)-enantiomer
(33.0)
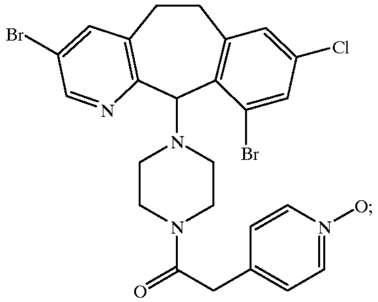
(-)-enantiomer
-continued
(34.0)
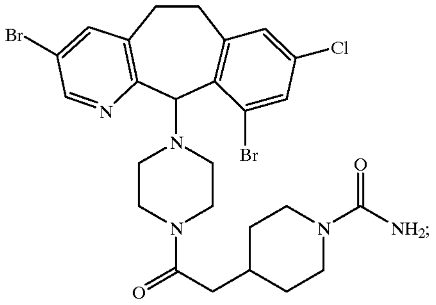
(+)-enantiomer
(35.0)
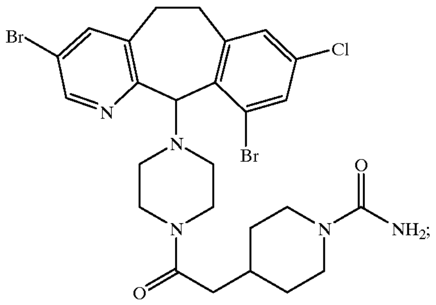
(-)-enantiomer
(36.0)
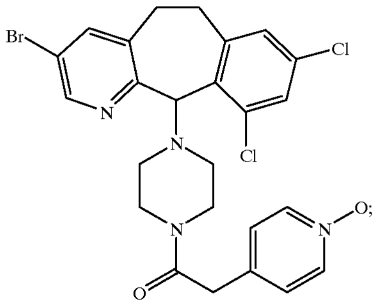
(+)-enantiomer
(37.0)
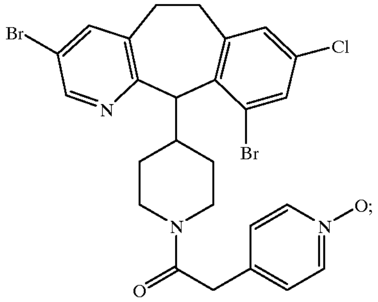
(+)-enantiomer -continued
(38.0)
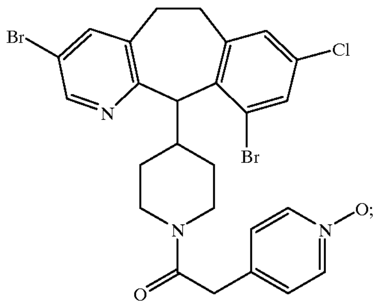
(-)-enantiomer
(39.0)
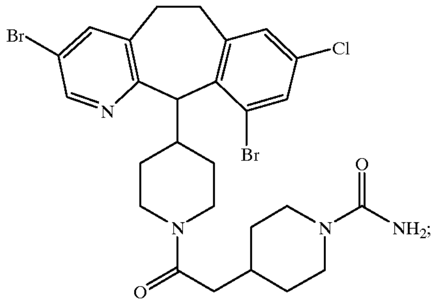
(+)-enantiomer
(40.0)
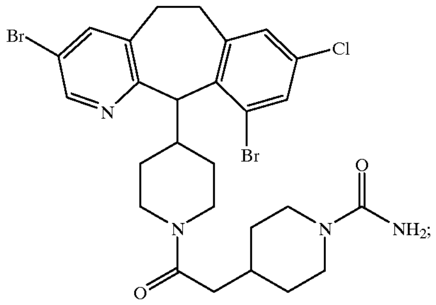
(-)-enantiomer
(41.0)
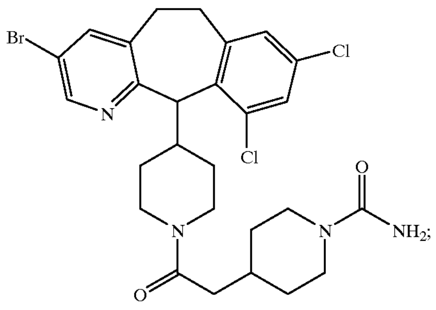
(+)-enantiomer
-continued
(42.0)
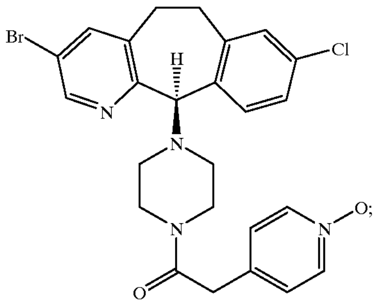
(43.0)
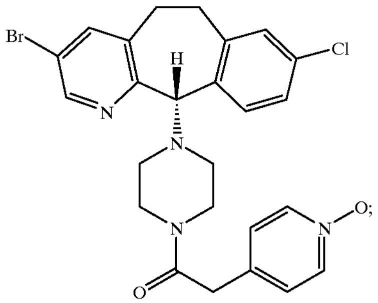
(44.0)
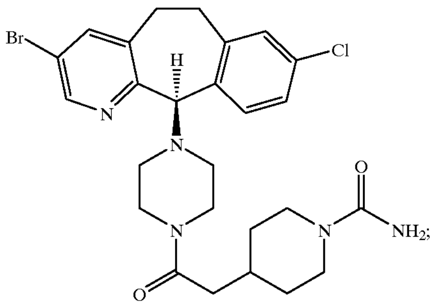
(45.0)
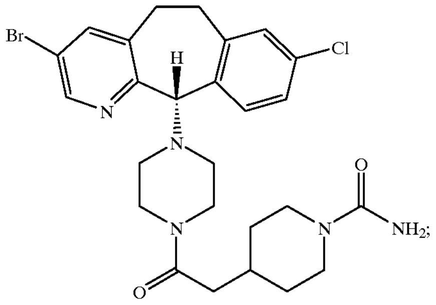
(46.0)
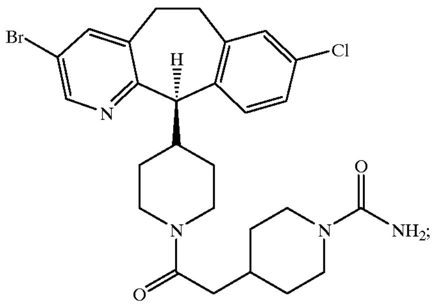

-continued
(47.0)
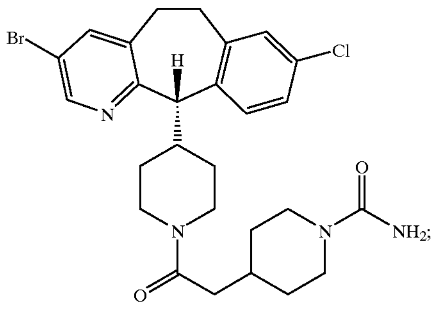
(48.0)
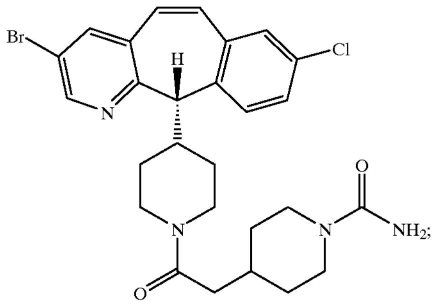
(49.0)
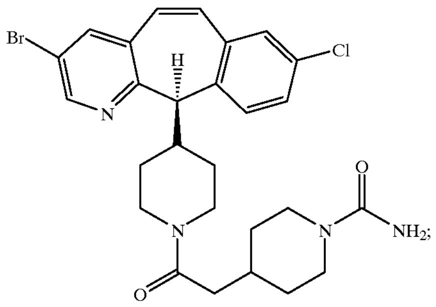
(50.0)
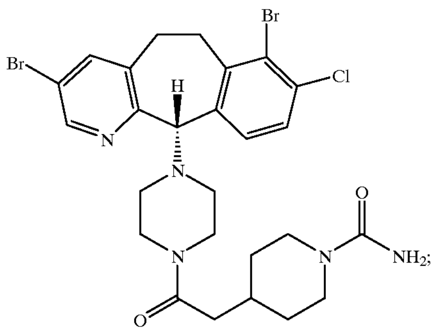
-continued
(51.0)
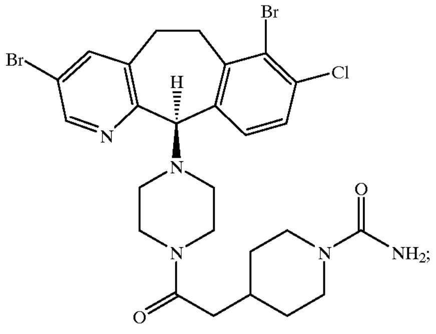
(52.0)
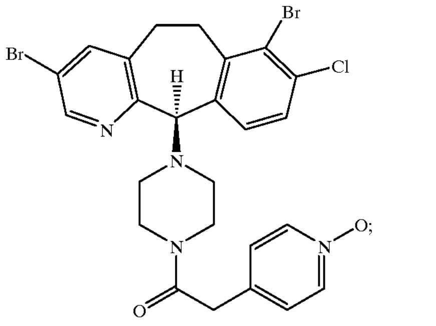
(53.0)
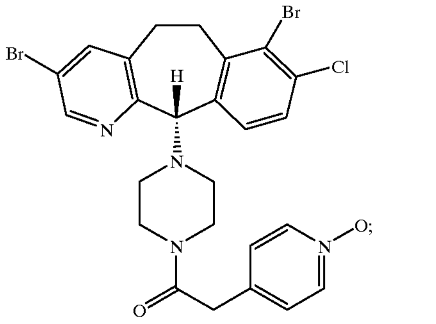
(54.0)
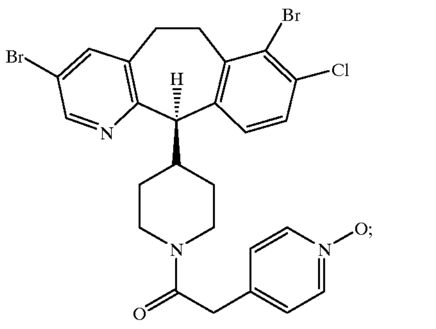

-continued
(55.0)
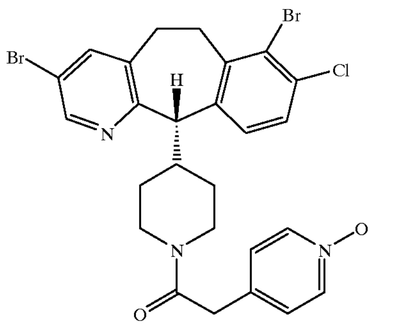
(56.0)
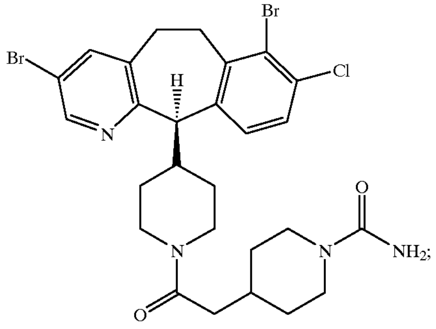
(57.0)
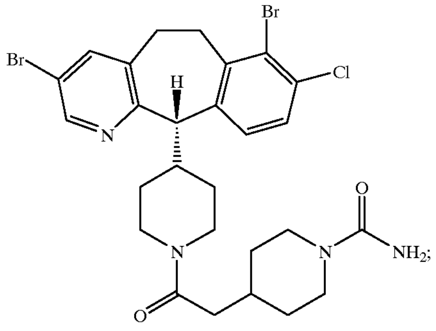
(58.0)
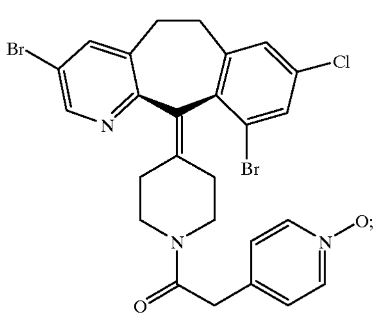
-continued
(59.0)
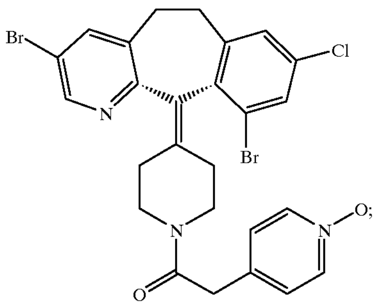
(60.0)
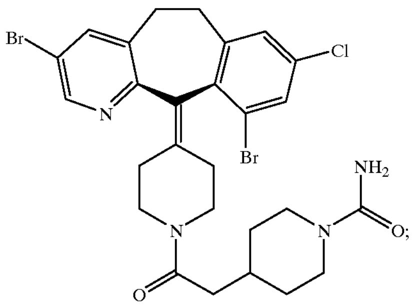
(61.0)
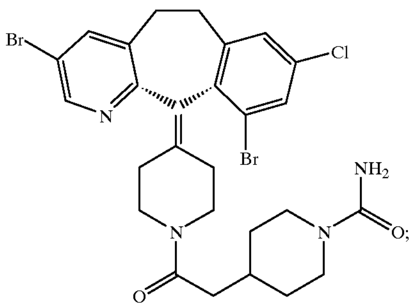
(62.0)
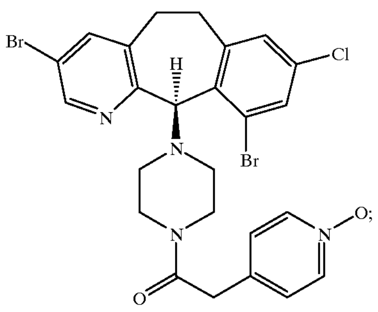
(63.0)
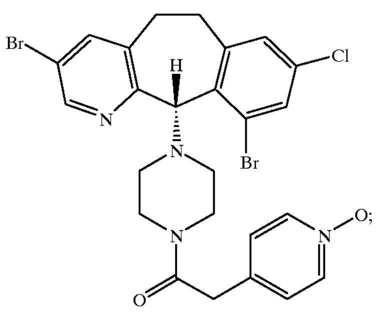

-continued
(64.0)
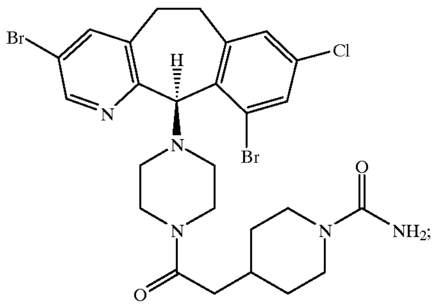
(65.0)
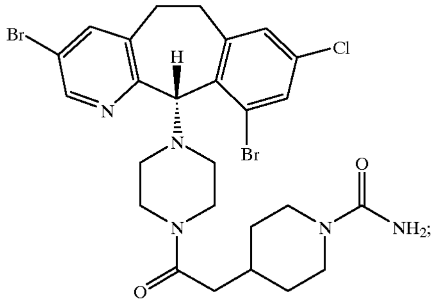
(66.0)
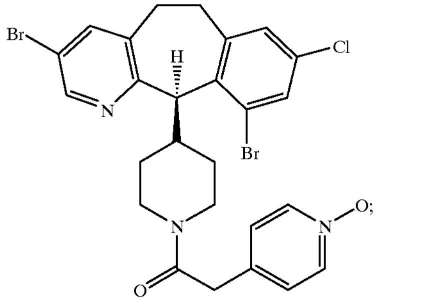
(67.0)
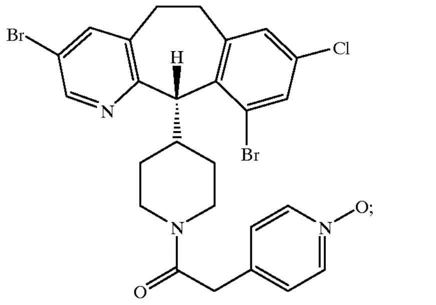
(68.0)
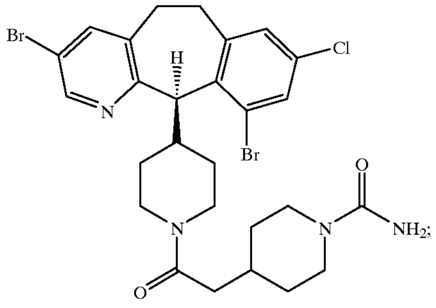
-continued
(69.0)
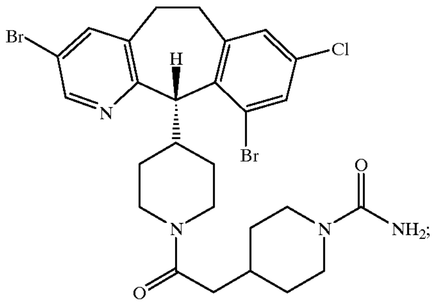
(70.0)
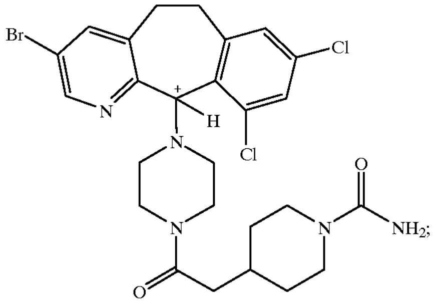
(71.0)
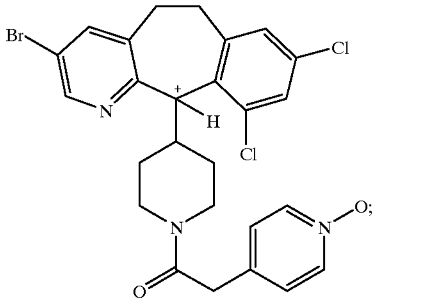
(72.0)
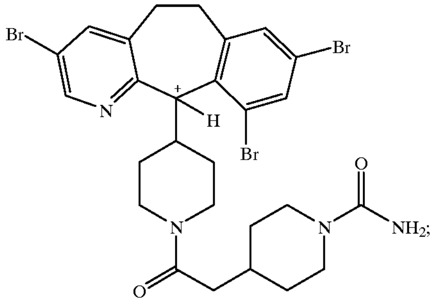
(73.0)
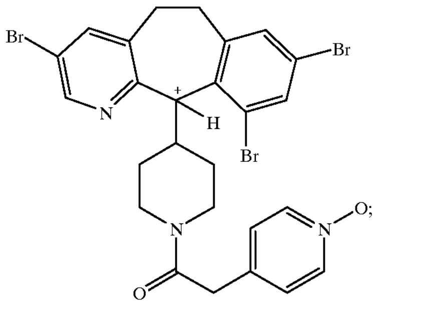

-continued (74.0)

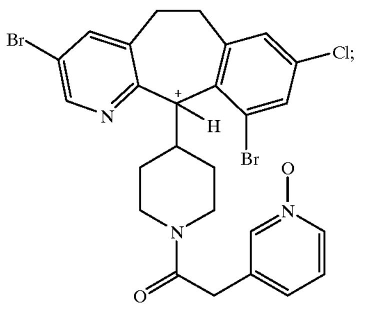

(75.0)

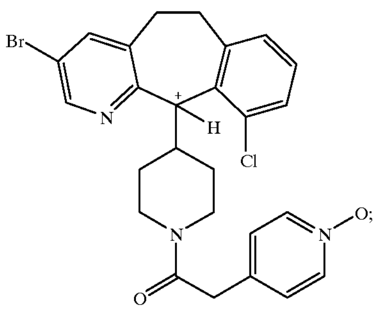

(76.0)

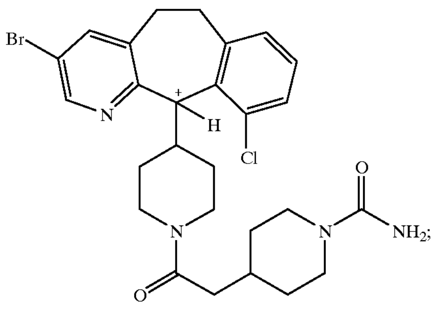

(77.0)

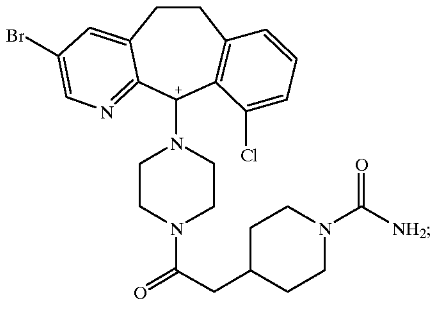

(78.0)

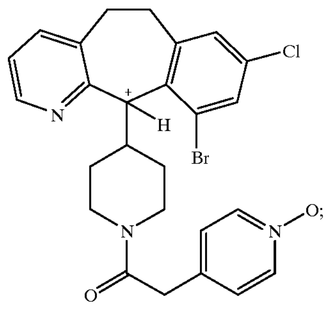

-continued (79.0)

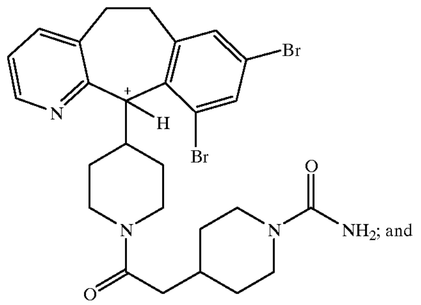

and

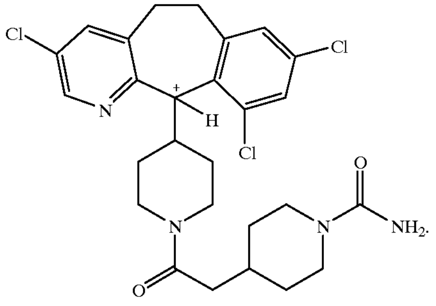

or pharmaceutically acceptable salts thereof.

A preferred compound for use as an FPT inhibitor in the method of the present invention has the formula:

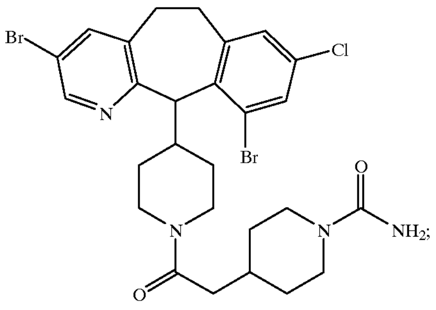

i.e., the compound 4-[2-[4-[(8-chloro-3,10-dibromo-6,11-dihydro-5H-benzo[5,6]cyclohepta[1,2-b]pyridin-11-yl)-1-piperidinyl]-2-oxoethyl]-1-piperidinecarboxamide, preferably the (+)-isomer thereof, which has the structure

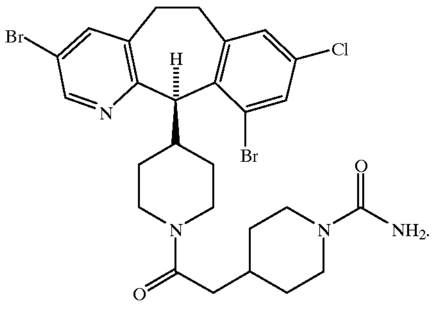

See also U.S. Pat. No. 5,719,148, which issued on Feb. 17, 1998, and is expressly incorporated herein by reference.

WO 96/31501 published Oct. 10, 1996 discloses compounds of formula (1.0):

(1.0)

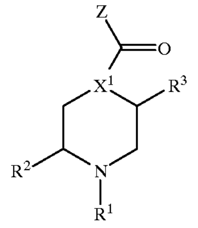

and (1.1)

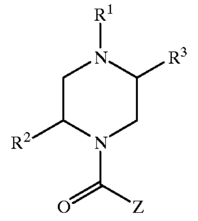

or a pharmaceutically acceptable salt or solvate thereof, wherein:

(1) Z is a group which is:

(-i-)

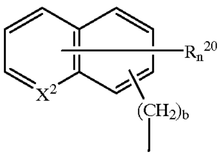

(-ii-)

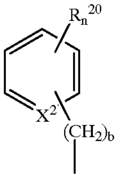

(-iii-)

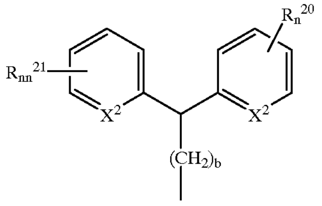

wherein $X^1$ is CH or N;

$X^2$ can be the same or different and can be CH, N or N—O;

b is 0, 1, 2, 3 or 4;

n and nn independently represent 0, 1, 2, 3, 4 or when $X^2$ is CH, n and nn can be 5;

$R^{20}$ and $R^{21}$ can be the same group or different groups when n or nn is 2, 3, 4 or 5, and can be:

(a) hydrogen, $C_1$ to $C_6$ alkyl, aryl, aralkyl, heteroaryl, heteroarylalkyl or heterocycloalkyl, wherein each of said $C_1$ to $C_6$ alkyl, aryl, aralkyl, heteroaryl, heteroarylalkyl or heterocycloalkyl can be optionally substituted with one or more of the following:

$C_1$ to $C_4$ alkyl, $C_3$–$C_6$ cycloalkyl, $(CH_2)_tOR^8$ wherein t is 0, 1, 2, 3 or 4, $(CH_2)_tNR^8R^9$ wherein t is 0, 1, 2, 3 or 4, or halogen;

(b) $C_3$ to $C_6$ cycloalkyl; (c) $—OR^8$; (d) $—SR^8$; (e) $—S(O)R^8$; (f) $—SO_2R^8$; (g) $—NR^8R^9$; (h) —CN; (i) $—NO_2$, (j) $—CF_3$ or (k) halogen (l) $—CONR^8R^9$ or (m) $—COR^{13}$ wherein $R^8$ and $R^9$ can independently represent:

H, $C_1$ to $C_4$ alkyl, $C_3$ to $C_6$ cycloalkyl, heteroaryl, heteroarylalkyl, heterocycloalkyl, aryl or aralkyl and each of said alkyl, cycloalkyl, heteroaryl, heteroarylalkyl, heterocycloalkyl, aryl or aralkyl can be optionally substituted with one to three of the following:

$C_1$ to $C_4$ alkoxy, aryl, aralkyl, heteroaryl, heteroarylalkyl, heterocycloalkyl, halogen, —OH, $—C(O)R^{13}$, $—NR^{14}R^{15}$; $—CONR^8R^9$ or $—N(R^8)COR^{13}$; —CN; $C_3$–$C_6$ cycloalkyl, $S(O)_qR^{13}$; or $C_3$–$C_{10}$ alkoxyalkoxy wherein q is 0, 1 or 2;

wherein $R^{13}$ is selected from $C_1$ to $C_4$ alkyl, aryl or aralkyl, and $R^{14}$ and $R^{15}$ are independently selected from H, $C_1$ to $C_4$ alkyl or aralkyl;

and optionally, when $R^8$ and $R^9$ are bound to the same nitrogen, $R^8$ and $R^9$, together with the nitrogen to which they are bound, can form a 5 to 7 membered heterocycloalkyl ring which may optionally contain O, $NR^8$, S(O)q wherein q is 0, 1 or 2;

with the proviso that $R^8$ is not H in substituents (e) and (f), and with the proviso that $R^8$ or $R^9$ is not $—CH_2OH$ or $—CH_2NR^{14}R^{15}$ when $R^8$ or $R^9$ is directly attached to a heteroatom;

(2) $R^1$ is a group which is:

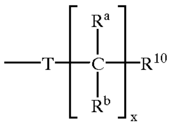

wherein

T can be

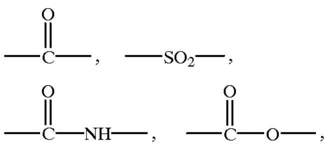

or a single bond, x=0, 1, 2, 3, 4, 5 or 6, $R^a$ and $R^b$ independently represent H, aryl, alkyl, amino, alkylamino, alkoxy, aralkyl, heterocyloalkyl, $—COOR^{16}$, $—NH(CO)_zR^{16}$ wherein z=0 or 1, $—(CH_2)_wS(O)_mR^{16}$ wherein w=0, 1, 2 or 3 such that when x is greater than 1, then $R^a$ and $R^b$ can be independent of the substituents on an adjacent carbon atom provided $R^a$ and $R^b$ are not both selected from alkoxy, amino, alkylamino, and $—NH(CO)_z R^{16}$;

m=0, 1 or 2 wherein $R^{16}$ represent H, alkyl, aryl or aralkyl, or $R^a$ and $R^b$ taken together can represent cycloalkyl, =O, =N—O-alkyl or heterocycloalkyl, and $R^{10}$ can represent H, alkyl, aryl, aryloxy, arylthio, aralkoxy, aralkthio, aralkyl, heteroaryl, heterocycloalkyl, or $R^1$ can also be

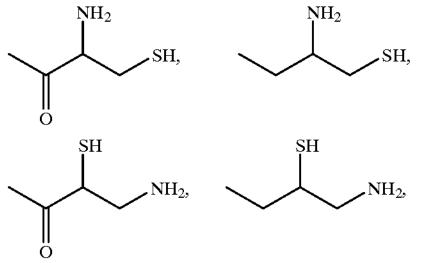

or disulfide dimers thereof;

(3) $R^2$ and $R^3$ are independently selected from the group which is:

hydrogen, $C_1$ to $C_8$ alkyl, $C_2$ to $C_8$ alkenyl, $C_2$ to $C_8$ alkynyl,

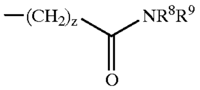

or

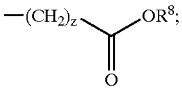

wherein z is 0, 1, 2, 3 or 4; and said alkyl, alkenyl, or alkynyl group is optionally substituted with one or more groups which can independently represent:

(a) aryl, aralkyl, heteroaryl, heteroarylalkyl or heterocycloalkyl, wherein each of said aryl, aralkyl, heteroaryl, heteroarylalkyl or heterocycloalkyl group can be optionally substituted with one or more of the following:

$C_1$ to $C_4$ alkyl, $(CH_2)_tOR^8$ wherein t is 0, 1, 2, 3 or 4, $(CH_2)_tNR^8R^9$ wherein t is 0, 1, 2, 3 or 4, or halogen;

(b) $C_3$ to $C_6$ (c) $—OR^8$; (d) $—SR^8$; (e) $—S(O)R^8$; cycloalkyl;

(f) $—SO_2R^8$; (g) $—NR^8R^9$;

(h)

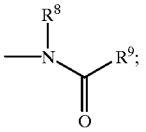

(i)

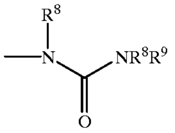

(j)

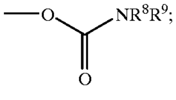

(k)

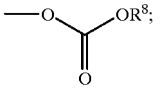

-continued (l)

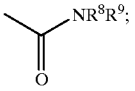

(m)

$—SO_2—NR^8R^9$ (n)

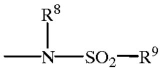

(o)

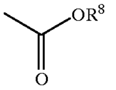

or (p)

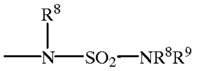

wherein $R^8$ and $R^9$ are defined hereinbefore; and and optionally, when $R^8$ and $R^9$ are bound to the same nitrogen, $R^8$ and $R^9$, together with the nitrogen to which they are bound, can form a 5 to 7 membered heterocycloalkyl ring which may optionally contain O, $NR^8$, S(O)q wherein q is 0, 1 or 2;

with the proviso that for compound (1.0) when $X^1$ is CH, then $R^3$ is hydrogen, and with the further proviso that $R^2$ and $R^3$ cannot both be hydrogen;

and with the provision that when $X^1$ is N, then $R^1$ is not

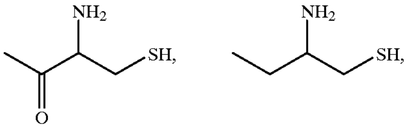

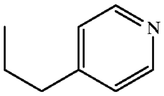

or

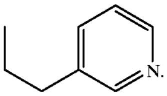

WO 95/10514 published Apr. 20, 1995 discloses compounds of the formula:

(1.0)

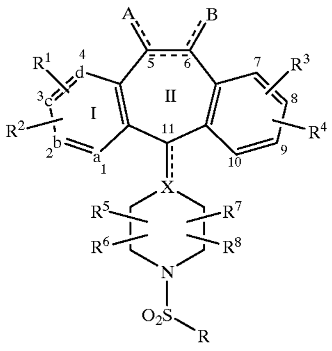

or a pharmaceutically acceptable salt or solvate thereof, wherein:

one of a, b, c and d represents N or $NR^9$ wherein $R^9$ is $O^-$, $—CH_3$ or $—(CH_2)_nCO_2H$ wherein n is 1 to 3, and the remaining a, b, c and d groups represent $CR^1$ or $CR^2$;

$R^1$ and $R^2$ are the same or different and each independently represents H, halo, benzotriazol-lyloxy, —$CF_3$, —$OR^{10}$, —$COR^{10}$, —$SR^{10}$, —$S(O)_tR^{11}$ (wherein t is 0, 1 or 2), —$N(R^{10})_2$, —$NO_2$, —$OC(O)R^{10}$, —$CO_2R^{11}$, —$OCO_2R^{11}$, —CN, —$NR^{10}COOR^{11}$, alkynyl, alkenyl or alkyl, which alkyl or alkenyl group may be substituted with halo, —$OR^{10}$ or —$CO_2R^{10}$;

$R^3$ and $R^4$ are the same or different and each independently represents, any of the substituents of $R^1$ and $R^2$, or $R^3$ and $R^4$ together may represent a saturated or unsaturated $C_5$–$C_7$ ring fused to the benzene ring (Ring III);

$R^5$, $R^6$, $R^7$ and $R^8$ each independently represent H, —$CF_3$, —$COR^{10}$, alkyl or aryl, which alkyl or aryl may be substituted with —$OR^{10}$, —$SR^{10}$, $S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or one of $R^5$, $R^6$, $R^7$ and $R^8$ may be taken in combination with R as defined below to represent —$(CH_2)_r$— wherein r is 1 to 4 which may be substituted with lower alkyl, lower alkoxy, —$CF_3$ or aryl;

$R^{10}$ represents H, alkyl or aryl;

$R^{11}$ represents alkyl or aryl;

X represents N or C, which C may contain an optional double bond to carbon atom 11;

the dotted lines represent optional double bonds;

the dotted line between carbon atoms 5 and 6 represents an optional double bond, such that when a double bond is present, A and B independently represent —$R^{10}$, —$OR^{11}$, $OCO_2R^{11}$ or —$OC(O)R^{10}$, and when no double bond is present between carbon atoms 5 and 6, A and B each independently represent $H_2$, —$(OR^{11})_2$, H and halo, dihalo, alkyl and H, $(alkyl)_2$, —H and —$OC(O)R^{10}$, H and —$OR^{10}$, =O, aryl and H, =$NOR^{10}$ or —O—$(CH_2)_p$—O— wherein p is 2, 3 or 4;

R is selected from the group consisting of:

(1) $C_1$ to $C_4$ alkyl (e.g., methyl, ethyl, and butyl);

(2) phenyl substituted with 1 to 3 substituents selected from $R^1$, $R^2$ or $C(O)OR^{20}$, wherein $R^{20}$ is selected from the group consisting of: $C_1$ to $C_6$ alkyl (e.g., methyl) and H;

(3) bridged polycyclic hydrocarbons having from 5 to 10 carbon atoms (e.g., adamantyl, norbornyl, norcamphoryl—i.e., the radical formed from 2-norbornaneone, and 2-norboranol);

(4) substituted bridged polycyclic hydrocarbons, wherein the bridged unsubstituted polycyclic hydrocarbon contains 5 to 10 carbon atoms, wherein the substituents are selected from the group consisting of $C_1$ to $C_6$ alkyl (e.g., methyl), said substituted bridged polycyclic hydrocarbon having from 1 to 8 substituents with two being preferred, and each substituent being the same or different (with the same being preferred);

(5) —$CH_2R^{21}$ wherein $R^{21}$ is aryl (e.g., phenyl or substituted phenyl—i.e., phenyl substituted with 1 to 3, preferably 1, group selected from halo, alkyl, haloalkyl or alkoxy), heteroaryl (e.g., thiophene, thiazole, pyridyl, such as 3- or 4-pyridyl, or pyridyl N-oxide, such as 3- or 4-pyridyl N-oxide), 2-,3- or 4-piperidyl or N-substituted piperidyl, wherein the substituent on said N-substituted piperidyl is $C_1$ to $C_4$ alkyl, alkylcarbonyl or —$C(O)NH(R^{10})$ wherein $R^{10}$ is H or alkyl, a bridged polycyclic hydrocarbon, or a substituted bridged polycyclic hydrocarbon as described above, e.g.,

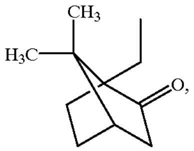

and

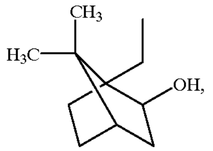

(6) heteroaryl (e.g., thiophene, thiazole, pyridyl, such as 3- or 4-pyridyl, or pyridyl N-oxide, such as 3- or 4-pyridyl N-oxide);

(7) substituted heteroaryl wherein said substituents are selected from the group consisting of: $C_1$ to $C_6$ alkyl (e.g., methyl) and —$NHC(O)R^{22}$ wherein $R^{22}$ is a $C_1$ to $C_6$ alkyl (e.g., methyl), e.g.,

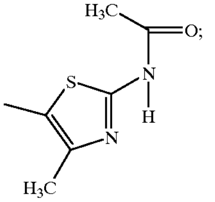

(8) $C_2$ to $C_6$ alkenyl (e.g., —CH=$CH_2$);

(9) benzyl; and

(10) —$N(R^{23})_2$ wherein each $R^{23}$ is independently selected from the group consisting of: $C_1$ to $C_6$ alkyl, H, aryl (e.g., phenyl and substituted phenyl), 2-,3- or 4-piperidyl or N-substituted piperidyl, wherein the substituent on said N-substituted piperidyl is $C_1$ to $C_4$ alkyl, alkylcarbonyl or —$C(O)NH(R^{10})$ wherein $R^{10}$ is H or alkyl (preferably, 3- or 4-N-substituted piperidyl wherein the substituent on the nitrogen is $C_1$ to $C_4$ alkyl, most preferably methyl), heteroaryl (e.g., pyridyl, such as 3- or 4-pyridyl, or 3- or 4-pyridyl N-oxide), preferably, each $R^{23}$ is selected such that there is no more than one H bound to the nitrogen (i.e., preferably there is 0 or 1 H attached to the nitrogen), most preferably one of the two $R^{23}$ substituents is H, more preferably one of the two $R^{23}$ substituents is H and the other $R^{23}$ substituent is other than H.

International Patent Application No. PCT/US97/17314 filed Oct. 7, 1997 discloses compounds of the formula:

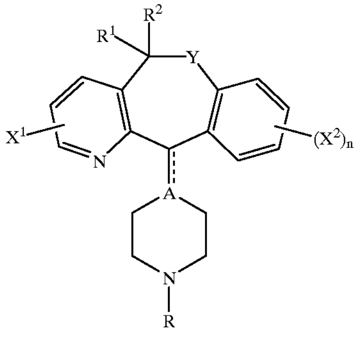

I wherein:

$X^1$ is hydrogen, halogen, $CF_3$, nitro, $NH_2$ or lower alkyl;

each $X^2$ is independently selected from the group consisting of hydrogen, halogen, lower alkoxy and lower alkyl;

n is 1 or 2;

Y is selected from the group consisting of $S(O)_p$, O, and $NR^5$, wherein p is 0, 1 or 2, and $R^5$ is hydrogen, alkyl, aryl, cycloalkyl, lower alkoxycarbonyl, aminocarbonyl or acyl;

$R^1$ and $R^2$ are the same or different and are selected from the group consisting of hydrogen and lower alkyl groups, or taken together can form an oxygen atom when Y is $NR^5$;

the dotted line indicates a single or double bond—i.e., the dotted line indicates that the bond from A to C-11 of the tricyclic ring can be a single bond or a double bond;

A is a C atom (when the dotted line indicates a double bond, i.e., when there is a double bond from A to the C-11 of the tricyclic ring) or CH or an N atom (when the dotted line indicates a single bond, i.e., when there is a single bond from A to the C-11 of the tricyclic ring);

R is —CZ—$Y^1$—$Y^2$—$R^3$, wherein:

Z is O, =CH—CN, or =N—CN;

one of $Y^1$ and $Y^2$ is a bond, —CO—, O, S, or —$NR^4$—, and the other is $(CH_2)_m$, where m is 0 or an integer of 1 to 4, and $R^4$ is H or alkyl, with the proviso that when Z is O and m is 0 then $Y^1$ or $Y^2$ is selected from —CO—, O, S, or —$NR^4$;

$R^3$ is aryl, heteroaryl or heterocycloalkyl, with the proviso that $R^3$ can also be lower alkyl when Z is =N—CN;

and their pharmaceutically acceptable acid addition salts.

International Patent Application No. PCT/US97/15899 filed Sep. 11, 1997 discloses compounds of the formula:

(1.0)

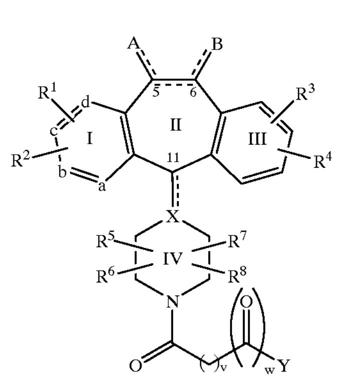

wherein:

X is N, CH, or C when the double bond is present at the C-11 position;

one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COR^{11}$,

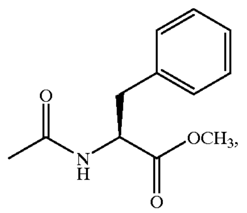

—$SR^{11}C(O)OR^{11}$ (e.g., —$SCH_2CO_2CH_3$), —$SR^{11}N(R^{12})_2$ wherein each $R^{12}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$, or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, $(alkyl)_2$, —H and —$OC(O)R^{10}$, H and —$OR^{10}$, =O, aryl and H, =$NOR^{10}$ or —O—$(CH_2)_p$—O— wherein p is 2, 3 or 4;

v is 0 to 5;

w is 0 or 1;

Y is

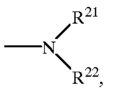

—O—$C_1$–$C_6$-alkyl or OM+, wherein M+ is an alkali metal cation;

$R^{21}$ and $R^{22}$ are each independently H, $C_1$–$C_6$ alkyl, —$CH_2CONH_2$, phenyl, benzyl, —$SO_2$—($C_1$–$C_6$-alkyl), —NH-phenyl, acyl, $C_3$–$C_6$ cycloalkyl, pyridyl, chlorophenyl,

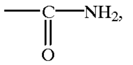

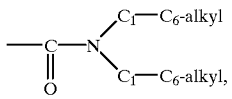

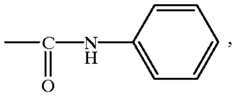

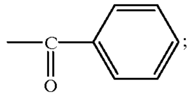

or $R^{21}$ and $R^{22}$ taken together with the nitrogen to which they are attached form

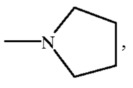

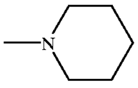

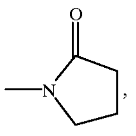

-continued

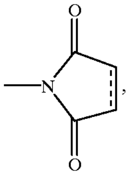, 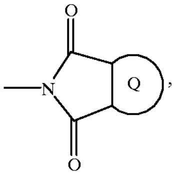, 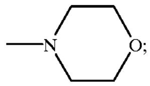;

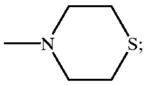; 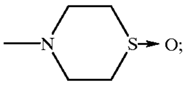; or

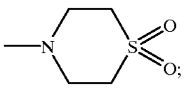;

a dashed line means an optional chemical bond;

wherein Q is benzene, or a heterocyclic ring such as pyridine, pyrazine, or thiophene;

or a pharmaceutically acceptable salt thereof.

International Patent Application No. PCT/US97/15900 filed Sep. 11, 1997 discloses compounds of formula:

(1.0)

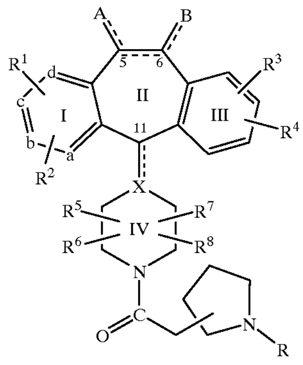

or a pharmaceutically acceptable salt or solvate thereof, wherein: one of a, b, c and d represents N or $NR^9$ wherein $R^9$ is $O^-$, $—CH_3$ or $—(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, $—CF_3$, $—OR^{10}$ (e.g., $—OCH_3$), $—COR^{10}$, $—SR^{10}$ (e.g., $—SCH_3$ and $—SCH_2C_6H_5$), $—S(O)_tR^{11}$ (wherein t is 0, 1 or 2, e.g., $—SOCH_3$ and $—SO_2CH_3$), —SCN, $—N(R^{10})_2$, $—NR^{10}R^{11}$, $—NO_2$, $—OC(O)R^{10}$, $—CO_2R^{10}$, $—OCO_2R^{11}$, —CN, $—NHC(O)R^{10}$, $—NHSO_2R^{10}$, $—CONHR^{10}$, $—CONHCH_2CH_2OH$, $—NR^{10}COOR^{11}$,

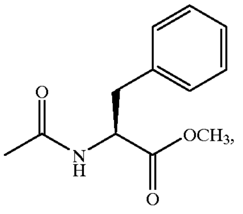

$—SR^{11}C(O)OR^{11}$ (e.g., $—SCH_2CO_2CH_3$), $—SR^{11}N(R^{75})_2$ wherein each $R^{75}$ is independently selected from H and $—C(O)OR^{11}$ (e.g., $—S(CH_2)_2NHC(O)O$-t-butyl and $—S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, $—OR^{10}$ or $—CO_2R^{10}$;

$R^3$ and $R^4$ are independently selected from the group consisting of H, $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ are independently selected from the group consisting of H, $—CF_3$, $—COR^{10}$, alkyl and aryl, said alkyl or aryl optionally being substituted with $—OR^{10}$, $—SR^{10}$, $—S(O)_tR^{11}$, $—NR^{10}COOR^{11}$, $—N(R^{10})_2$, $—NO_2$, $—COR^{10}$, $—OCOR^{10}$, $—OCO_2R^{11}$, $—CO_2R^{10}$ or $OPO_3R^{10}$, or $R^5$ is combined with $R^6$ to represent =O or =S, or $R^7$ is combined with $R^8$ to represent =O or =S;

$R^{10}$ represents H, alkyl, aryl, or aralkyl (e.g., benzyl);

$R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent $—R^{10}$, halo, $—OR^{11}$, $—OCO_2R^{11}$ or $—OC(O)R^{10}$, and when no double bond is present between carbon atoms 5 and 6, A and B each independently represent (H, H), ($—OR^{11}$, $—OR^{11}$), (H, halo), (halo, halo), (alkyl, H), (alkyl, alkyl), (H, $—OC(O)R^{10}$), (H, $—OR^{10}$), =O, (aryl, H) or $=NOR^{10}$, or A and B together are $—O—(CH_2)_p—O—$ wherein p is 2, 3 or 4; and R represents:

(1) $—C(O)N(R^{10})_2$;

(2) $—CH_2C(O)N(R^{10})_2$;

(3) $—SO_2$-alkyl, $—SO_2$-aryl, $—SO_2$-aralkyl, $—SO_2$-heteroaryl or $—SO_2$-heterocycloalkyl;

(4) cyano (i.e., CN);

(5) an imidate represented by the formula:

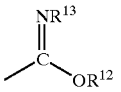

wherein $R^{13}$ is selected from e group consisting of H, CN, $—SO_2$—alkyl (e.g., $—SO_2CH_3$), —C(O)-aryl (e.g., $—C(O)C_6H_5$, i.e., —C(O)phenyl), $—SO_2NR^{10}R^{14}$ (e.g., $—SO_2NH_2$), $—C(O)NR^{10}R^{14}$ (e.g., $—C(O)NH_2$) and $—OR^{10}$ (e.g., OH and $—OCH_3$); $R^{12}$ is aryl; and $R^{14}$ is independently selected from the group consisting of H, alkyl, aryl and aralkyl;

(6) an imidamido group formula:

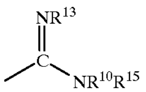

wherein $R^{10}$ and $R^{13}$ are ed above; $R^{15}$ is alkyl, aryl, aralkyl, cycloalkyl, heteroaryl, heteroaralkyl or heterocycloalkyl;

(7) a 1-amino-2-nitroethylene derivative of the formula:

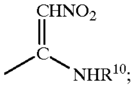;

(8) —C(O)$R^{16}$, wherein $R^{16}$ is alkyl, aryl, aralkyl or heteroaryl;

(9) —C(O)—O—$R^{16}$;

(10)

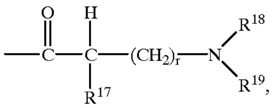

wherein $R^{17}$ is selected from the group consisting of H, alkyl, aralkyl (e.g., benzyl) and heteroaralkyl (e.g., —$CH_2$-imidazolyl); $R^{18}$ and $R^{19}$ are each independently selected from the group consisting of: H; —C(O)$OR^{20}$, wherein $R^{20}$ represents alkyl, aralkyl, and heteroaralkyl; —$SO_2R^{21}$ wherein $R^{21}$ is selected from the group consisting of alkyl (e.g., $C_{1-6}$ alkyl, such as methyl), aryl, aralkyl, heteroaryl and heteroaralkyl; —C(O)$R^{21}$; $C_{1-6}$ alkyl; alkaryl; and $C_{3-6}$ cycloalkyl; and r is 0, 1 or 2;

(11) alkyl, aryl, aralkyl, cycloalkyl, heterocycloalkyl or heteroaryl;

(12) —$SO_2NR^{10}R^{14}$;

(13) —P(O)$(R^{10})_2$;

(14) a sugar group of the formula

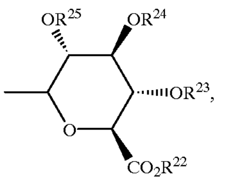

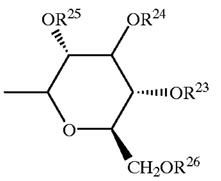

or

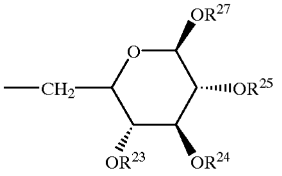

wherein $R^{22}$ and $R^{26}$ are independently selected from the group consisting of H, ($C_1$–$C_6$)alkyl, aryl and aryl($C_1$–$C_6$) alkyl; and $R^{23}$, $R^{24}$, $R^{25}$ and $R^{27}$ are independently selected from the group consisting of H, ($C_1$–$C_6$)alkyl, aryl($C_1$–$C_6$) alkyl, —C(O)($C_1$–$C_6$)alkyl and —C(O)aryl; or

(15) —$CH_2C(O)OR^{28}$, wherein $R^{28}$ is selected from the group consisting of H, alkyl (e.g., —$C(CH_3)_3$), aryl and heteroaryl.

International Patent Application No. PCT/US97/15901 filed Sep. 11, 1997 discloses the compounds:

4-[8-Chloro-3,7-dibromo-5,6-dihydro-11H-benzo [5,6]-cyclohepta[1, 2-b]pyridin-11-yl]-1-(4-thiomorpholinylacetyl)-piperidine 4-[8-Chloro-3,7-dibromo-6,11 -dihydro-5H-benzo[5,6] cyclo-hepta[1, 2-b]pyridin-11-yl]-1-(4-thiomorpholinylacetyl)piperidine S-oxide;

(+,−)-1-(3-bromo-8,10-dichloro-5-ethyl-6,11-dihydro-5H-benzo[5,6]cyclohepta[1,2-b]pyridin-11-yl)-4-(4-pyridinylacetyl)-piperazine N4-oxide (+)-4-(3-bromo-8,10-dichloro-6,11-dihydro-5H-benzo[5,6]-cyclohepta[1,2-b]pyridin-11-yl)-1-[2-(1,3-dihydro-1,3-dioxo-2H-isoindol-2-yl)-1-oxoethyl]piperidine; and (+)-4-(3,10-Dibromo-8-chloro-6,11-dihydro-5H-benzo[5,6]-cyclohepta[1,2-b]pyridin-11(R)-yl)-1-[(1-oxopropyl-4-piperidinyl)acetyl]piperidine;

or a pharmaceutically acceptable salt or solvate thereof.

International Patent Application No. PCT/US97/ 15902 filed Sep. 11, 1997 discloses compounds of the formula:

(1.0)

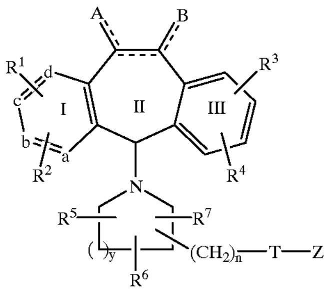

or a pharmaceutically acceptable salt or solvate thereof, wherein:

one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —OC(O)$R^{10}$, —$CO_2R^{10}$, —$OCO_2R^{11}$, —CN, —NHC(O)$R^{10}$, —$NHSO_2R^{11}$, —$CONHR^{10}$, —$CONHCH_2CH_2OH$, —$NR^{10}COOR^{11}$, —$SR^{11}C(O)OR^{11}$(e.g., —$SCH_2CO_2CH_3$), —$SR^{11}N(R^{75})_2$ wherein each $R^{75}$ is independently selected from H and —C(O)$OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$ and $R^6$ (y=0) or $R^5$, $R^6$ and $R^7$ (y=1) each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or one of $R^5$, $R^6$ and $R^7$ can be taken in combination with $R^{40}$ as defined below to represent —$(CH_2)_r$— wherein r is 1 to 4 which can be substituted with lower alkyl, lower alkoxy, —$CF_3$ or aryl, or $R^5$ is combined with $R^6$ or $R^7$ to represent =O or =S;

$R^{10}$ independently represents H, alkyl, cycloalkyl, cycloalkylalkyl, heteroaryl, aryl, aralkyl or —$NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl, cycloalkylalkyl, alkenyl and alknyl;

$R^{11}$ represents alkyl or aryl;

the dotted line between carbon atoms 5 and 6 represents an optional double bond, such that when a double bond is present, A and B independently represent —$NO_2$, —$R^{10}$, halo, —$OR^{11}$, —$OCO_2R^{11}$ or —OC(O)$R^{10}$, and when no double bond is present between carbon atoms 5 and 6, A and B each independently represent $H_2$, —$(OR^{11})_2$, H and halo, dihalo, alkyl and H, $(alkyl)_2$, —H and —OC(O)$R^{10}$, H and —$OR^{10}$, oxy, aryl and H, =$NOR^{10}$ or —O—$(CH_2)_p$—O— wherein p is 2, 3 or 4; and y is 0 (zero) or 1;

n is 0, 1, 2, 3, 4, 5 or 6;

T is —CO—; —SO—; —$SO_2$—; or —$CR^{30}R^{31}$— wherein $R^{30}$ and $R^{31}$ independently represent H, alkyl, aryl, aralkyl, heteroalkyl, heteroaryl, heteroarylalkyl, heterocycloalkyl or heterocycloalkylalkyl;

Z represents alkyl, aryl, aralkyl, heteroalkyl, heteroaryl, heteroarylalkyl, heterocycloalkyl, heterocycloalkylalkyl, —$OR^{40}$, —$SR^{40}$, —$CR^{40}R^{42}$ or —$NR^{40}R^{42}$ wherein $R^{40}$ and $R^{42}$ are defined hereinbefore

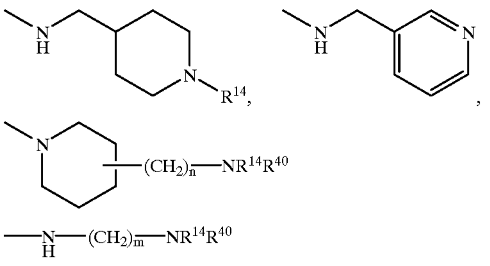

wherein n, $R^{40}$ and $R^{42}$ are defined hereinbefore, m is 2, 3 4, 5, 6, 7 or 8;

and $R^{14}$ represents H, $C_{1-6}$ alkyl, aralkyl, acyl, carboxamido, cyano, alkoxycarbonyl, aralkyloxycarbonyl, D- and L-amino acids covalently bonded through the carboxyl group, imido, imidamido, sulfamoyl, sulfonyl, dialkylphoshinyl, N-glycosyl,

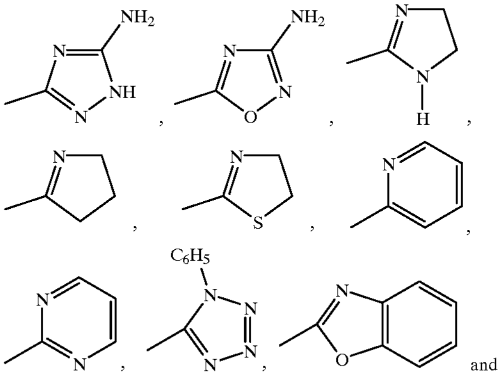

and

—$C(NHCH_3){=}CHNO_2$, with the proviso that when T is —SO—, Z is not —$NR^{40}R^{42}$.

International Patent Application No. PCT/US97/15903 filed Sep. 11, 1997 discloses compounds of formula 1.0:

(1.0)

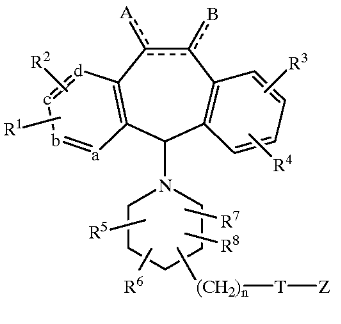

or a pharmaceutically acceptable salt or solvate thereof, wherein:

one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, —$CF_3$, —$OR^{10}$, —$COR^{10}$, —$SR^{10}$, —$S(O)_tR^{11}$ (wherein t is 0, 1 or 2), —SCN, —$N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COOR^{11}$, —$SR^{11}C(O)OR^{11}$, —$SR^{11}N(R^{75})_2$ wherein each $R^{75}$ is independently selected from H and —$C(O)OR^{11}$, benzotriazol-1-yloxy, tetrazol-5-ylthio, or substituted tetrazol-5-ylthio, alkynyl, alkenyl or alkyl, said alkyl or alkenyl group optionally being substituted with halo, —$OR^{10}$ or —$CO_2R^{10}$;_

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$, or $R^5$ is combined with $R^6$ to represent =O or =S and/or $R^7$ is combined with $R^8$ to represent =O or =S;

$R^{10}$ represents H, alkyl, cycloalkyl, cycloalkylalkyl, heteroaryl, aryl, aralkyl or —$NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl, cycloalkylalkyl, alkenyl and alkynyl;

$R^{11}$ represents alkyl or aryl;

the dotted line between carbon atoms 5 and 6 represents an optional double bond, such that when a double bond is present, A and B independently represent —$NO_2$, —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$, H and halo, dihalo, alkyl and H, $(alkyl)_2$, —H and —$OC(O)R^{10}$, H and —$OR^{10}$, oxy, aryl and H, =$NOR^{10}$ or —O—$(CH_2)_p$—O— wherein p is 2, 3 or 4;

n is 0 (zero), 1, 2, 3, 4, 5 or 6;

T is —CO—; —SO—; —$SO_2$—; or —$CR^{30}R^{31}$— wherein $R^{30}$ and $R^{31}$ independently represent H, alkyl, aryl, aralkyl, heteroalkyl, heteroaryl, heteroarylalkyl, heterocycloalkyl or heterocycloalkylalkyl; and Z represents alkyl, aryl, aralkyl, heteroalkyl, heteroaryl, heteroarylalkyl, heterocycloalkyl, heterocycloalkylalkyl, —$OR^{40}$,

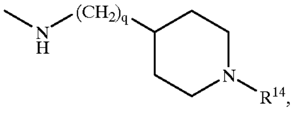

—$SR^{40}$, —$CR^{40}R^{42}$, $NR^{40}R^{42}$,

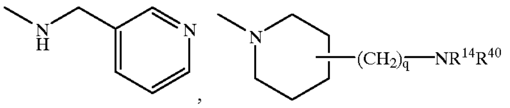

-continued

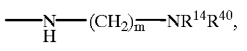

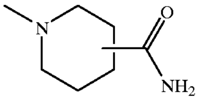

and

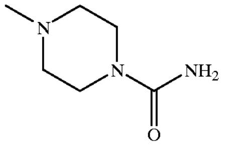

wherein n, $R^{40}$ and $R^{42}$ are defined hereinbefore, m is 2, 3 4, 5, 6, 7 or 8;

q is 0 (zero), 1 or 2;

and $R^{14}$ represents H, $C_{1-6}$ alkyl, aralkyl, heteroaryl, acyl, carboxamido, carboxamidoalkyl, cyano, alkoxycarbonyl, aralkyloxycarbonyl, D- and L-amino acids covalently bonded through the carboxyl group, imido, imidamido, sulfamoyl, sulfonyl, dialkylphosphinyl, N-glycosyl, (1.0)

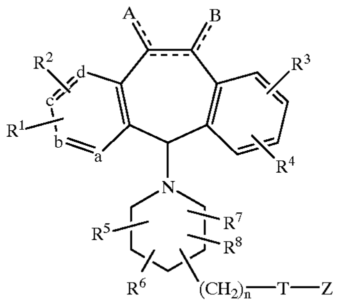

—$C(NHCH_3)$=$CHNO_2$, with the proviso that when T is —SO—, Z is not —$NR^{40}R^{42}$, International Patent Application No. PCT/US97/15904 filed Sep. 11, 1997 discloses compounds of the formula:

(1.0)

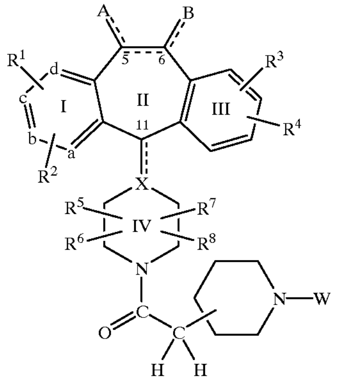

or a pharmaceutically acceptable salt or solvate thereof, wherein:

one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $OR^1$ or $CR^2$; or each of a, b, c, and d are independently selected from $CR^1$ or $CR^2$;

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COOR^{11}$,

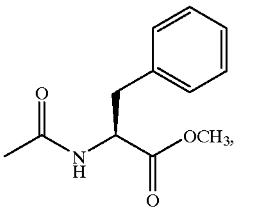

—$SR^{11}C(O)OR^{11}$ (e.g., —$SCH_2CO_2CH_3$), —$SR^{11}N(R^{75})_2$ wherein each $R^{75}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$, or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, $(alkyl)_2$, —H and —$OC(O)R^{10}$, H and —$OR^{10}$, =O, aryl and H, =$NOR^{10}$ or —O—$(CH_2)_p$—O— wherein p is 2, 3 or 4; and W represents a group selected from the group consisting of:

(1)

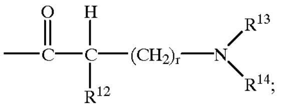

(2)

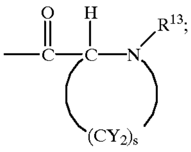

-continued (3)

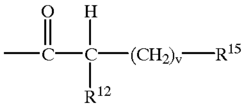 and (4)

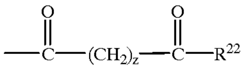

wherein:

$R^{12}$ is selected from the group consisting of: (a) H; (b) alkyl; (c) aralkyl (e.g., benzyl); and (d) heteroarylalkyl (heteroaralkyl) (e.g., —$CH_2$-imidazolyl);

$R^{13}$ and $R^{14}$ are each independently selected from the group consisting of: (a) H; (b) —C(O)O$R^{16}$ wherein $R^{16}$ represents alkyl, aralkyl, and heteroaralkyl; (c) —$SO_2R^{17}$ wherein $R^{17}$ is selected from the group consisting of: —$NH_2$, —N$(alkyl)_2$ wherein each alkyl is the same or different (e.g., —$N(CH_3)_2$), alkyl (e.g., $C_{1-6}$ alkyl, such as methyl), aryl, aralkyl, heteroaryl and heteroaralkyl; (d) —C(O)$R^{18}$ wherein $R^{18}$ is selected from the group consisting of: aryl (e.g., phenyl), alkyl, aralkyl, heteroaryl, and heteroaralkyl; (e) $C_{1-6}$ alkyl; (f) alkaryl; and (g) $C_{3-6}$ cycloalkyl;

r is 0, 1 or 2;

s represents 1, 2, 3, 4, or 5 (preferably 3 or 4), and each Y for each —$CY_2$— group is independently selected from H or —OH, provided that both Y substituents of each —$CY_2$— group are not —OH, and provided that for the —$CY_2$— group alpha to the nitrogen both Y substituents are H, preferably each Y is H such that each —$CY_2$— group is a —$CH_2$— group such that the group

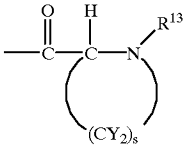 , e.g., 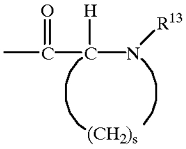 , forms a 3, 4, 5, 6, or 7 (preferably 5 or 6) membered ring (e.g., piperidyl or pyrrolidinyl),;

v is 0, 1 or 2;

$R^{15}$ is selected from the group consisting of:

(a) heteroaryl (e.g., imidazolyl);

(b) a group selected from:

(1)

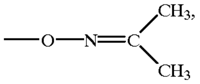

(2)

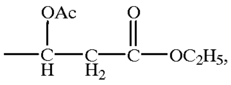

(3)

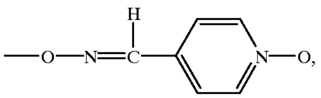

-continued (4)

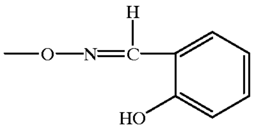 , (5) —$CH(OCH_2CH_3)_2$, (6) —OH, and (7) —CN; and (c) heterocycloalkyl selected from the group consisting of:

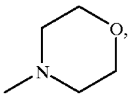 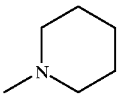 , 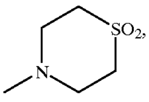

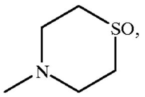 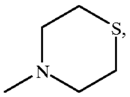

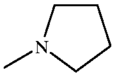 , 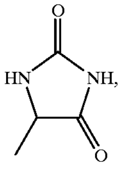 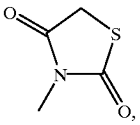

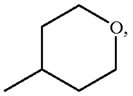 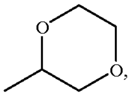 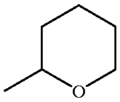 and

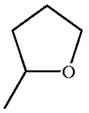 ;

z is 0, 1, 2, 3, 4, or 5 wherein each —$CH_2$— group is optionally substituted with a —OH group, i.e., each H of each —$CH_2$— group can optionally be replaced with a —OH group and the optional substitution on each —$CH_2$— group is independent of the substitution on any other —$CH_2$— group, generally each —$CH_2$— is unsubstituted;

$R^{22}$ represents a group selected from:

(1)

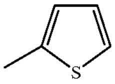 , (2)

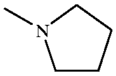 , (3)

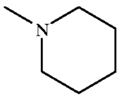 ,

-continued (4)

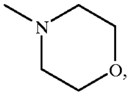

(5) alkyl (e.g., $—CH_3$), (6) $—OR^{23}$ wherein $R^{23}$ is selected from the group consisting of: alkyl, aryl and H, and (7)

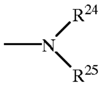

wherein $R^{24}$ and $R^{25}$ are independently selected from the group consisting of: $—NH_2$, alkoxy (e.g., $—OCH_3$), —OH, $—CH_2CO_2H$, $—OCH_2Ph$ (i.e., $—OCH_2C_6H_5$), $—CH(OCH_3)CH(CH_3)_2$

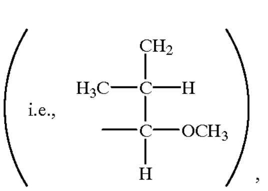

alkyl, aryl, H, aralkyl, and heteroaralkyl; or $R^{24}$ and $R^{25}$ taken together form a carbon chain having 4 or 5 ($—CH_2—$) groups such that $R^{24}$ and $R^{25}$ taken together with the nitrogen to which they are bound form a 5 or 6 membered heterocycloalkyl ring.

International Patent Application No. PCT/US97/15905 filed Sep. 11, 1997 discloses compounds of the formula:

(1.0)

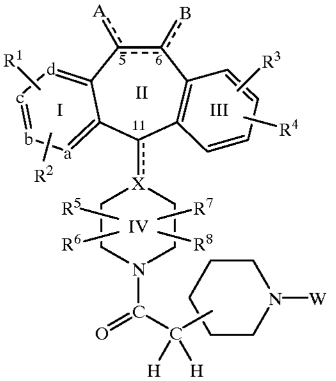

or a pharmaceutically acceptable salt or solvate thereof, wherein: one of a, b, c and d represents N or $NR^9$ wherein $R^9$ is $O^-$, $—CH_3$ or $—(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, $—CF_3$, $—OR^{10}$ (e.g., $—OCH_3$), $—COR^{10}$, $—SR^{10}$ (e.g., $—SCH_3$ and $—SCH_2C_6H_5$), $—S(O)_tR^{11}$ (wherein t is 0, 1 or 2, e.g., $—SOCH_3$ and $—SO_2CH_3$), —SCN, $—N(R^{10})_2$, $—NR^{10}R^{11}$, $—NO_2$, $—OC(O)R^{10}$, $—CO_2R^{10}$, $—OCO_2R^{11}$, —CN, $—NHC(O)R^{10}$, $—NHSO_2R^{10}$, $—CONHR^{10}$, $—CONHCH_2CH_2OH$, $—NR^{10}COOR^{11}$,

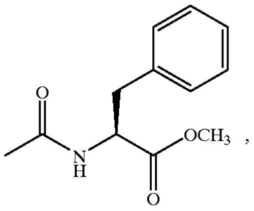

$—SR^{11}C(O)OR^{11}$ (e.g., $—SCH_2CO_2CH_3$), $—SR^{11}N(R^{75})_2$ wherein each $R^{75}$ is independently selected from H and $—C(O)OR^{11}$ (e.g., $—S(CH_2)_2NHC(O)O$-t-butyl and $—S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, $—OR^{10}$ or $—CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, $—CF_3$, $—COR^{10}$, alkyl or aryl, said alkyl or aryl optionally being substituted with $—OR^{10}$, $—SR^{10}$, $—S(O)_tR^{11}$, $—NR^{10}COOR^{11}$, $—N(R^{10})_2$, $—NO_2$, $—COR^{10}$, $—OCOR^{10}$, $—OCO_2R^{11}$, $—CO_2R^{10}$, $OPO_3R^{10}$ or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent $—R^{10}$, halo, $—OR^{11}$, $—OCO_2R^{11}$ or $—OC(O)R^{10}$, and when no double bond is present between carbon atoms 5 and 6, A and B each independently represent $H_2$, $—(OR^{11})_2$; H and halo, dihalo, alkyl and H, $(alkyl)_2$, —H and $—OC(O)R^{10}$, H and $—OR^{10}$, =O, aryl and H, $=NOR^{10}$ or $—O—(CH_2)_p—O—$ wherein p is 2, 3 or 4; and W represents a group selected from:

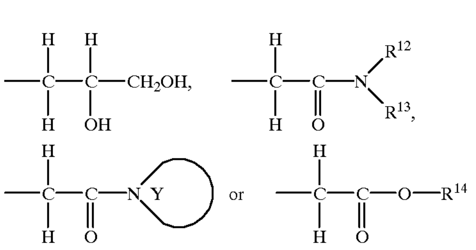

wherein:

$R^{12}$ is selected from the group consisting of: (1) H; (2) alkyl (e.g., methyl and ethyl); (3) aryl; (4) arylalkyl (aralkyl);

$R^{13}$ is selected from the group consisting of: (1) H; (2) alkyl (e.g., methyl and ethyl); (3) alkoxy (e.g., methoxy); (4) heterocycloalkyl, e.g., (a) tetrahydopyranyl, and (b) substituted tetrahydropyranyl wherein said substituents are selected from hydroxy and hydroxyalkyl (e.g., hydroxymethyl), for example D-galactosyl, i.e.,

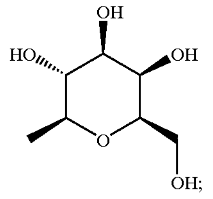

(5) aryl; and (6) aralkyl, e.g., benzyl;

$R^{14}$ is selected from the group consisting of: (1) H; (2) alkyl (e.g., $-C(CH_3)_3$); (3) aryl; and (4) heteroaryl;

ring

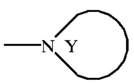

represents a heterocycloalkyl ring wherein Y represents the remainder of the ring, said remainder comprising carbon atoms and optionally a hetero atom selected from the group consisting of: NH, $NR^{15}$, O and S, and said remainder optionally having an aryl ring (e.g., phenyl) fused thereto; generally the heterocycloalkyl ring contains 4 or 5 carbon atoms and usually 4 carbon atoms, examples include:

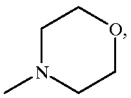 , 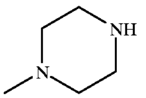 and 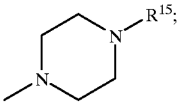;

examples of a heterocycloalkyl ring having a aryl ring fused to the remainder Y include

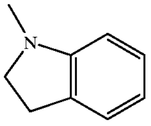 ;

$R^{15}$ represents $-C(O)OR^{16}$; and $R^{16}$ represents alkyl, preferably $-C(CH_3)_3$.

International Patent Application No. PCT/US97/15906 filed Sep. 11, 1997 discloses compounds of the formula:

(1.0)

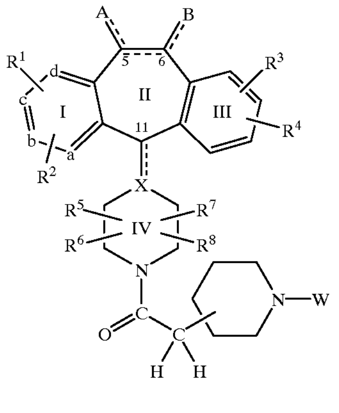

or a pharmaceutically acceptable salt or solvate thereof, wherein: one of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, $-CF_3$, $-OR^{10}$ (e.g., $-OCH_3$), $-COR^{10}$, $-SR^{10}$ (e.g., $-SCH_3$ and $-SCH_2C_6H_5$), $-S(O)_tR^{11}$ (wherein t is 0, 1 or 2, e.g., $-SOCH_3$ and $-SO_2CH_3$), $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR^{10}$, $-CONHCH_2CH_2OH$, $-NR^{10}COOR^{11}$,

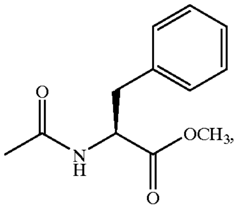

$-SR^{11}C(O)OR^{11}$ (e.g., $-SCH_2CO_2CH_3$), $-SR^{11}N(R^{75})_2$ wherein each $R^{75}$ is independently selected from H and $-C(O)OR^{11}$ (e.g., $-S(CH_2)_2NHC(O)O$-t-butyl and $-S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, $-OR^{10}$ or $-CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, $-CF_3$, $-COR^{10}$, alkyl or aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R^{11}$, $-CO_2R^{11}$, $OPO_3R^{10}$ or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent $-R^{10}$, halo, $-OR^{11}$, $-OCO_2R^{11}$ or $-OC(O)R^{10}$, and when no double bond is present between carbon atoms 5 and 6, A and B each independently represent $H_2$, $-(OR^{11})_2$; H and halo, dihalo, alkyl and H, $(alkyl)_2$, $-H$ and $-OC(O)R^{10}$, H and $-OR^{10}$, =O, aryl and H, $=NOR^{10}$ or $-O-(CH_2)_p-O-$ wherein p is 2, 3 or 4; and W represents a group selected from: $-SO_2R^{12}$ or $-P(O)R^{13}R^{14}$;

$R^{12}$ is selected from the group consisting of:

(1) alkyl, e.g., methyl, ethyl and propyl (such as n-propyl and iso-propyl);

(2) aralkyl, e.g., benzyl;

(3) cycloalkyl;

(4) aryl, e.g., phenyl;

(5) heteroaryl, e.g., pyridyl, thienyl and imidazolyl (e.g., 4- or 5-imidazolyl);

(6) substituted heteroaryl wherein said heteroaryl is as defined above and said substituents are selected from:

(a) heteroaryl (e.g., pyridyl, and imidazolyl), (b) alkyl (e.g., methyl), (c) aryl (e.g., phenyl), (d) aralkyl (e.g., benzyl), (e) —$OR^{10}$, and (f) $N(R^{10})_2$;

(7) camphor, e.g.,

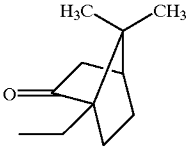

or

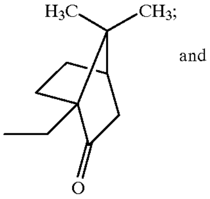

and (8) —$NR^{15}R^{16}$ wherein $R^{15}$ and $R^{16}$ are independently selected from the group consisting of: (a) H, (b) alkyl (e.g., methyl), (c) aryl (e.g., phenyl), (d) aralkyl (e.g., benzyl), (e) heteroaryl (e.g., pyridyl), and (f) heterocycloalkyl (e.g., piperidinyl), and preferably, $R^{15}$ and $R^{16}$ are the same; and $R^{13}$ and $R^{14}$ are independently selected from the group consisting of:

(1) H;

(2) alkyl, e.g., methyl;

(3) aryl, e.g., phenyl;

(4) aralkyl, e.g., benzyl; and (5) —$OR^{13}$ wherein $R^{13}$ is as defined above;

preferably $R^{13}$ and $R^{14}$ are the same.

International Patent Application No. PCT/US97/15907 filed Sep. 11, 1997 discloses compounds of the formula:

(1.0)

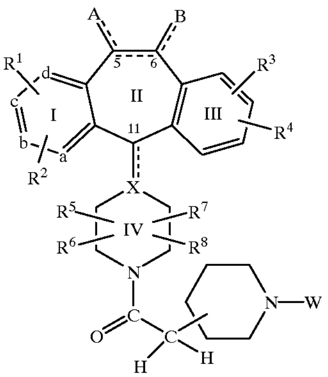

or a pharmaceutically acceptable salt or solvate thereof, wherein: one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COOR^{11}$,

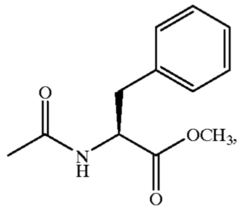

—$SR^{11}C(O)OR^{11}$ (e.g., —$SCH_2CO_2CH_3$), —$SR^{11}N(R^{75})_2$ wherein each $R^{75}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, $(alkyl)_2$, —H and —$OC(O)R^{10}$, H and —$OR^{10}$, =O, aryl and H, =$NOR^{10}$ or —O—$(CH_2)_p$—O— wherein p is 2, 3 or 4; and W represents a heteroaryl, aryl, heterocyloalkyl or cycloalkyl group.

International Patent Application No. PCT/US97/ 19976 filed Sep. 11, 1997 discloses compounds of the formula:

(1.0)

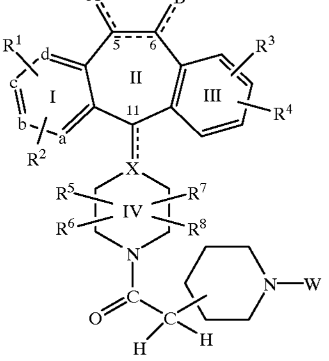

or a pharmaceutically acceptable salt or solvate thereof, wherein: one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COOR^{11}$,

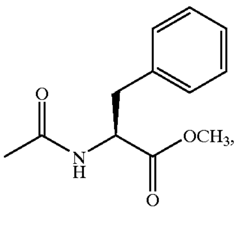

—$SR^{11}C(O)OR^{11}$ (e.g., —$SCH_2CO_2CH_3$), —$SR^{11}N(R^{75})_2$ wherein each —$R^{75}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-yl-thio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$, or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, $(alkyl)_2$, —H and —$OC(O)R^{10}$, H and —$OR^{10}$, =O, aryl and H, =$NOR^{10}$ or —O— $(CH_2)_p$—O— wherein p is 2, 3 or 4; and W is selected from the group consisting of:

(1) cyano (i.e., CN);

(2) —$C(O)R^{12}$ wherein $R^{12}$ is selected from:

(a) a heteroaryl group, for example, pyridyl (e.g., 3-pyridyl), indolyl (e.g., 2-indolyl), pyrrolyl (e.g., 2-pyrrolyl) and N-substituted pyrrolyl (e.g., N-alkylpyrrolyl such as N-alkylpyrrol-2-yl, such as, N-methylpyrrol-2-yl);

(b) H;

(c) alkyl (e.g., —$CH_3$); or (d) a substituent of the formula:

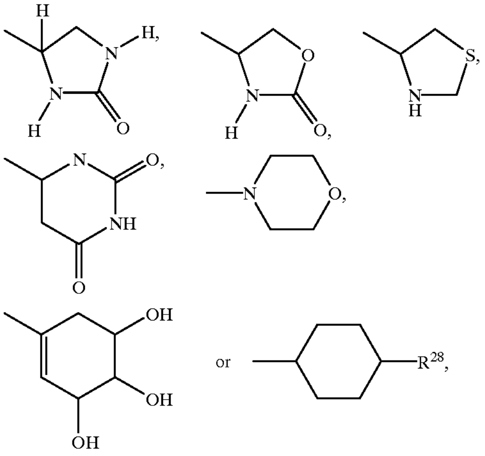

wherein $R^{28}$ is selected from —$OC(O)R^{29}$, —OH, —$OC(O)NHC(O)CCl_3$, or —$OC(O)NH_2$, wherein $R^{29}$ is alkyl (e.g., —$CH_3$);

(3) an imidate represented by the formula:

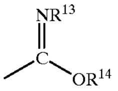

wherein $R^{13}$ is selected from the group consisting of: (a) H, (b) CN, (c) —$SO_2$-alkyl (e.g., —$SO_2CH_3$), (d) —C(O)-aryl (e.g., —$C(O)C_6H_5$, i.e., —C(O)phenyl), (e) —$SO_2NR^{10}R^{15}$ (e.g., —$SO_2NH_2$), (f) —$C(O)NR^{10}R^{15}$ (e.g., —$C(O)NH_2$), (g) —$OR^{10}$ (e.g., —OH and —$OCH_3$); and (h) —$C(O)NR^{10}C(O)NR^{10}R^{15}$ (e.g., —$C(O)NHC(O)NH_2$); $R^{14}$ is aryl; and $R^{10}$ and $R^{15}$ are independently selected from the group consisting of: H, alkyl, aryl and aralkyl;

(4) an imidamido (amidino) represented by the formula:

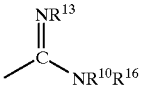

wherein $R^{13}$ is selected from the group consisting of (a)H, (b) CN, (c) —$SO_2$-alkyl (e.g., —$SO_2CH_3$), (d) —C(O)-aryl (e.g., —$C(O)C_6H_5$, i.e., —C(O)phenyl), (e) —$SO_2NR^{10}R^{15}$ (e.g., —$SO_2NH_2$), (f) —$C(O)NR^{10}R^{15}$ (e.g., —$C(O)NH_2$), (g) —$OR^{10}$ (e.g., —OH and —$OCH_3$); and (h) —$C(O)NR^{10}C(O)NR^{10}R^{15}$ (e.g., —$C(O)NHC(O)NH_2$); $R^{16}$ is selected from the group consisting of: alkyl, aralkyl, aryl, cycloalkyl, heteroaryl, heteroaralkyl and heterocycloalkyl; $R^{10}$ and $R^{15}$ are as defined above; and $R^{10}$ and $R^{16}$ are independently selected from the above defined groups;

(5) 1-amino-2-nitroethylene derivatives of the formula:

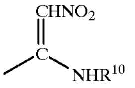

wherein $R^{10}$ is as defined above; and (6) a substituent of the formula:

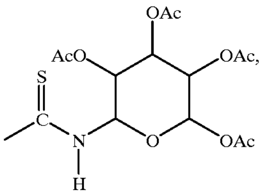

e.g.,

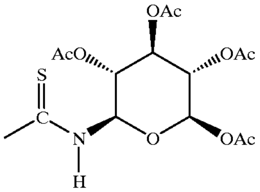

U.S. application Ser. No. 08/877,049 filed Jun. 17, 1997 now abandoned discloses compounds of the formula:

(1.0)

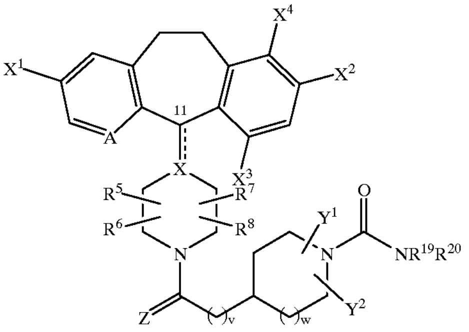

or a pharmaceutically acceptable salt or solvate thereof, wherein:

A represents N or N-oxide;

X represents N, CH or C, such that when X is N or CH, there is a single bond to carbon atom 11 as represented by the solid line; or when X is C, there is a double bond to carbon atom 11, as represented by the solid and dotted lines;

$X^1$ and $X^2$ are independently selected from bromo or chloro, and $X^3$ and $X^4$ are independently selected from hydrogen, bromo or chloro provided that at least one of $X^3$ and $X^4$ is hydrogen;

$Y^1$ and $Y^2$ are independently selected from hydrogen or alkyl;

Z is =O or =S;

$R^5$, $R^6$, $R^7$ and $R^8$ each independently represents hydrogen, —$CF_3$, —$COR^{10}$, alkyl or aryl, and further wherein $R^5$ may be combined with $R^6$ to represent =O or =S and/or $R^7$ may be combined with $R^8$ to represent =O or =S;

$R^{10}$, $R^{19}$ and $R^{20}$ independently represent hydrogen, alkyl, alkoxy, aryl, aralkyl, heteroaryl, heteroarylalkyl, cycloalkyl, cycloalkylalkyl, heterocycloalkyl and heterocycloalkylalkyl, with the proviso that $R^{19}$ and $R^{20}$ are not both hydrogen;

v is zero, 1, 2 or 3; and w is zero or 1.

U.S. application Ser. No. 08/877,366 filed Jun. 17, 1997 U.S. Pat. No. 5,939,416 discloses compounds of the formula:

I

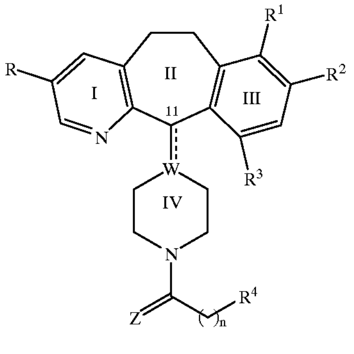

or an N-oxide thereof, or a pharmaceutically acceptable salt or solvate thereof, wherein:

R and $R^2$ are independently selected from halo;

$R^1$ and $R^3$ are independently selected from the group consisting of H and halo, provided that at least one of $R^1$ and $R^3$ is H;

W is N, CH or C, when the double bond is present at the C-11 position;

$R^4$ is 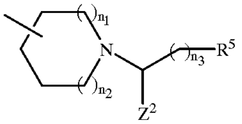 or $R^5$;

$R^5$ is 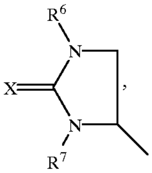, 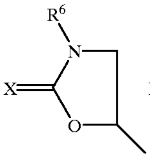, 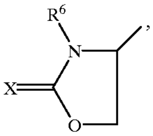,

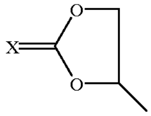, 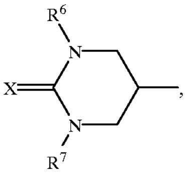,

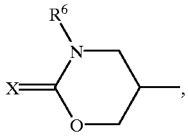, 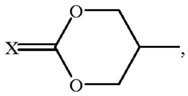,

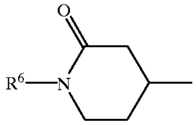 or 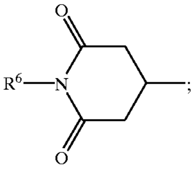;

$R^6$ and $R^7$ are independently selected from the group consisting of H, alkyl, substituted alkyl, acyl, aryl, aralkyl, heterocycloalkyl and heteroaryl;

X is =O or =S;

$Z^1$ and $Z^2$ are independently =O or =S;

n and $n_3$ are independently 0, 1 or 2; and $n_1$ and $n_2$ are independently 0 or 1.

U.S. application Ser. No. 08/877,399 filed Jun. 17, 1997 U.S. Pat. No. 5,852,034 discloses compounds of the formula:

I

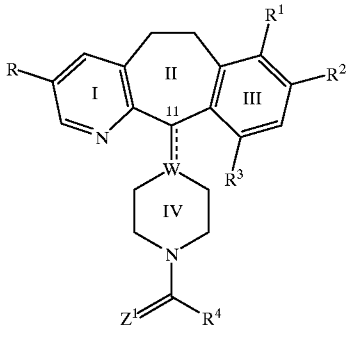

or an N-oxide thereof, or a pharmaceutically acceptable salt or solvate thereof, wherein:

R and $R^2$ are independently selected from halo;

$R^1$ and $R^3$ are independently selected from the group consisting of H and halo, provided that at least one of $R^1$ and $R^3$ is H;

W is N, CH or C when the double bond is present at the C-11 position;

$R^4$ is $-(CH_2)_n-R^5$

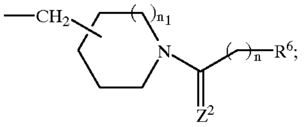

or $R^5$

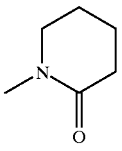

,

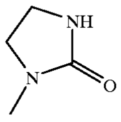

or

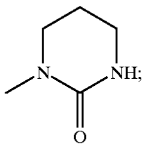

is $R^6$ is $R^5$ or

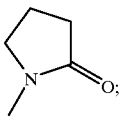

$Z^1$ and $Z^2$ are independently selected from the group consisting of =O and =S;

n is 1–6; and $n_1$ is 0 or 1.

U.S. application Ser. No. 08/877,336 filed Jun. 17, 1997 U.S. Pat. No. 5,877,177 discloses compounds of the formula:

I

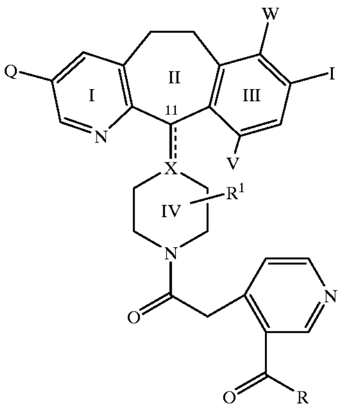

or an N-oxide thereof, or a pharmaceutically acceptable salt or solvate thereof, wherein:

Q and T are independently selected from halo;

W and V are independently selected from H and halo, provided that at least one of W and V is H;

$R^1$ is H or alkyl;

X represents N, CH, or C when the double bond is present at the C-11 position;

R is $-OR^3$, $-NR^3R^4$ or $-SR^3$; and $R^3$ and $R^4$ are independently selected form the group consisting of H, alkyl, arylalkyl, substituted arylalkyl, heteroarylalkyl and substituted heteroarylalkyl.

U.S. application Ser. No. 08/877,269 filed Jun. 17, 1997 now abandoned discloses compounds of the formula:

I

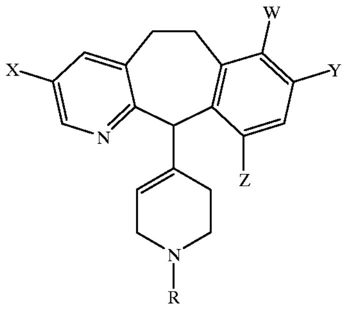

or an N-oxide thereof, or a pharmaceutically acceptable salt or solvate thereof, wherein:

W is H or halo;

X is H, halo, $CH_3$, isopropyl, t-butyl, cyclopropyl,

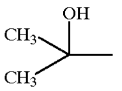

or

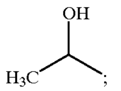

Y and Z are independently selected from the group consisting of halo, $CH_3$, $OCH_3$, $CF_3$, $OCF_3$ and $CH_2OH$;

R is $R'-(CH_2)_nC(O)-$, $R'-(CH_2)_nSO_2-$ or $R'-OC(O)-$, wherein n is 0 to 2; and R' is aryl, heteroaryl or heterocycloalkyl.

U.S. application Ser. No. 08/877,050 filed Jun. 17, 1997 discloses compounds of the formula:

(1.0)

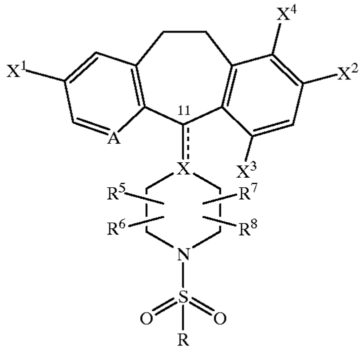

or a pharmaceutically acceptable salt or solvate thereof, wherein:

A represents N or N-oxide;

X represents N, CH or C, such that when X is N or CH, there is a single bond to carbon atom 11 as represented by the solid line; or when X is C, there is a double bond to carbon atom 11, as represented by the solid and dotted lines;

$X^1$ and $X^2$ are independently selected from bromo, iodo or chloro;

$X^3$ and $X^4$ are independently selected from bromo, iodo, chloro, fluro or hydrogen provided only one of $X^3$ or $X^4$ is hydrogen;

R can represent alkyl, aryl, arylalkyl, heteroaryl, heteroarylalkyl, cycloalkyl, cycloalkylalkyl, heterocycloalkyl, heterocycloalkylalkyl or $—NR^{10}R^{11}$, wherein $R^{10}$ and $R^{11}$ can independently represent hydrogen, alkenyl, alkyl, aryl, aralkyl, heteroaryl, heteroarylalkyl, cycloalkyl, cycloalkylalkyl, heterocycloalkyl or heterocycloalkylalkyl.

U.S. application Ser. No. 08/877,052 filed Jun. 17, 1997 now abandoned discloses compounds of the formula:

(1.0)

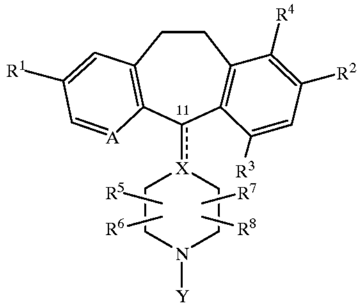

or a pharmaceutically acceptable salt or solvate thereof, wherein:

A represents N or N-oxide;

X represents N, CH or C, such that when X is N or CH, there is a single bond to carbon atom 11 as represented by the solid line; or when X is C, there is a double bond to carbon atom 11, as represented by the solid and dotted lines;

$R^1$ is hydrogen, bromo, chloro, trifluoromethyl, acyl, alkyl, cycloalkyl, amino, acylamino or alkoxy;

$R^2$ is hydrogen, halo, trifluoromethyl, alkyl, alkoxy, $—OCF_3$, hydroxy, amino or acylamino;

$R^3$ is hydrogen, bromo, chloro, alkoxy, $—OCF_3$ or hydroxy;

$R^4$ is hydrogen, halo, trifluoromethyl, alkyl or alkoxy;

provided that at least one of $R^2$ or $R^3$ or $R^4$ is alkyl or alkoxy and provided that at least two of $R^1$, $R^2$, $R^3$ or $R^4$ are substituents other than hydrogen;

$R^5$, $R^6$, $R^7$ and $R^8$ independently represent hydrogen, alkyl or $—CONHR^{50}$ wherein $R^{50}$ can be any of the values represented for R, below;

Y is

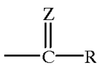

or $—SO_2—R$, wherein;

Z is =O or =S; and

R is aryl, aralkyl, cycloalkyl, cycloalkylalkyl, heteroalkyl, heteroaryl, heteroarylalkyl, heterocycloalkyl or heterocycloalkylalkyl.

U.S. application Ser. No. 08/877,051 filed Jun. 17, 1997 now abandoned discloses compounds of the formula:

(1.0)

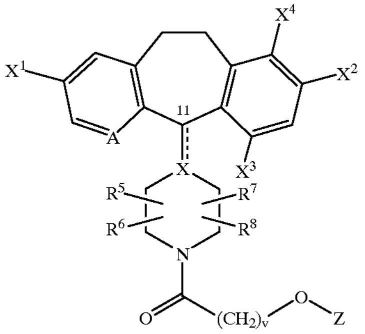

or a pharmaceutically acceptable salt or solvate thereof, wherein:

A represents N or N-oxide;

X represents N, CH or C, such that when X is N or CH, there is a single bond to carbon atom 11 as represented by the solid line; or when X is C, there is a double bond to carbon atom 11, as represented by the solid and dotted lines;

$X^1$ and $X^2$ are independently selected from bromo, iodo or chloro;

$X^3$ and $X^4$ are independently selected from bromo, iodo, chloro or hydrogen provided only one of $X^3$ or $X^4$ is hydrogen;

v is 1, 2, 3, 4, 5 or 6;

Z represents $—NR^{19}R^{20}$ or $—N{=}CR^{19}R^{20}$; wherein $R^{19}$ and $R^{20}$ are independently selected from hydrogen, alkyl, alkoxy, aryl, aralkyl, heteroaryl, heteroarylalkyl, cycloalkyl, cycloalkylalkyl, heterocycloalkyl, heterocycloalkylalkyl, $CONR^{10}R^{12}$, $—COOR^{10}$, $—COR^{10}$, $—SO_2R^{10}$ and $—SO_2NR^{10}R^{12}$, or $R^{19}$ and $R^{20}$ taken together can form a cycloalkyl or a heterocycloalkyl ring, wherein $R^{10}$ and $R^{12}$ are independently selected from hydrogen, alkyl, alkoxy, aryl, aralkyl, heteroaryl, heteroarylalkyl, cycloalkyl, cycloalkylalkyl, heterocycloalkyl or heterocycloalkylalkyl.

U.S. application Ser. No. 08/877,498 filed Jun. 17, 1997 now abandoned discloses compounds of the formula:

(1.0)

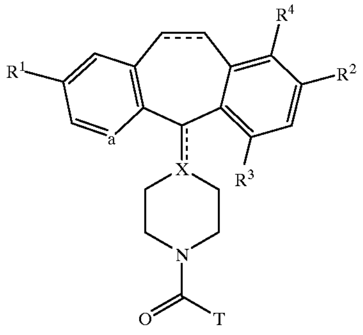

or a pharmaceutically acceptable salt or solvate thereof, wherein:

a represents N or $NO^-$;

$R^1$ and $R^3$ are the same or different halo atom;

$R^2$ and $R^4$ are selected from H and halo, provided that at least one of $R^2$ and $R^4$ is H;

the dotted line (---) represents an optional bond;

X is N, C when the optional bond is present, or CH when the optional bond is absent;

T is a substituent selected from:

(1)

(2.0)

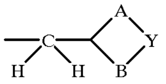

wherein:

A represents $-(CH_2)_b-$;

B represents $-(CH_2)_d-$;

b and d are independently selected from: 0, 1, 2, 3, or 4 such that the sum of b and d is 3 or 4; and Y is selected from: O, S, SO, or $SO_2$;

(2)

(3.0)

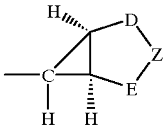

wherein:

D represents $-(CH_2)_e-$;

B represents $-(CH_2)_f-$;

e and f are independently selected from: 0, 1, 2, or3 such that the sum of e and f is 2 or 3; and Z is O;

(3)

(4.0)

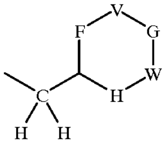

wherein:

F represents $-(CH_2)_g-$;

G represents $-(CH_2)_h-$;

H represents $-(CH_2)_i-$;

h represents 1, 2, or 3 g and i are independently selected from: 0, 1 or 2 such that the sum of h, g and i is 2 or 3; and V and W are independently selected from O, S, SO, or $SO_2$;

(4)

(5.0)

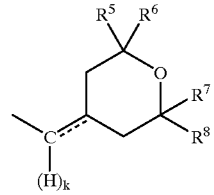

wherein:

the dotted line (---) represents an optional bound;

k is 1 or 2 such that when the optional bond is present k represents 1, and when the optional double bond is absent then k represents 2;

$R^5$, $R^6$, $R^7$ and $R^8$ are the same alkyl (preferably methyl); or $R^5$ and $R^7$ are the same alkyl (preferably methyl), and $R^6$ and $R^8$ are H;

(6.0)

(5)

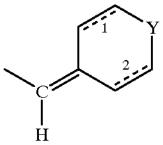

wherein:

the dotted lines (---) represent optional bonds 1 and 2 such that optional bonds 1 and 2 are both present, or optional bonds 1 and 2 are both absent;

Y represents O, S, SO, or $SO_2$;

(7.0)

(6)

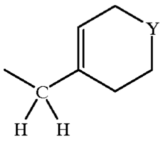

wherein:

Y represents O, S, SO, or $SO_2$;

(8.0)

(7)

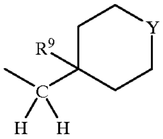

wherein:
$R^9$ is selected from: —CN, —$CO_2H$, or —C(O)N$(R^{10})_2$;
each $R^{10}$ is the same or different alkyl group (preferably, methyl);
(9.0)
(8)
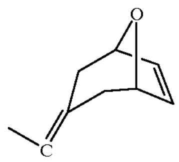
(10.0A)
(9)
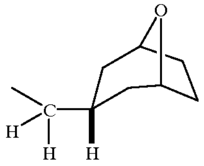
or
(10.0B)
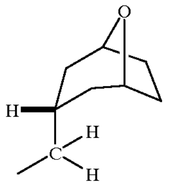
;
(11.0A)
(10)
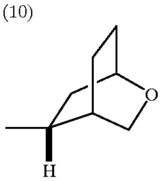
or
Isomer 1
(11.0B)
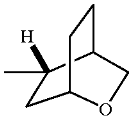
Isomer 2 ; and
(12.0)
(11)
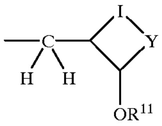
wherein:
I represents —$(CH_2)_m$—;
m represents 2 or 3;
Y represents O, S, SO, or $SO_2$; and
$R^{11}$ represents alkyl (preferably ethyl).
U.S. application Ser. No. 08/877,057 filed Jun. 17, 1997 now abandoned discloses compounds of the formula:
(1.0)
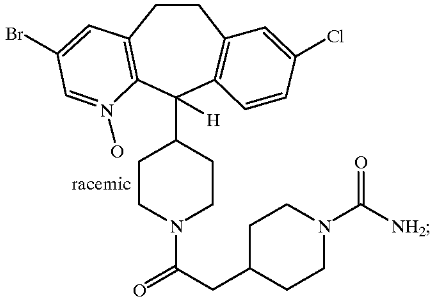
(2.0)
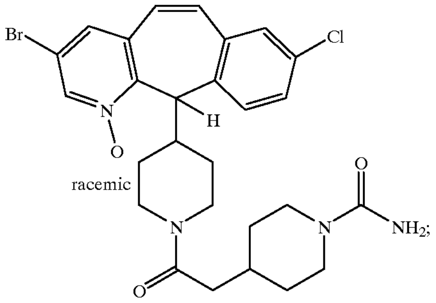
(3.0)
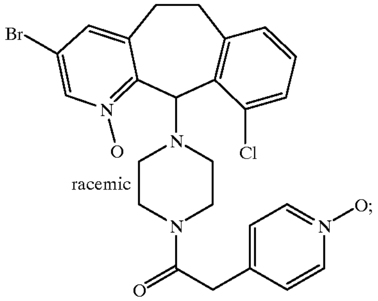
(3.0A)
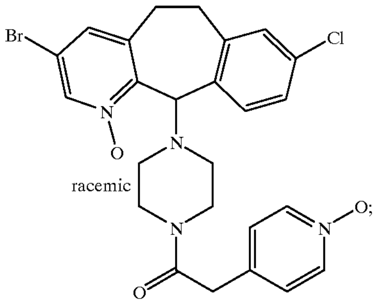
(3.0B)
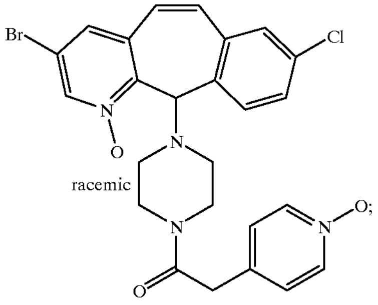

-continued
(5.0)
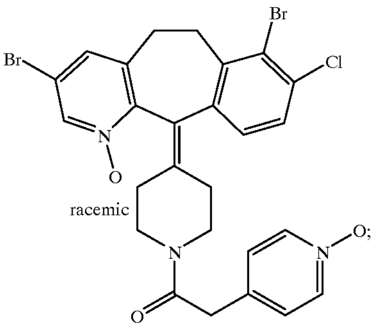
(6.0)
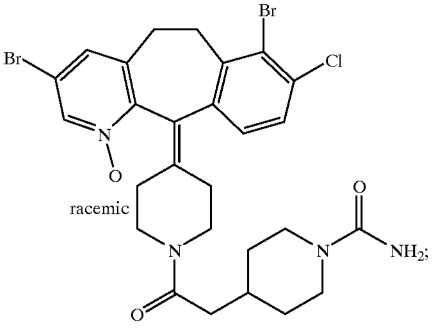
(7.0)
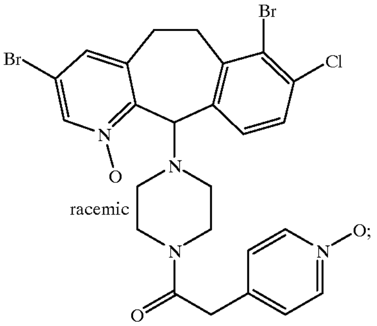
(7.0A)
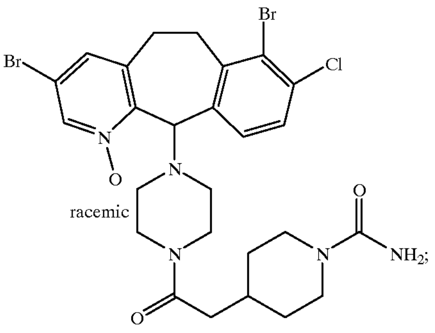
-continued
(8.0)
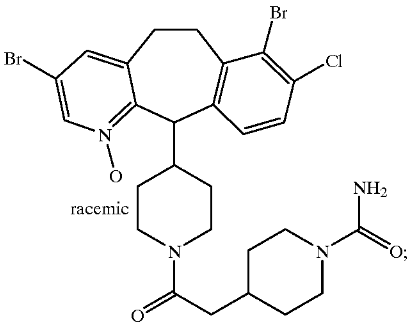
(8.0A)
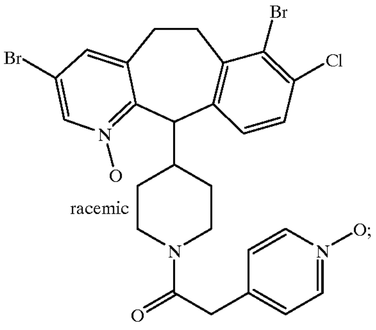
(9.0)
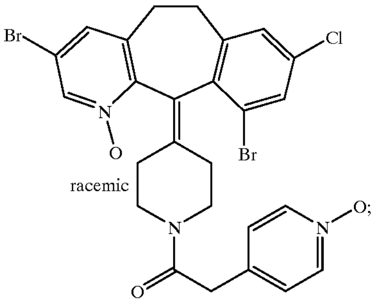
(10.0)
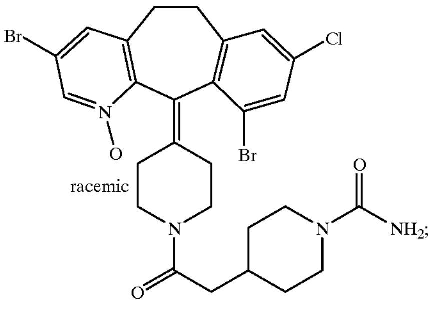
(11.0)
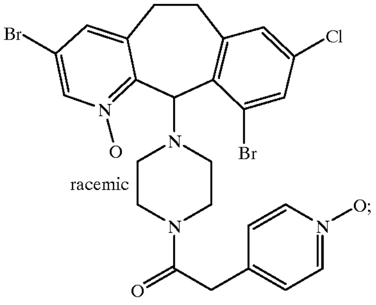

-continued
(12.0)
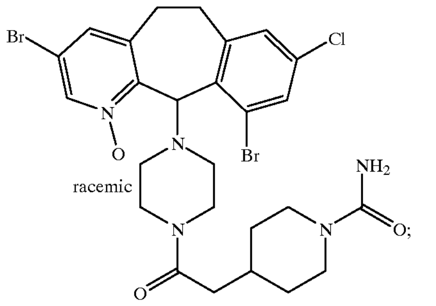
racemic
(13.0)
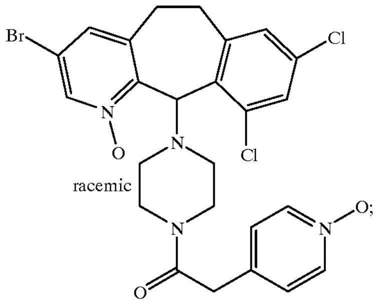
racemic
(14.0)
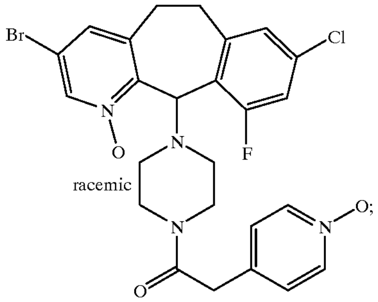
racemic
(15.0)
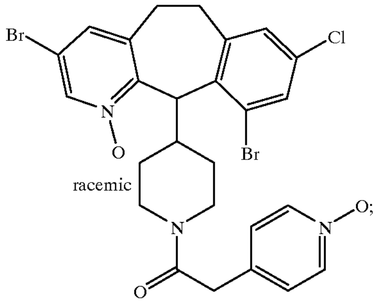
racemic
(16.0)
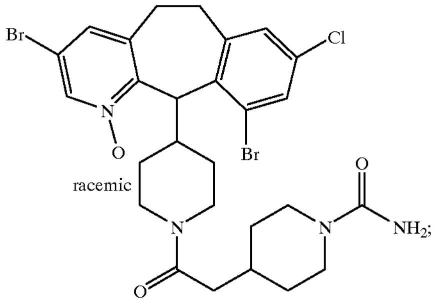
racemic
-continued
(17.0)
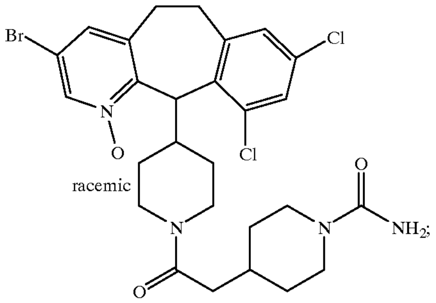
racemic
(18.0)
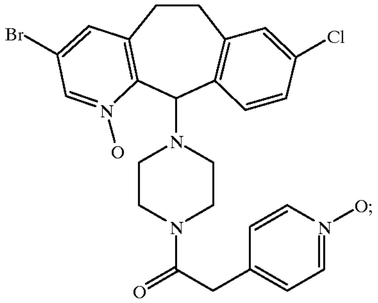
(+)-enantiomer
(19.0)
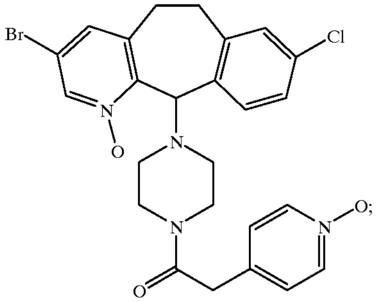
(-)-enantiomer
(20.0)
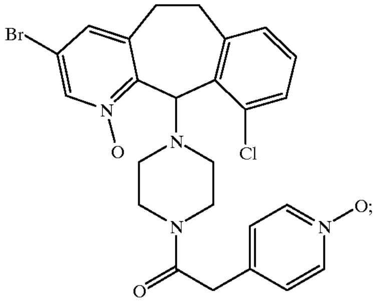
(+)-enantiomer -continued
(21.0)
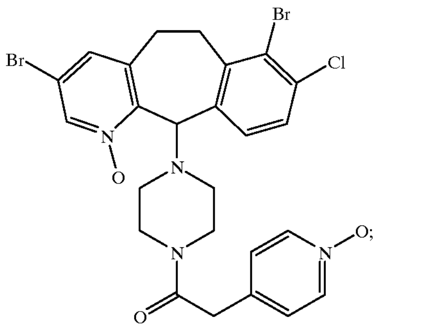
(+)-enantiomer
(22.0)
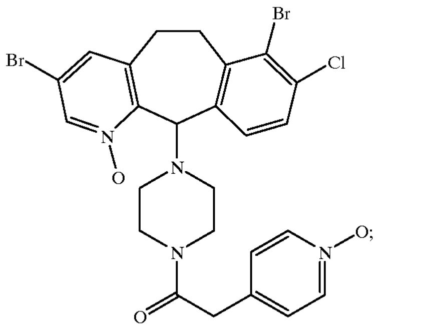
(-)-enantiomer
(23.0)
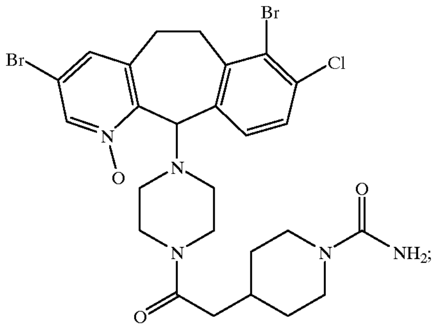
(-)-enantiomer
(24.0)
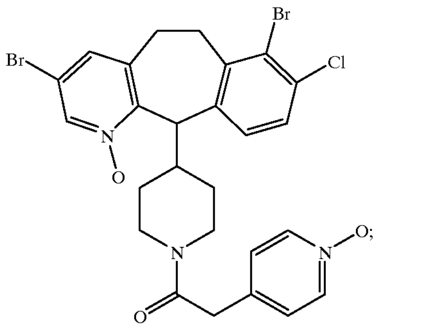
(+)-enantiomer
-continued
(25.0)
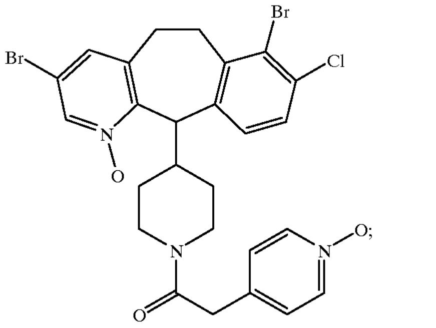
(-)-enantiomer
(26.0)
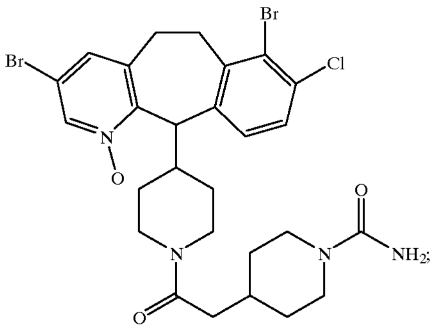
(+)-enantiomer
(27.0)
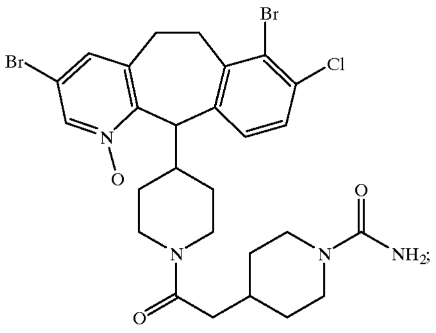
(-)-enantiomer
(28.0)
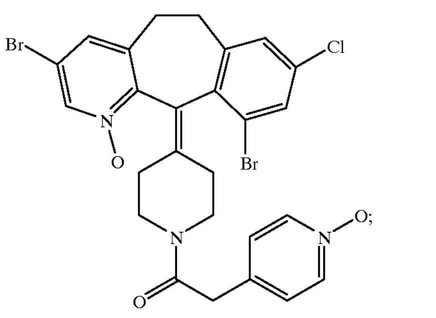
(-)-enantiomer -continued
(29.0)
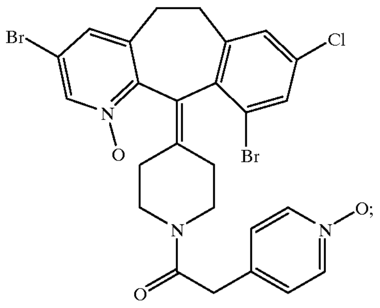
(+)-enantiomer
(30.0)
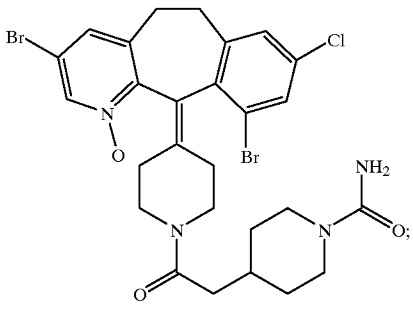
(-)-enantiomer
(31.0)
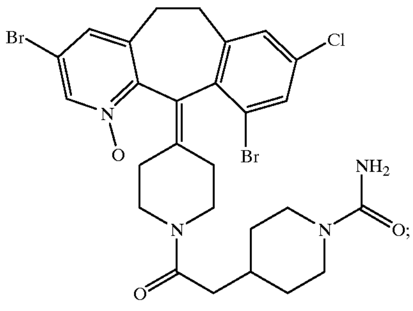
(+)-enantiomer
(32.0)
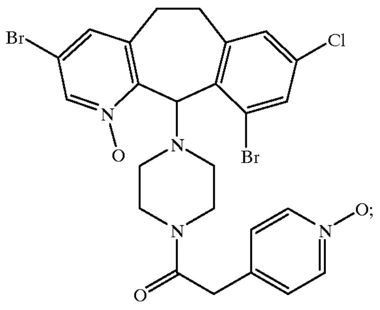
(+)-enantiomer
-continued
(33.0)
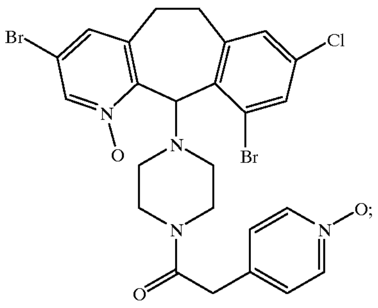
(-)-enantiomer
(34.0)
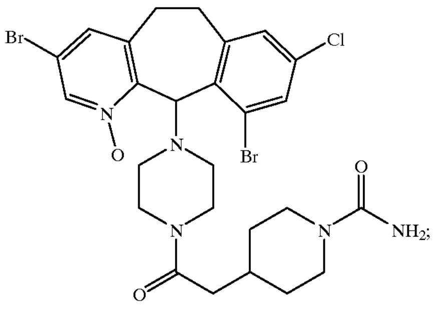
(+)-enantiomer
(35.0)
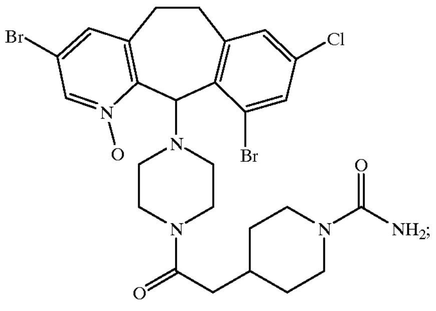
(-)-enantiomer
(36.0)
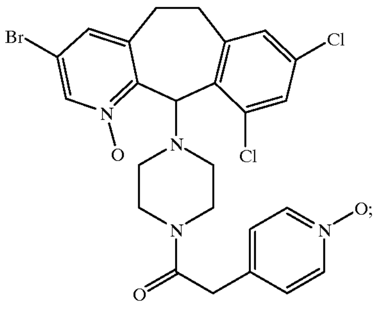
(+)-enantiomer -continued
(37.0)
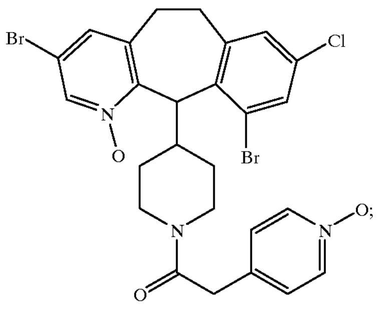
(+)-enantiomer
(38.0)
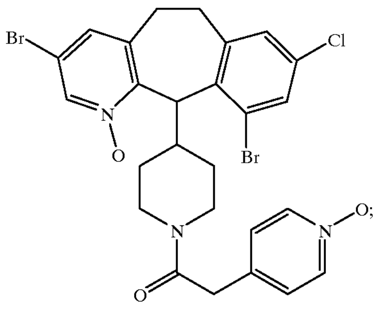
(-)-enantiomer
(39.0)
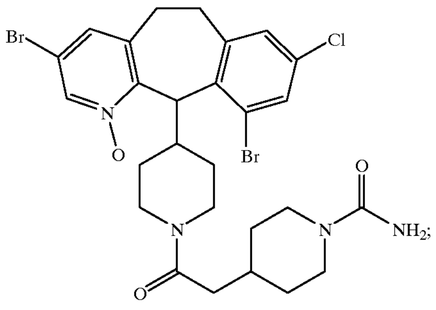
(+)-enantiomer
(40.0)
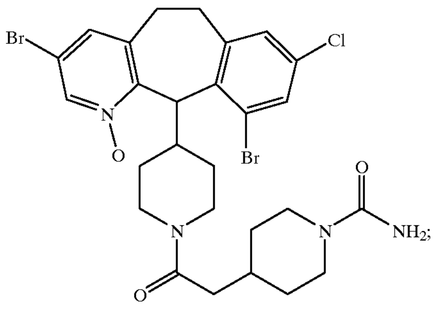
(-)-enantiomer
-continued
(41.0)
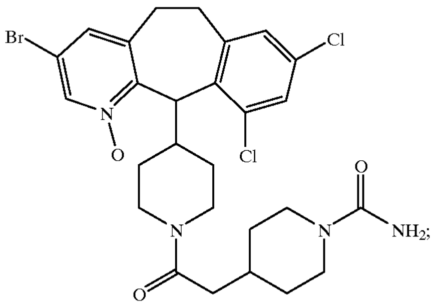
(+)-enantiomer
(42.0)
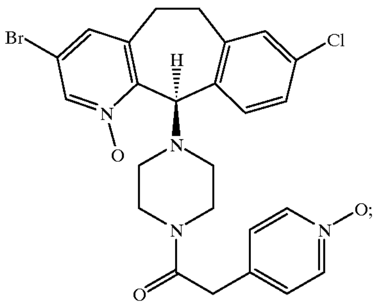
(43.0)
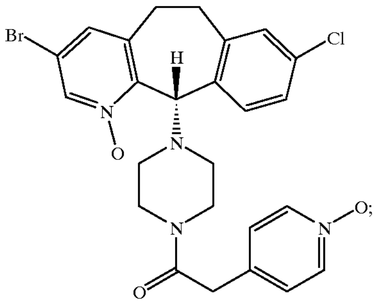
(44.0)
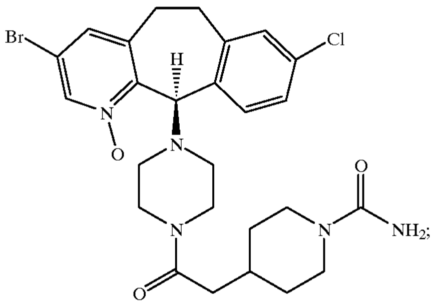
(45.0)
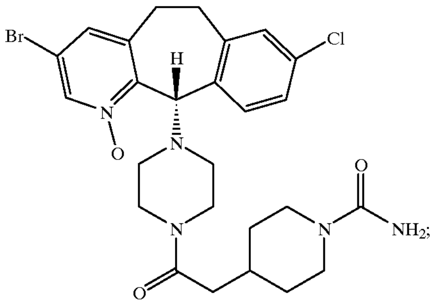

-continued
(46.0)
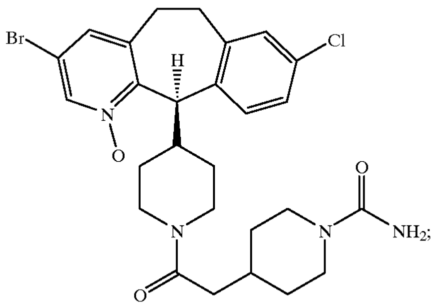
(47.0)
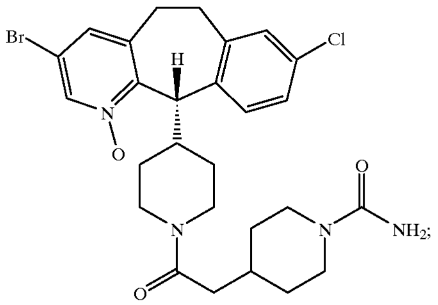
(48.0)
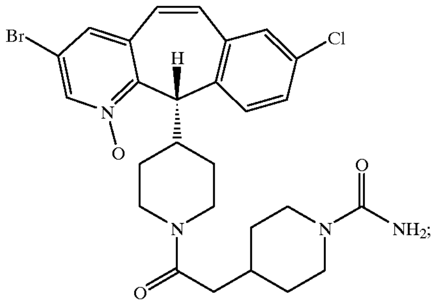
(49.0)
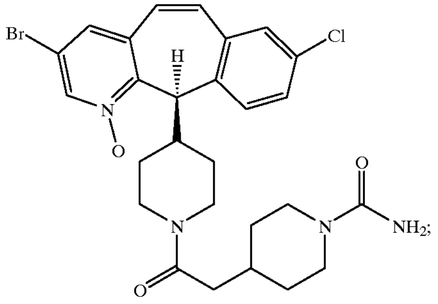
(50.0)
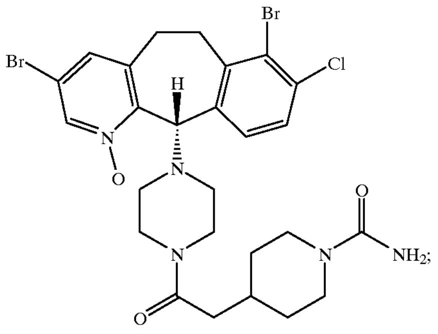
-continued
(51.0)
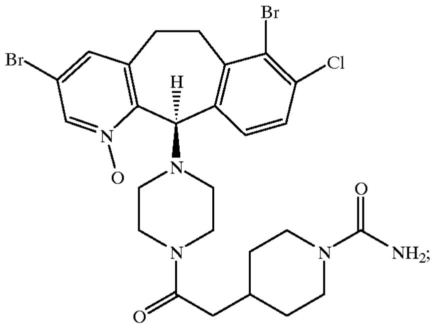
(52.0)
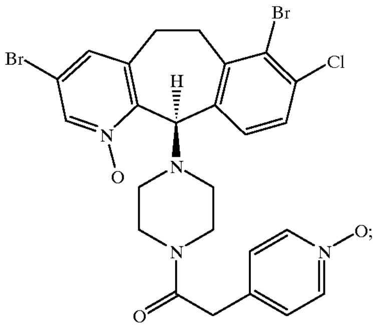
(53.0)
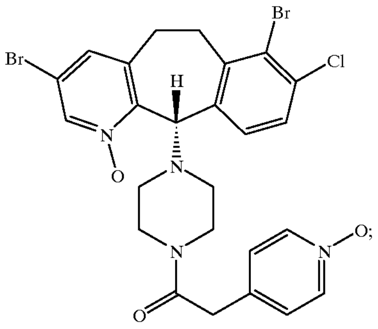
(54.0)
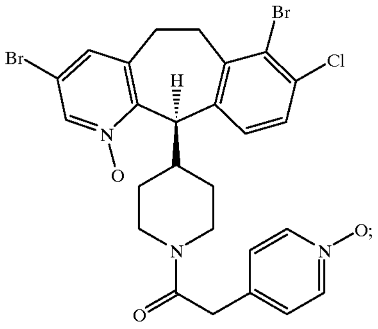

-continued
(55.0)
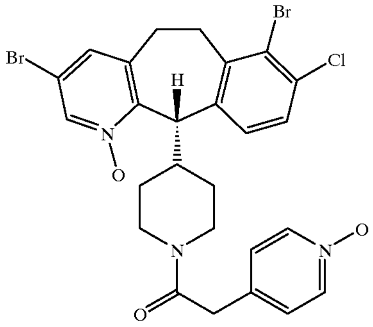
(56.0)
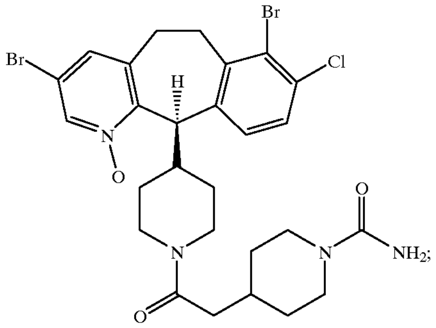
(57.0)
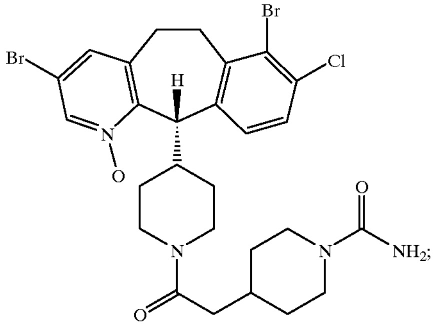
(58.0)
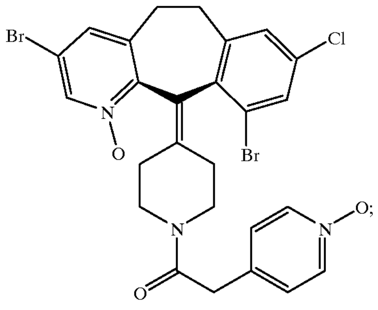
-continued
(59.0)
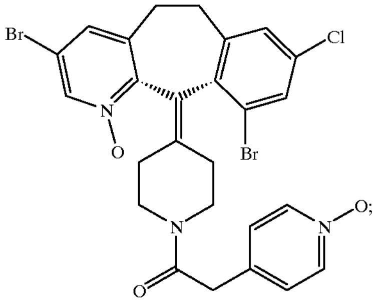
(60.0)
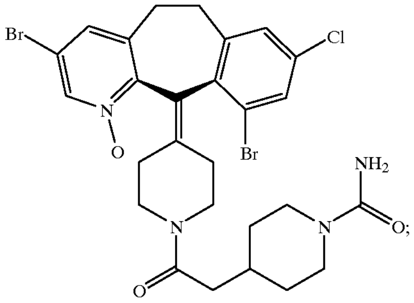
(61.0)
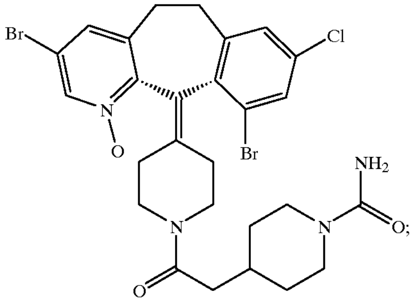
(62.0)
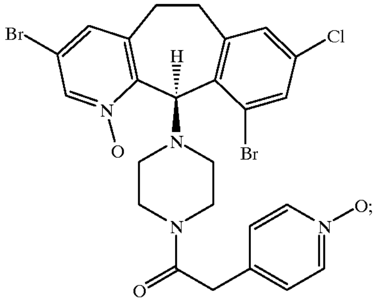
(63.0)
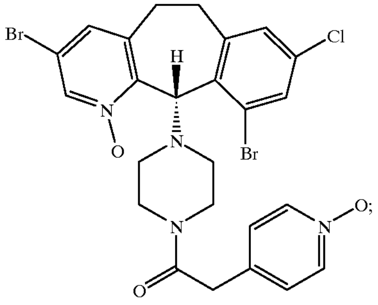

-continued
(64.0)
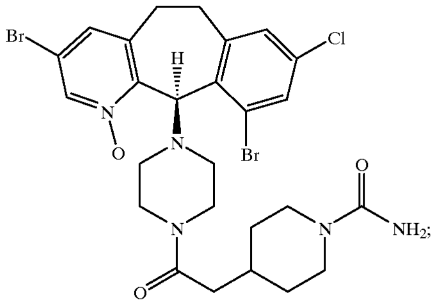
(65.0)
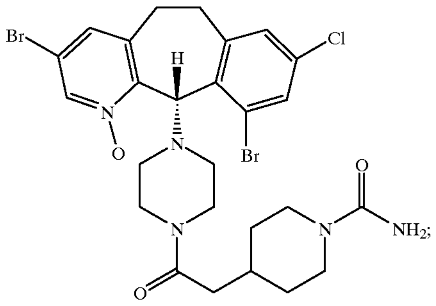
(66.0)
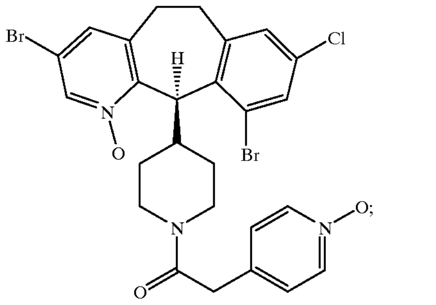
(67.0)
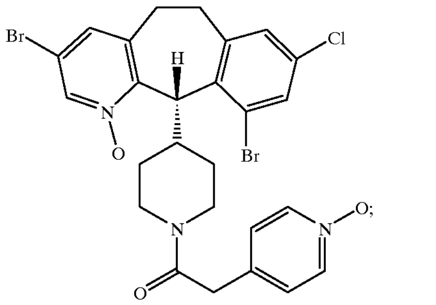
(68.0)
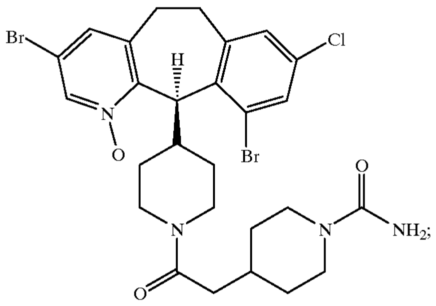
-continued
(69.0)
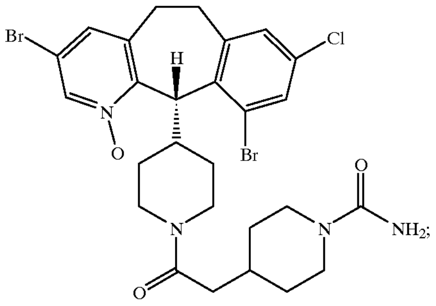
(70.0)
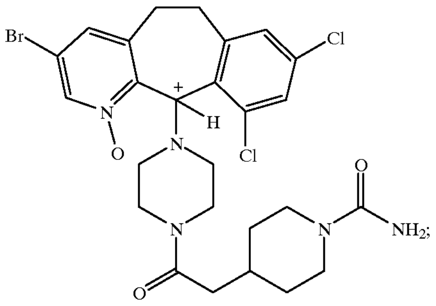
(71.0)
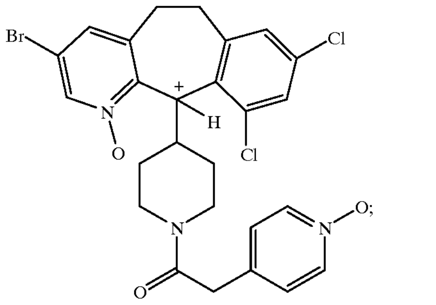
(72.0)
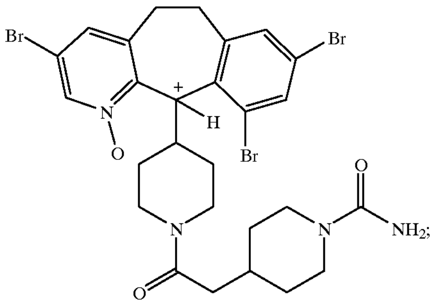
(73.0)
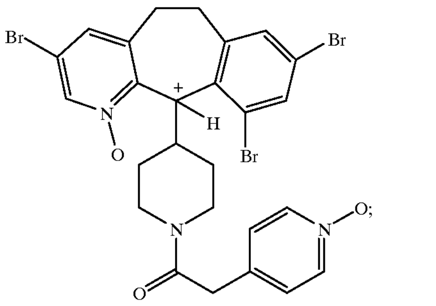

-continued (74.0)

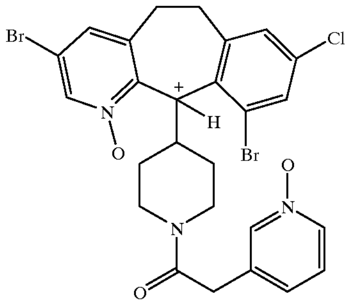

;

(75.0)

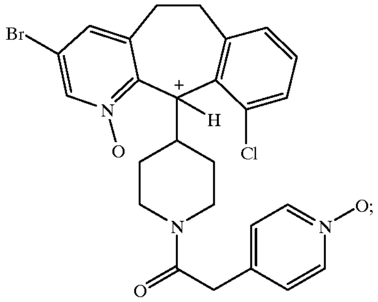

(76.0)

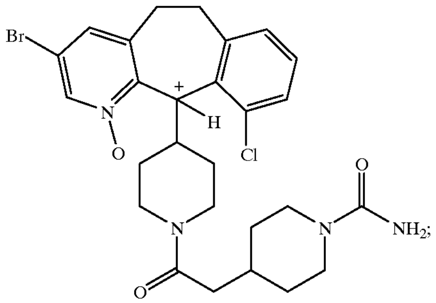

(77.0)

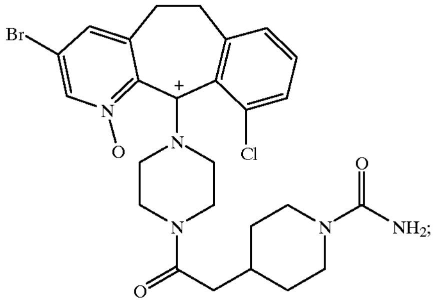

(78.0)

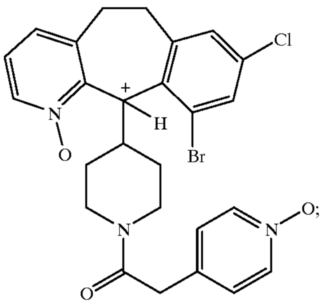

-continued (79.0)

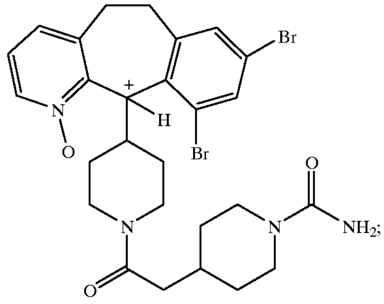

and (80.0)

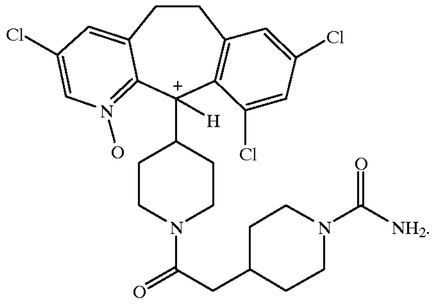

or pharmaceutically acceptable salts or solvates thereof.

U.S. application Ser. No. 08/877,739 filed Jun. 17, 1997 now abandoned discloses compounds of the formula:

(1.0)

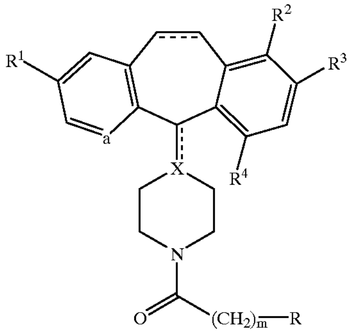

or a pharmaceutically acceptable salt or solvate thereof, wherein:

(A) a represents N or $NO^-$;

(B) $R^1$ and $R^3$ are the same or different halo atom;

(C) $R^2$ and $R^4$ are selected from H and halo, provided that at least one of $R^2$ and $R^4$ is H;

(D) the dotted line (---) represents an optional bond;

(E) X is N, C when the optional bond to X is present, or CH when the optional bond to X is absent;

(F) m is 0, 1 or 2;

(G) R represents:

1. a cycloalkyl ring selected from:

2.0

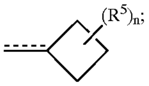

-continued 3.0

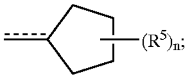

4.0

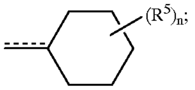

5.0

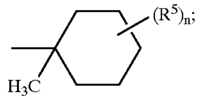

6.0

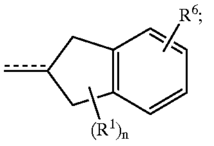

7.0

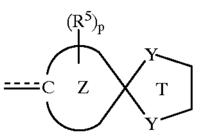

; or 8.0

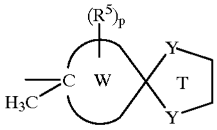

; or 2. a heterocycloalkyl ring selected from:

9.0

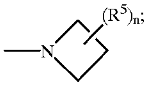

10.0

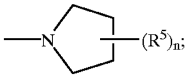

11.0

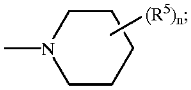

or 12.0

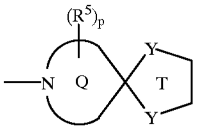

;

(H) p is 0, 1 or 2;

(I) when n or p is 1 then $R^5$ is selected from:

(1) =O;

(2) =N—OH;

(3) =N—$OR^7$ wherein $R^7$ represents a $C_1$ to $C_6$ alkyl group;

(4) =N—N(H)—C(O)—$R^8$ wherein $R^8$ represents —$NH_2$ or $C_1$ to $C_6$ alkyl;

(5) =N—O—$(CH_2)_r$—C(O)—$R^{11}$ wherein r is 1, 2, or 3, and $R^{11}$ is selected from: —OH, —O-alkyl or —$NH_2$;

(6) =N—O—$(CH_2)_s$—O—$R^{12}$, wherein s is 2, 3, or 4 and $R^{12}$ is selected from: H, alkyl or trialkylsilyl (e.g., $Si(CH_3)_2$—$C(CH_3)_3$);

(7) —$NR^{13}R^{14}$ wherein $R^{13}$ and $R^{14}$ are independently selected from:

(a) H;

(b) acyl;

(c) alkyl;

(d) aralkyl;

(d) cycloalkyl;

(e) heterocycloalkyl;

(f) heteroaralkyl;

(g) —$S(O)_2R^{15}$ wherein $R^{15}$ is $C_1$ to $C_6$ alkyl or aryl; or (h) an aralkyl, cycloalkyl, heterocycloalkyl, heteroaryl or heteroaralkyl having from 1 to 3 substituents selected from: =O, halo, —OH or —O-alkyl, wherein said substituents being bound to substitutable ring carbons;

or (8) $OR^{16}$ wherein $R^{16}$ is selected from:

(a) H;

(b) $C_1$ to $C_6$ alkyl;

(c) —$C(O)R^{17}$ wherein $R^{17}$ is selected from: alkyl, aryl, heteroaryl or aralkyl; or (d) —$C(O)NHR^{18}$ wherein $R^{18}$ is selected from: H, —$C(O)R^{19}$ wherein $R^{19}$ is selected from: —$C(Cl)_3$, alkyl or —$(CH_2)_2OH$;

(J) when n or p is 2, then each $R^5$ is the same or different and each $R^5$ is selected from:

(1) —$NR^{13}R^{14}$ wherein $R^{13}$ and $R^{14}$ are independently selected from:

(a) H;

(b) acyl;

(c) alkyl;

(d) aralkyl;

(d) cycloalkyl;

(e) heterocycloalkyl;

(f) heteroaralkyl;

(g) —$S(O)_2R^{15}$ wherein $R^{15}$ is $C_1$ to $C_6$ alkyl or aryl; or (h) an aralkyl, cycloalkyl, heterocycloalkyl, heteroaryl or heteroaralkyl having from 1 to 3 substituents selected from: =O, halo, —OH or —O-alkyl, wherein said substituents being bound to substitutable ring carbons; or;

(2) $OR^{16}$ wherein $R^{16}$ is selected from:

(a) H;

(b) $C_1$ to $C_6$ alkyl;

(c) —$C(O)R^{17}$ wherein $R^{17}$ is selected from: alkyl, aryl, heteroaryl or aralkyl; or (d) —$C(O)NHR^{18}$ wherein $R^{18}$ is selected from: H, —$C(O)R^{19}$ wherein $R^{19}$ is selected from: —$C(Cl)_3$, alkyl or —$(CH_2)_2OH$; or (K) provided that $R^1$ is not bound to a carbon atom adjacent to the nitrogen atom in Rings 9.0, 10.0, 11.0 or 12.0;

(L) Y is selected from O or S, provided that each Y is the same;

(M) Z represents the remainder of cycloalkyl Rings 2.0, 3.0 or 4.0, such that spiro ring T is bound to one of the carbon atoms in said cycloalkyl ring;

(N) W represents the remainder of cycloalkyl Ring 5.0, such that spiro ring T is bound to one of the carbon atoms in said cycloalkyl ring;

(O) Q represents the remainder of heterocycloalkyl Rings 9.0, 10.0 or 11.0, such that spiro ring T is bound to one of the carbon atoms in said heterocycloalkyl ring, provided that spiro Ring T is not bound to a carbon atom adjacent to the nitrogen atom; and (P) $R^6$ is selected from: alkoxy, alkyl or —OH.

U.S. application Ser. No. 08/877,677 filed Jun. 17, 1997 U.S. Pat. No. 5,925,639 discloses compounds of the formula:

I

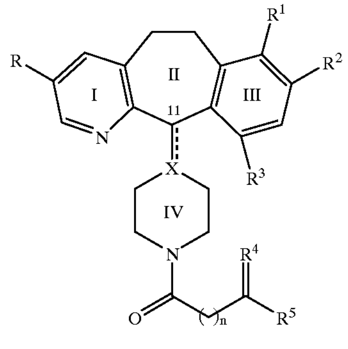

or an N-oxide thereof, or a pharmaceutically acceptable salt or solvate thereof, wherein:

R and $R^2$ are independently selected from halo;

$R^1$ and $R^3$ are independently selected from the group consisting of H and halo, provided that at least one of $R^1$ and $R^3$ is H;

X is N, CH or C, when the double bond is present at the C-11 position;

$R^4$ is =O, —NHOH, —N=NHR$^6$, —N=NHSO$_2$R$^6$, —N=NHCOR$^6$, —N=NHCONH$_2$, —N=NHCOCONH$_2$, (H, OH), (H, —OR$^6$), (H, —OCOR$^6$), (H, OSO$_2$R$^6$) or —E—(CH$_2$)$_{n1}$—G—, wherein $n_1$ is 1 to 5, and E and G are independently selected from the group consisting of O, S, and N, and are joined to the same carbon to form a cyclic structure;

$R^5$ is H, lower alkyl, aryl, heteroaryl, aralkyl, heteroaralkyl, heterocycloalkyl-alkyl, substituted aryl, substituted heteroaryl, substituted aralkyl, substituted heteroaralkyl or substituted heterocycloalkyl-alkyl, wherein the substituents are 1 to 3 groups independently selected from the group consisting of hydroxy, lower alkyl, halo, —NR$^7$R$^8$, —COOH, —CONH$_2$, —COR$^9$ and —SOR$^9$;

$R^6$ is lower alkyl, aryl, heteroaryl, aralkyl, heteroaralkyl, heterocycloalkyl-alkyl, substituted aryl, substituted heteroaryl, substituted aralkyl, substituted heteroaralkyl or substituted heterocycloalkyl-alkyl, wherein the substitution is as defined above for $R^5$;

$R^7$, $R^8$ and $R^9$ are independently selected from the group consisting of H, lower alkyl, aryl, and aralkyl; and n is 0, 1, 2, 3, 4 or 5.

U.S. application Ser. No. 08/877,741 filed Jun. 17, 1997 now abandoned discloses compounds of the formula:

(1.0)

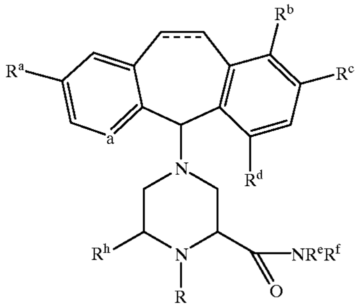

or a pharmaceutically acceptable salt or solvate thereof, wherein:

a represents N or NO$^-$;

$R^a$, $R^b$, $R^c$, and $R^d$ are the same or different, and are selected from the group consisting of H, halo, alkyl, and alkoxy, with the proviso that at least one, but not more than two of $R^a$, $R^b$, $R^c$ and $R^d$ are H;

the dotted line (---) represents an optional double bond;

R is selected from the group consisting of H, —S(O)$_2$R$^1$, —S(O)$_2$NR$^1$R$^2$, —C(O)R$^1$, and —C(O)NR$^1$R$^2$, wherein $R^1$ and $R^2$ are independently selected from the group consisting of H, alkyl, aryl, arylalkyl, heteroaryl, heteroarylalkyl, (C$_3$–C$_7$) cycloalkyl, cycloalkylalkyl, heterocycloalkyl, substituted alkyl, substituted aryl, substituted arylalkyl, substituted heteroaryl, substituted heteroarylalkyl, substituted (C$_3$–C$_7$) cycloalkyl, substituted cycloalkylalkyl, substituted heterocycloalkyl, wherein said substituted groups have one or more substituents selected from: alkyl, alkoxy, aralkyl, heteroarylalkyl, —NO$_2$, alkyloxyalkyl, alkyloxyalkyloxyalkyl, C$_3$–C$_7$ cycloalkyl, aryl, —CN, heteroaryl, heterocycloalkyl, =O, —OH, amino, substituted amino, nitro and halo;

$R^e$ and $R^f$ are independently selected from H, alkyl, alkyloxyalkyl, alkyloxyalkyloxyalkyl, aryl, arylalkyl, heteroaryl, heteroarylalkyl, (C$_3$–C$_7$) cycloalkyl, cycloalkylalkyl, heterocycloalkyl, substituted alkyl, substituted alkyloxyalkyl, substituted alkyloxyalkyloxyalkyl, substituted aryl, substituted arylalkyl, substituted heteroaryl, substituted heteroarylalkyl, substituted (C$_3$–C$_7$) cycloalkyl, substituted cycloalkylalkyl, substituted heterocycloalkyl, wherein said substituted groups have one or more substituents selected from: alkyl, alkoxy, aralkyl, heteroarylalkyl, —NO$_2$, alkyloxyalkyl, alkyloxyalkyloxyalkyl, C$_3$–C$_7$ cycloalkyl, aryl, —CN, heteroaryl, heterocycloalkyl, =O, —OH, amino, substituted amino, nitro and halo; or $R^e$ is selected from the group consisting of H, alkyl and aryl and $R^f$ is represented by —(CH$_2$)$_n$—R$^{15}$, wherein n is an integer from 0 to 8 and $R^{15}$ is selected from —C(O)NH$_2$, —SO$_2$NH$_2$, aryl, heteroaryl, cycloalkyl, heterocycloalkyl, optionally substituted by alkyl, alkoxy, aralkyl, heteroarylalkyl, —NO$_2$, alkyloxyalkyl, alkyloxyalkyloxyalkyl, C$_3$–C$_7$ cycloalkyl, aryl, —CN, heterocycloalkyl, =O, —OH, amino, substituted amino, nitro and halo;

or $R^{15}$ is

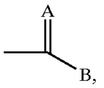

wherein B is OH or NH$_2$ and A is NH, O, NOH or NCN, or $R^{15}$ is NR$^{16}$R$^{17}$, wherein $R^{16}$ is H or alkyl and $R^{17}$ is H, alkyl, $SO_2CH_3$, or $C(O)NH_2$; or $R^e$ and $R^f$ together with the nitrogen to which they are bound, form a 5 or 6 membered heterocycloalkyl ring which is optionally substituted by OH, $NH_2$, $NHR^{16}$, $NHR^{17}$, $NR^{16}R^{17}$, or $(CH_2)_nR^{18}R^{19}$, wherein $R^{16}$ and $R^{17}$ are as defined above, $R^{18}$ is H or $C_1$–$C_6$ alkyl, and $R^{19}$ is selected from H, $C_1$–$C_6$ alkyl, substituted alkyl, arylalkyl, acyl (e.g., acetyl, benzoyl, etc.), carboxamido, alkyloxycarbonyl (e.g., methoxycarbonyl), arylalkyloxycarbonyl (e.g., benzyloxycarbonyl), amido derivatives derived from amino acids (e.g., glycine, alnine, serine, etc.), imidate (e.g., phenoxyimidate), cyanide, imidamido (e.g., C(=NH)$NH_2$, (C=$NSO_2NH_2$)$NH_2$, etc.), sulfonamido (e.g., $SO_2NH_2$, $SO_2N(CH_3)_2$) sulfonyl (e.g., $SO_2CH_3$, $SO_2C_6H_5$, $SO_2CH_2C_6H_5$, etc.), phosphinate (e.g., P(=O) $(CH_3)_2$), heterocyclyl and imidamido (e.g., (C=$NC_6H_5$)$C_6H_5$), (C=NH)$C_6H_5$ ,etc.), wherein n is as defined above; and $R^h$ is H or =O; with the further proviso that when $R^h$ is H and $R^b$ and $R^d$ are both H, $R^e$ is H and $R^f$ is

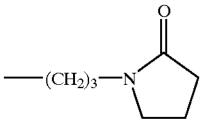

,

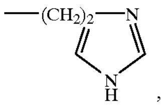

,

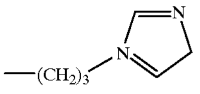

,

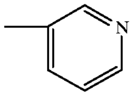

, or

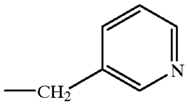

.

U.S. application Ser. No. 08/877,743 filed Jun. 17, 1997 now abandoned discloses compounds of the formula:

(1.0)

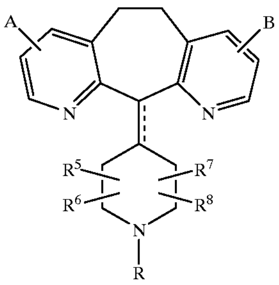

or (2.0)

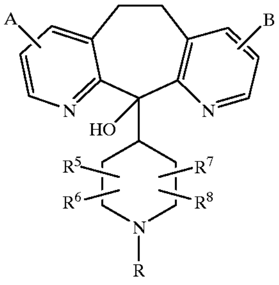

or a pharmaceutically acceptable salt or solvate thereof, wherein:

A is alkyl, halo or H;

B is methyl, halo or H;

the dotted line represents an optional double bond;

$R^5$, $R^6$ , $R^7$ and $R^8$ are independently selected from the group consisting of H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or one of $R^5$, $R^6$, $R^7$ and $R^8$ can be taken in combination with $R^{40}$ as defined below to represent —$(CH_2)_r$— wherein r is 1 to 4 which can be substituted with lower alkyl, lower alkoxy, —$CF_3$ or aryl, or $R^5$ is combined with $R^6$ to represent =O or =S and/or $R^7$ is combined with $R^8$ to represent =O or =S;

$R^{10}$ represents H, alkyl, aryl, or aralkyl (e.g., benzyl);

$R^{11}$ represents alkyl or aryl;

$R^{40}$ represents H, aryl, alkyl, cycloalkyl, alkenyl, alkynyl or —D wherein —D represents

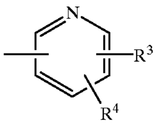

,

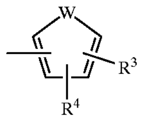

,

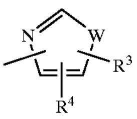

,

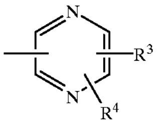

or

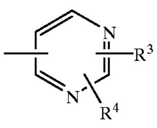

wherein $R^3$ and $R^4$ are independently selected from the group consisting of H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —OC(O)$R^{10}$, —$CO_2R^{10}$, —$OCO_2R^{11}$, —CN, —NHC(O)$R^{10}$, —$NHSO_2R^{10}$, —$CONHR^{10}$, —$CONHCH_2CH_2OH$, —$NR^{10}COOR^{11}$,

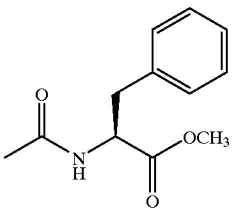

,

—$SR^{11}C(O)OR^{11}$ (e.g., —$SCH_2CO_2CH_3$), —$SR^{11}N(R^{75})_2$ wherein each $R^{75}$ is independently selected from H and —$C(O)OR^{11}$ (e.g., —$S(CH_2)_2NHC(O)O$-t-butyl and —$S(CH_2)_2NH_2$), benzotriazol-1-yloxy, tetrazol-5-ylthio, or substituted tetrazol-5-ylthio (e.g., alkyl substituted tetrazol5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

and W is O, S or $NR^{10}$ wherein $R^{10}$ is as defined above; said $R^{40}$ cycloalkyl, alkenyl and alkynyl groups being optionally substituted with from 1–3 groups selected from halo, —$CON(R^{10})_2$, aryl, —$CO_2R^{10}$, —$OR^{12}$, —$SR^{12}$, —$N(R^{10})_2$, —$N(R^{10})CO_2R^{11}$, —$COR^{12}$, —$NO_2$ or D, wherein —D, $R^{10}$ and $R^{11}$ are as defined above and $R^{12}$ represents $R^{10}$, —$(CH_2)_mOR^{10}$ or —$(CH_2)_qCO_2R^{10}$ wherein $R^{10}$ is as previously defined, m is 1 to 4 and q is 0 to 4; said alkenyl and alkynyl $R^{40}$ groups not containing —OH, —SH or —$N(R^{10})_2$ on a carbon containing a double or triple bond respectively; or $R^{40}$ represents phenyl substituted with a group selected from —$SO_2NH_2$, —$NHSO_2CH_3$, —$SO_2NHCH_3$, —$SO_2CH_3$, —$SOCH_3$, —$SCH_3$, or —$NHSO_2CF_3$, preferably, said group is located in the para (p-) position of the phenyl ring; and R is —$C(O)R^1$, —C(O)—$OR^1$, —$C(O)NR^1R^2$, —$S(O)_2$—$R^1$, or —$S(O)_2NR^1R^2$ wherein $R^1$ and $R^2$ are independently selected from the group consisting of H, alkyl, aryl, arylalkyl, heteroaryl, heteroarylalkyl, C3–C6 cycloalkyl, cycloalkylalkyl, heterocycloalkyl, substituted alkyl, substituted aryl, substituted arylalkyl, substituted heteroaryl, substituted heteroarylalkyl, substituted (C3–C6) cycloalkyl, substituted cycloalkylalkyl, substituted heterocycloalkyl, wherein said substituted groups have one or more substituents selected from: $C_1$–$C_6$ alkyl, alkoxy, aralkyl, heteroarylalkyl, —$NO_2$, alkyloxyalkyl, alkyloxyalkyloxyalkyl, $C_3$–$C_6$ cycloalkyl, aryl, —CN, heteroaryl, heterocycloalkyl, ═O, —OH, amino, substituted amino, nitro and halo, with the proviso that $R^1$ is not H for —C(O)—$OR^1$ or for —$S(O)^2R^1$.

U.S. application Ser. No. 08/877,457 filed Jun. 17, 1997 now abandoned discloses compounds of the formula:

(1.0)

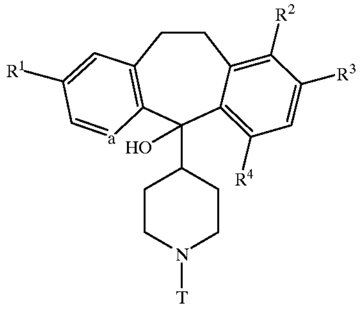

or a pharmaceutically acceptable salt or solvate thereof, wherein:

a represents N or $NO^-$;

$R^1$ and $R^3$ are the same or different and each represents halo;

$R^2$ and $R^4$ are the same or different and each is selected from H and halo, provided that at least one of $R^2$ and $R^4$ is H;

T is a substituent selected from $SO_2R$ or

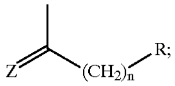

Z is O or S;

n is zero or an integer from 1 to 6;

R is alkyl, aryl, arylalkyl, heteroaryl, heteroarylalkyl, cycloalkyl, heterocycloalkyl, or $N(R^5)_2$;

$R^5$ is H, alkyl, aryl, heteroaryl or cycloalkyl.

U.S. application Ser. No. 08/877,673 filed Jun. 17, 1997 now abandoned discloses compounds of the formula:

(1.0)

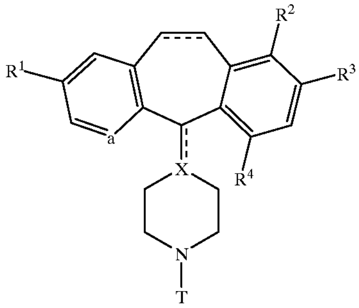

or a pharmaceutically acceptable salt or solvate thereof, wherein:

a represents N or $NO^-$;

$R^1$ and $R^3$ are the same or different and each represents halo;

$R^2$ and $R^4$ are each independently selected from H and halo, provided that at least one of $R^2$ and $R^4$ is H;

each dotted line (---) represents an optional bond;

X is N, C when the optional bond to X is present, or CH when the optional bond to X is absent;

T is a substituent selected from:

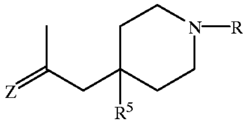

or

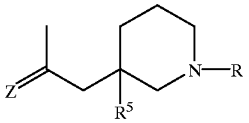

Z represents O or S;

R represents —$C(O)N(R^{10})_2$, —$CH_2C(O)N(R^{10})_2$, —$SO_2R^{10}$, —$SO_2N(R^{10})_2$, —$C(O)R^{11}$, —C(O)—O—$R^{11}$, alkyl, aryl, aralkyl, cycloalkyl, heterocycloalkyl or heteroaryl;

$R^5$ represents alkyl, aryl, aralkyl, heteroaryl, heteroarylalkyl, cycloalkyl, $OR^{12}$, $NR^{12}H$, $SR^{12}$, $SOR^{12}$ (where $R^{12}$ is not H), or $SO_2R^{12}$ (where $R^{12}$ is not H); and each $R^{10}$ independently represents H, alkyl, aryl, or aralkyl (e.g., benzyl);

$R^{11}$ is alkyl, aryl, aralkyl, heteroaryl or heterocycloalkyl;

$R^{12}$ is selected from H, alkyl, aryl, aralkyl, heteroaryl, heteroarylalkyl, or heterocycloalkyl.

U.S. application Ser. No. 08/876,507 filed Jun. 17, 1997 now abandoned discloses compounds of the formula:

(1.0)

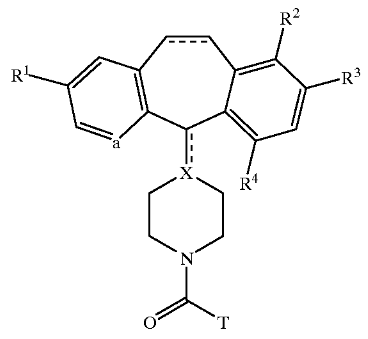

or a pharmaceutically acceptable salt or solvate thereof, wherein:

a represents N or $NO^-$;

$R^1$ and $R^3$ are the same or different halo atom;

$R^2$ and $R^4$ are selected from H and halo, provided that at least one of $R^2$ and $R^4$ is H;

the dotted line (---) represents an optional bond;

X is N, C when the optional bond is present, or CH when the optional bond is absent;

T represents

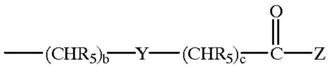

wherein $R_5$ represents H, $(C_1-C_6)$alkyl or a bond; b and c are independently 0 to 3; and Y represents

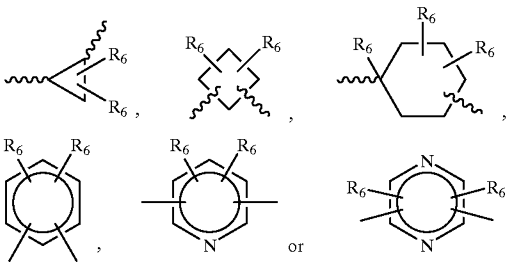

$R_6$ represents $(C_1-C_6)$alkyl or H;

Z represents $OR_7$, $R_7$ or $NR_8R_9$;

$R_7$ represents H, $(C_1-C_6)$alkyl or $(C_1-C_6)$alkyl substituted by $OR_5$, $COR_5$, phenyl or heteroaryl; and $R_8$ and $R_9$ independently represent H, OH, $(C_1-C_6)$alkyl or $(C_1-C_6)$ alkyl substituted by $OR_5$, $COR_5$, phenyl, heteroaryl or $R_8$ and $R_9$ taken together with the nitrogen atom in $NR_8R_9$ form an unsubstituted or substituted five or six membered heterocyclic ring system containing carbon and one to four heteroatoms selected from N, O and S, SO and $SO_2$ said heterocyclic substituents being $(C_1-C_8)$ alkanoyl, $(C_1-C_6)$alkyl or $(C_1-C_6)$penthalo alkyl.

U.S. application Ser. No. 08/876,507 also discloses now abandoned compounds represented by the formula:

(1.3a)

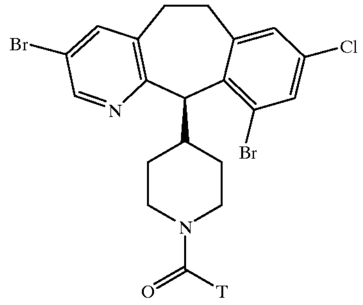

wherein T represents

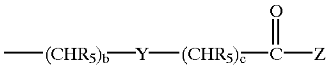

wherein $R_5$ represents H, $(C_1-C_6)$alkyl or a bond; b and c are independently 0 to 3; and Y represents

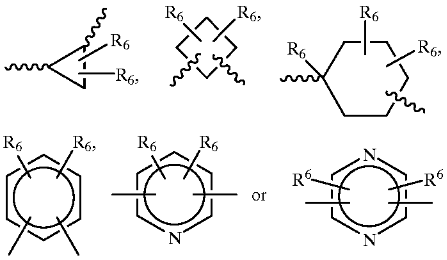

$R_6$ represents $(C_1-C_6)$alkyl or H;

Z represents $OR_7$; $R_7$ or $NR_8R_9$; $R_7$ represents H,$(C_1-C_6)$ alkyl or $(C_1-C_6)$ alkyl substituted by; $OR_5$, $COR_5$, phenyl or heteroaryl; and $R_8$ and $R_9$ independently represent H, OH or $(C_1-C_6)$ alkyl, $(C_1-C_6)$alkyl substituted by $OR_5$, $COR_5$, phenyl, heteroaryl or $R_8$ and $R_9$ taken together with the nitrogen atom in $NR_8R_9$ form an unsubstituted or substituted five or six membered heterocyle ring system containing carbon and one to four heteroatoms selected from N, O and S, SO and $SO_2$ said heterocyclic substituents being $(C_1-C_8)$alkanoyl, $(C_1-C_6)$alkyl or $(C_1-C_6)$perhalo alkyl.

Preferred FPT inhibitors include peptides and peptidomimetic compounds and fused-ring tricyclic compounds of the above documents (which have already been incorporated herein by reference thereto). More preferred are the fused-ring tricyclic compounds, and most preferred are the compounds of WO 97/23478.

The FPT inhibition and anti-tumor activity of the compounds used as FPT inhibitors in this invention can be determined by methods known in the art—see, for example, the in vitro Enzyme Assays, Cell-Based Assays, Cell Mat Assays, and in vivo Anti-Tumor Studies in WO 95/10516 published Apr. 20, 1995, and the soft agar assay in WO 97/23478 published Jul. 3, 1997.

EXAMPLES

The examples A through G below investigated the in vitro effect of combining paclitaxel with the following FPT inhibitory compound (referred to as "Compound X" in the Tables below):

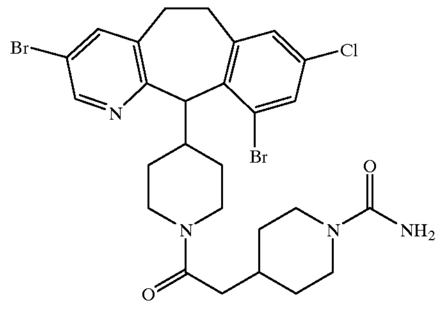

(+)- enantiomer

As mentioned previously, FIGS. 1 through 15 show three examples where clear synergy was observed. These three examples are Examples A through C as discussed below. Similar results were observed in the DLD-1 colon, HTB177 lung, PA-1 ovarian, LNCaP prostate, AsPC-1 pancreatic and PANC-1 pancreatic models (summarized in the table below; data not shown). Clear Antagonism was observed in one cell line MDA-MB-231 (FIGS. 16–20, Example D). Mixed results were seen in MDA-MB-468 (FIGS. 21–35, Examples E through G).

Analysis of in vitro Drug Interactions between Compound X and Paclitaxel

| Cell Line | Tumor Type | p53 Protein | Ras Mutation | Isobole Analysis |
|---|---|---|---|---|
| DLD-1 | Human Colorectal | Mutant | K-ras | Synergy (p = 0.0592) |
| NCI-H460 | Human Lung | Wild-type | K-ras | Synergy (p = 0.0309) |
| MDA-MB-468 | Human Breast | Mutant | Wild-type | Antagonism (p = 0.0001) |
| MDA-MB-468 | Human Breast | Mutant | Wild-type | Synergy (p = 0.0237) |
| MDA-MB-468 | Human Breast | Mutant | Wild-type | Synergy (p = 0.0094) |
| MDA-MB-231 | Human Breast | Mutant | Mutant | Antagonism (p = 0.0093) |
| Mid T #2-1 | Mouse Mammary | ? | ? | Synergy (p = 0.011) |
| PA-1 | Human Ovarian | Wild-type | Kras | Synergy (p = 0.0122) |
| DU-145 | Human Prostate | Mutant | Wild-type | Synergy (p = 0.0238) |
| LNCaP | Human Prostate | Wild-type | Wild-type | Synergy (p = 0.0021) |
| AsPC-1 | Human Pancreatic | Null | K-ras | Synergy (p = 0.0328) |
| MiaPaCa2 | Human Pancreatic | Mutant | K-ras | Synergy (p = 0.0002) |
| PANC-1 | Human Pancreatic | Mutant | K-ras | Synergy (p = 0.0011) |

To prepare compositions of Compound X for the following examples, the compound was dissolved in 100% DMSO. The final concentration of DMSO within cells was ≦0.02% DMSO in cell culture medium. In the case of paclitaxel, stock paclitaxel was dissolved in 100% ethanol. The final concentration of ethanol was ≦0.001% in cell culture medium.

Example A

Compound X Synergizes with Paclitaxel to Inhibit Proliferation of MiaPaCa2 Pancreatic Tumor Cells Methods: MiaPaCa2 pancreatic tumor cells were aliquoted into culture wells and allowed to attach for 3 hrs. The cells were incubated with paclitaxel for 4 hrs., washed, then Compound X was added and the incubation continued for 7 days. Cell proliferation was quantified using the MTT assay of Mosmann (see Mosmann, T. (1983) *J. Immunol. Meth.,* 65: 55–63). The data was analyzed using the Thin Plate Spline methodology of O'Connell and Wolfinger (1997) (See O'Connell, M. A., and Wolfinger, R. D., *J. Computational and Graphical Statistics* 6: 224–241, 1997).

Results: Compound X and paclitaxel had synergistic efficacy (p=0.0002). FIG. 1 shows the Isobole analysis for the interaction of these drugs while FIG. 2 shows the 3-dimensional model of cell proliferation from which FIG. 1 was derived. FIGS. 3 4, and 5 show the dose response curves before statistical analysis.

Example B

Compound X Synergizes with Paclitaxel to Inhibit Proliferation of p53$^{mut}$ DU-145 Prostate Tumor Cells Methods: p53$^{mut}$ DU-145 prostate tumor cells were aliquoted into culture wells and allowed to attach for 3 hrs. The cells were incubated with paclitaxel for 4 hrs., washed, then Compound X was added and the incubation continued for 7 days. Cell proliferation was quantitated using the MTT assay of Mosmann. The data was analyzed using the Thin Plate Spline methodology of O'Connell and Wolfinger (1997).

Results: Compound X and paclitaxel had synergistic efficacy (p=0.0238). FIG. 6 shows the Isobole analysis for the interaction of these drugs while FIG. 7 shows the three dimensional model of cell proliferation from which FIG. 6 was derived. FIGS. 8, 9, and 10 show the dose response curves before statistical analysis.

Example C

Compound X Synergizes with Paclitaxel to Inhibit Proliferation of MidT#2-1 Transgenic Mouse Mammary Tumor Cells Methods: MidT#2-1 mouse tumor cells were aliquoted into culture wells and allowed to attach for 3 hrs. The cells were incubated with paclitaxel for 4 hrs., washed, then Compound X was added and the incubation continued for 7 days. Cell proliferation was quantitated using the MTT assay of Mosmann. The data was analyzed using the Thin Plate Spline methodology of O'Connell and Wolfinger (1997).

Results: Compound X and paclitaxel had synergistic efficacy (p=0.0110). FIG. 11 shows the Isobole analysis for the interaction of these drugs while while FIG. 12 shows the 3-dimensional model of cell proliferation from which FIG. 11 was derived. FIGS. 13, 14, and 15 show the dose response curves before statistical analysis.

Example D

Compound X and Paclitaxel Have an Antagonistic Interaction in p53$^{mut}$ MDA-MB-231 Breast Cancer Cells Methods: p53$^{mut}$ MDA-MB-231 tumor cells were aliquoted into culture wells and allowed to attach for 3 hrs. The cells were incubated with paclitaxel for 4 hrs., washed, then Compound X was added and the incubation continued for 7 days. Cell proliferation was quantitated using the MTT assay of Mosmann. The data was analyzed using the Thin Plate Spline methodology of O'Connell and Wolfinger (1997).

Results: Compound X and paclitaxel had antagonistic interaction (p=0.0093). FIG. 16 shows the Isobole analysis for the interaction of these drugs while FIG. 17 shows the 3-dimensional model of cell proliferation from which FIG. 16 was derived. FIGS. 18, 19, and 20 show the dose response curves before statistical analysis.

Examples E, F and G

Studies of Compound X and Paclitaxel in $p53^{mut}$ MDA-MB-468 Breast Cancer Cells In the following three Examples (E through G), the effects of Compound X and paclitaxel were studied in $p53^{mut}$ MDA-MB-468 breast cancer cells. In two of the examples (Examples F and G), Compound X and paclitaxel had synergistic interaction, but in Example E the interaction was found to be antagonistic. The cells in Examples F and G appear to have had a better proliferative rate than the cells in Example E, which may have influenced the outcome, although the Isobole curves are atypical in all three of these studies with $p53^{mut}$ MDA-MB-468 breast cancer cells.

Data based on combining a particular peptido-mimetic FTI compound with several different chemotherapeutic agents (e.g., taxol (paclitaxel), doxorubicin, cisplatin, and vinblastine) in breast cancer cell lines MDA-MB-468 and MCF-7 are presented in Moasser, MM, et aL. Proc. Natl. Acad. Sci. USA 95: 1369–1374, 1998. Results of additional experiments combining the FTI compound with taxol were reported in the Moasser publication (data not shown) for T47D, MDA-MB-231, and MCF-7 breast cancer cells, and for DU-145 prostate cancer cells. Additional results were reported in the publication (data not shown) for fluorouracil in breast cancer cells.

Example E

Compound X and Paclitaxel Have an Antagonistic Interaction in $p53^{mut}$ MDA-MB-468 Breast Cancer Cells (Study #1)

Methods: $p53^{mut}$ MDA-MB-468 tumor cells were aliquoted into culture wells and allowed to attach for 3 hrs. The cells were incubated with paclitaxel for 4 hrs., washed, then Compound X was added and the incubation continued for 7 days. Cell proliferation was quantitated using the MTT assay of Mosmann. The data was analyzed using the Thin Plate Spline methodology of O'Connell and Wolfinger (1997).

Results: Compound X and paclitaxel had antagonistic interaction (p=0.0001). FIG. 21 shows the Isobole analysis for the interaction of these drugs while FIG. 22 shows the 3-dimensional model of cell proliferation from which FIG. 21 was derived. FIGS. 23, 24, and 25 show the dose response curves before statistical analysis.

Example F

Compound X and Paclitaxel Have a Synergistic Interaction in $p53^{mut}$ MDA-MB-468 Breast Cancer Cells (Study #2)

Methods: $p53^{mut}$ MDA-MB-468 tumor cells were aliquoted into culture wells and allowed to attach for 3 hrs. The cells were incubated with paclitaxel for 4 hrs., washed, then Compound X was added and the incubation continued for 7 days. Cell proliferation was quantified using the MTT assay of Mosmann. The data was analyzed using the Thin Plate Spline methodology of O'Connell and Wolfinger (1997).

Results: Compound X and paclitaxel had a synergistic interaction (p=0.0237). FIG. 26 shows the Isobole analysis for the interaction of these drugs, while FIG. 27 shows the 3-dimensional model of all proliferation from which FIG. 26 was derived. FIGS. 28, 29, and 30 show the dose response curves before statistical analysis. The cells in this study had a better proliferative rate than the cells in the previous study (Example E), which may have influenced the outcome, although the Isobole curves are atypical in both studies.

Example G

Compound X and Paclitaxel Have a Synergistic Interaction in $p53^{mut}$ MDA-MB-468 Breast Cancer Cells (Study #3)

Methods: $p53^{mut}$ MDA-MB-468 tumor cells were aliquoted into culture wells and allowed to attach for 3 hrs. The cells were incubated with paclitaxel for 4 hrs., washed, then Compound X was added and the incubation continued for 7 days. Cell proliferation was quantified using the MTT assay of Mosmann. The data was analyzed using the Thin Plate Spline methodology of O'Connell and Wolfinger (1997).

Results: Compound X and paclitaxel had a synergistic interaction (p=0.0094). FIG. 31 shows the Isobole analysis for the interaction of these drugs, while FIG. 32 shows the 3-dimensional model of all proliferation from which FIG. 31 was derived. FIGS. 33, 34, and 35 show the dose response curves before statistical analysis. As was the case with Example F, the cells in Example G appear to have had a better proliferative rate than the cells in Example E, which may have influenced the outcome, although the Isobole curves are atypical in all these studies with $p53^{mut}$ MDA-MB-468 breast cancer cells.

Example H

IN VIVO COMBINATION THERAPY—B.I.D.

The effect of in vivo combination therapy of an FPT inhibitory compound (referred to as "Compound X" in the Tables below)

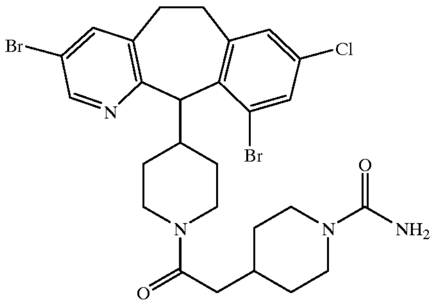

(+)- enantiomer with paclitaxel on HTB 177 xenografts (NCI-H460, a human lung large cell carcinoma) using two times a day dosing was determined.

Athymic nu/nu female mice, 5–6 weeks old were used. On Day 0, HTB 177 cells, $3 \times 10^6$, were injected s.c. into the flank of 120 mice. An overview of the groups is set forth below:

| | | | |
|---|---|---|---|
| Group 1 | No treatment | | 10 mice |
| Group 2 | Vehicle control I | p.o. | 10 mice |
| Group 3 | Compound X, 80 mpk/dosing, | p.o. | 10 mice |
| Group 4 | Compound X, 20 mpk/dosing, | p.o. | 10 mice |
| Group 5 | paclitaxel 20 mpk/dosing | i.p. | 10 mice |
| Group 6 | paclitaxel 5 mpk/dosing | i.p. | 10 mice |
| Group 7 | Compound X 80 mpk & paclitxel 20 | | 10 mice |

-continued

| | | | |
|---|---|---|---|
| | mpk | | |
| Group 8 | Compound X 80 mpk & paclitaxel 5 mpk | | 10 mice |
| Group 9 | Compound X 20 mpk & paclitaxel 20 mpk | | 10 mice |
| Group 10 | Compound X 20 mpk & paclitaxel 5 mpk | | 10 mice |
| Group 11 | Vehicle control II | p.o. & i.p. | 10 mice |

Formulation: Compound X for groups 3, 4, 7, 8, 9, and 10 was dissolved in 20% hydroxyl-propyl-betacyclodexatrin (Vehicle I). 0.2 ml of Compound X solution was the dosing volume. Paclitaxel was dissolved in a diluted ethanol/cremophor EL solution (Vehicle II) and the i.p. dosing volume for paclitaxel was 0.1 ml.

The 80 mpk dosing solution of Compound X was made by adding 17 ml of 20% HPBCD to a 50 ml tube containing 136 mg of Compound X to dissolve the compound. The mixture was sonicated until a complete solution was made.

The 20 mpk dosing solution was made by placing 2 ml of the 80 mpk solution into a 15 ml tube, adding 6 ml of 20% HPBCD, and vortexing the solution to mix it.

Protocol: Tumor cells were inoculated into 120 mice in the morning of Day 0, and the mice are weighed, randomized, and ear-marked afterwards. Drug treatment began at 7:30 am on Day 4. The animals in groups 2, 3, 4, 7, 8, 9, 10, and 11 were dosed p.o., B.I.D. with Compound X or vehicle I solution (HPBCD), at 7:30 am, and 7:30 pm, 7 days a week. Groups 5, 6, 7, 8, 9, 10 and 11 are dosed i.p., on Day 4 to Day 7, with paclitaxel or vehicle II solution. Tumor growth is quantitated by measuring tumor volume on Day 7 and Day 14.

The results are given in Table 1 below:

TABLE 1

| Group | Days of Treatment | Median Tumor Vol. | Mean Tumor Vol. | Standard Deviation | Average Inhibition |
|---|---|---|---|---|---|
| 1. No treatment | 7 | 114.58 | 124.36 | 37.32 | |
| | 14 | 632.81 | 718.82 | 338.44 | |
| 2. Vehicle | 7 | 130.29 | 156.17 | 62.78 | |
| | 14 | 738.8 | 760.87 | 379.45 | |
| 3. Compound X | 7 | 32.83 | 34.84 | 13.44 | |
| (80 mpk) | 14 | 28.08 | 34.68 | 27.95 | 95% |
| 4. Compound X | 7 | 95.61 | 90.55 | 28.56 | |
| (20 mpk) | 14 | 357.72 | 364.59 | 114.83 | 52% |
| 5. paclitaxel | 7 | 37.75 | 48.52 | 20.34 | |
| (20 mpk) | 14 | 75.19 | 91.61 | 57.08 | 88% |
| 6. paclitaxel | 7 | 78.93 | 91.59 | 35.14 | |
| (5 mpk) | 14 | 178.73 | 298.20 | 280.59 | 61% |
| 7. Compound X | 7 | 23.88 | 23.63 | 6.58 | |
| (80 mpk) & paclitaxel (20 mpk) | 14 | 0 | 0 | 0 | 100% |
| 8. Compound X | 7 | 32.76 | 33.19 | 27 | |
| (80 mpk) & paclitaxel (5 mpk) | 14 | 23.60 | 30.75 | 72.78 | 95% |
| 9. Compound X | 7 | 30.03 | 32.49 | 11 | |
| (20 mpk) & paclitaxel (20 mpk) | 14 | 48.32 | 65.18 | 36.18 | 91% |
| 10. Compound X | 7 | 38.49 | 40.37 | 9.66 | |
| (20 mpk) & paclitaxel (5 mpk) | 14 | 97.65 | 103.25 | 46.19 | 86% |
| 11. Ethanol/ | 7 | 194.77 | 190.48 | 61.81 | |
| Cremaphor | 14 | 1147.61 | 1080.01 | 632.87 | |

With regard to Table 1 above, it is particularly noteworthy that while Compound X alone at 20 mpk exhibited only 52% average inhibition (Experiment 4) and paclitaxel alone at 5 mpk exhibited only 61% average inhibition (Experiment 6), the combination of Compound X at 20 mpk plus paclitaxel at 5 mpk resulted in 86% average inhibition (see Experiment 10).

Example J

IN VIVO COMBINATION THERAPY—Q.I.D.

The effect of in vivo combination therapy of an FPT inhibitory compound (referred to as "Compound X" in Table 2 below)

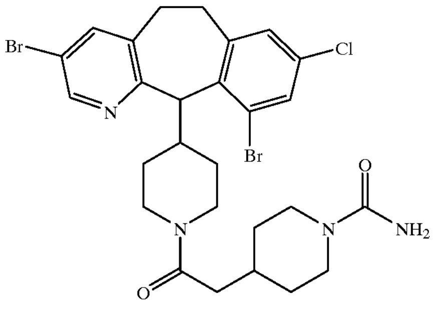

(+)- enantiomer with chemotherapeutic agents on HTB 177 (NCI-H460, a human lung large cell carcinoma) using four times a day dosing was determined.

Athymic nu/nu female mice, 5–6 weeks old were used. On Day 0, HTB 177, $3\times10^6$, was injected s.c. into the flank of 170 mice. Afterwards the mice were weighed and randomly divided into 17 groups of 10 mice per group. Drug treatment began at about 6:00 am on Day 1. The mice in groups 2, 3, 4, 5, 9, 10, 11, 12, 13, 14, 15, 16, and 17 were dosed p.o., q.i.d., at about 6 am, 12 noon, 6 pm, and 12 midnight, 7 days a week for 4 weeks. The mice in Groups 6–17 were dosed i.p. once with the indicated cytotoxic agent (see Table 1) on Day 13. The primary tumors were measured two times a week. The results are given in Table 2.

TABLE 2

| Group | Treatment | % Average Inhibition |
|---|---|---|
| 1 | No treatment - control | — |
| 2 | Vehicle, 20% HPBCD, QID, Days 1–26, p.o. | — |
| 3 | Compound X, 40 mpk, QID, Days 1–26, p.o. | 68 |
| 4 | Compound X, 40 mpk, QID, Days 1–12, p.o.<br>Vehicle, 40 mpk, QID, Days 13–26, p.o. | 64 |
| 5 | Vehicle, 40 mpk, QID, Days 1–12, p.o.<br>Compound X, 40 mpk, QID, Days 13–26, p.o. | 25 |
| 6 | Cytoxan, 200 mpk, once on Day 13, i.p. | 9 |
| 7 | 5-FU, 50 mpk, once on Day 13, i.p. | 28 |
| 8 | Vincrisitine, 1 mpk, once on Day 13, i.p. | 7 |
| 9 | Compound X, 40 mpk, QID, Days 1–26<br>Cytoxan, 200 mpk, once on Day 13, i.p. | 81 |
| 10 | Compound X, 40 mpk, QID, Days 1–26<br>5-FU, 50 mpk, once on Day 13, i.p. | 80 |
| 11 | Compound X, 40 mpk, QID, Days 1–26<br>Vincristine, 1 mpk, once on Day 13, i.p. | 80 |
| 12 | Vehicle, 40 mpk, QID, Days 1–12<br>Cytoxan, 200 mpk, once on Day 13, i.p.<br>Compound X, 40 mpk, QID, Days 13–26. p.o. | 36 |
| 13 | Vehicle, 40 mpk, QID, Days 1–12, p.o.<br>5-FU, 50 mpk, once on Day 13, i.p.<br>Compound, 40 mpk, QID, Days 13–26. p.o. | 25 |
| 14 | Vehicle, 40 mpk, QID, Days 1–12, p.o.<br>Vincristine, 1 mpk, once on Day 13, i.p.<br>Compound X, 40 mpk, QID, Days 13–26. p.o. | 12 |
| 15 | Compound X, 40 mpk, QID, Days 1–12, p.o.<br>Cytoxan, 200 mpk, once on Day 13, i.p.<br>Vehicle, 40 mpk, QID, Days 13–26. p.o. | 83 |
| 16 | Compound X, 40 mpk, QID, Days 1–12, p.o.<br>5-FU, 50 mpk, once on Day 13, i.p.<br>Vehicle, 40 mpk, QID, Days 13–26. p.o. | 68 |
| 17 | Compound X, 40 mpk, QID, Days 1–12, p.o.<br>Vincristine, 1 mpk, once on Day 13, i.p.<br>Vehicle, 40 mpk, QID, Days 13–26. p.o. | 85 |

The Compound X (FPT Inhibitory Compound) for Groups 3, 4, 5, 9, 10, 11, 12, 13, 14, 15, 16, and 17 was dissolved in 20% hydroxypropylbetacyclodextran (HPBCD). Cytoxan, 5-FU, and Vincristine were dissolved in sterile water.

The 40 mpk dosing solution of Compound X was made by adding 39.6 ml of 20% HPBCD to a 50 ml tube containing 320 mg of Compound X to dissolve the compound. The mixture was sonicated until a complete solution was made. Aliquots of the solution were prepared ahead of time for the needed number of doses for the following 24 hour period. Aliquots of the 20% HPBCD were period ahead of time for the needed number of dosings with Vehicle Control on the specific day of dosing.

The 20 mpk dosing solution was made by placing 2 ml of the 80 mpk solution into a 15 ml tube, adding 6 ml of 40% HPBCD, and vortexing the solution to mix it.

Example K

IN VIVO COMBINATION THERAPY—B.I.D.

The effect of in vivo combination therapy of an FPT inhibitory compound (referred to as "Compound X" in Table 3 below)

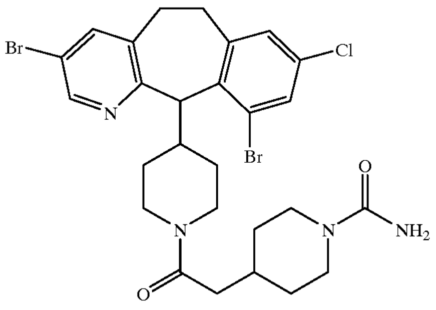

(+)- enantiomer with the chemotherapeutic agent Cytoxan on HTB 177 (NCI-H460, a human lung large cell carcinoma) using twice a day dosing was determined.

Athymic nu/nu female mice, 5–6 weeks old were used. On Day 0, HTB 177, $3\times10^6$, was injected s.c. into the flank of 100 mice. Afterwards the mice were weighed and randomly divided into 10 groups of 10 mice per group. Drug treatment began at about 8:00 am on Day 1. The mice in groups 2, 5, 6, 7, 8, 9, and 10 were dosed p.o., b.i.d., at about 8 am and 8 pm, 7 days a week for 4 weeks. The mice in Groups 3, 4, 6, 7, 9, and 10 were dosed i.p. with the indicated dosage of Cytoxan (see Table 2) on Days 5, 12, and d 19. The primary tumors were measured once a week starting when the average size was about 50–100 $mm^3$. The results are given in Table 3.

TABLE 3

| Group | Treatment | % Average Inhibition |
|---|---|---|
| 1 | No treatment - control | — |
| 2 | Vehicle, 40% HPBCD, BID, p.o. | — |
| 3 | Cytoxan, 200 mpk, BID, Days 5, 12, & 19, i.p. | 75.38 |
| 4 | Cytoxan, 100 mpk, BID, Days 5, 12, & 19, i.p. | 61.87 |
| 5 | Compound X, 80 mpk, BID, p.o., | 74.77 |
| 6 | Compound X, 80 mpk, BID, p.o.<br>Cytoxan, 200 mpk, BID, i.p. | 89.29 |
| 7 | Compound X, 80 mpk, BID, p.o.<br>Cytoxan, 100 mpk, BID, i.p. | 89.32 |
| 8 | Compound X, 20 mpk, BID, p.o., | 49.47 |
| 9 | Compound X, 20 mpk, BID, p.o.<br>Cytoxan, 200 mpk, BID, i.p. | 90.29 |
| 10 | Compound X, 20 mpk, BID, p.o.<br>Cytoxan, 100 mpk, BID, i.p. | 68.71 |

The Compound X (FPT Inhibitory Compound) for Groups 5, 6, 7, 8, 9, and 10 was dissolved in 40% hydroxypropylbetacyclodextran (HPBCD). Cytoxan was dissolved in sterile water.

The 80 mpk dosing solution of Compound X was made by adding 10.8 ml of 40% HPBCD to a 50 ml tube containing 176 mg of Compound X to dissolve the compound. The mixture was sonicated until a complete solution was made.

The 20 mpk dosing solution was made by placing 2 ml of the 80 mpk solution into a 15 ml tube, adding 6 ml of 40% HPBCD, and vortexing the solution to mix it.

Example L

IN VIVO COMBINATION THERAPY—B.I.D.

The effect of in vivo combination therapy of the following FPT inhibitory compound (referred to as "Compound X" in the Tables below)

(Compound X)

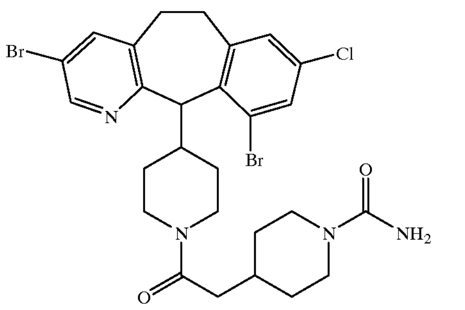

(+)- enantiomer with Gemzar® (Gemcitabine HCl) on MIA PaCa xenografts (a human pancreatic carcinoma) was determined. Athymic nu/nu female mice, 7 weeks old, were used. On day 0, human pancreatic cancer MIA PaCa cells, 6×10$^6$, were injected s.c. into the flank of each of 50 mice. An overview of the groups is set forth below:

| | | |
|---|---|---|
| Group 1 | Vehicle control I | 10 mice |
| Group 2 | Vehicle control II | 10 mice |
| Group 3 | Compound X (80 mpk/dosing) | 10 mice |
| Group 4 | Compound X (80 mpk) & Gemzar ® (120 mpk qid x 3) | 10 mice |
| Group 5 | Gemzar ® 120 mpk qid x 3 | 10 mice |

Formulation: Gemzar® was dissolved in Normal Saline (Vehicle I). Compound X was dissolved in 20% hydroxy-propyl-betacyclodexatrin (Vehicle II). 0.2 ml of Compound X solution was the oral dosing volume and the i.p. dosing volume for Gemzar® was 0.1 ml.

The 80 mpk dosing solution of Compound X was made by adding 15 ml of 20% HPBCD to a 50 ml tube containing 120 mg of Compound X to dissolve the compound. The mixture was sonicated until a complete solution was made.

The Gemzar® dosing solution was made by adding 16.6 ml of Saline to a vial of Gemzar® for Injection (200 mg of gemcitabine HCl), and vortexing to mix the solution. (Gemzar® is a commercially available form of gemcitabine (2', 2'-difluoro-deoxycytidine, dFdC, Gemzar®), which is a pyrimidine analogue of deoxycytidine in which the deoxyribose moiety contains two fluorine atoms at the 2'-position. (See Heinemann et al. Cancer Res 1988 48:4024). As noted in DeVita et al. (Eds.), *Cancer: Principles and Practice of Oncology* (Lippencott-Raven, Phila., Pa., 5th Ed. 1997), gemcitabine is known to have a broad spectrum of antitumor activity against leukemias and solid tumors. (reference: Hertel et al., Evaluation of the antitumor activity of gemcitabine (2', 2'-difluoro-2'deoxycytidine). Cancer Res 1990, 50:4417.) According to DeVita et al., "The most commonly used clinical schedule is a 30-minute IV infusion weekly for 3 weeks followed by a 1-week rest, and the recommended dose is 1000 mg/m$^2$. In phase II trials using this schedule (800 to 1250 dFdC mg/m$^2$ per week), response rates in the 16% to 24% range were reported in patients with non-small cell lung cancer (previously untreated) and small cell lung cancer, breast cancer patients who had received no more than one prior regimen for metastatic disease, and patients with refractory ovarian cancer, hormone-refractory prostate cancer, and head and neck cancer." DeVita et al. (Eds.), *Cancer: Principles and Practice of Oncology* (Lippencott-Raven, Phila., Pa., 5th Ed. 1997).)

Protocol: Tumor cells were inoculated into 50 mice in the morning of Day 0, and the mice were weighed, randomized, and ear-marked afterwards. Drug treatments with Compound X or Vehicle II started on Day 1 and continued twice a day at 7 am and 7 pm until Day 32. Gemzar® and Vehicle I treatments started on Day 7 and continued on every 3rd day (Day 10 and Day 13). Tumor growth was quantitated by measuring tumor volumes in 3 dimensions on Day 10, 15, 21, 26, and 32.

The results are given Table 4 below:

TABLE 4

| Group | Days of Treatment | Median Tumor Vol. | Mean Tumor Vol. | Standard Deviation | Average Inhibition |
|---|---|---|---|---|---|
| 1. Vehicle I | 10 | 6.12 | 13.15 | 17.94 | |
| | 15 | 33.3 | 47.41 | 39.47 | |
| | 21 | 63.9 | 74.32 | 34.38 | |
| | 26 | 90.33 | 83.88 | 30.16 | |
| | 32 | 166.9 | 154.17 | 70.5 | |
| 2. Vehicle II | 10 | 2.46 | 7.51 | 10.0 | |
| | 15 | 63.1 | 63.86 | 21.85 | |
| | 21 | 84.81 | 83.25 | 34.4 | |
| | 26 | 90.9 | 92.61 | 44.43 | |
| | 32 | 139.76 | 125.76 | 48.07 | |
| 3. Compound X | 10 | 4.96 | 8.87 | 10.7 | |
| (80 mpk) | 15 | 12.84 | 16.91 | 8.78 | |
| | 21 | 13.0 | 14.63 | 25.03 | |
| | 26 | 41.21 | 34.53 | 20.07 | |
| | 32 | 43.3 | 54.2 | 44.61 | 57% |
| 4. Compound X | 10 | 4.12 | 5.57 | 6.28 | |
| (80 mpk) | 15 | 6.66 | 12.21 | 14.06 | |
| & Gemzar ® | 21 | 0.40 | 0.67 | 0.68 | |
| (120 mpk) | 26 | 0.53 | 0.76 | 0.48 | |
| | 32 | 0.34 | 15.03 | 23.67 | 88% |
| 5. Gemzar ® | 10 | 12.29 | 13.26 | 11.56 | |
| (120 mpk) | 15 | 31.82 | 34.91 | 22.67 | |
| | 21 | 0.84 | 5.95 | 14.56 | |

TABLE 4-continued

| Group | Days of Treatment | Median Tumor Vol. | Mean Tumor Vol. | Standard Deviation | Average Inhibition |
|---|---|---|---|---|---|
| | 26 | 20.06 | 20.03 | 17.18 | |
| | 32 | 49.3 | 49.25 | 50.29 | 60% |

With regard to Table 4 above, it is particularly noteworthy that while Compound X alone at 80 mpk exhibited only 57% average inhibition and Gemzar® alone at 120 mpk exhibited only 60% average inhibition, the combination of Compound X at 80 mpk plus Gemzar® at 120 mpk resulted in 88% average inhibition. The percent inhibition observed in the case of the combination of Compound X with Gemzar® is statistically significant over the percentage observed with either agent alone ($p<0.05$).

Example M

IN VIVO THERAPY IN THE WAP-RAS TRANSGENIC MODEL

Compound X and Paclitaxel combination efficacy was also evaluated in the Wap-ras transgenic model. This model was used in a therapeutic mode in which treatments were initiated after mice had well developed tumors. An overview of the groups is set forth below:

| Groups: | | |
|---|---|---|
| Group 1 | No treatment | 10 mice |
| Group 2 | Vehicle control I p.o. | 10 mice |
| Group 3 | Compound X, 20 mpk/dosing, p.o. | 10 mice |
| Group 4 | Paclitaxel 5 mpk/dosing i.p. | 10 mice |
| Group 5 | Compound X, 20 mpk & Paclitaxel 5 mpk | 10 mice |
| Group 6 | Vehicle control II p.o. & i.p. | 10 mice |

Formulation: Compound X was dissolved in 20% hydroxyl-propyl-betacyclodexatrin (Vehicle I). 0.2 ml of Compound X solution is the oral dosing volume. Paclitaxel was dissolved in a diluted ethanol/cremophor EL solution (vehicle II) and the i.p. dosing volume for paclitaxel was 0.1 ml.

Protocol: The mice were weighed, randomized, and ear-marked on Day 0. Compound X treatment and Vehicle I treatment began on Day 1 and continued every 12 hours until Day 21. Paclitaxel and Vehicle II treatments started on Day 4 and continued daily on Day 5, 6, and 7.

Result: The results are illustrated in FIG. 38. Wap-ras tumors did not respond to treatment with Paclitaxel. They did respond (89% growth inhibition) to Compound X treatment at 20 mpk alone. When 20 mpk of Compound X and 5 mpk of Paclitaxel were combined, enhanced efficacy (tumor regression, equivalent to 180% growth inhibition) was seen compared to single agent alone. In addition to enhanced efficacy resulting from the combination of Compound X and Paclitaxel, the results also indicated that Compound X was able to sensitize Paclitaxel-resistant tumors.

PHARMACEUTICAL COMPOSITIONS

Inert, pharmaceutically acceptable carriers used for preparing pharmaceutical compositions of the FPT inhibitors and the chemotherapeutic agents described herein can be either solid or liquid. Solid preparations include powders, tablets, dispersible granules, capsules, cachets and suppositories. The powders and tablets may comprise from about 5 to about 70% active ingredient. Suitable solid carriers are known in the art, e.g., magnesium carbonate, magnesium stearate, talc, sugar, and/or lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into conveniently sized molds, allowed to cool and thereby solidify.

Liquid preparations include solutions, suspensions and emulsions. As an example may be mentioned water or water-propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The FPT inhibitors and the chemotherapeutic agents described herein may also be deliverable transdermally. The transdermal compositions can take the form of creams, lotions, aerosols and/or emulsions and can be included in a transdermal patch of the matrix or reservoir type as are conventional in the art for this purpose.

Preferably the compounds are administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, preferably from about 1 mg to 300 mg, more preferably 10 mg to 200 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the FPT inhibitors and the chemotherapeutic agents and/or radiation therapy will be regulated according to the judgment of the attending clinician (physician) considering such factors as age, condition and size of the patient as well as severity of the disease being treated. A dosage regimen of the FPT inhibitors can be oral administration of from 10 mg to 2000 mg/day, preferably 10 to 1000 mg/day, more preferably 50 to 600 mg/day, in two to four (preferably two) divided doses, to block tumor growth. In a preferred embodiment, in cases where the FPT inhibitor is a fused-ring tricyclic benzocycloheptapyridine, the preferred dosage of the inhibitor is oral administration of from 50 to 600 mg/day, more preferably 50 to 400 mg/day, in two divided doses. Intermittant therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

In a preferred example of combination therapy in the treatment of pancreatic cancer, the FPT inhibitor is "Compound X", as identified previously, administered orally in a range of from 50 to 400 mg/day, in two divided doses, on a continuous dosing regimen; and the antineoplastic agent is gemcitabine administered at a dosage of from 750 to 1350 $mg/m^2$ weekly for three out of four weeks during the course of treatment.

In a preferred example of combination therapy in the treatment of lung cancer, the FPT inhibitor is "Compound X", as identified previously, administered orally in a range of from 50 to 400 mg/day, in two divided doses, on a continuous dosing regimen; and the antineoplastic agent is paclitaxel administered at a dosage of from 65 to 175 $mg/m^2$ once every three weeks.

In a preferred example of combination therapy in the treatment of gliomas, the FPT inhibitor is "Compound X", as identified previously, administered orally in a range of from 50 to 400 mg/day, in two divided doses; and the antineoplastic agent is temozolomide administered at a dosage of from 100 to 250 $mg/m^2$.

In another example of combination therapy, the FPT inhibitor is "Compound X", as identified previously, administered orally in a range of from 50 to 400 mg/day, in two divided doses, on a continuous dosing regimen; and the antineoplastic agent is 5-Fluorouracil (5-FU) administered either at a dosage of 500 $mg/m^2$ per week (once a week), or at a dosage of 200–300 $mg/m^2$ per day in the case of continuous infusion of the 5-FU. In the case of 5-FU administration on a weekly injection, 5-FU may be administered in combination with a foliate agonist (e.g., Leucovoran (at a dosage of 20 $mg/m^2$/week).

In the methods of this invention, an FPT inhibitor is administered concurrently or sequentially with a chemotherapeutic agent and/or radiation. Thus, it is not necessary that, for example, the chemotherapeutic agent and the FPT inhibitor, or the radiation and the FPT inhibitor, should be administered simultaneously or essentially simultaneously. The advantage of a simultaneous or essentially simultaneous administration is well within the determination of the skilled clinician.

Also, in general, the FPT inhibitor and the chemotherapeutic agent do not have to be administered in the same pharmaceutical composition, and may, because of different physical and chemical characteristics, have to be administered by different routes. For example, the FPT inhibitor may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of FPT inhibitor, and chemotherapeutic agent and/or radiation will depend upon the diagnosis of the attending physicians and their judgement of the condition of the patient and the appropriate treatment protocol.

The FPT inhibitor, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the FPT inhibitor.

If the FPT inhibitor, and the chemotherapeutic agent and/or radiation are not administered simultaneously or essentially simultaneously, then the initial order of administration of the FPT inhibitor, and the chemotherapeutic agent and/or radiation, may not be important. Thus, the FPT inhibitor may be administered first followed by the administration of the chemotherapeutic agent and/or radiation; or the chemotherapeutic agent and/or radiation may be administered first followed by the administration of the FPT inhibitor. This alternate administration may be repeated during a single treatment protocol. The determination of the order of administration, and the number of repititions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the FPT inhibitor followed, where determined advantageous, by the administration of the chemotherapeutic agent and/or radiation, and so on until the treatment protocol is complete.

Thus, in accordance with experience and knowledge, the practising physician can modify each protocol for the administration of a component (therapeutic agent—i.e., FPT inhibitor, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The following are examples (Examples 1–4) of capsule formulations for the FPT Inhibitory Compound:

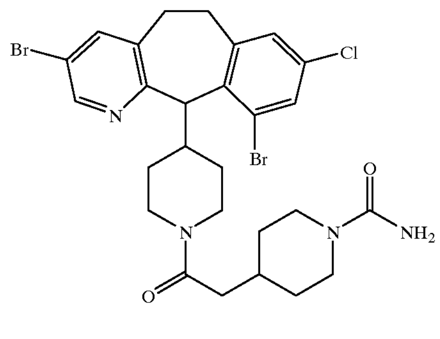

(+)- enantiomer

| Capsule Formulation Composition | Example 1 mg/capsule | Example 2 mg/capsule | % Composition |
|---|---|---|---|
| Solid Solution | 100 | 400.0 | 84.2 |
| Silicon Dioxide NF(1) | 0.625 | 2.5 | 0.5 |
| Magnesium Stearate NF(2) | 0.125 | 0.5 | 0.1 |
| Croscarmellose Sodium NF | 11.000 | 44.0 | 9.3 |
| Pluronic F68 NF | 6.250 | 25.0 | 5.3 |
| Silicon Dioxide NF(3) | 0.625 | 2.5 | 0.5 |
| Magnesium Stearate NF(4) | 0.125 | 0.5 | 0.1 |
| TOTAL | 118.750 | 475.00 | |
| Capsule size | No. 4 | No. 0 | |

METHOD (Examples 1 and 2)

Preparation of Solid Solution

| Composition | g/batch | % Composition |
|---|---|---|
| FPT Inhibitory Compound | 80 | 33.3 |
| Povidone NF K29/32 | 160 | 66.6 |
| Methylene Chloride | 5000 mL | evaporates |

Crystalline FPT Inhibitory Compound and the povidone were dissolved in methylene chloride. The solution was dried using a suitable solvent spray dryer. The residue was then reduced to fine particles by grinding. The powder was then passed through a 30 mesh screen. The powder was found to be amorphous by x-ray analysis.

The solid solid solution, silicon dioxide(1) and magnesium stearate(2) were mixed in a suitable mixer for 10 minutes. The mixture is compacted using a suitable roller compactor and milled using a suitable mill fitted with 30 mesh screen. Croscarmellose sodium, Pluronic F68 and silicon dioxide(3) are added to the milled mixture and mixed further for 10 minutes. A premix was made with magnesium stearate(4) and equal portions of the mixture. The premix was added to the remainder of the mixture and mixed for 5 minutes. the mixture was encapsulated in hard shell gelatin capsule shells.

Examples 3 and 4

| Capsule Formulation Composition | Example 3 mg/capsule | Example 4 mg/capsule | % Composition |
|---|---|---|---|
| Solid Solution | 400 | 200.0 | 80.0 |
| Silicon Dioxide NF(1) | 3.75 | 1.875 | 0.75 |
| Magnesium Stearate NF(2) | 0.125 | 0.625 | 0.25 |
| Croscarmellose Sodium NF | 40.00 | 20.00 | 8.0 |
| Pluronic F68 NF | 50.00 | 25.00 | 10 |
| Silicon Dioxide NF(3) | 3.75 | 1.875 | 0.75 |
| Magnesium Stearate NF(4) | 1.25 | 0.625 | 0.25 |
| TOTAL | 500.00 | 250.00 | |
| Capsule size | No. 0 | No. 2 | |

METHOD (Examples 3 and 4)

Preparation of Solid Solution

| Composition | g/batch | % Composition |
|---|---|---|
| FPT Inhibitory Compound | 15 | 50 |
| Povidone NF K29/32 | 15 | 50 |
| Methylene Chloride | 140 mL | evaporates |
| Methanol | 60 mL | evaporates |

For information on formulations, reference can also be made to U.S. patent application Ser. Nos. 08/997,168 and 60/068,387 (filed Dec. 22, 1997), incorporated herein by reference.

Crystalline FPT Inhibitory Compound and the povidone were dissolved in a mixture of methylene chloride and methanol. The solution was dried using a suitable solvent spray dryer. The residue was then reduced to fine particles by grinding. The powder was then passed through a 30 mesh screen. The powder was found to be amorphous by x-ray analysis.

The solid solid solution, silicon dioxide(1) and magnesium stearate(2) were mixed in a suitable mixer for 10 minutes. The mixture is compacted using a suitable roller compactor and milled using a suitable mill fitted with 30 mesh screen. Croscarmellose sodium, Pluronic F68 and silicon dioxide(3) are added to the milled mixture and mixed further for 10 minutes. A premix was made with magnesium stearate(4) and equal portions of the mixture. The premix was added to the remainder of the mixture and mixed for 5 minutes. The mixture was encapsulated in hard shell gelatin capsule shells.

The scope of the invention in its pharmaceutical composition aspect is not to be limited by the examples provided.

All documents (e.g., publications and patent applications) cited herein are incorporated by reference to the same extent as if each individual document was specifically and individually indicated to be incorporated by reference.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method of treating proliferative disease in a patient in need of such treatment, said treatment comprising administering, concurrently or sequentially, an effective amount of (1) the FPT inhibitor

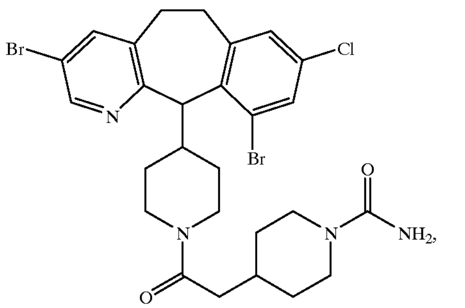

(+)-enantiomer and (2) an antineoplastic agent and/or radiation therapy.

2. The method of claim 1 wherein said antineoplastic agent is selected from: Uracil mustard, Chlormethine, Cyclophosphamide, Ifosfamide, Melphalan, Chlorambucil, Pipobroman, Triethylenemelamine, Triethylenethiophosphoramine, Busulfan, Carmustine, Lomustine, Streptozocin, Dacarbazine, Temozolomide, Methotrexate, 5-Fluorouracil, Floxuridine, Cytarabine, 6-Mercaptopurine, 6-Thioguanine, Fludarabine phosphate, Pentostatine, Gemcitabine, Vinblastine, Vincristine, Vindesine, Bleomycin, Dactinomycin, Daunorubicin, Doxorubicin, Epirubicin, Idarubicin, Paclitaxel, Mithramycin, Deoxycoformycin, Mitomycin-C, L-Asparaginase, Interferons, Etoposide, Teniposide 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Goserelin, Cisplatin, Carboplatin, Hydroxyurea, Amsacrine, Procarbazine, Mitotane, Mitoxantrone, Levamisole, Navelbene, CPT-11, Anastrazole, Letrazole, Capecitabine, Reloxafine, Droloxafine, or Hexamethylmelamine.

3. The method of claim 1 wherein said antineoplastic agent is selected from: Cyclophosphamide, 5-Fluorouracil, or Vincristine.

4. The method of claim 1 wherein said antineoplastic agent is Cyclophosphamide.

5. The method of claim 1 wherein said antineoplastic agent is 5-Fluorouracil.

6. The method of claim 1 wherein said antineoplastic agent is temozolomide.

7. The method of claim 1 wherein said proliferative disease is: lung cancer, pancreatic cancer, colon cancer, myeloid leukemia, melanoma, glioma, thyroid follicular cancer, bladder carcin-oma, myelodysplastic syndrome, breast cancer or prostate cancer.

8. The method of claim 1 wherein said FPT inhibitor, and said antineoplastic agent and/or radiation are administered concurrently.

9. The method of claim 1 wherein said FPT inhibitor, and said antineoplastic agent and/or radiation are administered simultaneously.

10. The method of claim 1 wherein said FPT inhibitor, and said antineoplastic agent and/or radiation are administered sequentially.

11. The method of claim 1 wherein said antineoplastic agent and/or radiation therapy is administered first.

12. The method of claim 1 wherein said FPT inhibitor is administered first.

13. A method of treating proliferative diseases in a patient in need of such treatment, said treatment comprising administering, concurrently or sequentially, an effective amount of (1) the FPT inhibitor

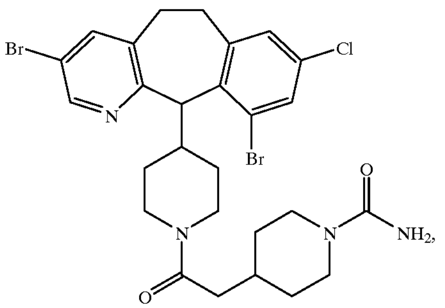

(+)-enantiomer and (2) gemcitabine.

14. The method of claim 13 wherein the proliferative disease is: prostate cancer, lung cancer, or pancreatic cancer.

15. The method of claim 13 wherein the proliferative disease is pancreatic cancer.

16. The method of claim 15 wherein the FPT inhibitor is administered orally in an amount of from 50 to 400 mg/day, and the gemcitabine is administered in an amount of from 750 to 1350 $mg/m^2$ weekly for three out of four weeks.

17. A method of treating proliferative diseases in a patient in need of such treatment, said treatment comprising administering, concurrently or sequentially, an effective amount of (1) the FPT inhibitor

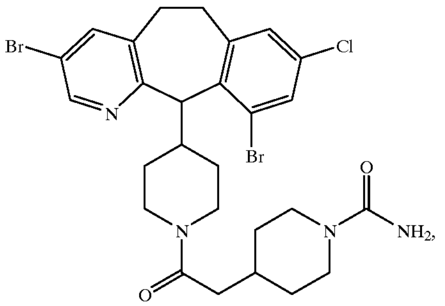

(+)-enantiomer and (2) a microtubule affecting agent.

18. The method of claim 17 wherein the microtubule affecting agent is paclitaxel or a paclitaxel derivative.

19. The method of claim 17 wherein the proliferative disease is prostate cancer.

20. The method of claim 17 wherein the proliferative disease is pancreatic cancer.

21. The method of claim 17 wherein the proliferative disease is lung cancer.

* * * * *